(12) United States Patent
Dyckman et al.

(10) Patent No.: US 11,420,973 B2
(45) Date of Patent: Aug. 23, 2022

(54) AMIDE SUBSTITUTED INDOLE COMPOUNDS USEFUL AS TLR INHIBITORS

(71) Applicant: BRISTOL-MYERS SQUIBB COMPANY, Princeton, NJ (US)

(72) Inventors: Alaric J. Dyckman, Lawrenceville, NJ (US); Dharmpal S. Dodd, Monmouth Junction, NJ (US); Christopher P. Mussari, Princeton, NJ (US); Trevor C. Sherwood, West Windsor, NJ (US); Tasir Shamsul Haque, Yardley, PA (US); Shoshana L. Posy, Highland Park, NJ (US); Sreekantha Ratna Kumar, Bangalore (IN); Laxman Pasunoori, Warangal (IN); Subramanya Hegde, Bangalore (IN); Rushith Kumar Anumula, Secunderabad (IN)

(73) Assignee: Bristol-Myers Squibb Company, Princeton, NJ (US)

( * ) Notice: Subject to any disclaimer, the term of this patent is extended or adjusted under 35 U.S.C. 154(b) by 40 days.

(21) Appl. No.: 16/954,543

(22) PCT Filed: Dec. 18, 2018

(86) PCT No.: PCT/US2018/066106
§ 371 (c)(1),
(2) Date: Jun. 17, 2020

(87) PCT Pub. No.: WO2019/126081
PCT Pub. Date: Jun. 27, 2019

(65) Prior Publication Data
US 2020/0331920 A1     Oct. 22, 2020

Related U.S. Application Data

(60) Provisional application No. 62/607,388, filed on Dec. 19, 2017.

(51) Int. Cl.
| | |
|---|---|
| *C07D 487/04* | (2006.01) |
| *C07D 209/42* | (2006.01) |
| *C07D 401/10* | (2006.01) |
| *C07D 401/12* | (2006.01) |
| *C07D 401/14* | (2006.01) |
| *C07D 403/10* | (2006.01) |
| *C07D 403/14* | (2006.01) |
| *C07D 405/14* | (2006.01) |
| *C07D 417/12* | (2006.01) |
| *C07D 417/14* | (2006.01) |
| *C07D 491/08* | (2006.01) |

(52) U.S. Cl.
CPC ......... *C07D 487/04* (2013.01); *C07D 209/42* (2013.01); *C07D 401/10* (2013.01); *C07D 401/12* (2013.01); *C07D 401/14* (2013.01); *C07D 403/10* (2013.01); *C07D 403/14* (2013.01); *C07D 405/14* (2013.01); *C07D 417/12* (2013.01); *C07D 417/14* (2013.01); *C07D 491/08* (2013.01)

(58) Field of Classification Search
CPC .. C07D 487/04; C07D 209/42; C07D 401/10; C07D 401/12; C07D 401/14; C07D 403/10; C07D 403/14; C07D 405/14; C07D 417/12; C07D 417/14; C07D 491/04
See application file for complete search history.

(56) References Cited

U.S. PATENT DOCUMENTS

| | | |
|---|---|---|
| 6,187,777 B1 | 2/2001 | Norman et al. |
| 6,306,874 B1 | 10/2001 | Fraley et al. |
| 6,867,200 B1 | 3/2005 | Allen et al. |
| 7,410,975 B2 | 8/2008 | Lipford et al. |
| 8,138,187 B2 | 3/2012 | Zemolka et al. |
| 8,354,400 B2 | 1/2013 | Zheng et al. |

(Continued)

FOREIGN PATENT DOCUMENTS

| | | |
|---|---|---|
| EP | 2738172 A1 | 6/2014 |
| WO | 03057696 A1 | 7/2003 |

(Continued)

OTHER PUBLICATIONS

Bobko, M. et al., "Synthesis of 2,5-disubstituted-3-cyanoindoles", Tetrahedron Letters, 53 (2012) 200-202.

(Continued)

*Primary Examiner* — Rebecca L Anderson
(74) *Attorney, Agent, or Firm* — Gary Greenblatt

(57) ABSTRACT

N-oxides, or salts thereof, wherein G, $L_2$, $R_1$, $R_5$, $R_9$, $R_{10}$, and n are defined herein. Also disclosed are methods of using such compounds as inhibitors of signaling through Toll-like receptor 7, or 8, or 9, and pharmaceutical compositions comprising such compounds. These compounds are useful in treating inflammatory and autoimmune diseases.

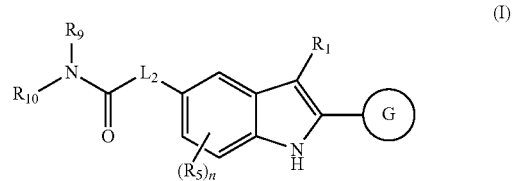

9 Claims, No Drawings

(56) References Cited

U.S. PATENT DOCUMENTS

| | | | |
|---|---|---|---|
| 8,691,814 B2* | 4/2014 | Daun | A61P 17/06 514/234.2 |
| 9,126,996 B2 | 9/2015 | Lipford et al. | |
| 9,126,999 B2 | 9/2015 | Bolvin et al. | |
| 9,241,991 B2 | 1/2016 | Ji et al. | |
| 9,353,115 B2 | 5/2016 | Lipford et al. | |
| 9,376,398 B2 | 6/2016 | Hori et al. | |
| 9,428,495 B2 | 8/2016 | Carlson et al. | |
| 9,643,967 B2 | 5/2017 | Koul et al. | |
| 2006/0235037 A1 | 10/2006 | Purandare et al. | |
| 2010/0160314 A1 | 6/2010 | Lipford et al. | |
| 2010/0197657 A1 | 8/2010 | Chang et al. | |
| 2011/0015219 A1 | 1/2011 | Trawick et al. | |
| 2011/0071150 A1 | 3/2011 | Alam et al. | |
| 2011/0105427 A1 | 5/2011 | Daun et al. | |
| 2011/0183967 A1 | 7/2011 | Zheng et al. | |
| 2011/0275631 A1 | 11/2011 | Abeywardane et al. | |
| 2013/0045986 A1 | 2/2013 | Nagarathnam et al. | |
| 2013/0324547 A1 | 12/2013 | Boivin et al. | |
| 2014/0066432 A1 | 3/2014 | Howbert et al. | |
| 2014/0088085 A1 | 3/2014 | Burgess et al. | |
| 2014/0242121 A1 | 8/2014 | Lipford et al. | |
| 2015/0231142 A1 | 8/2015 | van Goor et al. | |
| 2017/0008885 A1 | 1/2017 | Koul et al. | |
| 2017/0273983 A1 | 9/2017 | Ding et al. | |
| 2018/0000790 A1 | 1/2018 | Dyckman et al. | |

FOREIGN PATENT DOCUMENTS

| | | | |
|---|---|---|---|
| WO | 2006113458 A1 | 10/2006 | |
| WO | 2007115306 A2 | 10/2007 | |
| WO | 2008065198 A1 | 6/2008 | |
| WO | 2008152471 A1 | 12/2008 | |
| WO | 2009030996 A1 | 3/2009 | |
| WO | 2010149769 A1 | 12/2010 | |
| WO | 2013010904 A1 | 1/2013 | |
| WO | 2013181579 A2 | 12/2013 | |
| WO | 2015088045 A1 | 6/2015 | |
| WO | 2016029077 A1 | 2/2016 | |
| WO | 2018005586 A1 | 1/2018 | |
| WO | 2018026620 A1 | 2/2018 | |
| WO | 2018049089 A1 | 3/2018 | |

OTHER PUBLICATIONS

International Preliminary Report on Patentability for PCT/US2018/066106, dated Jun. 23, 2020.

International Search Report for PCT/US2018/066106, dated Dec. 18, 2018.

Kawai, T., et al., "The Role of Pattern-Recognition Receptors in Innate Immunity: Update on Toll-like Receptors", Nature Immunol., 2011, 11, 373-384.

Lamphier, M. et al., "Novel Small Molecule Inhibitors of TLR7 and TLR9: Mechanism of Action and Efficacy in Vivo", Mol Pharmacol, 2014, 85:429-440.

Patra, Mahesh Chandra, et al., "Recent Progress in the Development of Toll-like Receptor (TLR) antagonists", Exp. Opin. On Therapeutic Patents, 2016, vol. 26, No. 6, 719-730.

Roy, et al., "Design and developmen of benzoxazole derivatives with toll-like receptor 9 antagonism", Eur J Med Chem, 2017, vol. 134, 334-347.

Sims, et al., "The IL-1 Family: Regulators of Immunity", Nature Rev. Immunol., 2010, 10, 89-102.

* cited by examiner

AMIDE SUBSTITUTED INDOLE COMPOUNDS USEFUL AS TLR INHIBITORS

CROSS REFERENCE

This application is a national phase application under 35 U.S.C. § 371 of International Patent Application No. PCT/US2018/066106, filed Dec. 18, 2018, which claims priority to U.S. Provisional Application Ser. 62/607,388, filed Dec. 19, 2017, the contents of which are specifically incorporated fully herein by reference.

DESCRIPTION

The present invention generally relates to amide substituted indole compounds useful as inhibitors of signaling through Toll-like receptor 7, 8, or 9 (TLR7, TLR8, TLR9) or combinations thereof. Provided herein are amide substituted indole compounds, compositions comprising such compounds, and methods of their use. The invention further pertains to pharmaceutical compositions containing at least one compound according to the invention that are useful for the treatment of conditions related to TLR modulation, such as inflammatory and autoimmune diseases, and methods of inhibiting the activity of TLRs in a mammal.

Toll/IL-1 receptor family members are important regulators of inflammation and host resistance. The Toll-like receptor family recognizes molecular patterns derived from infectious organisms including bacteria, fungi, parasites, and viruses (reviewed in Kawai, T. et al., Nature Immunol., 11:373-384 (2010)). Ligand binding to the receptor induces dimerization and recruitment of adaptor molecules to a conserved cytoplasmic motif in the receptor termed the Toll/IL-1 receptor (TIR) domain. With the exception of TLR3, all TLRs recruit the adaptor molecule MyD88. The IL-1 receptor family also contains a cytoplasmic TIR motif and recruits MyD88 upon ligand binding (reviewed in Sims, J. E. et al., Nature Rev. Immunol., 10:89-102 (2010)).

Toll-like receptors (TLRs) are a family of evolutionarily conserved, transmembrane innate immune receptors that participate in the first-line defense. As pattern recognition receptors, the TLRs protect against foreign molecules, activated by pathogen associated molecular patterns (PAMPs), or from damaged tissue, activated by danger associated molecular patterns (DAMPs). A total of 13 TLR family members have been identified, 10 in human, that span either the cell surface or the endosomal compartment. TLR7/8/9 are among the set that are endosomally located and respond to single-stranded RNA (TLR7 and TLR8) or unmethylated single-stranded DNA containing cytosine-phosphate-guanine (CpG) motifs (TLR9).

Activation of TLR7/8/9 can initiate a variety of inflammatory responses (cytokine production, B cell activation and IgG production, Type I interferon response). In the case of autoimmune disorders, the aberrant sustained activation of TLR7/8/9 leads to worsening of disease states. Whereas overexpression of TLR7 in mice has been shown to exacerbate autoimmune disease, knockout of TLR7 in mice was found to be protective against disease in lupus-prone MRL/lpr mice. Dual knockout of TLR7 and 9 showed further enhanced protection.

As numerous conditions may benefit by treatment involving modulation of cytokines, IFN production and B cell activity, it is immediately apparent that new compounds capable of modulating TLR7 and/or TLR8 and/or TLR9 and methods of using these compounds could provide substantial therapeutic benefits to a wide variety of patients.

The present invention relates to a new class of amide substituted indole compounds found to be effective inhibitors of signaling through TLR7/8/9. These compounds are provided to be useful as pharmaceuticals with desirable stability, bioavailability, therapeutic index, and toxicity values that are important to their drugability.

DETAILED DESCRIPTION

The present invention provides compounds of Formula (I) that are useful as inhibitors of signaling through Toll-like receptor 7, 8, or 9 and are useful for the treatment of proliferative diseases, allergic diseases, autoimmune diseases and inflammatory diseases, or stereoisomers, N-oxides, tautomers, pharmaceutically acceptable salts, solvates or prodrugs thereof.

The present invention also provides pharmaceutical compositions comprising a pharmaceutically acceptable carrier and at least one of the compounds of the present invention or stereoisomers, tautomers, pharmaceutically acceptable salts, solvates, or prodrugs thereof.

The present invention also provides a method for inhibition of Toll-like receptor 7, 8, or 9 comprising administering to a host in need of such treatment a therapeutically effective amount of at least one of the compounds of the present invention or stereoisomers, tautomers, pharmaceutically acceptable salts, solvates, or prodrugs thereof.

The present invention also provides a method for treating proliferative, metabolic, allergic, autoimmune and inflammatory diseases, comprising administering to a host in need of such treatment a therapeutically effective amount of at least one of the compounds of the present invention or stereoisomers, tautomers, pharmaceutically acceptable salts, solvates, or prodrugs thereof.

The present invention also provides a method of treating a disease or disorder associated with Toll-like receptor 7, 8, or 9 activity, the method comprising administering to a mammal in need thereof, at least one of the compounds of Formula (I) or salts, solvates, and prodrugs thereof.

The present invention also provides processes and intermediates for making the compounds of Formula (I) including salts, solvates, and prodrugs thereof.

The present invention also provides at least one of the compounds of Formula (I) or salts, solvates, and prodrugs thereof, for use in therapy.

The present invention also provides the use of at least one of the compounds of Formula (I) or salts, solvates, and prodrugs thereof, for the manufacture of a medicament for the treatment of prophylaxis of Toll-like receptor 7, 8, or 9 related conditions, such as allergic disease, autoimmune diseases, inflammatory diseases, and proliferative diseases.

The compound of Formula (I) and compositions comprising the compounds of Formula (I) may be used in treating, preventing, or curing various Toll-like receptor 7, 8, or 9 related conditions. Pharmaceutical compositions comprising these compounds are useful for treating, preventing, or slowing the progression of diseases or disorders in a variety of therapeutic areas, such as allergic disease, autoimmune diseases, inflammatory diseases, and proliferative diseases.

These and other features of the invention will be set forth in expanded form as the disclosure continues.

DETAILED DESCRIPTION

The first aspect of the present invention provides at least one compound of Formula (I):

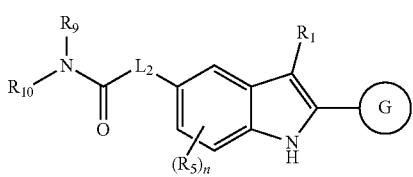
(I)
N-oxide, or a salt thereof, wherein:
G is:
(i)
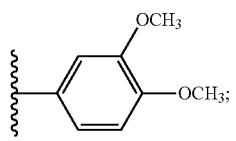 [SMILES: *c1ccc(OC)c(OC)c1]
(ii)
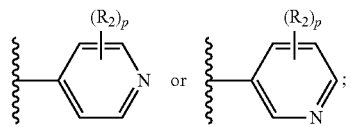
(iii)
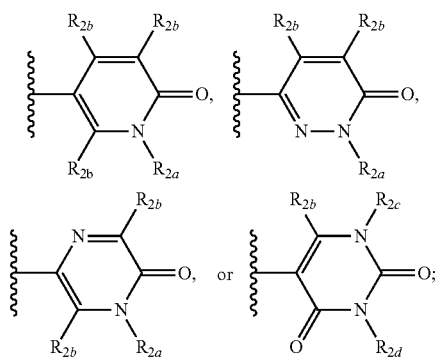
(iv) a 9-membered heterocyclic ring selected from:
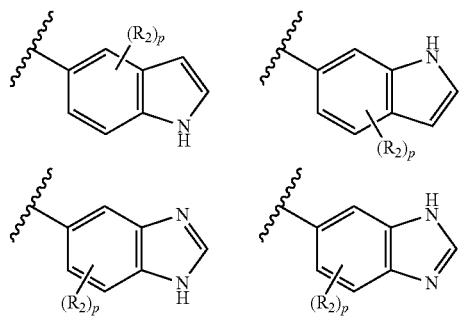
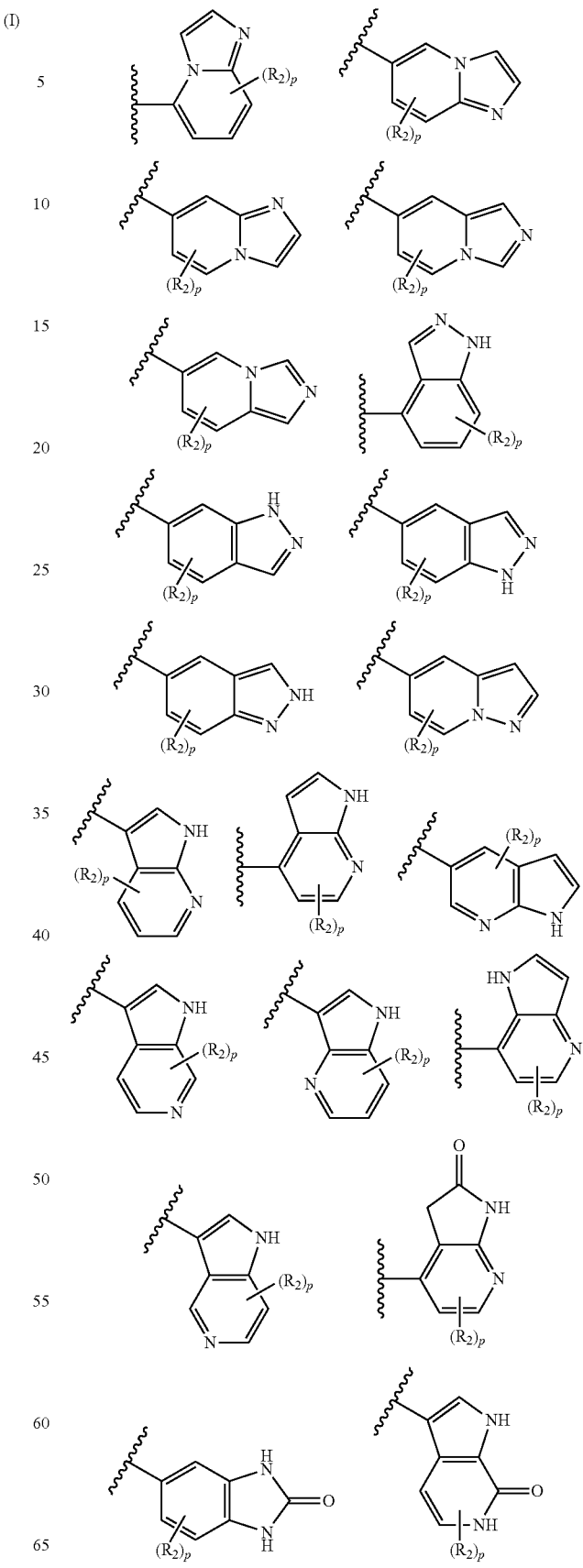

-continued
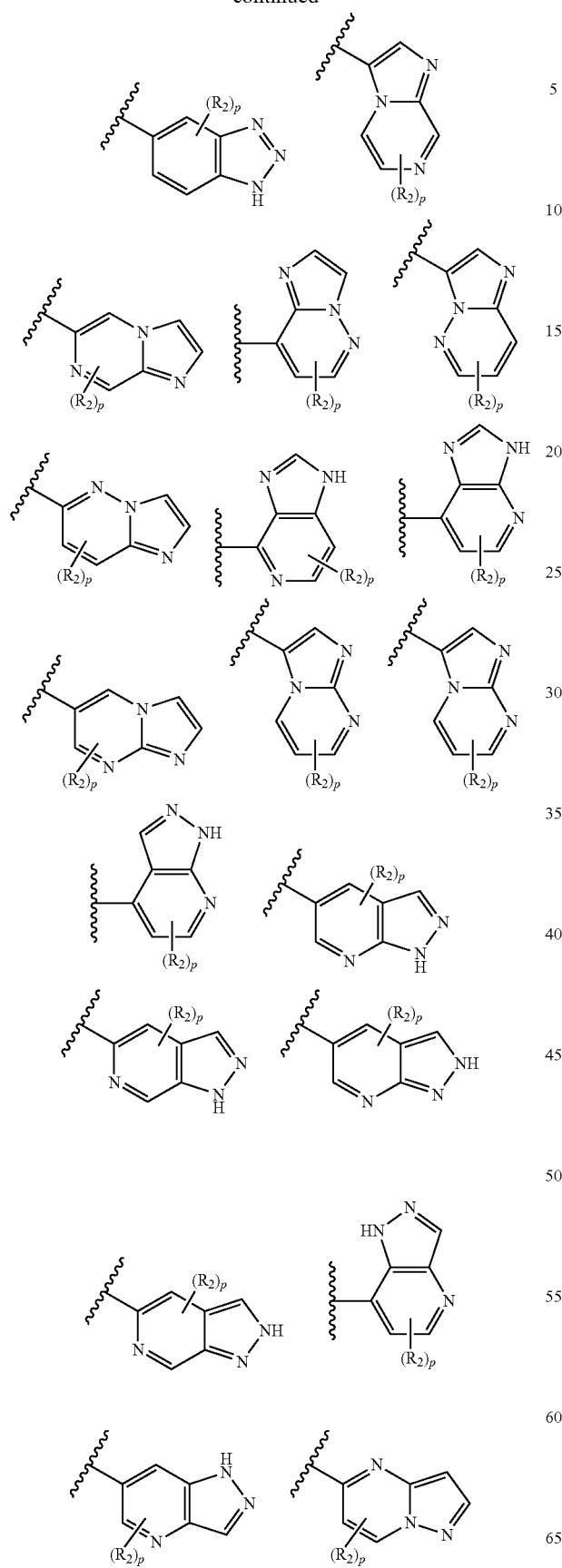
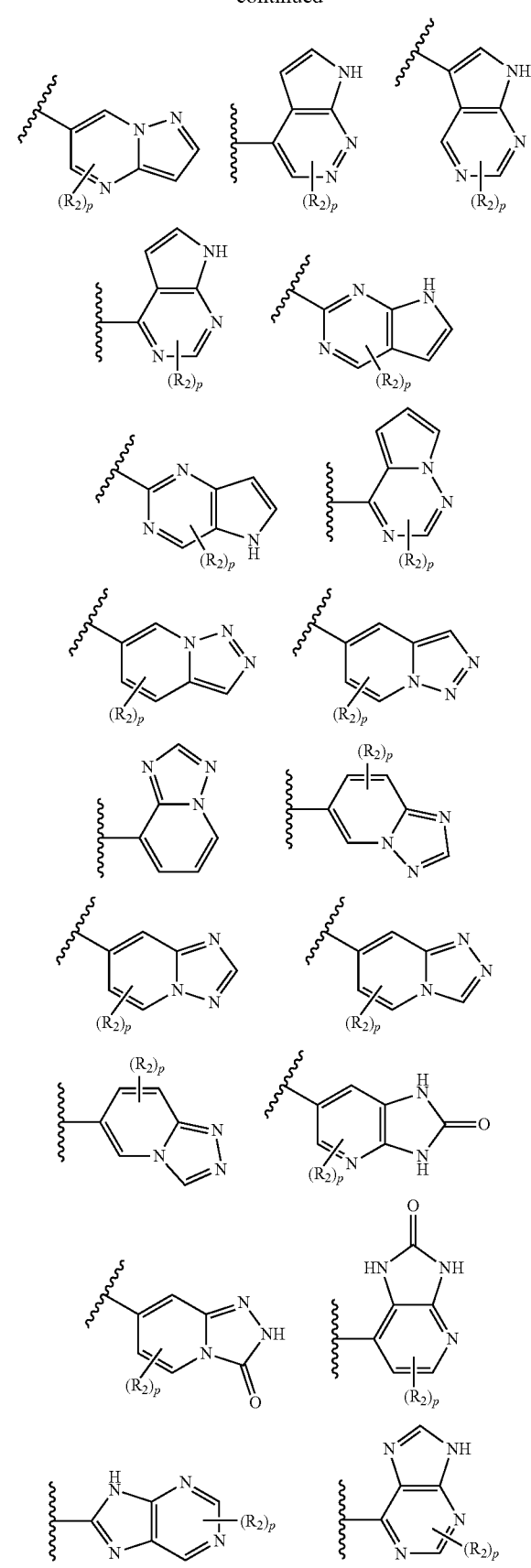

-continued
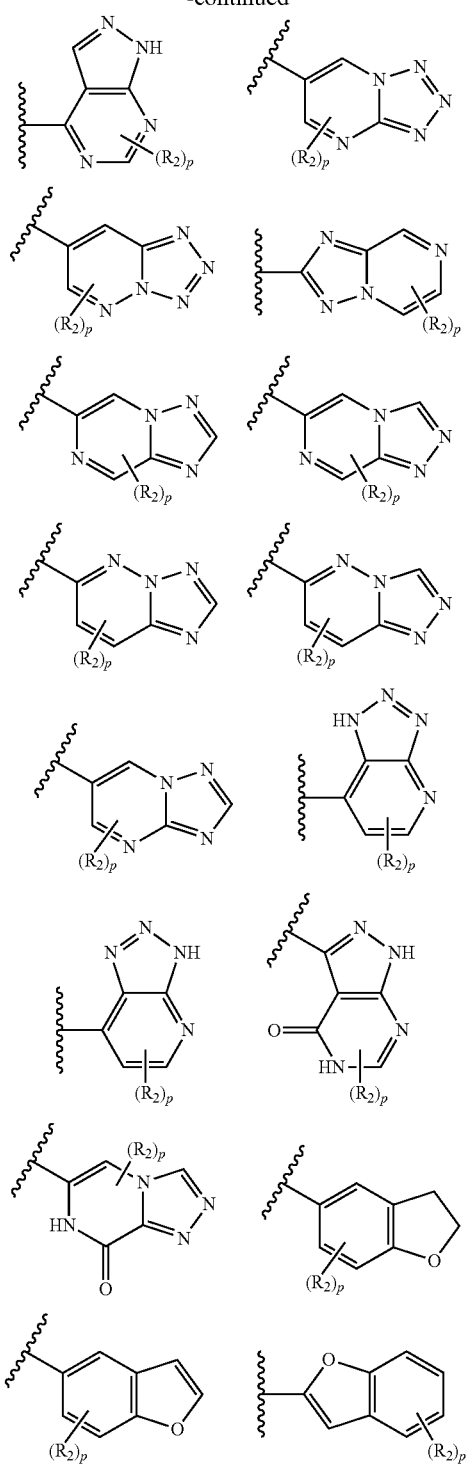
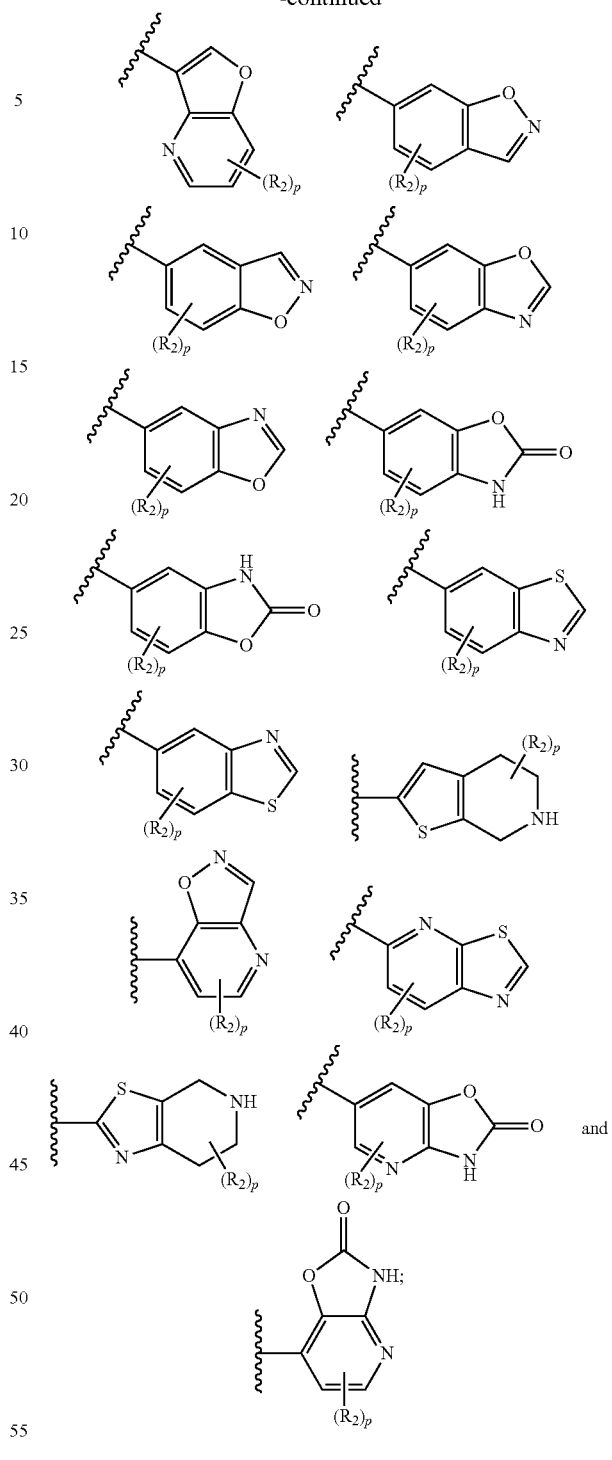
or
(v) a 10-membered heterocyclic ring selected from:
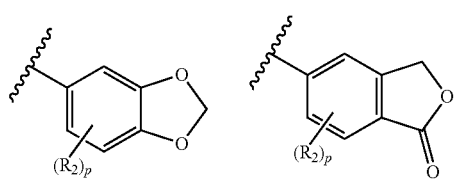
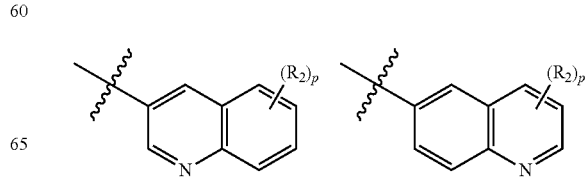

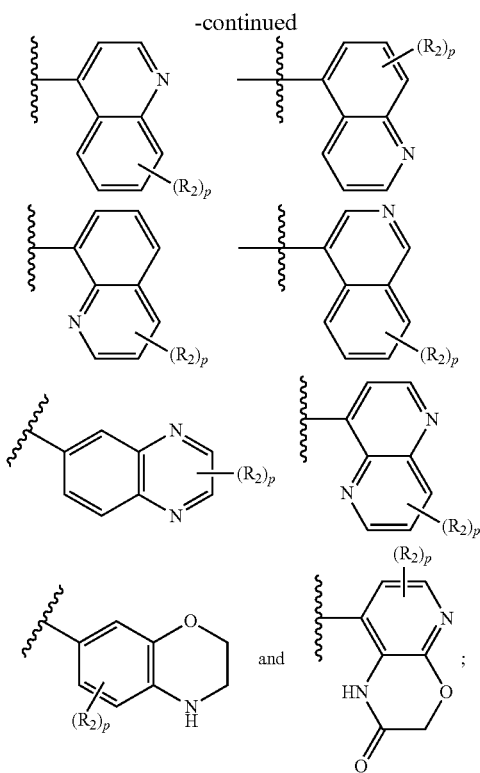

L$_2$ is a bond or —(CR$_x$R$_x$)$_{1-3}$—,

R$_1$ is H, Cl, —CN, C$_{1-4}$ alkyl, C$_{1-3}$ fluoroalkyl, C$_{1-3}$ hydroxyalkyl, C$_{1-3}$ hydroxy-fluoroalkyl, —CR$_y$=CH$_2$, C$_{3-6}$ cycloalkyl, —CH$_2$(C$_{3-6}$ cycloalkyl), —C(O)O(C$_{1-3}$ alkyl), or tetrahydropyranyl, each R$_2$ is independently halo, —CN, —OH, —NO$_2$, C$_{1-4}$ alkyl, C$_{1-2}$ fluoroalkyl, C$_{1-2}$ cyanoalkyl, C$_{1-3}$ hydroxyalkyl, C$_{1-3}$ aminoalkyl, —O(CH$_2$)$_{1-2}$OH, —(CH$_2$)$_{0-4}$O(C$_{1-4}$ alkyl), C$_{1-3}$ fluoroalkoxy, —(CH$_2$)$_{1-4}$O(C$_{1-3}$ alkyl), —O(CH$_2$)$_{1-2}$OC(O)(C$_{1-3}$ alkyl), —O(CH$_2$)$_{1-2}$NR$_x$R$_x$, —C(O)O(C$_{1-3}$ alkyl), —(CH$_2$)$_{0-2}$C(O)NR$_y$R$_y$, —C(O)NR$_x$(C$_{1-5}$ hydroxyalkyl), —C(O)NR$_x$(C$_{2-6}$ alkoxyalkyl), —C(O)NR$_x$(C$_{3-6}$ cycloalkyl), —NR$_y$R$_y$, —NR$_y$(C$_{1-3}$ fluoroalkyl), —NR$_y$(C$_{1-4}$ hydroxyalkyl), —NR$_x$CH$_2$(phenyl), —NR$_x$S(O)$_2$(C$_{3-6}$ cycloalkyl), —NR$_x$C(O)(C$_{1-3}$ alkyl), —NR$_x$CH$_2$(C$_{3-6}$ cycloalkyl), —S(O)$_2$(C$_{1-3}$ alkyl), —(CH$_2$)$_{0-2}$(C$_{3-6}$ cycloalkyl), —(CH$_2$)$_{0-2}$(phenyl), morpholinyl, dioxothiomorpholinyl, dimethyl pyrazolyl, methylpiperidinyl, methylpiperazinyl, amino-oxadiazolyl, imidazolyl, triazolyl, or —C(O)(thiazolyl);

R$_{2a}$ is C$_{1-6}$ alkyl, C$_{1-3}$ fluoroalkyl, C$_{1-6}$ hydroxyalkyl, C$_{1-3}$ aminoalkyl, —(CH$_2$)$_{0-4}$O(C$_{1-3}$ alkyl), C$_{3-6}$ cycloalkyl, —(CH$_2$)$_{1-3}$C(O)NR$_x$R$_x$, —CH$_2$(C$_{3-6}$ cycloalkyl), —CH$_2$(phenyl), tetrahydrofuranyl, tetrahydropyranyl, or phenyl;

each R$_{2b}$ is independently H, halo, —CN, —NR$_x$R$_x$, C$_{1-6}$ alkyl, C$_{1-3}$ fluoroalkyl, C$_{1-3}$ hydroxyalkyl, C$_{1-3}$ fluoroalkoxy, —(CH$_2$)$_{0-2}$O(C$_{1-3}$ alkyl), —(CH$_2$)$_{0-3}$C(O)NR$_x$R$_x$, —(CH$_2$)$_{1-3}$(C$_{3-6}$ cycloalkyl), —C(O)O(C$_{1-3}$ alkyl), —C(O)NR$_x$(C$_{1-3}$ alkyl), —CR$_x$=CR$_x$R$_x$, or —CR$_x$=CH(C$_{3-6}$ cycloalkyl);

R$_{2c}$ is R$_{2a}$ or R$_{2b}$;

R$_{2d}$ is R$_{2a}$ or R$_{2b}$; provided that one of R$_{2c}$ and R$_{2d}$ is R$_{2a}$, and the other of R$_{2c}$ and R$_{2d}$ is R$_{2b}$;

each R$_5$ is independently F, Cl, —CN, C$_{1-3}$ alkyl, C$_{1-2}$ fluoroalkyl, or —OCH$_3$;

R$_9$ is C$_{1-6}$ alkyl, C$_{1-6}$ hydroxyalkyl, C$_{1-6}$ hydroxy fluoroalkyl, C$_{1-3}$ aminoalkyl, —(CH$_2$)$_{1-2}$O(C$_{1-3}$ alkyl), —(CH$_2$)$_{1-3}$NR$_x$R$_x$, —(CH$_2$)$_{1-2}$C(O)NR$_x$R$_x$, —(CH$_2$)$_{1-3}$S(O)$_2$OH, —(CR$_x$R$_x$)$_{1-3}$NR$_x$S(O)$_2$(C$_{1-2}$ alkyl), or —(CH$_2$)$_{0-3}$R$_{9a}$;

R$_{9a}$ is C$_{3-7}$ cycloalkyl, furanyl, phenyl, piperazinyl, piperidinyl, pyrazolyl, pyridinyl, pyrrolidinyl, quinuclidinyl, thiazolyl, or octahydrocyclopenta[c]pyrrolyl, each substituted with zero to 3 substituents independently selected from F, Cl, —OH, C$_{1-4}$ alkyl, C$_{1-3}$ hydroxyalkyl, C$_{1-3}$ hydroxy fluoroalkyl, C$_{1-3}$ aminoalkyl, —NR$_y$R$_y$, oxetanyl, phenyl, piperazinyl, piperidinyl, and pyrrolidinyl;

R$_{10}$ is H, C$_{1-4}$ alkyl, —(CH$_2$)$_{1-3}$O(C$_{1-2}$ alkyl), or C$_{3-6}$ cycloalkyl;

or R$_9$ and R$_{10}$ together with the nitrogen atom to which they are attached form a heterocyclic ring selected from azabicyclo[3.1.1]heptanyl, azaspiro[5.5]undecanyl, diazabicyclo[2.2.1]heptanyl, diazabicyclo[3.1.1]heptanyl, diazabicyclo[3.2.0]heptanyl, diazaspiro[3.5]nonanyl, diazaspiro[4.4]nonanyl, diazaspiro[4.5]decanyl, diazepanyl, indolinyl, morpholinyl, octahydropyrrolo[3,4-c]pyrrolyl, piperazinonyl, piperazinyl, piperidinyl, and pyrrolidinyl, each substituted with zero to 3 R$_{10a}$;

each R$_{10a}$ is independently selected from C$_{1-4}$ alkyl, C$_{1-4}$ hydroxyalkyl, —(CH$_2$)$_{1-3}$O(C$_{1-3}$ alkyl), —(CH$_2$)$_{1-3}$NR$_x$R$_x$, —(CH$_2$)$_{1-2}$C(O)NR$_x$R$_x$, —(CH$_2$)$_{1-2}$(methyltriazolyl), —CH$_2$CH$_2$(phenyl), —CH$_2$CH$_2$(morpholinyl), —C(O)(C$_{1-2}$ alkyl), —C(O)NR$_y$R$_y$, —C(O)CH$_2$NR$_y$R$_y$, —NR$_y$R$_y$, —NHC(O)(C$_{1-3}$ alkyl), —C(O)(furanyl), —O(piperidinyl), —C(O)CH$_2$(diethylcarbamoylpiperidinyl), methylpiperazinyl, piperidinyl, methylpiperidinyl, diethylcarbamoylpiperidinyl, isopropylpiperidinyl, pyridinyl, trifluoromethylpyridinyl, pyrimidinyl, and dihydrobenzo[d]imidazolonyl;

R$_y$ is H, C$_{1-2}$ alkyl, or C$_{1-2}$ fluoroalkyl;

each R$_x$ is independently H or —CH$_3$;

each R$_y$ is independently H or C$_{1-6}$ alkyl;

each R$_z$ is independently H or —CH$_3$;

n is zero, 1, or 2; and p is zero, 1, 2, 3, or 4.

One embodiment provides a compound of Formula (I) or a salt thereof wherein G is:

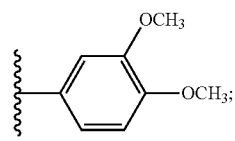 [SMILES: *c1ccc(OC)c(OC)c1]

and L$_2$, R$_1$, R$_5$, R$_9$, R$_{10}$, and n are defined in the first aspect.

One embodiment provides a compound of Formula (I), N-oxide, or a salt thereof wherein G is:

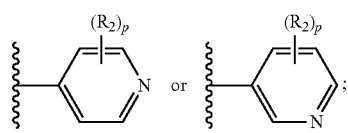

and L$_2$, R$_1$, R$_2$, R$_5$, R$_9$, R$_{10}$, n, and p are defined in the first aspect.

One embodiment provides a compound of Formula (I) or a salt thereof wherein G is

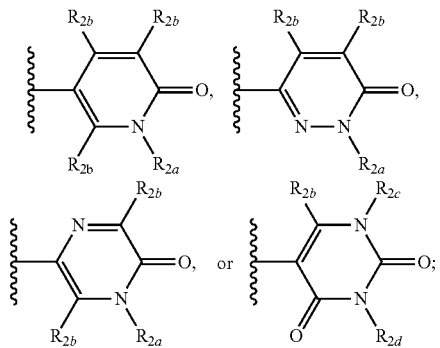

and $L_2$, $R_1$, $R_{2a}$, $R_{2b}$, $R_{2c}$, $R_{2d}$, $R_5$, $R_9$, $R_{10}$, n, and p are defined in the first aspect. Included in this embodiment are compounds in which $R_{2a}$ is $C_{1-4}$alkyl, $C_{1-2}$ fluoroalkyl, $C_{1-4}$ hydroxyalkl, —$(CH_2)_{1-3}OCH_3$, $C_{3-6}$cycloalkyl, —$CH_2C(O)NR_xR_x$, —$CH_2(C_{3-6}$cycloalkyl), —$CH_2$(phenyl), tetrahydrofuranyl or phenyl; and each $R_{2b}$ is independently H, F, Cl, —CN, —$NR_xR_x$ $C_{1-6}$alkyl, $C_{1-2}$ fluoroalkyl, $C_{1-3}$ hydroxyalkyl, —$(CH_2)_{0-2}(C_{1-2}$ alkyl), —$(CH_2)_{0-2}C(O)NR_xR_x$, —$(CH_2)_{1-3}$(cyclopropyl), —$C(O)O(C_{1-2}$ alkyl), —$C(O)NR_x$ $(C_{1-3}$ alkyl), —$CR_x$=$CH_2$, or —CH=CH($C_{3-6}$ cycloalkyl). Also included in this embodiment are compounds in which $R_{2a}$ is —$CH_3$; and each $R_{2b}$ is independently H, Cl, or —$CH_3$.

One embodiment provides a compound of Formula (I) or a salt thereof wherein G is a 9-membered heterocyclic ring selected from:

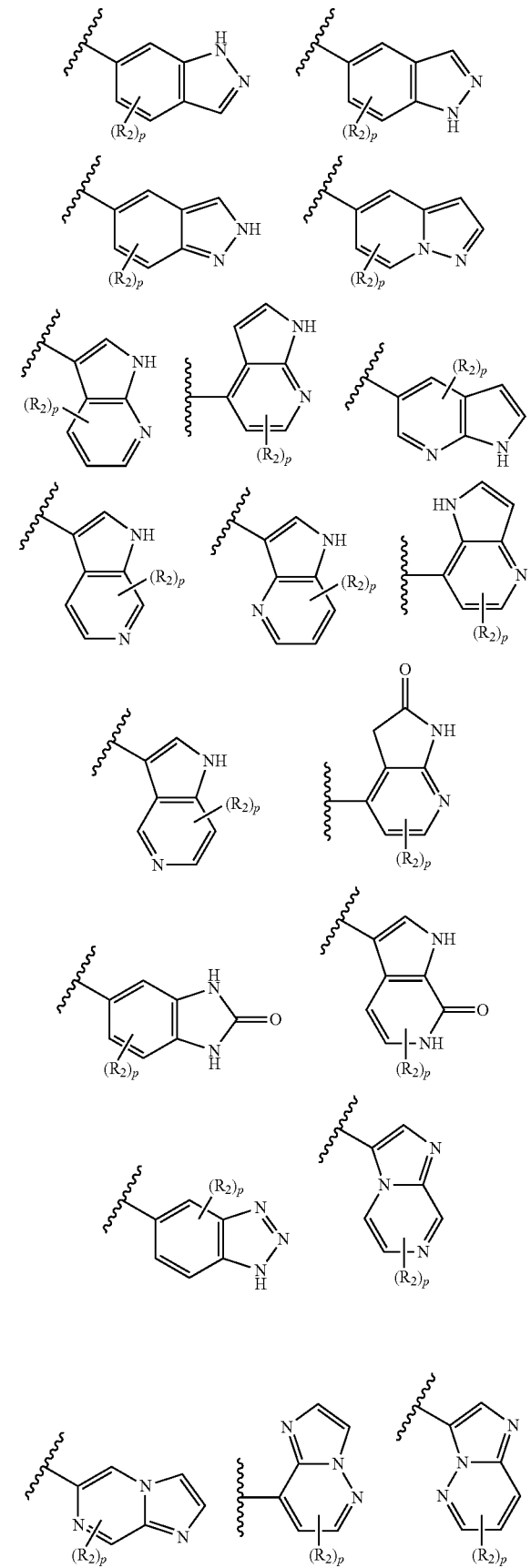

-continued
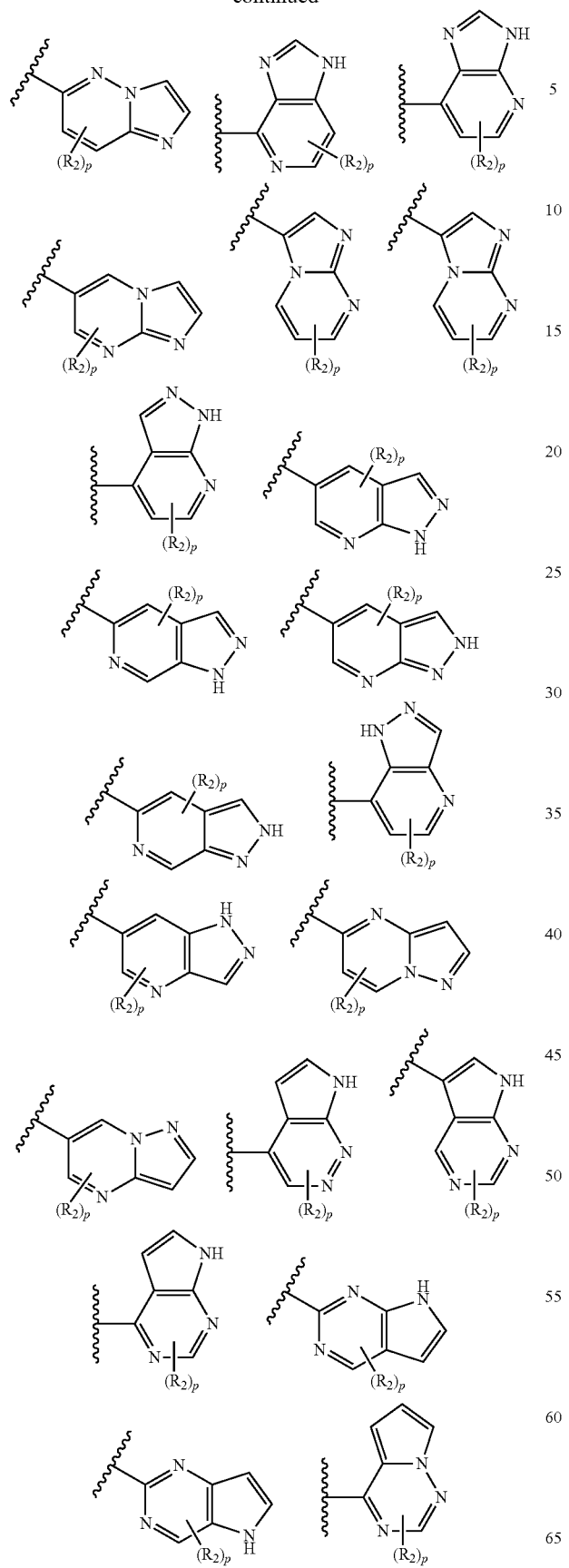
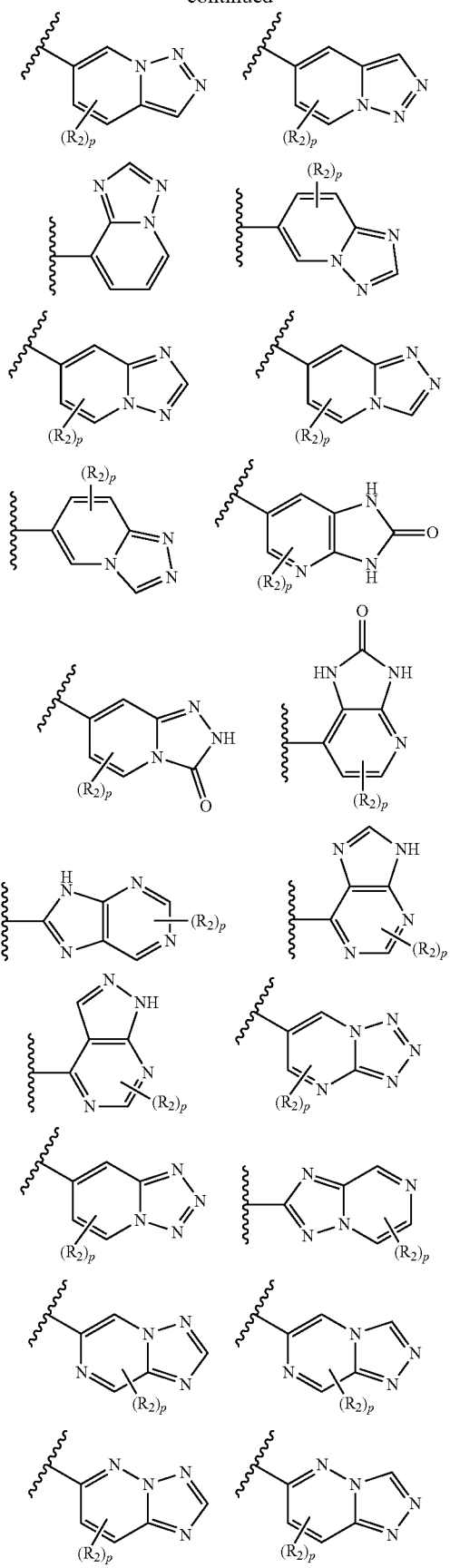

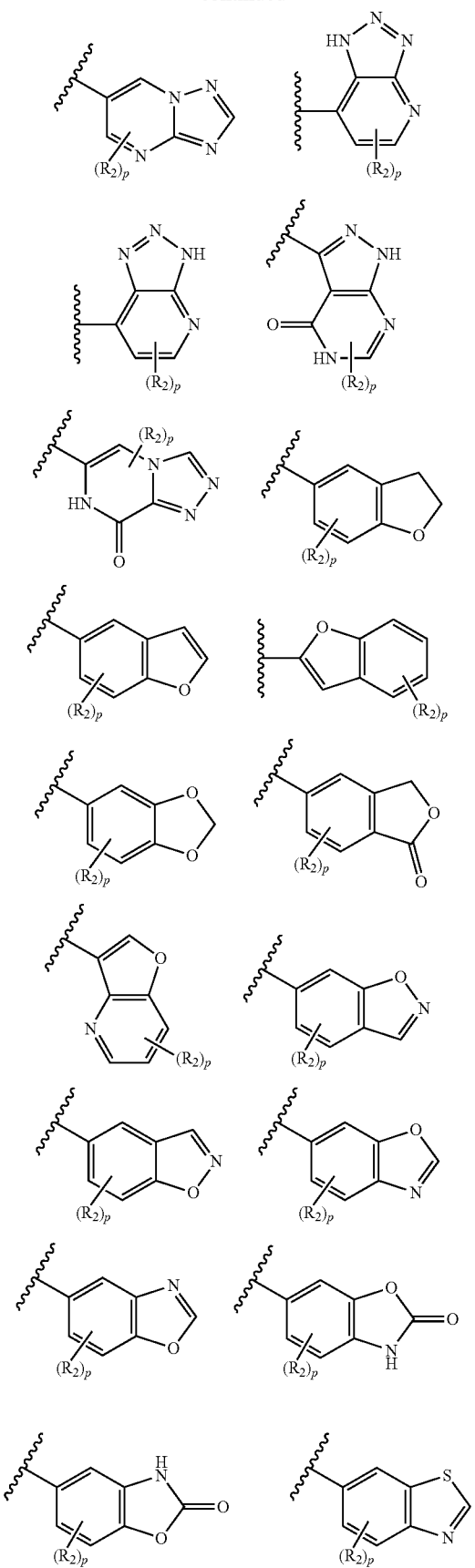
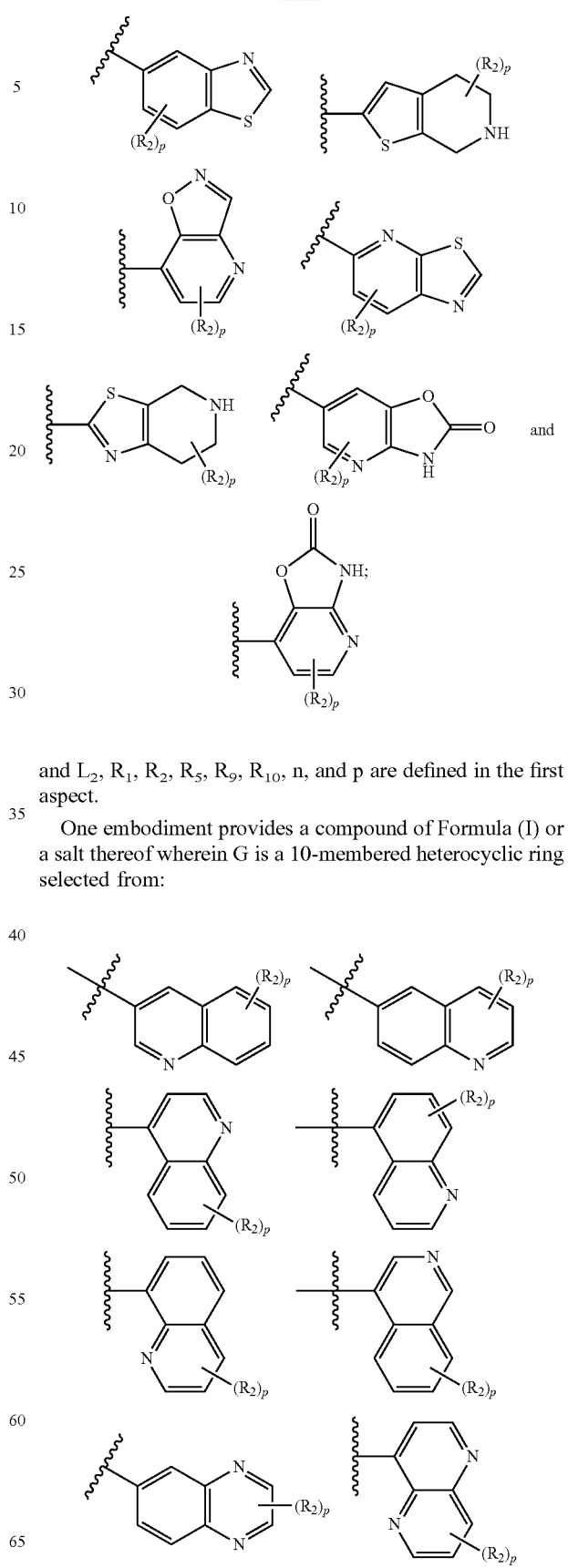
and $L_2$, $R_1$, $R_2$, $R_5$, $R_9$, $R_{10}$, n, and p are defined in the first aspect.
One embodiment provides a compound of Formula (I) or a salt thereof wherein G is a 10-membered heterocyclic ring selected from:
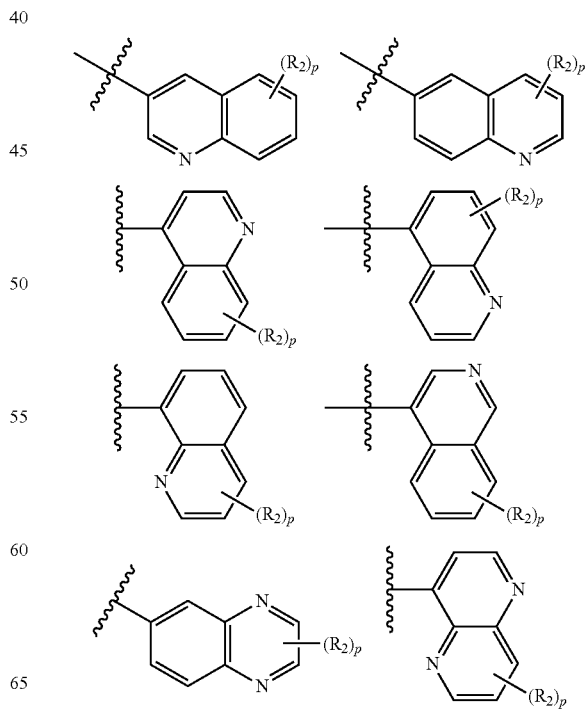

17

-continued

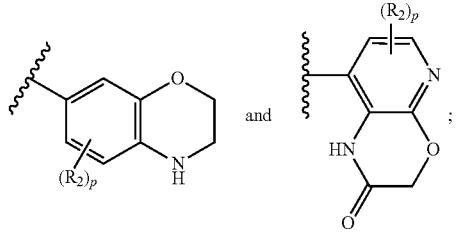

and and $L_2$, $R_1$, $R_2$, $R_5$, $R_9$, $R_{10}$, n, and p are defined in the first aspect.

One embodiment provides a compound of Formula (I), N-oxide, or a salt thereof wherein $R_1$ is H, Cl, —CN, $C_{1-4}$ alkyl, $C_{1-2}$ fluoroalkyl, $C_{1-2}$ hydroxyalkyl, or —C(O)O($C_{1-2}$ alkyl); each $R_2$ is independently F, Cl, —CN, —OH, $C_{1-3}$ alkyl, $C_{1-2}$ fluoroalkyl, $C_{1-2}$ cyanoalkyl, $C_{1-3}$ hydroxyalkyl, $C_{1-2}$ aminoalkyl, —(CH$_2$)$_{0-2}$O($C_{1-3}$ alkyl), $C_{3-6}$ cycloalkyl, —NR$_x$R$_x$, —(CH$_2$)$_{0-2}$C(O)NR$_x$R$_x$, —CH$_2$($C_{3-6}$ cycloalkyl), —CH$_2$(phenyl), or phenyl; $R_{2a}$ is $C_{1-4}$ alkyl, $C_{1-2}$ fluoroalkyl, $C_{1-4}$ hydroxyalkyl, —(CH$_2$)$_{1-3}$OCH$_3$, $C_{3-6}$ cycloalkyl, —CH$_2$C(O)NR$_x$R$_x$, —CH$_2$($C_{3-6}$ cycloalkyl), —CH$_2$(phenyl), tetrahydrofuranyl, or phenyl; each $R_{2b}$ is independently H, F, Cl, —CN, —NR$_x$R$_x$, $C_{1-6}$ alkyl, $C_{1-2}$ fluoroalkyl, $C_{1-3}$ hydroxyalkyl, —(CH$_2$)$_{0-2}$O($C_{1-2}$ alkyl), —(CH$_2$)$_{0-2}$C(O)NR$_x$R$_x$, —(CH$_2$)$_{1-3}$(cyclopropyl), —C(O)O($C_{1-2}$ alkyl), —C(O)NR$_x$($C_{1-3}$ alkyl), —CR$_x$=CH$_2$, or —CH=CH($C_{3-6}$ cycloalkyl); $L_2$ is a bond or —(CR$_x$R$_x$)$_{1-2}$—; $R_9$ is $C_{1-3}$ alkyl, $C_{1-5}$ hydroxyalkyl, $C_{2-5}$ hydroxy fluoroalkyl, $C_{1-2}$ aminoalkyl, —(CH$_2$)$_{1-2}$O($C_{1-2}$ alkyl), —(CH$_2$)$_{1-3}$N(CH$_3$)$_2$, —(CH$_2$)$_{1-2}$C(O)NH$_2$, —(CH$_2$)$_{1-2}$S(O)$_2$OH, —(CH$_2$)$_{1-2}$CR$_x$R$_x$NHS(O)$_2$CH$_3$, or —(CH$_2$)$_{0-3}$R$_{9a}$; $R_{9a}$ is $C_{5-7}$ cycloalkyl, furanyl, phenyl, piperazinyl, piperidinyl, pyrazolyl, pyridinyl, pyrrolidinyl, quinuclidinyl, thiazolyl, or octahydrocyclopenta[c]pyrrolyl, each substituted with zero to 2 substituents independently selected from —OH, $C_{1-3}$ alkyl, —NR$_x$, oxetanyl, phenyl, piperazinyl, piperidinyl, and pyrrolidinyl; $R_{10}$ is H, $C_{1-3}$ alkyl, —(CH$_2$)$_{1-2}$O($C_{1-2}$ alkyl), or $C_{3-6}$ cycloalkyl; or $R_9$ and $R_{10}$ together with the nitrogen atom to which they are attached form a heterocyclic ring selected from azabicyclo[3.1.1]heptanyl, azaspiro[5.5]undecanyl, diazabicyclo[2.2.1]heptanyl, diazabicyclo[3.1.1]heptanyl, diazabicyclo[3.2.0]heptanyl, diazaspiro[3.5]nonanyl, diazaspiro[4.4]nonanyl, diazaspiro[4.5]decanyl, diazepanyl, indolinyl, morpholinyl, octahydropyrrolo[3,4-c] pyrrolyl, piperazinonyl, piperazinyl, piperidinyl, and pyrrolidinyl, each substituted with zero to 3 $R_{10a}$; each $R_{10a}$ is independently selected from $C_{1-3}$ alkyl, $C_{1-3}$ hydroxyalkyl, —(CH$_2$)$_{1-2}$O($C_{1-2}$ alkyl), —(CH$_2$)$_{1-2}$NR$_x$R$_x$, —CH$_2$C(O)NR$_x$R$_x$, —CH$_2$(methyltriazolyl), —CH$_2$CH$_2$(phenyl), —CH$_2$CH$_2$(morpholinyl), —C(O)($C_{1-2}$ alkyl), —C(O)NH$_2$, —C(O)N($C_{1-2}$ alkyl)$_2$, —C(O)CH$_2$NR$_x$R$_x$, —NR$_x$R$_x$, —NHC(O)($C_{1-2}$ alkyl), —C(O)(furanyl), —O(piperidinyl), —C(O)CH$_2$(diethylcarbamoylpiperidinyl), methylpiperazinyl, piperidinyl, methylpiperidinyl, diethylcarbamoylpiperidinyl, isopropylpiperidinyl, pyridinyl, trifluoromethylpyridinyl, pyrimidinyl, and dihydrobenzo[d]imidazolonyl; each $R_5$ is independently F, Cl, —CN, $C_{1-2}$ alkyl, or —OCH$_3$; n is zero or 1; and p is zero, 1, 2, or 3; and G and $R_x$ are defined in the first aspect.

18

One embodiment provides a compound of Formula (I), N-oxide, or a salt thereof wherein G is

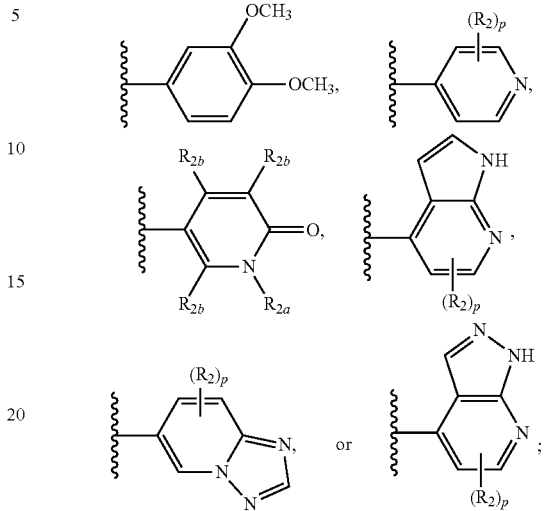

$R_1$ is —CH$_2$CH$_3$, —CH(CH$_3$)$_2$, —CH$_2$CHF$_2$, or —CH$_2$CF$_3$; each $R_2$ is independently —CH$_3$, —OCH$_3$, or —NH$_2$; $R_{2a}$ is —CH$_3$; each $R_{2b}$ is independently H, Cl, or —CH$_3$; L is a bond, —CH(CH$_3$)—, —C(CH$_3$)$_2$—, or —CH$_2$CH$_2$—; $R_9$ is —CH$_3$, —CH$_2$CH$_2$OH, —CH$_2$C(CH$_3$)$_2$OH, —CH$_2$C(CH$_3$)$_2$CH$_2$OH, —CH$_2$CHFC(CH$_3$)$_2$OH, —CH$_2$CH$_2$C(CH$_3$)$_2$OH, —CH(CH$_2$OH)$_2$, —CH$_2$CH$_2$OCH$_3$, —CH$_2$CH$_2$NH$_2$, —CH$_2$CH$_2$N(CH$_3$)$_2$, —CH$_2$CH$_2$CH$_2$N(CH$_3$)$_2$, —CH$_2$CH$_2$C(O)NH$_2$, —CH$_2$S(O)$_2$OH, —CH$_2$CH$_2$C(CH$_3$)$_2$NHS(O)$_2$CH$_3$, or —(CH$_2$)$_{0-3}$R$_{9a}$; $R_{9a}$ is cyclohexyl, cycloheptyl, furanyl, phenyl, piperazinyl, piperidinyl, pyrazolyl, pyridinyl, pyrrolidinyl, quinuclidinyl, thiazolyl, or octahydrocyclopenta[c]pyrrolyl, each substituted with zero to 2 substituents independently selected from —OH, $C_{1-3}$ alkyl, —NH$_2$, —N(CH$_3$)$_2$, oxetanyl, phenyl, piperazinyl, piperidinyl, and pyrrolidinyl; $R_{10}$ is H, —CH$_3$, —CH$_2$CH$_3$, —CH$_2$CH$_2$OCH$_3$, or cyclopropyl; or $R_9$ and $R_{10}$ together with the nitrogen atom to which they are attached form a heterocyclic ring selected from azabicyclo[3.1.1]heptanyl, azaspiro[5.5]undecanyl, diazabicyclo[2.2.1]heptanyl, diazabicyclo[3.1.1]heptanyl, diazabicyclo[3.2.0]heptanyl, diazaspiro[3.5]nonanyl, diazaspiro[4.4]nonanyl, diazaspiro[4.5]decanyl, diazepanyl, indolinyl, morpholinyl, octahydropyrrolo[3,4-c] pyrrolyl, piperazinonyl, piperazinyl, piperidinyl, and pyrrolidinyl, each substituted with zero to 2 $R_{10a}$; each $R_{10a}$ is independently selected from —CH$_3$, —CH$_2$CH$_3$, —CH(CH$_3$)$_2$, —CH$_2$OH, —CH$_2$CH$_2$OH, —CH$_2$OCH$_3$, —CH$_2$CH$_2$OCH$_3$, —CH$_2$NH$_2$, —CH$_2$CH$_2$NH$_2$, —CH$_2$CH$_2$NH(CH$_3$), —CH$_2$C(O)NH(CH$_3$), —CH$_2$C(O)N(CH$_3$)$_2$, —CH$_2$(methyltriazolyl), —CH$_2$CH$_2$(phenyl), —CH$_2$CH$_2$(morpholinyl), —C(O)CH$_3$, —C(O)NH$_2$, —C(O)N(CH$_2$CH$_3$)$_2$, —C(O)CH$_2$NH(CH$_3$), —C(O)CH$_2$N(CH$_3$)$_2$, —NH$_2$, —N(CH$_3$)$_2$, —NHC(O)CH$_3$, —C(O)(furanyl), —O(piperidinyl), —C(O)CH$_2$(diethylcarbamoylpiperidinyl), methylpiperazinyl, piperidinyl, methylpiperidinyl, diethylcarbamoylpiperidinyl, isopropylpiperidinyl, pyridinyl, trifluoromethylpyridinyl, pyrimidinyl, and dihydrobenzo[d]imidazolonyl; n is zero; and p is zero, 1, or 2.

One embodiment provides a compound of Formula (I), N-oxide, or a salt thereof wherein $L_2$ is a bond or —(CR$_x$R$_x$)$_{1-2}$—; and G, R$_1$, R$_5$, R$_9$, R$_{10}$, and n are defined in the first aspect. Included in this embodiment are compounds in which L$_2$ is a bond, —CR$_x$R$_x$—, or —CR$_x$R$_x$CH$_2$—. Also included in this embodiment are compounds in which L$_2$ is a bond, —CH(CH$_3$)—, —C(CH$_3$)$_2$—, or —CH$_2$CH$_2$—.

One embodiment provides a compound of Formula (I), N-oxide, or a salt thereof wherein R$_1$ is H, Cl, —CN, C$_{1-4}$ alkyl, C$_{1-3}$ fluoroalkyl, C$_{1-3}$ hydroxyalkyl, C$_{1-3}$ hydroxyfluoroalkyl, C$_{3-6}$ cycloalkyl, —CH$_2$(C$_{3-6}$ cycloalkyl), or —C(O)O(C$_{1-3}$ alkyl); and G, L$_2$, R$_5$, R$_9$, R$_{10}$, and n are defined in the first aspect. Included in this embodiment are compounds in which R$_1$ is H, Cl, —CN, C$_{1-4}$ alkyl, C$_{1-2}$ fluoroalkyl, C$_{1-2}$ hydroxyalkyl, or —C(O)O(C$_{1-2}$ alkyl). Also included in this embodiment are compounds in which R$_1$ is —CH$_2$CH$_3$, —CH(CH$_3$)$_2$, —CH$_2$CHF$_2$, or —CH$_2$CF$_3$.

One embodiment provides a compound of Formula (I), N-oxide, or a salt thereof wherein each R$_2$ is independently F, Cl, Br, —CN, —OH, C$_{1-4}$ alkyl, C$_{1-2}$ fluoroalkyl, C$_{1-2}$ cyanoalkyl, C$_{1-3}$ hydroxyalkyl, C$_{1-3}$ aminoalkyl, —O(CH$_2$)$_{1-2}$OH, —(CH$_2$)$_{0-4}$O(C$_{1-4}$ alkyl), C$_{1-3}$ fluoroalkoxy, —(CH$_2$)$_{1-3}$O(C$_{1-3}$ alkyl), —O(CH$_2$)$_{1-2}$OC(O)(C$_{1-2}$ alkyl), —O(CH$_2$)$_{1-2}$NR$_x$R$_x$, —C(O)O(C$_{1-2}$ alkyl), —(CH$_2$)$_{0-2}$C(O)NR$_y$R$_y$, —C(O)NR$_x$(C$_{1-5}$ hydroxyalkyl), —C(O)NR$_x$(C$_{2-6}$ alkoxyalkyl), —C(O)NR$_x$(C$_{3-6}$ cycloalkyl), —NR$_x$R$_y$, —NR$_y$(C$_{1-3}$ fluoroalkyl), —NR$_y$(C$_{1-4}$ hydroxyalkyl), —NR$_x$CH$_2$(phenyl), —NR$_x$S(O)$_2$(C$_{3-6}$ cycloalkyl), —NR$_x$C(O)(C$_{1-2}$ alkyl), —NR$_x$CH$_2$(cyclopropyl), —S(O)$_2$(C$_{1-2}$ alkyl), —(CH$_2$)$_{0-2}$(C$_{3-6}$ cycloalkyl), —(CH$_2$)$_{0-2}$(phenyl), morpholinyl, dioxothiomorpholinyl, dimethyl pyrazolyl, methylpiperidinyl, methylpiperazinyl, amino-oxadiazolyl, imidazolyl, or triazolyl; and G, L$_2$, R$_1$, R$_5$, R$_9$, R$_{10}$, and n are defined in the first aspect. Included in this embodiment are compounds in which each R$_2$ is independently F, Cl, —CN, —OH, C$_{1-3}$ alkyl, C$_{1-2}$ fluoroalkyl. C$_{1-2}$ cyanoalkyl, C$_{1-3}$ hydroxyalkyl, C$_{1-2}$ aminoalkyl, —(CH$_2$)$_{0-2}$O(C$_{1-3}$ alkyl), C$_{3-6}$ cycloalkyl, —NR$_x$R$_x$, —(CH$_2$)$_{0-2}$C(O)NR$_x$R$_x$, —CH$_2$(C$_{3-6}$ cycloalkyl), —CH$_2$ (phenyl), or phenyl. Also included in this embodiment are compounds in which each R$_2$ is independently —CH$_3$, —OCH$_3$, or —NH$_2$.

One embodiment provides a compound of Formula (I), N-oxide, or a salt thereof wherein R$_9$ is C$_{1-6}$ alkyl, C$_{1-6}$ hydroxyalkyl, C$_{1-6}$ hydroxy fluoroalkyl, C$_{1-3}$ aminoalkyl, —(CH$_2$)$_{1-2}$O(C$_{1-3}$ alkyl), —(CH$_2$)$_{1-3}$NR$_x$R$_x$, —(CH$_2$)$_{1-2}$C(O)NR$_x$R$_x$, —(CH$_2$)$_{1-3}$S(O)$_2$OH, —(CR$_x$R$_x$)$_{1-3}$NR$_x$S(O)$_2$(C$_{1-2}$ alkyl), or —(CH$_2$)$_{0-3}$R$_{9a}$; R$_{10}$ is H, C$_{1-4}$ alkyl, —(CH$_2$)$_{1-3}$O(C$_{1-2}$ alkyl), or C$_{1-6}$ cycloalkyl; and G, L$_2$, R$_1$, R$_5$, R$_{9a}$, R$_x$, and n are defined in the first aspect. Included in this embodiment are compounds in which R$_9$ is C$_{1-3}$ alkyl, C$_{1-5}$ hydroxyalkyl, C$_{2-5}$ hydroxy fluoroalkyl, C$_{1-2}$ aminoalkyl, —(CH$_2$)$_{1-2}$O(C$_{1-2}$ alkyl), —(CH$_2$)$_{1-3}$N(CH$_3$)$_2$, —(CH$_2$)$_{1-2}$C(O)NH$_2$, —(CH$_2$)$_{1-2}$S(O)$_2$OH, —(CH$_2$)$_{1-2}$CR$_x$R$_x$NHS(O)$_2$CH$_3$, or —(CH$_2$)$_{0-3}$R$_{9a}$; and R$_{10}$ is H, C$_{1-3}$ alkyl, —(CH$_2$)$_{1-2}$O(C$_{1-2}$ alkyl), or C$_{3-6}$ cycloalkyl. Also included in this embodiment are compounds in which R$_9$ is —CH$_3$, —CH$_2$CH$_2$OH, —CH$_2$C(CH$_3$)$_2$OH, —CH$_2$C(CH$_3$)$_2$CH$_2$OH, —CH$_2$CHFC(CH$_3$)$_2$OH, —CH$_2$CH$_2$C (CH$_3$)$_2$OH, —CH(CH$_2$OH)$_2$, —CH$_2$CH$_2$OCH$_3$, —CH$_2$CH$_2$NH$_2$, —CH$_2$CH$_2$N(CH$_3$)$_2$, —CH$_2$CH$_2$CH$_2$N (CH$_3$)$_2$, —CH$_2$CH$_2$C(O)NH$_2$, —CH$_2$S(O)$_2$OH, —CH$_2$CH$_2$C(CH$_3$)$_2$NHS(O)$_2$CH$_3$, or —(CH$_2$)$_{0-3}$R$_{9a}$; and R$_{10}$ is H, —CH$_3$, —CH$_2$CH$_3$, —CH$_2$CH$_2$OCH$_3$, or cyclopropyl.

One embodiment provides a compound of Formula (I), N-oxide, or a salt thereof wherein R$_9$ is C$_{1-3}$ alkyl, C$_{1-5}$ hydroxyalkyl, C$_{2-5}$ hydroxy fluoroalkyl, C$_{1-2}$ aminoalkyl, —(CH$_2$)$_{1-2}$O(C$_{1-2}$ alkyl), —(CH$_2$)$_{1-3}$N(CH$_3$)$_2$, —(CH$_2$)$_{1-2}$C (O)NH$_2$, —(CH$_2$)$_{1-2}$S(O)$_2$OH, —(CH$_2$)$_{1-2}$CR$_x$R$_x$ NHS(O)$_2$CH$_3$, or —(CH$_2$)$_{0-3}$R$_{9a}$; R$_{9a}$ is C$_{5-7}$ cycloalkyl, furanyl, phenyl, piperazinyl, piperidinyl, pyrazolyl, pyridinyl, pyrrolidinyl, quinuclidinyl, thiazolyl, or octahydrocyclopenta[c]pyrrolyl, each substituted with zero to 2 substituents independently selected from —OH, C$_{1-3}$ alkyl, —NR$_x$R$_x$ oxetanyl, phenyl, piperazinyl, piperidinyl, and pyrrolidinyl; R$_{10}$ is H, C$_{1-3}$ alkyl, —(CH$_2$)$_{1-2}$O(C$_{1-2}$ alkyl), or C$_{3-6}$ cycloalkyl; and G, L$_2$, R$_1$, R$_5$, R$_x$, and n are defined in the first aspect.

One embodiment provides a compound of Formula (I), N-oxide, or a salt thereof wherein R$_9$ is —CH$_3$, —CH$_2$CH$_2$OH, —CH$_2$C(CH$_3$)$_2$OH, —CH$_2$ C(CH$_3$)$_2$CH$_2$OH, —CH$_2$CHFC(CH$_3$)$_2$OH, —CH$_2$CH$_2$C (CH$_3$)$_2$OH, —CH(CH$_2$OH)$_2$, —CH$_2$CH$_2$OCH$_3$, —CH$_2$CH$_2$NH$_2$, —CH$_2$CH$_2$N(CH$_3$)$_2$, —CH$_2$CH$_2$CH$_2$N (CH$_3$)$_2$, —CH$_2$CH$_2$C(O)NH$_2$, —CH$_2$S(O)$_2$OH, —CH$_2$CH$_2$C(CH$_3$)$_2$NHS(O)$_2$CH$_3$, or —(CH$_2$)$_{0-3}$R$_{9a}$; R$_{9a}$ is cyclohexyl, cycloheptyl, furanyl, phenyl, piperazinyl, piperidinyl, pyrazolyl, pyridinyl, pyrrolidinyl, quinuclidinyl, thiazolyl, or octahydrocyclopenta[c]pyrrolyl, each substituted with zero to 2 substituents independently selected from —OH, C$_{1-3}$ alkyl, —NH$_2$, —N(CH$_3$)$_2$, oxetanyl, phenyl, piperazinyl, piperidinyl, and pyrrolidinyl; R$_{10}$ is H, —CH$_3$, —CH$_2$CH$_3$, —CH$_2$CH$_2$OCH$_3$, or cyclopropyl; and G, L$_2$, R$_1$, R$_5$, and n are defined in the first aspect.

One embodiment provides a compound of Formula (I), N-oxide, or a salt thereof wherein R$_9$ and R$_{10}$ together with the nitrogen atom to which they are attached form a heterocyclic ring selected from azabicyclo[3.1.1]heptanyl, azaspiro[5.5]undecanyl, diazabicyclo[2.2.1]heptanyl, diazabicyclo[3.1.1]heptanyl, diazabicyclo[3.2.0]heptanyl, diazaspiro[3.5]nonanyl, diazaspiro[4.4]nonanyl, diazaspiro[4.5]decanyl, diazepanyl, indolinyl, morpholinyl, octahydropyrrolo[3,4-c]pyrrolyl, piperazinonyl, piperazinyl, piperidinyl, and pyrrolidinyl, each substituted with zero to 3 R$_{10a}$; and G, L$_2$, R$_1$, R$_5$, R$_{10a}$, and n are defined in the first aspect. Included in this embodiment are compounds in which R$_9$ and R$_{10}$ together with the nitrogen atom to which they are attached form a heterocyclic ring selected from azabicyclo[3.1.1]heptanyl, azaspiro[5.5]undecanyl, diazabicyclo[2.2.1]heptanyl, diazabicyclo[3.1.1]heptanyl, diazabicyclo[3.2.0]heptanyl, diazaspiro[3.5]nonanyl, diazaspiro [4.4]nonanyl, diazaspiro[4.5]decanyl, diazepanyl, indolinyl, morpholinyl, octahydropyrrolo[3,4-c]pyrrolyl, piperazinonyl, piperazinyl, piperidinyl, and pyrrolidinyl, each substituted with zero to 2 R$_{10a}$. Also included in this embodiment are compounds in which each R$_{10a}$ is independently selected from —CH$_3$, —CH$_2$CH$_3$, —CH(CH$_3$)$_2$, —CH$_2$OH, —CH$_2$CH$_2$OH, —CH$_2$OCH$_3$, —CH$_2$CH$_2$OCH$_3$, —CH$_2$NH$_2$, —CH$_2$CH$_2$NH$_2$, —CH$_2$CH$_2$NH(CH$_3$), —CH$_2$C(O)NH(CH$_3$), —CH$_2$C(O)N(CH$_3$)$_2$, —CH$_2$(methyltriazolyl), —CH$_2$CH$_2$(phenyl), —CH$_2$CH$_2$(morpholinyl), —C(O)CH$_3$, —C(O)NH$_2$, —C(O)N(CH$_2$CH$_3$)$_2$, —C(O) CH$_2$NH(CH$_3$), —C(O)CH$_2$N(CH$_3$)$_2$, —NH$_2$—N(CH$_3$)$_2$, —NHC(O)CH$_3$, —C(O)(furanyl), —O(piperidinyl), —C(O)CH$_2$(diethylcarbamoylpiperidinyl), methylpiperazinyl, piperidinyl, methylpiperidinyl, diethylcarbamoylpiperidinyl, isopropylpiperidinyl, pyridinyl, trifluoromethylpyridinyl, pyrimidinyl, and dihydrobenzo[d]imidazolonyl.

One embodiment provides a compound of Formula (I), N-oxide, or a salt thereof wherein G is

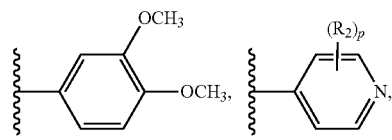

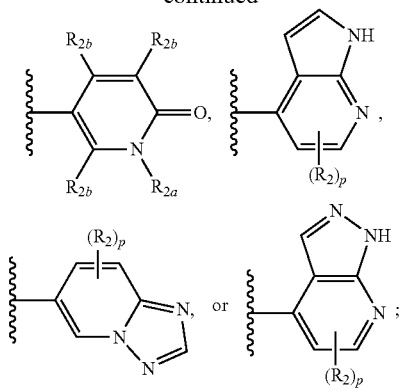

$L_2$ is a bond; and $R_1$, $R_2$, $R_{2a}$, $R_{2b}$, $R_5$, $R_9$, $R_{10}$, n, and p are defined in the first aspect. Included in this embodiment are compounds in which $R_9$ is —$CH_3$, —$CH_2CH_2OH$, —$CH_2C(CH_3)_2OH$, —$CH_2C(CH_3)_2CH_2OH$, —$CH_2CHFC(CH_3)_2OH$, —$CH_2CH_2C(CH_3)_2OH$, —$CH(CH_2OH)_2$, —$CH_2CH_2OCH_3$, —$CH_2CH_2NH_2$, —$CH_2CH_2N(CH_3)_2$, —$CH_2CH_2CH_2N(CH_3)_2$, —$CH_2CH_2C(O)NH_2$, —$CH_2S(O)_2OH$, —$CH_2CH_2C(CH_3)_2NHS(O)_2CH_3$, or —$(CH_2)_{0-3}R_9$; $R_{9a}$ is cyclohexyl, cycloheptyl, furanyl, phenyl, piperazinyl, piperidinyl, pyrazolyl, pyridinyl, pyrrolidinyl, quinuclidinyl, thiazolyl, or octahydrocyclopenta[c]pyrrolyl, each substituted with zero to 2 substituents independently selected from —OH, $C_{1-3}$ alkyl, —$NH_2$, —$N(CH_3)_2$, oxetanyl, phenyl, piperazinyl, piperidinyl, and pyrrolidinyl; and $R_{10}$ is H, —$CH_3$, —$CH_2CH_3$, —$CH_2CH_2OCH_3$, or cyclopropyl. Also included in this embodiment are compounds in which or $R_9$ and $R_{10}$ together with the nitrogen atom to which they are attached form a heterocyclic ring selected from azabicyclo[3.1.1]heptanyl, azaspiro[5.5]undecanyl, diazabicyclo[2.2.1]heptanyl, diazabicyclo[3.1.1]heptanyl, diazabicyclo[3.2.0]heptanyl, diazaspiro[3.5]nonanyl, diazaspiro[4.4]nonanyl, diazaspiro[4.5]decanyl, diazepanyl, indolinyl, morpholinyl, octahydropyrrolo[3,4-c]pyrrolyl, piperazinonyl, piperazinyl, piperidinyl, and pyrrolidinyl, each substituted with zero to 2 $R_{10a}$; and each $R_{10a}$ is independently selected from —$CH_3$, —$CH_2CH_3$, —$CH(CH_3)_2$, —$CH_2OH$, —$CH_2CH_2OH$, —$CH_2OCH_3$, —$CH_2CH_2OCH_3$, —$CH_2NH_2$, —$CH_2CH_2NH_2$, —$CH_2CH_2NH(CH_3)$, —$CH_2C(O)NH(CH_3)$, —$CH_2C(O)N(CH_3)_2$, —$CH_2$(methyltriazolyl), —$CH_2CH_2$(phenyl), —$CH_2CH_2$(morpholinyl), —$C(O)CH_3$, —$C(O)NH_2$, —$C(O)N(CH_2CH_3)_2$, —$C(O)CH_2NH(CH_3)$, —$C(O)CH_2N(CH_3)_2$, —$NH_2$, —$N(CH_3)_2$, —$NHC(O)CH_3$, —$C(O)$(furanyl), —$O$(piperidinyl), —$C(O)CH_2$(diethylcarbamoylpiperidinyl), methylpiperazinyl, piperidinyl, methylpiperidinyl, diethylcarbamoylpiperidinyl, isopropylpiperidinyl, pyridinyl, trifluoromethylpyridinyl, pyrimidinyl, and dihydrobenzo[d]imidazolonyl.

One embodiment provides a compound of Formula (I), N-oxide, or a salt thereof wherein G is

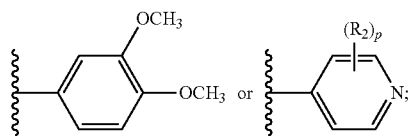

$L_2$ is a bond; and $R_1$, $R_2$, $R_5$, $R_9$, $R_{10}$, n, and p are defined in the first aspect.

One embodiment provides a compound of Formula (I), N-oxide, or a salt thereof wherein each $R_5$ is independently F, Cl, —CN, $C_{1-3}$ alkyl, —$CF_3$, or —$OCH_3$; n is zero, 1, or 2; and G, $L_2$, $R_1$, $R_9$, and $R_{10}$ are defined in the first aspect. Included in this embodiment are compounds in which each $R_5$ is independently F, Cl, —CN, $C_{1-2}$ alkyl, or —$OCH_3$; and n is zero, 1, or 2. Also included in this embodiment are compounds in which n is zero or 1.

One embodiment provides a compound of Formula (I), N-oxide, or a salt thereof wherein n is zero or 1; p is zero, 1, 2, or 3 and G, $L_2$, $R_1$, $R_2$, $R_5$, $R_9$, and $R_{10}$ are defined in the first aspect. Included in this embodiment are compounds in which n is zero or 1; and p is zero, 1, or 2. Also included in this embodiment are compounds in which n is zero.

One embodiment provides a compound of Formula (I) or a salt thereof, wherein said compound is selected from 2-(3,4-dimethoxyphenyl)-5-{octahydropyrrolo[3,4-c]pyrrole-2-carbonyl}-3-(propan-2-yl)-1H-indole (1); (2-(3,4-dimethoxyphenyl)-3-isopropyl-1H-indol-5-yl)(4-methyl-1,4-diazepan-1-yl)methanone (2); 2-(3,4-dimethoxyphenyl)-3-isopropyl-N,N-dimethyl-1H-indole-5-carboxamide (3); 2-(3,4-dimethoxyphenyl)-3-isopropyl-N-methyl-1H-indole-5-carboxamide (4); ((1S,4S)-2,5-diazabicyclo[2.2.1]heptan-2-yl)(2-(3,4-dimethoxyphenyl)-3-isopropyl-1H-indol-5-yl)methanone (5); 2-{5-[2-(3,4-dimethoxyphenyl)-3-(propan-2-yl)-1H-indole-5-carbonyl]-octahydropyrrolo[3,4-c]pyrrol-2-yl}-N,N-dimethylacetamide (6); 2-(5-(2-(3,4-dimethoxyphenyl)-3-isopropyl-1H-indole-5-carbonyl)hexahydropyrrolo[3,4-c]pyrrol-2(1H)-yl)-N-methylacetamide (7); 1-(2-{5-[2-(3,4-dimethoxyphenyl)-3-(propan-2-yl)-1H-indole-5-carbonyl]-octahydropyrrolo[3,4-c]pyrrol-2-yl}-2-oxoethyl)-N,N-diethylpiperidine-3-carboxamide (8); 1-(5-(2-(3,4-dimethoxyphenyl)-3-isopropyl-1H-indole-5-carbonyl)hexahydropyrrolo[3,4-c]pyrrol-2(1H)-yl)-2-(dimethylamino)ethan-1-one (9); 1-(2-{5-[2-(3,4-dimethoxyphenyl)-3-(propan-2-yl)-1H-indole-5-carbonyl]-octahydro pyrrolo[3,4-c]pyrrol-2-yl}-2-oxoethyl)-N,N-diethylpiperidine-3-carboxamide (10-11); 3,4-dimethoxyphenyl)-3-isopropyl-1H-indol-5-yl)(5-(2-(methylamino)ethyl) hexahydropyrrolo[3,4-c]pyrrol-2(1H)-yl)methanone (12); (2-(3,4-dimethoxyphenyl)-3-isopropyl-1H-indol-5-yl)(5-methylhexahydro pyrrolo[3,4-c] pyrrol-2 (1H)-yl)methanone (13); (2-(3,4-dimethoxyphenyl)-3-isopropyl-1H-indol-5-yl)(5-isopropylhexahydropyrrolo[3,4-c]pyrrol-2(1H)-yl)methanone (14); 2-(3,4-dimethoxyphenyl)-3-isopropyl-1H-indol-5-yl)(5-(1-methylpiperidin-4-yl)hexahydropyrrolo[3,4-c]pyrrol-2(1H)-yl)methanone (15); 1-(5-(2-(3,4-dimethoxyphenyl)-3-isopropyl-1H-indole-5-carbonyl)hexahydro pyrrolo[3,4-c]pyrrol-2(1H)-yl)-2-(methylamino)ethanone (16); 2-(3,4-dimethoxyphenyl)-N-[2-(dimethylamino)ethyl]-3-ethyl-1H-indole-5-carboxamide (17); (R)-2-(3,4-dimethoxyphenyl)-3-ethyl-N-(2-fluoro-3-hydroxy-3-methylbutyl)-1H-indole-5-carboxamide (18); 2-(3,4-dimethoxyphenyl)-N-(4-(dimethylamino)cyclohexyl)-3-ethyl-1H-indole-5-carboxamide (19); N-cycloheptyl-2-(3,4-dimethoxyphenyl)-3-ethyl-1H-indole-5-carboxamide (20); 2-(3,4-dimethoxyphenyl)-3-ethyl-N-(1-(oxetan-3-yl)-1H-pyrazol-4-yl)-1H-indole-5-carboxamide (21); 2-(3,4-dimethoxyphenyl)-3-ethyl-N-methyl-N-(pyridin-3-ylmethyl)-1H-indole-5-carboxamide (22); 2-(3,4-dimethoxyphenyl)-3-ethyl-N-methyl-N-((2-(piperidin-4-yl)thiazol-4-yl)methyl)-1H-indole-5-carboxamide (23); 2-(3,4-dimethoxyphenyl)-3-ethyl-N-methyl-N-(2-(pyridin-2-yl)ethyl)-1H-indole-5-carboxamide (24); (2-(3,4-dimethoxyphenyl)-3-ethyl-1H-indol-5-yl)(4-(4-methylpiperazin-1-yl)piperidin-1-yl)methanone (25); (R)-1-

(1-(2-(3,4-dimethoxyphenyl)-3-ethyl-1H-indole-5-carbonyl)pyrrolidin-3-yl)propan-2-one (26); (S)-(2-(3,4-dimethoxyphenyl)-3-ethyl-1H-indol-5-yl)(2-(methoxymethyl)pyrrolidin-1-yl)methanone (27); (S)-(2-(3,4-dimethoxyphenyl)-3-ethyl-1H-indol-5-yl)(2-(hydroxymethyl)pyrrolidin-1-yl)methanone (28); (R)-(2-(3,4-dimethoxyphenyl)-3-ethyl-1H-indol-5-yl)(3-(dimethylamino)pyrrolidin-1-yl)methanone (29); (S)-(2-(3,4-dimethoxyphenyl)-3-ethyl-1H-indol-5-yl)(3-(dimethylamino)pyrrolidin-1-yl)methanone (30); (2-(3,4-dimethoxyphenyl)-3-ethyl-1H-indol-5-yl)(4-(dimethylamino)piperidin-1-yl)methanone (31); (2-(3,4-dimethoxyphenyl)-3-ethyl-1H-indol-5-yl)(3,3-dimethylpiperidin-1-yl)methanone (32); 1-(2-(3,4-dimethoxy phenyl)-3-ethyl-1H-indole-5-carbonyl)-N,N-diethylpiperidine-3-carboxamide (33); 1-(2-(3,4-dimethoxyphenyl)-3-ethyl-1H-indole-5-carbonyl)piperidine-4-carboxamide (34); 1-(4-(2-(3,4-dimethoxyphenyl)-3-ethyl-1H-indole-5-carbonyl)-1,4-diazepan-1-yl)ethan-1-one (35); (2-(3,4-dimethoxyphenyl)-3-ethyl-1H-indol-5-yl)(4-(1-methylpiperidin-4-yl)piperazin-1-yl)methanone (36); (2-(3,4-dimethoxyphenyl)-3-ethyl-1H-indol-5-yl)(4-phenethylpiperazine-1-yl)methanone (37); (2-(3,4-dimethoxyphenyl)-3-ethyl-1H-indol-5-yl)(4-isopropylpiperazin-1-yl)methanone (38); (2-(3,4-dimethoxyphenyl)-3-ethyl-1H-indol-5-yl)(4-ethylpiperazin-1-yl)methanone (39); (2-(3,4-dimethoxyphenyl)-3-ethyl-1H-indol-5-yl)(4-(2-hydroxyethyl)piperazin-1-yl)methanone (40); (2-(3,4-dimethoxyphenyl)-3-ethyl-1H-indol-5-yl)(4-(2-methoxyethyl)piperazin-1-yl)methanone (41); (2-(3,4-dimethoxyphenyl)-3-ethyl-1H-indol-5-yl)(4-(2-morpholinoethyl)piperazin-1-yl)methanone (42); 2-(3,4-dimethoxyphenyl)-3-ethyl-N-(furan-2-ylmethyl)-1H-indole-5-carboxamide (43); 2-(3,4-dimethoxyphenyl)-3-ethyl-N-(pyridin-2-ylmethyl)-1H-indole-5-carboxamide (44); 2-(3,4-dimethoxyphenyl)-3-ethyl-N-((2-phenylthiazol-4-yl)methyl)-1H-indole-5-carboxamide (45); 2-(3,4-dimethoxyphenyl)-3-ethyl-N-(4-(piperazin-1-yl)benzyl)-1H-indole-5-carboxamide (46); N-((1r,4r)-4-aminocyclohexyl)-2-(3,4-dimethoxyphenyl)-3-ethyl-1H-indole-5-carboxamide (47); 2-(3,4-dimethoxyphenyl)-3-ethyl-N-(2-(pyrrolidin-1-yl)ethyl)-1H-indole-5-carboxamide (48); 2-(3,4-dimethoxyphenyl)-3-ethyl-N-(2-(piperidin-1-yl)ethyl)-1H-indole-5-carboxamide (49); 2-(2-aminophenyl)-3-ethyl-N-(2-(pyridin-4-yl)ethyl)-1H-indole-5-carboxamide (50); 2-(3,4-dimethoxyphenyl)-3-ethyl-N-(2-(pyridin-3-yl)ethyl)-1H-indole-5-carboxamide (51); N-(4-aminobenzyl)-2-(3,4-dimethoxyphenyl)-3-ethyl-1H-indole-5-carboxamide (52); 2-(3,4-dimethoxyphenyl)-3-ethyl-N-(3-(piperidin-1-yl)propyl)-1H-indole-5-carboxamide (53); 2-(3,4-dimethoxyphenyl)-3-ethyl-N-(2-(1-methylpyrrolidin-2-yl)ethyl)-1H-indole-5-carboxamide (54); 2-(3,4-dimethoxyphenyl)-3-ethyl-N-(3-(4-methylpiperazin-1-yl)propyl)-1H-indole-5-carboxamide (55); [1,4'-bipiperidin]-1'-yl(2-(3,4-dimethoxyphenyl)-3-ethyl-1H-indol-5-yl)methanone (56); (2-(3,4-dimethoxyphenyl)-3-ethyl-1H-indol-5-yl)(4-(pyrimidin-2-yl)piperazin-1-yl)methanone (57); (2-(3,4-dimethoxyphenyl)-3-ethyl-1H-indol-5-yl)(4-(pyrazin-2-yl)piperazin-1-yl)methanone (58); (2-(3,4-dimethoxyphenyl)-3-ethyl-1H-indol-5-yl)(4-(pyridin-2-yl)piperazin-1-yl)methanone (59); (2-(3,4-dimethoxyphenyl)-3-ethyl-1H-indol-5-yl)(4-(furan-2-carbonyl)piperazin-1-yl)methanone (60); (2-(3,4-dimethoxyphenyl)-3-ethyl-1H-indol-5-yl)(4-(5-(trifluoromethyl)pyridin-2-yl)piperazin-1-yl)methanone (61); 4-(2-(3,4-dimethoxyphenyl)-3-ethyl-1H-indole-5-carbonyl)piperazin-2-one (62); 1-(1-(2-(3,4-dimethoxyphenyl)-3-ethyl-1H-indole-5-carbonyl)piperidin-4-yl)-1,3-dihydro-2H-benzo[d]imidazol-2-one (63); (2-(3,4-dimethoxyphenyl)-3-ethyl-1H-indol-5-yl)(4-(pyrimidin-2-yl)-1,4-diazepan-1-yl)methanone ((4); (2-(3,4-dimethoxyphenyl)-3-ethyl-1H-indol-5-yl)(4-(pyridin-2-yl)-1,4-diazepan-1-yl)methanone (65); (2-(3,4-dimethoxyphenyl)-3-ethyl-1H-indol-5-yl)(indolin-1-yl)methanone (66); N-(1,3-dihydroxypropan-2-yl)-2-(3,4-dimethoxyphenyl)-3-ethyl-1H-indole-5-carboxamide (67); N-(3-amino-3-oxopropyl)-2-(3,4-dimethoxyphenyl)-3-ethyl-1H-indole-5-carboxamide (68); 2-(3,4-dimethoxyphenyl)-3-ethyl-N-(2-hydroxyethyl)-1H-indole-5-carboxamide (69); (2-(3,4-dimethoxyphenyl)-3-ethyl-1H-indole-5-carboxamido)methanesulfonic acid (70); 2-(3,4-dimethoxyphenyl)-3-ethyl-N-(3-methyl-3-(methylsulfonamido)butyl)-1H-indole-5-carboxamide (71); 2-(3,4-dimethoxyphenyl)-3-ethyl-N-(3-hydroxy-2,2-dimethylpropyl)-1H-indole-5-carboxamide (72); 2-(3,4-dimethoxyphenyl)-N-(2-(dimethylamino)ethyl)-N,3-diethyl-1H-indole-5-carboxamide (73); 2-(3,4-dimethoxyphenyl)-N-(3-(dimethylamino)propyl)-3-ethyl-N-methyl-1H-indole-5-carboxamide (74); 2-(3,4-dimethoxyphenyl)-N-(3-(dimethylamino)propyl)-3-ethyl-1H-indole-5-carboxamide (75); 2-(3,4-dimethoxyphenyl)-N-(2-(dimethylamino)ethyl)-3-ethyl-N-methyl-1H-indole-5-carboxamide (76); 2-(3,4-dimethoxyphenyl)-3-ethyl-N,N-bis(2-methoxyethyl)-1H-indole-5-carboxamide (77); (2-(3,4-dimethoxyphenyl)-3-ethyl-1H-indol-5-yl)(piperazin-1-yl)methanone hydrochloride (78); (2-(3,4-dimethoxyphenyl)-3-ethyl-1H-indol-5-yl)(hexahydropyrrolo[3,4-c]pyrrol-2(1H)-yl)methanone (79); (2-(3,4-dimethoxyphenyl)-3-ethyl-1H-indol-5-yl)(4-(1-isopropylpiperidin-4-yl) piperazin-1-yl)methanone (80); (2-(3,4-dimethoxyphenyl)-3-ethyl-1H-indol-5-yl)(5-isopropylhexahydropyrrolo[3,4-c]pyrrol-2(1H)-yl)methanone (81); 2-(5-(2-(3,4-dimethoxyphenyl)-3-ethyl-1H-indole-5-carbonyl)hexahydropyrrolo[3,4-c]pyrrol-2(1H)-yl)-N-methylacetamide (82); N-(2-(dimethylamino)ethyl)-N,3-diethyl-2-(1H-pyrrolo[2,3-b]pyridin-4-yl)-1H-indole-5-carboxamide (83); N-(2-(dimethylamino)ethyl)-N,3-diethyl-2-(2-methylpyridin-4-yl)-1H-indole-5-carboxamide (84); (3-ethyl-2-(2-methylpyridin-4-yl)-1H-indol-5-yl)(hexahydropyrrolo[3,4-c]pyrrol-2(1H)-yl)methanone (85); (3-ethyl-2-(2-methylpyridin-4-yl)-1H-indol-5-yl)(5-isopropylhexahydropyrrolo[3,4c]pyrrol-2(1H)-yl)methanone (86); 2-(2-aminopyridin-4-yl)-N-(4-(dimethylamino)cyclohexyl)-3-isopropyl-1H-indole-5-carboxamide (87); (2-(3,4-dimethoxyphenyl)-3-(2,2,2-trifluoroethyl)-1H-indol-5-yl)(hexahydropyrrolo[3,4-c]pyrrol-2(1H)-yl)methanone hydrochloride (88); 1-(5-(2-(3,4-dimethoxyphenyl)-3-(2,2,2-trifluoroethyl)-1H-indole-5-carbonyl) hexahydropyrrolo[3,4-c]pyrrol-2(1H)-yl)-2-(dimethylamino)ethan-1-one (89); 2-(5-(2-(3,4-dimethoxyphenyl)-3-(2,2,2-trifluoroethyl)-1H-indole-5-carbonyl) hexahydropyrrolo[3,4-c]pyrrol-2(1H)-yl)-N,N-dimethylacetamide (90); 2-(2,6-dimethylpyridin-4-yl)-3-isopropyl-N-(1-isopropylpiperidin-4-yl)-1H-indole-5-carboxamide (91); (2-(2,6-dimethylpyridin-4-yl)-3-isopropyl-1H-indol-5-yl)(4-methyl-1,4-diazepan-1-yl)methanone (92); N-(2-(dimethylamino)ethyl)-2-(2,6-dimethylpyridin-4-yl)-N-ethyl-3-isopropyl-1H-indole-5-carboxamide (93); 2-(2,6-dimethylpyridin-4-yl)-3-isopropyl-N,N-dimethyl-1H-indole-5-carboxamide (94); N-(3-(dimethylamino)propyl)-2-(2,6-dimethylpyridin-4-yl)-3-isopropyl-1H-indole-5-carboxamide (95); N-(2-(dimethylamino)ethyl)-2-(2,6-dimethylpyridin-4-yl)-3-isopropyl-1H-indole-5-carboxamide (96); 2-(2,6-dimethylpyridin-4-1)-3-isopropyl-N-methyl-1H-indole-5-carboxamide (97); (2-(2,6-dimethylpyridin-4-yl)-3-isopropyl-1H-indol-5-yl)

(4-((1-methyl-1H-1,2,4-triazol-3-yl)methyl)piperazin-1-yl) methanone (98); N-benzyl-2-(2,6-dimethylpyridin-4-yl)-3-isopropyl-N-methyl-1H-indole-5-carboxamide (99); 2-(2,6-dimethylpyridin-4-yl)-3-isopropyl-N-methyl-N-(pyridin-3-ylmethyl)-1H-indole-5-carboxamide (100); 2-(2,6-dimethylpyridin-4-yl)-3-isopropyl-N-methyl-N-(1-methylpiperidin-4-yl)-1H-indole-5-carboxamide (101); 2-(2,6-dimethylpyridin-4-yl)-3-isopropyl-N-methyl-N-phenethyl-1H-indole-5-carboxamide (102); N-(3-aminobenzyl)-2-(2,6-dimethylpyridin-4-yl)-3-isopropyl-N-methyl-1H-indole-5-carboxamide (103); (4-(dimethylamino) piperidin-1-yl)(2-(2,6-dimethylpyridin-4-yl)-3-isopropyl-1H-indol-5-yl)methanone (104); 2-(2,6-dimethylpyridin-4-yl)-N-(2-hydroxyethyl)-3-isopropyl-N-methyl-1H-indole-5-carboxamide (105); 2-(2,6-dimethylpyridin-4-yl)-3-isopropyl-N-(2-methoxyethyl)-N-methyl-1H-indole-5-carboxamide (106); (2-(2,6-dimethylpyridin-4-yl)-3-isopropyl-1H-indol-5-yl)(hexahydropyrrolo[3,4-c]pyrrol-2(1H)-yl)methanone, HCl (107); (2-(2,6-dimethylpyridin-4-yl)-3-isopropyl-1H-indol-5-yl)(piperazin-1-yl)methanone (108); (2-(2,6-dimethylpyridin-4-yl)-3-isopropyl-1H-indol-5-yl)(5-methylhexahydropyrrolo[3,4-c]pyrrol-2(1H)-yl) methanone (109); (2-(2,6-dimethylpyridin-4-yl)-3-isopropyl-1H-indol-5-yl)(5-isopropylhexahydropyrrolo[3,4-c]pyrrol-2(1H)-yl)methanone (110); 2-(dimethylamino)-1-(5-(2-(2,6-dimethylpyridin-4-yl)-3-isopropyl-1H-indole-5-carbonyl)hexahydropyrrolo[3,4-c]pyrrol-2(1H)-yl)ethanone (111); (hexahydropyrrolo[3,4-c]pyrrol-2(1H)-yl)(3-isopropyl-2-(2-methyl pyridin-4-yl)-1H-indol-5-yl)methanone, HCl (112); 3-isopropyl-N-(1-isopropylpiperidin-4-yl)-2-(2-methylpyridin-4-yl)-1H-indole-5-carboxamide (113); (3-isopropyl-2-(2-methylpyridin-4-yl)-1H-indol-5-yl)(4-methyl-1,4-diazepan-1-yl)methanone (114); (3-isopropyl-2-(2-methylpyridin-4-yl)-1H-indol-5-yl)(5-methylhexahydropyrrolo[3,4-c] pyrrol-2(1H)-yl)methanone (115); (3-isopropyl-2-(2-methylpyridin-4-yl)-1H-indol-5-yl)(5-isopropylhexahydropyrrolo[3,4-c]pyrrol-2(1H)-yl)methanone (116); 2-(5-(3-isopropyl-2-(2-methylpyridin-4-yl)-1H-indole-5-carbonyl)hexahydropyrrolo[3,4-c]pyrrol-2(1H)-yl)-N,N-dimethylacetamide (117); 2-(5-(3-isopropyl-2-(2-methylpyridin-4-yl)-1H-indole-5-carbonyl) hexahydropyrrolo[3,4-c]pyrrol-2(1H)-yl)-N-methylacetamide (118); 1-(5-(3-isopropyl-2-(2-methylpyridin-4-yl)-1H-indole-5-carbonyl) hexahydropyrrolo[3,4-c]pyrrol-2(1H)-yl)-2-(methylamino) ethanone (119); 2-(dimethylamino)-1-(5-(3-isopropyl-2-(2-methylpyridin-4-yl)-1H-indole-5-carbonyl) hexahydropyrrolo[3,4-c]pyrrol-2(1H)-yl)ethan-1-one (120); (hexahydropyrrolo[3,4-c]pyrrol-2(1H)-yl)(3-isopropyl-2-(1H-pyrazolo[3,4-b]pyridin-4-yl)-1H-indol-5-yl)methanone, HCl (121); (3-(2,2-difluoroethyl)-2-(2,6-dimethylpyridin-4-yl)-1H-indol-5-yl)(hexahydroprrolo[3,4-c]pyrrol-2(1H)-yl)methanone (122); 3-(2,2-difluoroethyl)-2-(2,6-dimethylpyridin-4-yl)-N-(1-isopropylpiperidin-4-yl)-1H-indole-5-carboxamide (123); (3-(2,2-difluoroethyl)-2-(2,6-dimethylpyridin-4-yl)-1H-indol-5-yl)(4-methyl-1,4-diazepan-1-yl)methanone (124); 3-(2,2-difluoroethyl)-N-(2-(dimethylamino)ethyl)-2-(2,6-dimethylpyridin-4-yl)-N-ethyl-1H-indole-5-carboxamide (125); (hexahydropyrrolo[3,4-c]pyrrol-2(1H)-yl)(3-isopropyl-2-(8-methoxy-[1,2,4] triazolo[1,5-a]pyridin-6-yl)-1H-indol-5-yl)methanone (126); 3-isopropyl-N-(1-isopropylpiperidin-4-yl)-2-(8-methoxy-[1,2,4]triazolo[1,5-a]pyridin-6-yl)-1H-indole-5-carboxamide (127); (3-isopropyl-2-(8-methoxy-[1,2,4]triazolo[1,5-a]pyridin-6-yl)-1H-indol-5-yl)(4-methyl-1,4-diazepan-1-yl)methanone (128) N-(2-(dimethylamino) ethyl)-3-isopropyl-2-(8-methoxy-[1,2,4]triazolo[1,5-a] pyridin-6-yl)-N-methyl-1H-indole-5-carboxamide (129); N—((R)-2-fluoro-3-hydroxy-3-methylbutyl)-2-(3-isopropyl-2-(2-methylpyridin-4-yl)-1H-indol-5-yl)propanamide (130); N-(2-hydroxy-2-methylpropyl)-2-(3-isopropyl-2-(2-methylpyridin-4-yl)-1H-indol-5-yl)propanamide (131); N-(3-hydroxy-3-methylbutyl)-2-(3-isopropyl-2-(2-methylpyridin-4-yl)-1H-indol-5-yl)propanamide (132); (R)—N-(2-fluoro-3-hydroxy-3-methylbutyl)-2-(3-isopropyl-2-(2-methylpyridin-4-yl)-1H-indol-5-yl)-2-methylpropanamide (133); N-(2-aminoethyl)-2-(3-isopropyl-2-(2-methylpyridin-4-yl)-1H-indol-5-yl)-2-methylpropanamide (134); N-(3-hydroxy-3-methylbutyl)-2-(3-isopropyl-2-(2-methylpyridin-4-yl)-1H-indol-5-yl)-2-methylpropanamide (135); 3-(3-isopropyl-2-(1H-pyrazolo[3,4-b]pyridin-4-yl)-1H-indol-5-yl)-1-morpholinopropan-1-one (136); 3-(2-(3,4-dimethoxyphenyl)-3-isopropyl-1H-indol-5-yl)-1-(hexahydropyrrolo[3,4-c]pyrrol-2(1H)-yl)propan-1-one (137); (S)-2-(3-isopropyl-2-(2-methylpyridin-4-yl)-1H-indol-5-yl)-2-methyl-N-(pyrrolidin-3-yl)propanamide (138); 2-(3-isopropyl-2-(2-methylpyridin-4-yl)-1H-indol-5-yl)-N-(1-isopropylpiperidin-4-yl)-2-methylpropanamide (139); (R)-2-(3-isopropyl-2-(2-methylpyridin-4-yl)-1H-indol-5-yl)-2-methyl-N-(piperidin-3-yl)propanamide (140); (R)-2-(3-isopropyl-2-(2-methylpyridin-4-yl)-1H-indol-5-yl)-2-methyl-N-(pyrrolidin-3-yl)propanamide (141); 2-(3-isopropyl-2-(2-methylpyridin-4-yl)-1H-indol-5-yl)-2-methyl-N-(quinuclidin-3-yl)propanamide (142); 2-(3-isopropyl-2-(2-methylpyridin-4-yl)-1H-indol-5-yl)-2-methyl-N-(piperidin-4-yl)propanamide (143); 2-(3-isopropyl-2-(2-methylpyridin-4-yl)-1H-indol-5-yl)-2-methyl-N-(octahydrocyclopenta[c]pyrrol-4-yl)propanamide (144); 2-(3-isopropyl-2-(2-methylpyridin-4-yl)-1H-indol-5-yl)-2-methyl-N-(1-(pyrrolidin-3-yl)piperidin-4-yl)propanamide (145); 2-(3-isopropyl-2-(2-methylpyridin-4-yl)-1H-indol-5-yl)-2-methyl-N-(octahydrocyclopenta[c]pyrrol-4-yl) propanamide (146); 2-(3-isopropyl-2-(2-methylpyridin-4-yl)-1H-indol-5-yl)-2-methyl-N-(octahydrocyclopenta[c] pyrrol-4-yl)propanamide (147); 1-(6-amino-3-azabicyclo [3.1.1]heptan-3-yl)-2-(3-isopropyl-2-(2-methylpyridin-4-yl)-1H-indol-5-yl)-2-methylpropan-1-one (148); 2-(3-isopropyl-2-(2-methylpyridin-4-yl)-1H-indol-5-yl)-2-methyl-1-(5-methylhexahydropyrrolo[3,4-c]pyrrol-2(1H)-yl)propan-1-one (149); 2-(3-isopropyl-2-(2-methylpyridin-4-yl)-1H-indol-5-yl)-2-methyl-1-(2-methyl-2,8-diazaspiro [4.5]decan-8-yl)propan-1-one (150); 1-(3-(aminomethyl) pyrrolidin-1-yl)-2-(3-isopropyl-2-(2-methylpyridin-4-yl)-1H-indol-5-yl)-2-methylpropan-1-one (151); 1-(7-amino-2-azaspiro[5.5]undecan-2-yl)-2-(3-isopropyl-2-(2-methylpyridin-4-yl)-1H-indol-5-yl)-2-methylpropan-1-one (152); 1-(4-aminopiperidin-1-yl)-2-(3-isopropyl-2-(2-methylpyridin-4-yl)-1H-indol-5-yl)-2-methylpropan-1-one (153); 1-(3-(2-aminoethyl)piperidin-1-yl)-2-(3-isopropyl-2-(2-methylpyridin-4-yl)-1H-indol-5-yl)-2-methylpropan-1-one (154); (S)-1-(3-aminopiperidin-1-yl)-2-(3-isopropyl-2-(2-methylpyridin-4-yl)-1H-indol-5-yl)-2-methylpropan-1-one (155); 1-(3-(aminomethyl)piperidin-1-yl)-2-(3-isopropyl-2-(2-methylpyridin-4-yl)-1H-indol-5-yl)-2-methylpropan-1-one (156); 1-(2-(aminomethyl)piperidin-1-yl)-2-(3-isopropyl-2-(2-methylpyridin-4-yl)-1H-indol-5-yl)-2-methylpropan-1-one (157); 1-(4-(aminomethyl) piperidin-1-yl)-2-(3-isopropyl-2-(2-methylpyridin-4-yl)-1H-indol-5-yl)-2-methylpropan-1-one (158) 2-(3-isopropyl-2-(2-methylpyridin-4-yl)-1H-indol-5-yl)-2-methyl-N-(piperidin-2-ylmethyl)propanamide (159); (S)-2-(3-isopropyl-2-(2-methylpyridin-4-yl)-1H-indol-5-yl)-2-methyl-N-(pyrrolidin-3-ylmethyl)propanamide (160); 2-(3-isopropyl-2-(2-methylpyridin-4-yl)-1H-indol-5-yl)-N,2- dimethyl-N-(piperidin-3-yl)propanamide (161); 2-(3-isopropyl-2-(2-methylpyridin-4-yl)-1H-indol-5-yl)-N,2-dimethyl-N-(quinuclidin-3-yl)propanamide (162); 2-(3-isopropyl-2-(2-methylpyridin-4-yl)-1H-indol-5-yl)-2-methyl-N-(piperidin-3-ylmethyl)propanamide (163); 2-(3-isopropyl-2-(2-methylpyridin-4-yl)-1H-indol-5-yl)-2-methyl-N-(piperidin-4-ylmethyl)propanamide (164); 2-(3-isopropyl-2-(2-methylpyridin-4-yl)-1H-indol-5-yl)-N,2-dimethyl-N-(piperidin-4-yl)propanamide (165); 2-(3-isopropyl-2-(2-methylpyridin-4-yl)-1H-indol-5-yl)-2-methyl-N-((1R,5S)-8-methyl-8-azabicyclo[3.2.1]octan-3-yl)propanamide (166); N-(4-aminocyclohexyl)-2-(3-isopropyl-2-(2-methylpyridin-4-yl)-1H-indol-5-yl)-2-methylpropanamide (167); N-(3-aminocyclohexyl)-2-(3-isopropyl-2-(2-methylpyridin-4-yl)-1H-indol-5-yl)-2-methylpropanamide (168); N—((R,2R)-2-aminocyclohexyl)-2-(3-isopropyl-2-(2-methylpyridin-4-yl)-1H-indol-5-yl)-2-methylpropanamide (169); N-((1S,2R)-2-aminocyclohexyl)-2-(3-isopropyl-2-(2-methylpyridin-4-yl)-1H-indol-5-yl)-2-methylpropanamide (170); 2-(3-isopropyl-2-(2-methylpyridin-4-yl)-1H-indol-5-yl)-2-methyl-N-(2-(piperidin-3-yl)ethyl)propanamide (171); N-(((1r,4r)-4-aminocyclohexyl)methyl)-2-(3-isopropyl-2-(2-methylpyridin-4-yl)-1H-indol-5-yl)-2-methylpropanamide (172); N-((4-hydroxy-1-methylpiperidin-4-yl)methyl)-2-(3-isopropyl-2-(2-methylpyridin-4-yl)-1H-indol-5-yl)-2-methylpropanamide (173); N-((3-hydroxyquinuclidin-3-yl)methyl)-2-(3-isopropyl-2-(2-methylpyridin-4-yl)-1H-indol-5-yl)-2-methylpropanamide (174); 2-(3-isopropyl-2-(2-methylpyridin-4-yl)-1H-indol-5-yl)-2-methyl-1-(piperazin-1-yl)propan-1-one (175); 1-(2,5-diazabicyclo[2.2.1]heptan-2-yl)-2-(3-isopropyl-2-(2-methylpyridin-4-yl)-1H-indol-5-yl)-2-methylpropan-1-one (176); 2-(3-isopropyl-2-(2-methylpyridin-4-yl)-1H-indol-5-yl)-2-methyl-1-(4-(piperidin-4-yloxy)piperidin-1-yl)propan-1-one (177); 2-(3-isopropyl-2-(2-methylpyridin-4-yl)-1H-indol-5-yl)-2-methyl-1-(2,7-diazaspiro[4.4]nonan-2-yl)propan-1-one (178); 2-(3-isopropyl-2-(2-methylpyridin-4-yl)-1H-indol-5-yl)-2-methyl-1-(2,7-diazaspiro[3.5]nonan-2-yl)propan-1-one (179); 2-(3-isopropyl-2-(2-methylpyridin-4-yl)-1H-indol-5-yl)-2-methyl-1-(2,6-diazaspiro[3.5]nonan-6-yl)propan-1-one (180); 2-(3-isopropyl-2-(2-methylpyridin-4-yl)-1H-indol-5-yl)-2-methyl-1-(2,8-diazaspiro[4.5]decan-8-yl)propan-1-one (181) 1-([2,4'-bipiperidin]-1-yl)-2-(3-isopropyl-2-(2-methylpyridin-4-yl)-1H-indol-5-yl)-2-methylpropan-1-one (182); 1-(hexahydropyrrolo[3,4-c]pyrrol-2(1H)-yl)-2-(3-isopropyl-2-(2-methylpyridin-4-yl)-1H-indol-5-yl)-2-methylpropan-1-one (183); 2-(3-isopropyl-2-(2-methylpyridin-4-yl)-1H-indol-5-yl)-2-methyl-1-(2,7-diazaspiro[4.5]decan-7-yl)propan-1-one (184); 1-(3,6-diazabicyclo[3.2.0]heptan-3-yl)-2-(3-isopropyl-2-(2-methylpyridin-4-yl)-1H-indol-5-yl)-2-methylpropan-1-one (185); 2-(3-isopropyl-2-(2-methylpyridin-4-yl)-1H-indol-5-yl)-N-(octahydrocyclopenta[c]pyrrol-4-yl)propanamide (186); 2-(3-isopropyl-2-(2-methylpyridin-4-yl)-1H-indol-5-yl)-N-(octahydrocyclopenta[c]pyrrol-4-yl)propanamide (187); 2-(3-isopropyl-2-(2-methylpyridin-4-yl)-1H-indol-5-yl)-N—((R)-pyrrolidin-3-yl)propanamide (188); 2-(3-isopropyl-2-(2-methylpyridin-4-yl)-1H-indol-5-yl)-N—((S)-pyrrolidin-3-yl)propanamide (189); 2-(3-isopropyl-2-(2-methylpyridin-4-yl)-1H-indol-5-yl)-N—((S)-pyrrolidin-3-yl)propanamide (190); 2-(3-isopropyl-2-(2-methylpyridin-4-yl)-1H-indol-5-yl)-N-(quinuclidin-3-yl)propanamide (191); 2-(3-isopropyl-2-(2-methylpyridin-4-yl)-1H-indol-5-yl)-N-(quinuclidin-3-yl)propanamide (192); 2-(3-isopropyl-2-(2-methylpyridin-4-yl)-1H-indol-5-yl)-N-(piperidin-4-yl)propanamide (193); 2-(3-isopropyl-2-(2-methylpyridin-4-yl)-1H-indol-5-yl)-N-(1-isopropylpiperidin-4-yl)propanamide (194); 2-(3-isopropyl-2-(2-methylpyridin-4-yl)-1H-indol-5-yl)-N—((R)-piperidin-3-yl)propanamide (195); 2-(3-isopropyl-2-(2-methylpyridin-4-yl)-1H-indol-5-yl)-N—((R)-piperidin-3-yl)propanamide (196); 2-(3-isopropyl-2-(2-methylpyridin-4-yl)-1H-indol-5-yl)-1-(5-methylhexahydropyrrolo[3,4-c]pyrrol-2(1H)-yl)propan-1-one (197); 2-(3-isopropyl-2-(2-methylpyridin-4-yl)-1H-indol-5-yl)-1-(2-methyl-2,8-diazaspiro[4.5]decan-8-yl)propan-1-one (198); 1-(3-(aminomethyl)pyrrolidin-1-yl)-2-(3-isopropyl-2-(2-methylpyridin-4-yl)-1H-indol-5-yl)propan-1-one (199); 1-(7-amino-2-azaspiro[5.5]undecan-2-yl)-2-(3-isopropyl-2-(2-methylpyridin-4-yl)-1H-indol-5-yl)propan-1-one (200); 1-(7-amino-2-azaspiro[5.5]undecan-2-yl)-2-(3-isopropyl-2-(2-methylpyridin-4-yl)-1H-indol-5-yl)propan-1-one (201); 1-(4-(aminomethyl)piperidin-1-yl)-2-(3-isopropyl-2-(2-methylpyridin-4-yl)-1H-indol-5-yl)propan-1-one (202); 1-(4-aminopiperidin-1-yl)-2-(3-isopropyl-2-(2-methylpyridin-4-yl)-1H-indol-5-yl)propan-1-one (203); 1-((S)-3-aminopiperidin-1-yl)-2-(3-isopropyl-2-(2-methylpyridin-4-yl)-1H-indol-5-yl)propan-1-one (204); 1-(3-(aminomethyl)piperidin-1-yl)-2-(3-isopropyl-2-(2-methylpyridin-4-yl)-1H-indol-5-yl)propan-1-one (205); 1-(3-(2-aminoethyl)piperidin-1-yl)-2-(3-isopropyl-2-(2-methylpyridin-4-yl)-1H-indol-5-yl)propan-1-one (206); 2-(3-isopropyl-2-(2-methylpyridin-4-yl)-1H-indol-5-yl)-N-methyl-N-(piperidin-4-yl)propanamide (207); 2-(3-isopropyl-2-(2-methylpyridin-4-yl)-1H-indol-5-yl)-N—(((R)-pyrrolidin-3-yl)methyl)propanamide (208) 2-(3-isopropyl-2-(2-methylpyridin-4-yl)-1H-indol-5-yl)-N-methyl-N-(piperidin-3-yl)propanamide (209); 2-(3-isopropyl-2-(2-methylpyridin-4-yl)-1H-indol-5-yl)-N-methyl-N-(piperidin-3-yl)propanamide (210); 2-(3-isopropyl-2-(2-methylpyridin-4-yl)-1H-indol-5-yl)-N-methyl-N-(quinuclidin-3-yl)propanamide (211); 2-(3-isopropyl-2-(2-methylpyridin-4-yl)-1H-indol-5-yl)-N—(((S)-pyrrolidin-3-yl)methyl)propanamide (212); 2-(3-isopropyl-2-(2-methylpyridin-4-yl)-1H-indol-5-yl)-N-(piperidin-3-ylmethyl)propanamide (213); 2-(3-isopropyl-2-(2-methylpyridin-4-yl)-1H-indol-5-yl)-N-((1R,5S)-8-methyl-8-azabicyclo[3.2.1]octan-3-yl)propanamide (214); N-((1R,2R)-2-aminocyclohexyl)-2-(3-isopropyl-2-(2-methylpyridin-4-yl)-1H-indol-5-yl)propanamide (215); N-((1R,2R)-2-aminocyclohexyl)-2-(3-isopropyl-2-(2-methylpyridin-4-yl)-1H-indol-5-yl)propanamide (216); N-(4-aminocyclohexyl)-2-(3-isopropyl-2-(2-methylpyridin-4-yl)-1H-indol-5-yl)propanamide (217); N-(3-aminocyclohexyl)-2-(3-isopropyl-2-(2-methylpyridin-4-yl)-1H-indol-5-yl)propanamide (218); N-(3-aminocyclohexyl)-2-(3-isopropyl-2-(2-methylpyridin-4-yl)-1H-indol-5-yl)propanamide (219); 3-chloro-5-(3-isopropyl-5-(4-methylpiperazine-1-carbonyl)-1H-indol-2-yl)-1,4-dimethylpyridin-2(1H)-one (220); 2-(5-chloro-1,4-dimethyl-6-oxo-1,6-dihydropyridin-3-yl)-N-cyclopropyl-3-isopropyl-N-(1-propylpiperidin-4-yl)-1H-indole-5-carboxamide (221); and 2-(5-chloro-1,4-dimethyl-6-oxo-1,6-dihydropyridin-3-yl)-N-(2-(dimethylamino)ethyl)-3-isopropyl-N-methyl-1H-indole-5-carboxamide (222).

The present invention may be embodied in other specific forms without departing from the spirit or essential attributes thereof. This invention encompasses all combinations of the aspects and/or embodiments of the invention noted herein. It is understood that any and all embodiments of the present invention may be taken in conjunction with any other embodiment or embodiments to describe additional embodiments. It is also to be understood that each individual element of the embodiments is meant to be combined with any and all other elements from any embodiment to describe an additional embodiment.

Definitions

The features and advantages of the invention may be more readily understood by those of ordinary skill in the art upon reading the following detailed description. It is to be appreciated that certain features of the invention that are, for clarity reasons, described above and below in the context of separate embodiments, may also be combined to form a single embodiment. Conversely, various features of the invention that are, for brevity reasons, described in the context of a single embodiment, may also be combined so as to form sub-combinations thereof. Embodiments identified herein as exemplary or preferred are intended to be illustrative and not limiting.

Unless specifically stated otherwise herein, references made in the singular may also include the plural. For example, "a" and "an" may refer to either one, or one or more.

As used herein, the phrase "compounds and/or salts thereof" refers to at least one compound, at least one salt of the compounds, or a combination thereof. For example, compounds of Formula (I) and/or salts thereof includes a compound of Formula (I); two compounds of Formula (I); a salt of a compound of Formula (I); a compound of Formula (I) and one or more salts of the compound of Formula (I); and two or more salts of a compound of Formula (I).

Unless otherwise indicated, any atom with unsatisfied valences is assumed to have hydrogen atoms sufficient to satisfy the valences.

The definitions set forth herein take precedence over definitions set forth in any patent, patent application, and/or patent application publication incorporated herein by reference.

Listed below are definitions of various terms used to describe the present invention. These definitions apply to the terms as they are used throughout the specification (unless they are otherwise limited in specific instances) either individually or as part of a larger group.

Throughout the specification, groups and substituents thereof may be chosen by one skilled in the field to provide stable moieties and compounds.

In accordance with a convention used in the art,

is used in structural formulas herein to depict the bond that is the point of attachment of the moiety or substituent to the core or backbone structure.

The terms "halo" and "halogen," as used herein, refer to F, Cl, Br, and I.

The term "cyano" refers to the group —CN.
The term "amino" refers to the group —$NH_2$.
The term "oxo" refers to the group =O.

The term "alkyl" as used herein, refers to both branched and straight-chain saturated aliphatic hydrocarbon groups containing, for example, from 1 to 12 carbon atoms, from 1 to 6 carbon atoms, and from 1 to 4 carbon atoms. Examples of alkyl groups include, but are not limited to, methyl (Me), ethyl (Et), propyl (e.g., n-propyl and i-propyl), butyl (e.g., n-butyl, i-butyl, sec-butyl, and t-butyl), and pentyl (e.g., n-pentyl, isopentyl, neopentyl), n-hexyl, 2-methylpentyl, 2-ethylbutyl, 3-methylpentyl, and 4-methylpentyl. When numbers appear in a subscript after the symbol "C", the subscript defines with more specificity the number of carbon atoms that a particular group may contain. For example, "$C_{1-4}$alkyl" denotes straight and branched chain alkyl groups with one to four carbon atoms.

The term "fluoroalkyl" as used herein is intended to include both branched and straight-chain saturated aliphatic hydrocarbon groups substituted with one or more fluorine atoms. For example, "$C_{1-4}$ fluoroalkyl" is intended to include $C_1$, $C_2$, $C_3$, and $C_4$ alkyl groups substituted with one or more fluorine atoms. Representative examples of fluoroalkyl groups include, but are not limited to, —$CF_3$ and —$CH_2CF_3$.

The term "aminoalkyl" includes both branched and straight-chain saturated alkyl groups substituted with one or more amine groups. For example, "aminoalkyl" includes —$CH_2NH_2$, —$CH_2CH_2NH_2$, and $C_{1-4}$ aminoalkyl.

The term "hydroxyalkyl" includes both branched and straight-chain saturated alkyl groups substituted with one or more hydroxyl groups. For example, "hydroxyalkyl" includes —$CH_2OH$, —$CH_2CH_2OH$, and $C_{1-4}$ hydroxyalkyl.

The term "hydroxy-fluoroalkyl" includes both branched and straight-chain saturated alkyl groups substituted with one or more hydroxyl groups and one or more fluorine atoms. For example, "hydroxy-fluoroalkyl" includes —$CHFCH_2OH$, —$CH_2CHFC(CH_3)_2OH$, and $C_{1-4}$ hydroxy-fluoroalkyl.

The term "cycloalkyl," as used herein, refers to a group derived from a non-aromatic monocyclic or polycyclic hydrocarbon molecule by removal of one hydrogen atom from a saturated ring carbon atom. Representative examples of cycloalkyl groups include, but are not limited to, cyclopropyl, cyclopentyl, and cyclohexyl. When numbers appear in a subscript after the symbol "C", the subscript defines with more specificity the number of carbon atoms that a particular cycloalkyl group may contain. For example, "$C_{3-6}$ cycloalkyl" denotes cycloalkyl groups with three to six carbon atoms.

The term "alkoxy," as used herein, refers to an alkyl group attached to the parent molecular moiety through an oxygen atom, for example, methoxy group (—$OCH_3$). For example, "$C_{1-3}$ alkoxy" denotes alkoxy groups with one to three carbon atoms.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The compounds of Formula (I) can form salts which are also within the scope of this invention. Unless otherwise indicated, reference to an inventive compound is understood to include reference to one or more salts thereof. The term "salt(s)" denotes acidic and/or basic salts formed with inorganic and/or organic acids and bases. In addition, the term "salt(s) may include zwitterions (inner salts), e.g., when a compound of Formula (I) contains both a basic moiety, such as an amine or a pyridine or imidazole ring, and an acidic moiety, such as a carboxylic acid. Pharmaceutically acceptable (i.e., non-toxic, physiologically acceptable) salts are preferred, such as, for example, acceptable metal and amine salts in which the cation does not contribute significantly to the toxicity or biological activity of the salt.

However, other salts may be useful, e.g., in isolation or purification steps which may be employed during preparation, and thus, are contemplated within the scope of the invention. Salts of the compounds of the formula (I) may be formed, for example, by reacting a compound of the Formula (I) with an amount of acid or base, such as an equivalent amount, in a medium such as one in which the salt precipitates or in an aqueous medium followed by lyophilization.

Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, maleates (formed with maleic acid), 2-hydroxyethanesulfonates, lactates, methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

Exemplary basic salts include ammonium salts, alkali metal salts such as sodium, lithium, and potassium salts; alkaline earth metal salts such as calcium and magnesium salts; barium, zinc, and aluminum salts; salts with organic bases (for example, organic amines) such as trialkylamines such as triethylamine, procaine, dibenzylamine, N-benzyl-β-phenethylamine, 1-ephenamine, N,N'-dibenzylethylenediamine, dehydroabietylamine, N-ethylpiperidine, benzylamine, dicyclohexylamine or similar pharmaceutically acceptable amines and salts with amino acids such as arginine, lysine and the like. Basic nitrogen-containing groups may be quaternized with agents such as lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl and stearyl chlorides, bromides and iodides), aralkyl halides (e.g., benzyl and phenethyl bromides), and others. Preferred salts include monohydrochloride, hydrogensulfate, methanesulfonate, phosphate or nitrate salts.

The compounds of Formula (I) can be provided as amorphous solids or crystalline solids. Lyophilization can be employed to provide the compounds of Formula (I) as a solid.

It should further be understood that solvates (e.g., hydrates) of the Compounds of Formula (I) are also within the scope of the present invention. The term "solvate" means a physical association of a compound of Formula (I) with one or more solvent molecules, whether organic or inorganic. This physical association includes hydrogen bonding. In certain instances the solvate will be capable of isolation, for example when one or more solvent molecules are incorporated in the crystal lattice of the crystalline solid. "Solvate" encompasses both solution-phase and isolable solvates. Exemplary solvates include hydrates, ethanolates, methanolates, isopropanolates, acetonitrile solvates, and ethyl acetate solvates. Methods of solvation are known in the art.

Various forms of prodrugs are well known in the art and are described in:

a) *The Practice of Medicinal Chemistry*, Camille G. Wermuth et al., Ch 31, (Academic Press, 1996);

b) *Design of Prodrugs*, edited by H. Bundgaard, (Elsevier, 1985);

c) *A Textbook of Drug Design and Development*, P. Krogsgaard-Larson and H. Bundgaard, eds. Ch 5, pgs 113-191 (Harwood Academic Publishers, 1991); and d) *Hydrolysis in Drug and Prodrug Metabolism*, Bernard Testa and Joachim M. Mayer, (Wiley-VCH, 2003).

In addition, compounds of Formula (I), subsequent to their preparation, can be isolated and purified to obtain a composition containing an amount by weight equal to or greater than 99% of a compound of Formula (I) ("substantially pure"), which is then used or formulated as described herein. Such "substantially pure" compounds of Formula (I) are also contemplated herein as part of the present invention.

"Stable compound" and "stable structure" are meant to indicate a compound that is sufficiently robust to survive isolation to a useful degree of purity from a reaction mixture, and formulation into an efficacious therapeutic agent. The present invention is intended to embody stable compounds.

"Therapeutically effective amount" is intended to include an amount of a compound of the present invention alone or an amount of the combination of compounds claimed or an amount of a compound of the present invention in combination with other active ingredients effective to act as an inhibitor to TLR7/8/9, or effective to treat or prevent autoimmune and/or inflammatory disease states, such as SLE, IBD, multiple sclerosis (MS), and Sjögren's syndrome, and rheumatoid arthritis.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting its development; and/or (c) relieving the disease-state. i.e., causing regression of the disease state.

The compounds of the present invention are intended to include all isotopes of atoms occurring in the present compounds. Isotopes include those atoms having the same atomic number but different mass numbers. By way of general example and without limitation, isotopes of hydrogen include deuterium (D) and tritium (T). Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed.

Compounds in accordance with Formula (I) and/or pharmaceutically acceptable salts thereof can be administered by any means suitable for the condition to be treated, which can depend on the need for site-specific treatment or quantity of Formula (I) compound to be delivered.

Also embraced within this invention is a class of pharmaceutical compositions comprising a compound of Formula (I) and/or pharmaceutically acceptable salts thereof; and one or more non-toxic, pharmaceutically-acceptable carriers and/or diluents and/or adjuvants (collectively referred to herein as "carrier" materials) and, if desired, other active ingredients. The compounds of Formula (I) may be administered by any suitable route, preferably in the form of a pharmaceutical composition adapted to such a route, and in a dose effective for the treatment intended. The compounds and compositions of the present invention may, for example, be administered orally, mucosally, or parenterally including intravascularly, intravenously, intraperitoneally, subcutaneously, intramuscularly, and intrasternally in dosage unit formulations containing conventional pharmaceutically acceptable carriers, adjuvants, and vehicles. For example, the pharmaceutical carrier may contain a mixture of mannitol or lactose and microcrystalline cellulose. The mixture may contain additional components such as a lubricating agent, e.g. magnesium stearate and a disintegrating agent such as crospovidone. The carrier mixture may be filled into a gelatin capsule or compressed as a tablet. The pharmaceutical composition may be administered as an oral dosage form or an infusion, for example.

For oral administration, the pharmaceutical composition may be in the form of, for example, a tablet, capsule, liquid capsule, suspension, or liquid. The pharmaceutical composition is preferably made in the form of a dosage unit containing a particular amount of the active ingredient. For example, the pharmaceutical composition may be provided as a tablet or capsule comprising an amount of active ingredient in the range of from about 0.1 to 1000 mg, preferably from about 0.25 to 250 mg, and more preferably from about 0.5 to 100 mg. A suitable daily dose for a human or other mammal may vary widely depending on the condition of the patient and other factors, but, can be determined using routine methods.

Any pharmaceutical composition contemplated herein can, for example, be delivered orally via any acceptable and suitable oral preparations. Exemplary oral preparations, include, but are not limited to, for example, tablets, troches, lozenges, aqueous and oily suspensions, dispersible powders or granules, emulsions, hard and soft capsules, liquid capsules, syrups, and elixirs. Pharmaceutical compositions intended for oral administration can be prepared according to any methods known in the art for manufacturing pharmaceutical compositions intended for oral administration. In order to provide pharmaceutically palatable preparations, a pharmaceutical composition in accordance with the invention can contain at least one agent selected from sweetening agents, flavoring agents, coloring agents, demulcents, antioxidants, and preserving agents.

A tablet can, for example, be prepared by admixing at least one compound of Formula (I) and/or at least one pharmaceutically acceptable salt thereof with at least one non-toxic pharmaceutically acceptable excipient suitable for the manufacture of tablets. Exemplary excipients include, but are not limited to, for example, inert diluents, such as, for example, calcium carbonate, sodium carbonate, lactose, calcium phosphate, and sodium phosphate; granulating and disintegrating agents, such as, for example, microcrystalline cellulose, sodium crosscarmellose, corn starch, and alginic acid; binding agents, such as, for example, starch, gelatin, polyvinyl-pyrrolidone, and acacia; and lubricating agents, such as, for example, magnesium stearate, stearic acid, and talc. Additionally, a tablet can either be uncoated, or coated by known techniques to either mask the bad taste of an unpleasant tasting drug, or delay disintegration and absorption of the active ingredient in the gastrointestinal tract thereby sustaining the effects of the active ingredient for a longer period. Exemplary water soluble taste masking materials, include, but are not limited to, hydroxypropyl-methylcellulose and hydroxypropyl-cellulose. Exemplary time delay materials, include, but are not limited to, ethyl cellulose and cellulose acetate butyrate.

Hard gelatin capsules can, for example, be prepared by mixing at least one compound of Formula (I) and/or at least one salt thereof with at least one inert solid diluent, such as, for example, calcium carbonate; calcium phosphate; and kaolin.

Soft gelatin capsules can, for example, be prepared by mixing at least one compound of Formula (I) and/or at least one pharmaceutically acceptable salt thereof with at least one water soluble carrier, such as, for example, polyethylene glycol; and at least one oil medium, such as, for example, peanut oil, liquid paraffin, and olive oil.

An aqueous suspension can be prepared, for example, by admixing at least one compound of Formula (I) and/or at least one pharmaceutically acceptable salt thereof with at least one excipient suitable for the manufacture of an aqueous suspension. Exemplary excipients suitable for the manufacture of an aqueous suspension, include, but are not limited to, for example, suspending agents, such as, for example, sodium carboxymethylcellulose, methylcellulose, hydroxypropylmethyl-cellulose, sodium alginate, alginic acid, polyvinyl-pyrrolidone, gum tragacanth, and gum acacia; dispersing or wetting agents, such as, for example, a naturally-occurring phosphatide, e.g., lecithin; condensation products of alkylene oxide with fatty acids, such as, for example, polyoxyethylene stearate; condensation products of ethylene oxide with long chain aliphatic alcohols, such as, for example heptadecaethyleneoxycetanol; condensation products of ethylene oxide with partial esters derived from fatty acids and hexitol, such as, for example, polyoxyethylene sorbitol monooleate; and condensation products of ethylene oxide with partial esters derived from fatty acids and hexitol anhydrides, such as, for example, polyethylene sorbitan monooleate. An aqueous suspension can also contain at least one preservative, such as, for example, ethyl and n-propyl p-hydroxybenzoate; at least one coloring agent; at least one flavoring agent; and/or at least one sweetening agent, including but not limited to, for example, sucrose, saccharin, and aspartame.

Oily suspensions can, for example, be prepared by suspending at least one compound of Formula (I) and/or at least one pharmaceutically acceptable salt thereof in either a vegetable oil, such as, for example, *arachis* oil; olive oil; sesame oil; and coconut oil; or in mineral oil, such as, for example, liquid paraffin. An oily suspension can also contain at least one thickening agent, such as, for example, beeswax; hard paraffin; and cetyl alcohol. In order to provide a palatable oily suspension, at least one of the sweetening agents already described hereinabove, and/or at least one flavoring agent can be added to the oily suspension. An oily suspension can further contain at least one preservative, including, but not limited to, for example, an anti-oxidant, such as, for example, butylated hydroxyanisol, and alpha-tocopherol.

Dispersible powders and granules can, for example, be prepared by admixing at least one compound of Formula (I) and/or at least one pharmaceutically acceptable salt thereof with at least one dispersing and/or wetting agent; at least one suspending agent; and/or at least one preservative. Suitable dispersing agents, wetting agents, and suspending agents are as already described above. Exemplary preservatives include, but are not limited to, for example, anti-oxidants, e.g., ascorbic acid. In addition, dispersible powders and granules can also contain at least one excipient, including, but not limited to, for example, sweetening agents; flavoring agents; and coloring agents.

An emulsion of at least one compound of Formula (I) and/or at least one pharmaceutically acceptable salt thereof can, for example, be prepared as an oil-in-water emulsion. The oily phase of the emulsions comprising compounds of Formula (I) may be constituted from known ingredients in a known manner. The oil phase can be provided by, but is not limited to, for example, a vegetable oil, such as, for example, olive oil and *arachis* oil; a mineral oil, such as, for example, liquid paraffin; and mixtures thereof. While the phase may comprise merely an emulsifier, it may comprise a mixture of at least one emulsifier with a fat or an oil or with both a fat and an oil. Suitable emulsifying agents include, but are not limited to, for example, naturally-occurring phosphatides, e.g., soy bean lecithin; esters or partial esters derived from fatty acids and hexitol anhydrides, such as, for example, sorbitan monooleate; and condensation products of partial esters with ethylene oxide, such as, for example, polyoxyethylene sorbitan monooleate. Preferably, a hydrophilic emulsifier is included together with a lipophilic emulsifier which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base which forms the oily dispersed phase of the cream formulations. An emulsion can also contain a sweetening agent, a flavoring agent, a preservative, and/or an antioxidant. Emulsifiers and emulsion stabilizers suitable for use in the formulation of the present invention include Tween 60. Span 80, cetostearyl alcohol, myristyl alcohol, glyceryl monostearate, sodium lauryl sulfate, glyceryl distearate alone or with a wax, or other materials well known in the art.

The compounds of Formula (I) and/or at least one pharmaceutically acceptable salt thereof can, for example, also be delivered intravenously, subcutaneously, and/or intramuscularly via any pharmaceutically acceptable and suitable injectable form. Exemplary injectable forms include, but are not limited to, for example, sterile aqueous solutions comprising acceptable vehicles and solvents, such as, for example, water. Ringer's solution, and isotonic sodium chloride solution; sterile oil-in-water microemulsions; and aqueous or oleaginous suspensions.

Formulations for parenteral administration may be in the form of aqueous or non-aqueous isotonic sterile injection solutions or suspensions. These solutions and suspensions may be prepared from sterile powders or granules using one or more of the carriers or diluents mentioned for use in the formulations for oral administration or by using other suitable dispersing or wetting agents and suspending agents. The compounds may be dissolved in water, polyethylene glycol, propylene glycol, ethanol, corn oil, cottonseed oil, peanut oil, sesame oil, benzyl alcohol, sodium chloride, tragacanth gum, and/or various buffers. Other adjuvants and modes of administration are well and widely known in the pharmaceutical art. The active ingredient may also be administered by injection as a composition with suitable carriers including saline, dextrose, or water, or with cyclodextrin (i.e. Captisol), cosolvent solubilization (i.e. propylene glycol) or micellar solubilization (i.e. Tween 80).

The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

A sterile injectable oil-in-water microemulsion can, for example, be prepared by 1) dissolving at least one compound of Formula (I) in an oily phase, such as, for example, a mixture of soybean oil and lecithin; 2) combining the Formula (I) containing oil phase with a water and glycerol mixture; and 3) processing the combination to form a microemulsion.

A sterile aqueous or oleaginous suspension can be prepared in accordance with methods already known in the art. For example, a sterile aqueous solution or suspension can be prepared with a non-toxic parenterally-acceptable diluent or solvent, such as, for example, 1,3-butane diol; and a sterile oleaginous suspension can be prepared with a sterile non-toxic acceptable solvent or suspending medium, such as, for example, sterile fixed oils, e.g., synthetic mono- or diglycerides; and fatty acids, such as, for example, oleic acid.

Pharmaceutically acceptable carriers, adjuvants, and vehicles that may be used in the pharmaceutical compositions of this invention include, but are not limited to, ion exchangers, alumina, aluminum stearate, lecithin, self-emulsifying drug delivery systems (SEDDS) such as d-alpha-tocopherol polyethyleneglycol 1000 succinate, surfactants used in pharmaceutical dosage forms such as Tweens, polyethoxylated castor oil such as CREMOPHOR surfactant (BASF), or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as alpha-, beta-, and gamma-cyclodextrin, or chemically modified derivatives such as hydroxyalkylcyclodextrins, including 2- and 3-hydroxypropyl-cyclodextrins, or other solubilized derivatives may also be advantageously used to enhance delivery of compounds of the formulae described herein.

The pharmaceutically active compounds of this invention can be processed in accordance with conventional methods of pharmacy to produce medicinal agents for administration to patients, including humans and other mammals. The pharmaceutical compositions may be subjected to conventional pharmaceutical operations such as sterilization and/or may contain conventional adjuvants, such as preservatives, stabilizers, wetting agents, emulsifiers, buffers etc. Tablets and pills can additionally be prepared with enteric coatings. Such compositions may also comprise adjuvants, such as wetting, sweetening, flavoring, and perfuming agents.

The amounts of compounds that are administered and the dosage regimen for treating a disease condition with the compounds and/or compositions of this invention depends on a variety of factors, including the age, weight, sex, the medical condition of the subject, the type of disease, the severity of the disease, the route and frequency of administration, and the particular compound employed. Thus, the dosage regimen may vary widely, but can be determined routinely using standard methods. A daily dose of about 0.001 to 100 mg/kg body weight, preferably between about 0.0025 and about 50 mg/kg body weight and most preferably between about 0.005 to 10 mg/kg body weight, may be appropriate. The daily dose can be administered in one to four doses per day. Other dosing schedules include one dose per week and one dose per two day cycle.

For therapeutic purposes, the active compounds of this invention are ordinarily combined with one or more adjuvants appropriate to the indicated route of administration. If administered orally, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose.

Pharmaceutical compositions of this invention comprise at least one compound of Formula (I) and/or at least one pharmaceutically acceptable salt thereof, and optionally an additional agent selected from any pharmaceutically acceptable carrier, adjuvant, and vehicle. Alternate compositions of this invention comprise a compound of the Formula (I) described herein, or a prodrug thereof, and a pharmaceutically acceptable carrier, adjuvant, or vehicle.

Utility

The human immune system has evolved to defend the body from micro-organisms, viruses, and parasites that can cause infection, disease or death. Complex regulatory mechanisms ensure that the various cellular components of the immune system target the foreign substances or organisms, while not causing permanent or significant damage to the individual. While the initiating events are not well understood at this time, in autoimmune disease states the immune system directs its inflammatory response to target organs in the afflicted individual. Different autoimmune diseases are typically characterized by the predominate or initial target organ or tissues affected; such as the joint in the case of rheumatoid arthritis, the thyroid gland in the case of Hashimoto's thyroiditis, the central nervous system in the case of multiple sclerosis, the pancreas in the case of type I diabetes, and the bowel in the case of inflammatory bowel disease.

The compounds of the invention inhibit signaling through Toll-like receptor 7, or 8, or 9 (TLR7, TLR8, TLR9) or combinations thereof. Accordingly, compounds of Formula (I) have utility in treating conditions associated with the inhibition of signaling through one or more of TLR7, TLR8, or TLR9. Such conditions include TLR7, TLR8, or TLR9 receptor associated diseases in which cytokine levels are modulated as a consequence of intracellular signaling.

As used herein, the terms "treating" or "treatment" encompass the treatment of a disease state in a mammal, particularly in a human, and include: (a) preventing or delaying the occurrence of the disease state in a mammal, in particular, when such mammal is predisposed to the disease state but has not yet been diagnosed as having it; (b) inhibiting the disease state, i.e., arresting its development; and/or (c) achieving a full or partial reduction of the symptoms or disease state, and/or alleviating, ameliorating, lessening, or curing the disease or disorder and/or its symptoms.

In view of their activity as selective inhibitors of TLR7, TLR8, or TLR9, compounds of Formula (I) are useful in treating TLR7, TLR8, or TLR9 family receptor associated diseases, but not limited to, inflammatory diseases such as Crohn's disease, ulcerative colitis, asthma, graft versus host disease, allograft rejection, chronic obstructive pulmonary disease; autoimmune diseases such as Graves' disease, rheumatoid arthritis, systemic lupus erythematosus, lupus nephritis, cutaneous lupus, psoriasis; auto-inflammatory diseases including Cryopyrin-Associated Periodic Syndromes (CAPS), TNF Receptor Associated Periodic Syndrome (TRAPS), Familial Mediterranean Fever (FMF), adult onset stills, systemic onset juvenile idiopathic arthritis, gout, gouty arthritis; metabolic diseases including type 2 diabetes, atherosclerosis, myocardial infarction; destructive bone disorders such as bone resorption disease, osteoarthritis, osteoporosis, multiple myeloma-related bone disorder; proliferative disorders such as acute myelogenous leukemia, chronic myelogenous leukemia; angiogenic disorders such as angiogenic disorders including solid tumors, ocular neovascularization, and infantile haemangiomas; infectious diseases such as sepsis, septic shock, and Shigellosis; neurodegenerative diseases such as Alzheimer's disease, Parkinson's disease, cerebral ischemias or neurodegenerative disease caused by traumatic injury, oncologic and viral diseases such as metastatic melanoma, Kaposi's sarcoma, multiple myeloma, and HIV infection and CMV retinitis, AIDS, respectively.

More particularly, the specific conditions or diseases that may be treated with the inventive compounds include, without limitation, pancreatitis (acute or chronic), asthma, allergies, adult respiratory distress syndrome, chronic obstructive pulmonary disease, glomerulonephritis, rheumatoid arthritis, systemic lupus erythematosus, scleroderma, chronic thyroiditis, Graves' disease, autoimmune gastritis, diabetes, autoimmune hemolytic anemia, autoimmune neutropenia, thrombocytopenia, atopic dermatitis, chronic active hepatitis, myasthenia gravis, multiple sclerosis, inflammatory bowel disease, ulcerative colitis, Crohn's disease, psoriasis, graft vs. host disease, inflammatory reaction induced by endotoxin, tuberculosis, atherosclerosis, muscle degeneration, cachexia, psoriatic arthritis, Reiter's syndrome, gout, traumatic arthritis, rubella arthritis, acute synovitis, pancreatic β-cell disease; diseases characterized by massive neutrophil infiltration; rheumatoid spondylitis, gouty arthritis and other arthritic conditions, cerebral malaria, chronic pulmonary inflammatory disease, silicosis, pulmonary sarcoidosis, bone resorption disease, allograft rejections, fever and myalgias due to infection, cachexia secondary to infection, keloid formation, scar tissue formation, ulcerative colitis, pyresis, influenza, osteoporosis, osteoarthritis, acute myelogenous leukemia, chronic myelogenous leukemia, metastatic melanoma, Kaposi's sarcoma, multiple myeloma, sepsis, septic shock, and Shigellosis; Alzheimer's disease, Parkinson's disease, cerebral ischemias or neurodegenerative disease caused by traumatic injury; angiogenic disorders including solid tumors, ocular neovascularization, and infantile haemangiomas; viral diseases including acute hepatitis infection (including hepatitis A, hepatitis B and hepatitis C), HIV infection and CMV retinitis, AIDS, ARC or malignancy, and herpes; stroke, myocardial ischemia, ischemia in stroke heart attacks, organ hypoxia, vascular hyperplasia, cardiac and renal reperfusion injury, thrombosis, cardiac hypertrophy, thrombin-induced platelet aggregation, endotoxemia and/or toxic shock syndrome, conditions associated with prostaglandin endoperoxidase syndase-2, and pemphigus vulgaris. Included in this embodiment are methods of treatment in which the condition is selected from lupus including lupus nephritis and systemic lupus erythematosus (SLE), Crohn's disease, ulcerative colitis, allograft rejection, rheumatoid arthritis, psoriasis, ankylosing spondylitis, psoriatic arthritis, and pemphigus vulgaris. Also included are methods of treatment in which the condition is selected from ischemia reperfusion injury, including cerebral ischemia reperfusions injury arising from stroke and cardiac ischemia reperfusion injury arising from myocardial infarction. Another method of treatment is one in which the condition is multiple myeloma.

In one embodiment, the compounds of Formula (I) are useful in treating cancer, including Waldenstrom's Macroglobulinemia (WM), diffuse large B cell lymphoma (DLBCL), chronic lymphocytic leukemia (CLL), cutaneous diffuse large B cell lymphoma, and primary CNS lymphoma.

In addition, the TLR7, TLR8, or TLR9 inhibitors of the present invention inhibit the expression of inducible pro-inflammatory proteins such as prostaglandin endoperoxide synthase-2 (PGHS-2), also referred to as cyclooxygenase-2 (COX-2), IL-1, IL-6, IL-18, chemokines. Accordingly, additional TLR7/8/9 associated conditions include edema, analgesia, fever and pain, such as neuromuscular pain, headache, pain caused by cancer, dental pain and arthritis pain. The inventive compounds also may be used to treat veterinary viral infections, such as lentivirus infections, including, but not limited to equine infectious anemia virus; or retrovirus infections, including feline immunodeficiency virus, bovine immunodeficiency virus, and canine immunodeficiency virus.

The present invention thus provides methods for treating such conditions, comprising administering to a subject in need thereof a therapeutically-effective amount of at least one compound of Formula (I) or a salt thereof. "Therapeutically effective amount" is intended to include an amount of a compound of the present invention that is effective when administered alone or in combination to inhibit autoimmune disease or chronic inflammatory disease.

The methods of treating TLR7, TLR8, or TLR9 associated conditions may comprise administering compounds of Formula (I) alone or in combination with each other and/or other suitable therapeutic agents useful in treating such conditions. Accordingly, "therapeutically effective amount" is also intended to include an amount of the combination of compounds claimed that is effective to inhibit TLR7. TLR8, or TLR9 and/or treat diseases associated with TLR7, TLR8, or TLR9.

Exemplary of such other therapeutic agents include corticosteroids, rolipram, calphostin, cytokine-suppressive anti-inflammatory drugs (CSAIDs), Interleukin-10, glucocorticoids, salicylates, nitric oxide, and other immunosuppressants; nuclear translocation inhibitors, such as deoxyspergualin (DSG); non-steroidal anti-inflammatory drugs (NSAIDs) such as ibuprofen, celecoxib and rofecoxib; steroids such as prednisone or dexamethasone; antiviral agents such as abacavir; antiproliferative agents such as methotrexate, leflunomide, FK506 (tacrolimus, PROGRAF®); anti-malarials such as hydroxychloroquine; cytotoxic drugs such as azathiprine and cyclophosphamide; TNF-α inhibitors such as tenidap, anti-TNF antibodies or soluble TNF receptor, and rapamycin (sirolimus or RAPAMUNE®) or derivatives thereof.

The above other therapeutic agents, when employed in combination with the compounds of the present invention, may be used, for example, in those amounts indicated in the *Physicians' Desk Reference* (PDR) or as otherwise determined by one of ordinary skill in the art. In the methods of the present invention, such other therapeutic agent(s) may be administered prior to, simultaneously with, or following the administration of the inventive compounds. The present invention also provides pharmaceutical compositions capable of treating TLR7/8/9 receptor-associated conditions, including IL-1 family receptor-mediated diseases as described above.

The inventive compositions may contain other therapeutic agents as described above and may be formulated, for example, by employing conventional solid or liquid vehicles or diluents, as well as pharmaceutical additives of a type appropriate to the mode of desired administration (e.g., excipients, binders, preservatives, stabilizers, flavors, etc.) according to techniques such as those well known in the art of pharmaceutical formulation.

Accordingly, the present invention further includes compositions comprising one or more compounds of Formula (I) and a pharmaceutically acceptable carrier.

A "pharmaceutically acceptable carrier" refers to media generally accepted in the art for the delivery of biologically active agents to animals, in particular, mammals. Pharmaceutically acceptable carriers are formulated according to a number of factors well within the purview of those of ordinary skill in the art. These include without limitation the type and nature of the active agent being formulated; the subject to which the agent-containing composition is to be administered; the intended route of administration of the composition; and, the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, *Remington's Pharmaceutical Sciences*, 17th Edition (1985), which is incorporated herein by reference in its entirety.

Compounds in accordance with Formula (I) can be administered by any means suitable for the condition to be treated, which can depend on the need for site-specific treatment or quantity of Formula (I) compound to be delivered.

Also embraced within this invention is a class of pharmaceutical compositions comprising a compound of Formula (I) and one or more non-toxic, pharmaceutically-acceptable carriers and/or diluents and/or adjuvants (collectively referred to herein as 'carrier' materials) and, if desired, other active ingredients. The compounds of Formula (I) may be administered by any suitable route, preferably in the form of a pharmaceutical composition adapted to such a route, and in a dose effective for the treatment intended. The compounds and compositions of the present invention may, for example, be administered orally, mucosally, or parenterally including intravascularly, intravenously, intraperitoneally, subcutaneously, intramuscularly, and intrasternally in dosage unit formulations containing conventional pharmaceutically acceptable carriers, adjuvants, and vehicles. For example, the pharmaceutical carrier may contain a mixture of mannitol or lactose and microcrystalline cellulose. The mixture may contain additional components such as a lubricating agent, e.g. magnesium stearate and a disintegrating agent such as crospovidone. The carrier mixture may be filled into a gelatin capsule or compressed as a tablet. The pharmaceutical composition may be administered as an oral dosage form or an infusion, for example.

For oral administration, the pharmaceutical composition may be in the form of for example, a tablet, capsule, liquid capsule, suspension, or liquid. The pharmaceutical composition is preferably made in the form of a dosage unit containing a particular amount of the active ingredient. For example, the pharmaceutical composition may be provided as a tablet or capsule comprising an amount of active ingredient in the range of from about 0.1 to 1000 mg, preferably from about 0.25 to 250 mg, and more preferably from about 0.5 to 100 mg. A suitable daily dose for a human or other mammal may vary widely depending on the condition of the patient and other factors, but, can be determined using routine methods.

Any pharmaceutical composition contemplated herein can, for example, be delivered orally via any acceptable and suitable oral preparations. Exemplary oral preparations, include, but are not limited to, for example, tablets, troches, lozenges, aqueous and oily suspensions, dispersible powders or granules, emulsions, hard and soft capsules, liquid capsules, syrups, and elixirs. Pharmaceutical compositions intended for oral administration can be prepared according to any methods known in the art for manufacturing pharmaceutical compositions intended for oral administration. In order to provide pharmaceutically palatable preparations, a pharmaceutical composition in accordance with the invention can contain at least one agent selected from sweetening agents, flavoring agents, coloring agents, demulcents, antioxidants, and preserving agents.

A tablet can, for example, be prepared by admixing at least one compound of Formula (I) with at least one non-toxic pharmaceutically acceptable excipient suitable for the manufacture of tablets. Exemplary excipients include, but are not limited to, for example, inert diluents, such as, for example, calcium carbonate, sodium carbonate, lactose, calcium phosphate, and sodium phosphate; granulating and disintegrating agents, such as, for example, microcrystalline cellulose, sodium crosscarmellose, corn starch, and alginic acid, binding agents, such as, for example, starch, gelatin, polyvinyl-pyrrolidone, and acacia; and lubricating agents, such as, for example, magnesium stearate, stearic acid, and talc. Additionally, a tablet can either be uncoated, or coated by known techniques to either mask the bad taste of an unpleasant tasting drug, or delay disintegration and absorption of the active ingredient in the gastrointestinal tract thereby sustaining the effects of the active ingredient for a longer period. Exemplary water soluble taste masking materials, include, but are not limited to, hydroxypropyl-methylcellulose and hydroxypropyl-cellulose. Exemplary time delay materials, include, but are not limited to, ethyl cellulose and cellulose acetate butyrate.

Hard gelatin capsules can, for example, be prepared by mixing at least one compound of Formula (I) with at least one inert solid diluent, such as, for example, calcium carbonate; calcium phosphate; and kaolin.

Soft gelatin capsules can, for example, be prepared by mixing at least one compound of Formula (I) with at least one water soluble carrier, such as, for example, polyethylene glycol; and at least one oil medium, such as, for example, peanut oil, liquid paraffin, and olive oil.

An aqueous suspension can be prepared, for example, by admixing at least one compound of Formula (I) with at least one excipient suitable for the manufacture of an aqueous suspension. Exemplary excipients suitable for the manufacture of an aqueous suspension, include, but are not limited to, for example, suspending agents, such as, for example, sodium carboxymethylcellulose, methylcellulose, hydroxypropylmethyl-cellulose, sodium alginate, alginic acid, polyvinyl-pyrrolidone, gum tragacanth, and gum acacia; dispersing or wetting agents, such as, for example, a naturally-occurring phosphatide, e.g., lecithin; condensation products of alkylene oxide with fatty acids, such as, for example, polyoxyethylene stearate; condensation products of ethylene oxide with long chain aliphatic alcohols, such as, for example heptadecaethyleneoxycetanol; condensation products of ethylene oxide with partial esters derived from fatty acids and hexitol, such as, for example, polyoxyethylene sorbitol monooleate; and condensation products of ethylene oxide with partial esters derived from fatty acids and hexitol anhydrides, such as, for example, polyethylene sorbitan monooleate. An aqueous suspension can also contain at least one preservative, such as, for example, ethyl and n-propyl p-hydroxybenzoate; at least one coloring agent; at least one flavoring agent; and/or at least one sweetening agent, including but not limited to, for example, sucrose, saccharin, and aspartame.

Oily suspensions can, for example, be prepared by suspending at least one compound of Formula (I) in either a vegetable oil, such as, for example, *arachis* oil; olive oil; sesame oil; and coconut oil; or in mineral oil, such as, for example, liquid paraffin. An oily suspension can also contain at least one thickening agent, such as, for example, beeswax; hard paraffin; and cetyl alcohol. In order to provide a palatable oily suspension, at least one of the sweetening agents already described hereinabove, and/or at least one flavoring agent can be added to the oily suspension. An oily suspension can further contain at least one preservative, including, but not limited to, for example, an anti-oxidant, such as, for example, butylated hydroxyanisol, and alpha-tocopherol.

Dispersible powders and granules can, for example, be prepared by admixing at least one compound of Formula (I) with at least one dispersing and/or wetting agent; at least one suspending agent; and/or at least one preservative. Suitable dispersing agents, wetting agents, and suspending agents are as already described above. Exemplary preservatives include, but are not limited to, for example, anti-oxidants, e.g., ascorbic acid. In addition, dispersible powders and granules can also contain at least one excipient, including, but not limited to, for example, sweetening agents; flavoring agents; and coloring agents.

An emulsion of at least one compound of Formula (I) thereof can, for example, be prepared as an oil-in-water emulsion. The oily phase of the emulsions comprising compounds of Formula (I) may be constituted from known ingredients in a known manner. The oil phase can be provided by, but is not limited to, for example, a vegetable oil, such as, for example, olive oil and *arachis* oil; a mineral oil, such as, for example, liquid paraffin; and mixtures thereof. While the phase may comprise merely an emulsifier, it may comprise a mixture of at least one emulsifier with a fat or an oil or with both a fat and an oil. Suitable emulsifying agents include, but are not limited to, for example, naturally-occurring phosphatides, e.g., soy bean lecithin; esters or partial esters derived from fatty acids and hexitol anhydrides, such as, for example, sorbitan monooleate; and condensation products of partial esters with ethylene oxide, such as, for example, polyoxyethylene sorbitan monooleate. Preferably, a hydrophilic emulsifier is included together with a lipophilic emulsifier which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base which forms the oily dispersed phase of the cream formulations. An emulsion can also contain a sweetening agent, a flavoring agent, a preservative, and/or an antioxidant. Emulsifiers and emulsion stabilizers suitable for use in the formulation of the present invention include Tween 60, Span 80, cetostearyl alcohol, myristyl alcohol, glyceryl monostearate, sodium lauryl sulfate, glyceryl distearate alone or with a wax, or other materials well known in the art.

The compounds of Formula (I) can, for example, also be delivered intravenously, subcutaneously, and/or intramuscularly via any pharmaceutically acceptable and suitable injectable form. Exemplary injectable forms include, but are not limited to, for example, sterile aqueous solutions comprising acceptable vehicles and solvents, such as, for example, water, Ringer's solution, and isotonic sodium chloride solution; sterile oil-in-water microemulsions; and aqueous or oleaginous suspensions.

Formulations for parenteral administration may be in the form of aqueous or non-aqueous isotonic sterile injection solutions or suspensions. These solutions and suspensions may be prepared from sterile powders or granules using one or more of the carriers or diluents mentioned for use in the formulations for oral administration or by using other suitable dispersing or wetting agents and suspending agents. The compounds may be dissolved in water, polyethylene glycol, propylene glycol, ethanol, corn oil, cottonseed oil, peanut oil, sesame oil, benzyl alcohol, sodium chloride solution, tragacanth gum, and/or various buffers. Other adjuvants and modes of administration are well and widely known in the pharmaceutical art. The active ingredient may also be administered by injection as a composition with suitable carriers including saline, dextrose, or water, or with cyclodextrin (i.e. Captisol), cosolvent solubilization (i.e. propylene glycol) or micellar solubilization (i.e. Tween 80).

The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

A sterile injectable oil-in-water microemulsion can, for example, be prepared by 1) dissolving at least one compound of Formula (I) in an oily phase, such as, for example, a mixture of soybean oil and lecithin; 2) combining the Formula (I) containing oil phase with a water and glycerol mixture; and 3) processing the combination to form a microemulsion.

A sterile aqueous or oleaginous suspension can be prepared in accordance with methods already known in the art. For example, a sterile aqueous solution or suspension can be prepared with a non-toxic parenterally-acceptable diluent or solvent, such as, for example, 1,3-butane diol; and a sterile oleaginous suspension can be prepared with a sterile nontoxic acceptable solvent or suspending medium, such as, for example, sterile fixed oils, e.g., synthetic mono- or diglycerides; and fatty acids, such as, for example, oleic acid.

Pharmaceutically acceptable carriers, adjuvants, and vehicles that may be used in the pharmaceutical compositions of this invention include, but are not limited to, ion exchangers, alumina, aluminum stearate, lecithin, self-emulsifying drug delivery systems (SEDDS) such as d-alpha-tocopherol polyethyleneglycol 1000 succinate, surfactants used in pharmaceutical dosage forms such as Tweens, polyethoxylated castor oil such as CREMOPHOR surfactant (BASF), or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as alpha-, beta-, and gamma-cyclodextrin, or chemically modified derivatives such as hydroxyalkylcyclodextrins, including 2- and 3-hydroxypropyl-cyclodextrins, or other solubilized derivatives may also be advantageously used to enhance delivery of compounds of the formulae described herein.

The pharmaceutically active compounds of this invention can be processed in accordance with conventional methods of pharmacy to produce medicinal agents for administration to patients, including humans and other mammals. The pharmaceutical compositions may be subjected to conventional pharmaceutical operations such as sterilization and/or may contain conventional adjuvants, such as preservatives, stabilizers, wetting agents, emulsifiers, buffers etc. Tablets and pills can additionally be prepared with enteric coatings. Such compositions may also comprise adjuvants, such as wetting, sweetening, flavoring, and perfuming agents.

The amounts of compounds that are administered and the dosage regimen for treating a disease condition with the compounds and/or compositions of this invention depends on a variety of factors, including the age, weight, sex, the medical condition of the subject, the type of disease, the severity of the disease, the route and frequency of administration, and the particular compound employed. Thus, the dosage regimen may vary widely, but can be determined routinely using standard methods. A daily dose of about 0.001 to 100 mg/kg body weight, preferably between about 0.0025 and about 50 mg/kg body weight and most preferably between about 0.005 to 10 mg/kg body weight, may be appropriate. The daily dose can be administered in one to four doses per day. Other dosing schedules include one dose per week and one dose per two day cycle.

For therapeutic purposes, the active compounds of this invention are ordinarily combined with one or more adjuvants appropriate to the indicated route of administration. If administered orally, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose.

Pharmaceutical compositions of this invention comprise at least one compound of Formula (I) and optionally an additional agent selected from any pharmaceutically acceptable carrier, adjuvant, and vehicle. Alternate compositions of this invention comprise a compound of the Formula (I) described herein, or a prodrug thereof, and a pharmaceutically acceptable carrier, adjuvant, or vehicle.

The present invention also encompasses an article of manufacture. As used herein, article of manufacture is intended to include, but not be limited to, kits and packages. The article of manufacture of the present invention, comprises: (a) a first container; (b) a pharmaceutical composition located within the first container, wherein the composition, comprises: a first therapeutic agent, comprising: a compound of the present invention or a pharmaceutically acceptable salt form thereof; and (c) a package insert stating that the pharmaceutical composition can be used for the treatment of a inflammatory disorder and/or an autoimmune disease (as defined previously). In another embodiment, the package insert states that the pharmaceutical composition can be used in combination (as defined previously) with a second therapeutic agent to treat an inflammatory disorder and/or an autoimmune disease. The article of manufacture can further comprise: (d) a second container, wherein components (a) and (b) are located within the second container and component (c) is located within or outside of the second container. Located within the first and second containers means that the respective container holds the item within its boundaries.

The first container is a receptacle used to hold a pharmaceutical composition. This container can be for manufacturing, storing, shipping, and/or individual/bulk selling. First container is intended to cover a bottle, jar, vial, flask, syringe, tube (e.g., for a cream preparation), or any other container used to manufacture, hold, store, or distribute a pharmaceutical product.

The second container is one used to hold the first container and, optionally, the package insert. Examples of the second container include, but are not limited to, boxes (e.g., cardboard or plastic), crates, cartons, bags (e.g., paper or plastic bags), pouches, and sacks. The package insert can be physically attached to the outside of the first container via tape, glue, staple, or another method of attachment, or it can rest inside the second container without any physical means of attachment to the first container. Alternatively, the package insert is located on the outside of the second container. When located on the outside of the second container, it is preferable that the package insert is physically attached via tape, glue, staple, or another method of attachment. Alternatively, it can be adjacent to or touching the outside of the second container without being physically attached.

The package insert is a label, tag, marker, etc. that recites information relating to the pharmaceutical composition located within the first container. The information recited will usually be determined by the regulatory agency governing the area in which the article of manufacture is to be sold (e.g., the United States Food and Drug Administration). In one embodiment, the package insert specifically recites the indications for which the pharmaceutical composition has been approved. The package insert may be made of any material on which a person can read information contained therein or thereon. For example, the package insert is a printable material (e.g., paper, plastic, cardboard, foil, adhesive-backed paper or plastic, etc.) on which the desired information has been formed (e.g., printed or applied).

Methods of Preparation

The compounds of the present invention can be prepared in a number of ways well known to one skilled in the art of organic synthesis. The compounds of the present invention can be synthesized using the methods described below, together with synthetic methods known in the art of synthetic organic chemistry, or variations thereon as appreciated by those skilled in the art. Preferred methods include, but are not limited to, those described below. All references cited herein are hereby incorporated in their entirety by reference.

The compounds of this invention may be prepared using the reactions and techniques described in this section. The reactions are performed in solvents appropriate to the reagents and materials employed and are suitable for the transformations being effected. Also, in the description of the synthetic methods described below, it is to be understood that all proposed reaction conditions, including choice of solvent, reaction atmosphere, reaction temperature, duration of the experiment and work up procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents that are compatible with the reaction conditions will be readily apparent to one skilled in the art and alternate methods must then be used. This will sometimes require a judgment to modify the order of the synthetic steps or to select one particular process scheme over another in order to obtain a desired compound of the invention. It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene and Wuts (*Protective Groups In Organic Synthesis*, Third Edition, Wiley and Sons, 1999).

Compounds of Formula (I) may be prepared by reference to the methods illustrated in the following Schemes. As shown therein the end product is a compound having the same structural formula as Formula (I). It will be understood that any compound of Formula (I) may be produced by the schemes by the suitable selection of reagents with appropriate substitution. Solvents, temperatures, pressures, and other reaction conditions may readily be selected by one of ordinary skill in the art. Starting materials are commercially available or readily prepared by one of ordinary skill in the art. Constituents of compounds are as defined herein or elsewhere in the specification.

EXAMPLES

Preparation of compounds of Formula (I), and intermediates used in the preparation of compounds of Formula (I), can be prepared using procedures shown in the following Examples and related procedures. The methods and conditions used in these examples, and the actual compounds prepared in these Examples, are not meant to be limiting, but are meant to demonstrate how the compounds of Formula (I) can be prepared. Starting materials and reagents used in these examples, when not prepared by a procedure described herein, are generally either commercially available, or are reported in the chemical literature, or may be prepared by using procedures described in the chemical literature.

Abbreviations

Ac acetyl
ACN acetonitrile
anhyd. anhydrous
aq. aqueous
Bn benzyl
Boc-anhydride di-tert-butyl dicarbonate
Bu butyl
Boc tert-butoxycarbonyl
CV Column Volumes
DCE dichloroethane
DCM dichloromethane
DMAP dimethylaminopyridine
DMF dimethylformamide DMSO dimethylsulfoxide
EtOAc ethyl acetate
Et ethyl
Et$_3$N triethylamine
H or H$_2$ hydrogen
h, hr or hrs hour(s)
hex hexane
i iso
HCl hydrochloric acid
HPLC high pressure liquid chromatography
LC liquid chromatography
LCMS liquid chromatography-mass spectrometry
LiAlH$_4$ lithium aluminum hydride
M molar
mM millimolar
Me methyl
MeOH methanol
MHz megahertz
min. minute(s)
mins minute(s)
M$^{+1}$ (M+H)$^+$
MS mass spectrometry
n or N normal
NBS n-bromosuccinimide
NCS n-chlorosuccinimide
nm nanometer
nM nanomolar
NMP N-methylpyrrolidinone
Pd/C palladium on carbon
PdCl$_2$(dppf) [1,1'-bis(diphenylphosphino)ferrocene]dichloropalladium(II)
Ph phenyl
Pr propyl
PSI pounds per square inch
Ret Time retention time
sat. saturated
SFC supercritical fluid chromatography
TEA triethylamine
TFA trifluoroacetic acid
THF tetrahydrofuran
Tr Trityl: Triphenylmethyl
Ts Tosyl: p-toluenesulfonyl
XPhos Precatalyst G2 chloro(2-dicyclohexylphosphino-2',4',6'-triisopropyl-1,1'-biphenyl)[2-(2'-amino-1,1'-biphenyl)]palladium(II)

Analytical and Preparative HPLC Conditions:

QC-ACN-AA-XB: Column: Waters Acquity UPLC BEH C18, 2.1×50 mm, 1.7 μm particles; Mobile Phase A: 5:95 acetonitrile:water with 10 mM ammonium acetate; Mobile Phase B: 95:5 acetonitrile:water with 10 mM ammonium acetate, Temperature: 50° C.; Gradient: 0-100% B over 3 minutes, then a 0.75-minute hold at 100% B; Flow: 1.0 mL/min; Detection: UV at 220 nm.

QC-ACN-TFA-XB: Column: Waters Acquity UPLC BEH C18, 2.1×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.0 mL/min; Detection: UV at 220 nm.

Method A1: L3 Acquity: Column: (LCMS) UPLC BEH C18, 2.1×50 mm, 1.7 μm particles; Mobile Phase: (A) water; (B) acetonitrile; Buffer: 0.05% TFA: Gradient Range: 2%-98% B (0 to 1 min) 98% B (to 1.5 min) 98%-2% B (to 1.6 min); Gradient Time: 1.6 min; Flow Rate: 0.8 mL/min; Analysis Time: 2.2 min; Detector 1: UV at 220 nm; Detector 2: MS (ESI$^+$).

Method B1: L2 Aquity; Column: (LCMS) UPLC BEH C18, 2.1×50 mm, 1.7 μm particles; Mobile Phase: (A) water; (B) acetonitrile; Buffer: 0.05% TFA; Gradient Range: 2%-98% B (0 to 1 min), 98%-2% B (to 1.5 min); Gradient Time: 1.8 min; Flow Rate: 0.8 mL/min; Analysis Time: 2.2 min; Detection: Detector 1: UV at 220 nm: Detector 2: MS (ESI$^+$).

Method C1 SCP: Column: Waters Acquity UPLC BEH C18, 2.1×50 mm, 1.7 μm particles; Mobile Phase A: 5:95 acetonitrile:water with 10 mM ammonium acetate; Mobile Phase B: 95:5 acetonitrile:water with 10 mM ammonium acetate. Temperature: 50° C.; Gradient: 0-100% B over 3 minutes, then a 0.75 minute hold at 100% B; Flow: 1.11 mL/min; Detection: UV at 220 nm.

Method D1 SCP: Column: Waters Acquity UPLC BEH C18, 2.1×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.11 mL/min; Detection: UV at 220 nm.

Method D2 SCP: Column: XBridge C18, 19×200 mm, 5 μm particles; Mobile Phase A: 5:95 acetonitrile:water with 10-mM ammonium acetate: Mobile Phase B: 95:5 acetonitrile:water with 10-mM ammonium acetate; Gradient: 10-50% B over 20 minutes, then a 5-minute hold at 100% B; Flow: 20 mL/min. Detection: UV at 220 nm.

Method D3 SCP: Column: XBridge C18, 19×200 mm, 5 μm particles; Mobile Phase A: 5:95 acetonitrile:water with 0.1% trifluoroacetic acid; Mobile Phase B: 95:5 acetonitrile:water with 0.1% trifluoroacetic acid; Gradient: 6-46% B over 20 minutes, then a 4-minute hold at 100% B; Flow: 20 mL/min. Detection: UV at 220 nm.

Method E1 iPAC: Column: Waters Xbridge C18 4.6×50 mm 5 μm particles; Mobile Phase A: 5:95 acetonitrile:water with 10 mM ammonium acetate; Mobile Phase B: 95:5 acetonitrile:water with 10 mM ammonium acetate. Temperature: 50° C.; Gradient: 0-100% B over 1 minute; Flow: 4 mL/min; Detection: UV at 220 nm.

Method F1 iPAC: Column: Waters Acquity BEH C18 2.1×50 mm 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 2.20 minutes; Flow: 0.800 mL/min; Detection: UV at 220 nm.

(A): Column-Ascentis Express C18 (50×2.1 mm-2.7 μm) Mphase A: 10 mM NH$_4$COOH in water:ACN (98:02); Mphase B: 10 mM NH$_4$COOH in water:ACN (02:98), Gradient: 0-100% B over 3 minutes, Flow=1 mL/min.

(B): Waters Acquity BEH C18 (2.1×50 mm) 1.7 micron; Buffer: 5 mM ammonium acetate pH 5 adjusted with HCOOH, Solvent A: Buffer:ACN (95:5), Solvent B: Buffer: ACN (5:95), Method: % B: 0 min-5%: 1.1 min-95%: 1.7 min-95%, Flow: 0.8 mL/min.

(C): Column-Ascentis Express C18 (50×2.1 mm-2.7 μm) Mobile phase A: 0.1% HCOOH in water; Mobile phase B: ACN. Temperature: 50° C.; Gradient: 0-100% B over 3 minutes; Flow rate: 1.0 mL/min.

(D): Kinetex XB-C18 (75×3 mm) 2.6 micron; Solvent A: 10 mM ammonium formate in water:acetonitrile (98:02); Mobile Phase B: 10 mM ammonium formate in water:

acetonitrile (02:98); Temperature: 50° C.; Gradient: 0-100% B over 3 minutes; Flow rate: 1.1 mL/min; Detection: UV at 220 nm.

(E): Column: Ascentis Express C18 (50×2.1) mm, 2.7 µm; Mobile Phase A: 5:95 acetonitrile:water with 10 mM NH₄OAc; Mobile Phase B: 95:5 acetonitrile:water with 10 mM NH₄OAc; Temperature: 50° C.; Gradient: 0-100% B over 3 minutes; Flow: 1.1 mL/min.

(F): Column: Ascentis Express C18 (50×2.1) mm, 2.7 µm; Mobile Phase A: 5:95 acetonitrile:water with 0.1% TFA; Mobile Phase B: 95:5 acetonitrile:water with 0.1% TFA; Temperature: 50° C.; Gradient: 0-100% B over 3 minutes; Flow: 1.1 mL/min.

(G): Column: Waters Acquity UPLC BEH C18 (2.1×50 mm), 1.7 micron; Solvent A=100% water with 0.05% TFA; Solvent B=100% acetonitrile with 0.05% TFA; gradient=2-98% B over 1 minute, then a 0.5-minute hold at 98% B; Flow rate: 0.8 mL/min; Detection: UV at 220 nm.

(H): Column: Acentis Express C18 (50×2.1 mm) 1.7 µm Acentis C8 NH₄COOH 5 min. M, Mobile Phase A: ~10 mM ammonium formate: ACN (98:2), Mobile Phase B: ~10 mM ammonium formate: ACN (2:98), gradient: 20%-100% B (0-4 min); 100% B (4-4.6 min); Flow: 1 mL/min (I) Column: Sunfire C18 (4.6×150) mm, 3.5 µm; Mobile Phase A: 5:95 acetonitrile:water with 0.05% TFA; Mobile Phase B: 95:5 acetonitrile:water with 0.05% TFA; Temperature: 50° C.; Gradient: 10-100% B over 12 minutes; Flow: 1 mL/min.

(J) Column: Sunfire C18 (4.6×150) mm, 3.5 µm; Mobile Phase A: 5:95 acetonitrile:water with 0.05% TFA; Mobile Phase B: 95:5 acetonitrile:water with 0.05% TFA;

(K) Waters Acquity SDS Mobile Phase: A: water B: ACN; 5%-95% B in 1 min; Gradient Range: 50%-98% B (0-0.5 min); 98% B (0.5 min-1 min); 98%-2% B (1-1.1 min); Run time: 1.2 min; Flow Rate: 0.7 mL/min; Analysis Time: 1.7 min; Detection: Detector 1: UV at 220 nm; Detector 2: MS (ES⁺).

(L) Acquity UPLC BEH C18 (3.0×50 mm) 1.7 µm. Buffer: 5 mM ammonium acetate; Mobile phase A: Buffer: ACN (95:5); Mobile phase B: Buffer:ACN (5:95) Method: % B: 0 min-20%:1.1 min-90%:1.7 min-90%. Run time: 2.25 min; Flow Rate: 0.7 mL/min; Detection: Detector 1: UV at 220 nm; Detector 2: MS (ES⁺).

(M): Kinetex SBC18 (4.6×50 mm) 5 micron; Solvent A: 10 mM ammonium formate in water:acetonitrile (98:02); Mobile Phase B: 10 mM ammonium formate in water: acetonitrile (02:98); Temperature: 50° C.; Gradient: 30-100% B (0-4 min), 100% B (44.6 min), 100-30% B (4.6-4.7 min), 30% B (4.7-5.0 min); Flow rate: 1.5 mL/min; Detection: UV at 220 nm.

(N): Column-Ascentis Express C18 (50×2.1 mm-2.7 µm) Mphase A: 10 mM NH₄COOH in water:ACN (98:02); Mphase B: 10 mM NH₄COOH in water:ACN (02:98), Gradient: 0-100% B (0-1.7 minutes); 100% B (1.7-3.4 minutes). Flow=1 mL/min.

(O) Waters Acquity SDS Column BEH C18 (2.1×50 mm) 1.7 µm. Phase A: buffer in water; Mphase B: buffer in ACN, Gradient: 20-98% B (0-1.25 minutes); 98% B (1.25-1.70 minutes); 98%-2% B (1.70-1.75 minutes); Flow=0.8 mL/min.

Example 1

2-(3,4-dimethoxyphenyl)-5-{octahydropyrrolo[3,4-c]pyrrole-2-carbonyl}-3-(propan-2-yl)-1H-indole

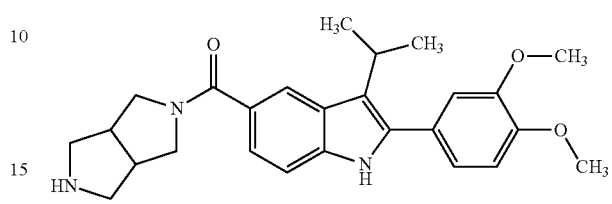

(1)

Intermediate 1A: Methyl 3-isopropyl-1H-indole-5-carboxylate

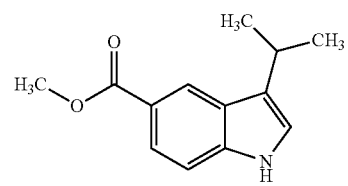

(1A)

To a solution of 5-bromo-3-isopropyl-1H-indole (4.00 g, 16.80 mmol) in MeOH (80.00 mL) and DMF (80.00 mL) were added palladium(II) acetate (0.754 g, 1.119 mmol) and DPPF (2.79 g, 5.04 mmol). The mixture was degassed with nitrogen for 5 min. and TEA (7.02 mL, 50.4 mmol) was added. The reaction mixture was stirred in an autoclave at 100° C. with 5 kg pressure in presence of CO gas for 16 h. Crude LCMS showed formation of product and no starting material. The reaction mass was concentrated and the residue was dissolved in EtOAc (50 mL). The solid was filtered and washed with EtOAc (2×30 mL), the combined filtrates was collected and concentrated to get crude compound. The crude material was purified by column chromatography using 120 g silica column. The compound was eluted in 35% ethyl acetate in hexanes, the fractions were collected and concentrated to afford methyl 3-isopropyl-1H-indole-5-carboxylate (3.42 g, 15.74 mmol, 94% yield) as an oil. LCMS retention time 0.96 min [G]. MS m/z: 218.6 [M+H]⁺.

Intermediate 1B: Methyl 2-bromo-3-isopropyl-1H-indole-5-carboxylate

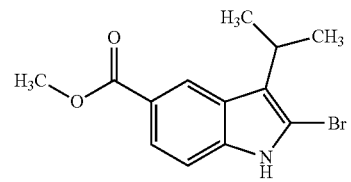

(1B)

To a solution of methyl 3-isopropyl-1H-indole-5-carboxylate (0.790 g, 2.69 mmol) in DCE (20 mL) was added NBS (0.479 g, 2.69 mmol) at room temperature. The mixture was stirred at the same temperature for 10 min. Crude LCMS showed formation of product and no starting material. The reaction was quenched with the addition of water (5 mL). The reaction mixture was extracted with DCM (2×20 mL), combined organic extracts were washed with brine (5 mL), dried (Na₂SO₄) and concentrated to get crude compound. The crude material was purified by column chromatography using 24 g silica column, the compound was eluted in 15% EtOAc in hexanes, the fractions were collected and concentrated to afford methyl 2-bromo-3-isopropyl-1H-indole-5-carboxylate (0.582 g, 1.965 mmol, 73.0% yield) as pale brown solid. LCMS retention time 1.05 min [G]. MS m/z: 298 [M+2)+H]⁺.

Intermediate 1C: Methyl-2-(3,4-dimethoxyphenyl)-3-isopropyl-1H-indole-5-carboxylate

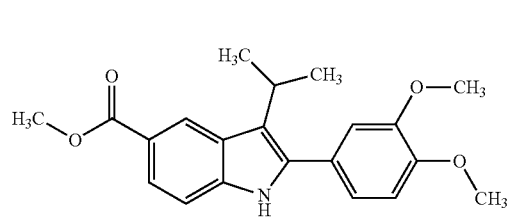

(1C)

A solution of methyl 2-bromo-3-isopropyl-1H-indole-5-carboxylate (0.570 g, 1.925 mmol), (3,4-dimethoxyphenyl) boronic acid (0.736 g, 4.04 mmol) and cesium carbonate (1.881 g, 5.77 mmol) in dioxane (12.00 mL) and water (3.00 mL) was degassed for 30 min. Next, Pd(Ph₃P)₄ (0.222 g, 0.192 mmol) was added and the reaction mixture was stirred at 90° C. for 4 h. Crude LCMS showed formation of product and no starting material. The reaction was quenched with the addition of water (5 mL). The reaction mixture was extracted with EtOAc (2×30 mL), combined organic extracts were washed with brine (10 mL), dried (Na₂SO₄), and concentrated to get crude compound. The crude material was purified by column chromatography, using 24 g silica column, the compound was eluted in 15% EtOAc in hexane, the fractions were collected and concentrated to afford methyl 2-(3,4-dimethoxyphenyl)-3-isopropyl-1H-indole-5-carboxylate (0.520 g, 1.471 mmol, 76% yield) as pale orange solid. LCMS retention time 1.13 min [G]. MS m/z: 354 [M+H]⁺.

Intermediate 1D: 2-(3,4-dimethoxyphenyl)-3-isopropyl-1H-indole-5-carboxylic Acid

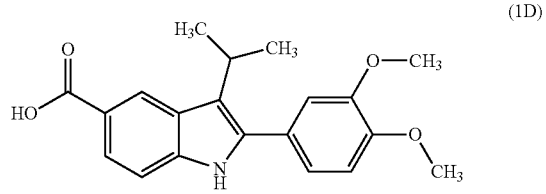 [SMILES: COc1ccc(-c2[nH]c3ccc(C(=O)O)cc3c2C(C)C)cc1OC]

(1D)

To a solution of methyl 2-(3,4-dimethoxyphenyl)-3-isopropyl-1H-indole-5-carboxylate (0.325 g, 0.920 mmol) in THF (8.00 mL), MeOH (4.00 mL) and water (2.000 mL) solvent mixture was added lithium hydroxide (0.110 g, 4.60 mmol) at room temperature. The reaction mixture was stirred at the same temperature for 4 h. Crude LCMS showed starting material remained. The reaction mixture was stirred at 75° C. for 16 h. Crude LCMS showed formation of product and no starting material. The reaction mixture was concentrated and the residue/solid was added to water (20 mL), washed with EtOAc (1×20 mL), then the aqueous slurry was brought to acid pH with 1.5 N HCl, the solids were filtered, washed with water and dried under vacuum to afford 2-(3,4-dimethoxyphenyl)-3-isopropyl-1H-indole-5-carboxylic acid (0.210 g, 0.619 mmol, 67% yield) as a white solid. LCMS retention time 0.97 min [G]. MS m/z: 340.1 [M+H]⁺.

Intermediate 1E: tert-butyl 5-(2-(3,4-dimethoxyphenyl)-3-isopropyl-1H-indole-5-carbonyl)hexahydro pyrrolo[3,4-c]pyrrole-2(1H)-carboxylate

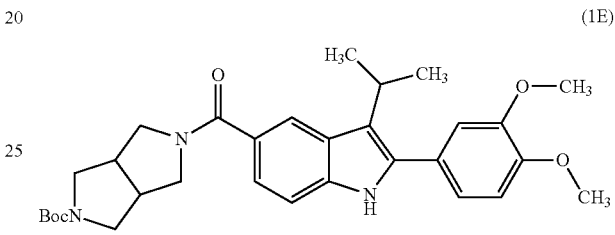

(1E)

To a solution of 2-(3,4-dimethoxyphenyl)-3-isopropyl-1H-indole-5-carboxylic acid (0.095 g, 0.280 mmol) in DCM (2.00 mL) and DMF (2.00 mL) were added tert-butyl hexahydropyrrolo[3,4-c]pyrrole-2(1H)-carboxylate (0.059 g, 0.280 mmol) and EDC (0.080 g, 0.420 mmol) at room temperature. The mixture was stirred at the same temperature for 2 h. Crude LCMS showed formation of product. The reaction was quenched with the addition of water (5 mL). The reaction mixture was extracted with 10% MeOH in CH₂Cl₂ (2×10 mL), combined organic extracts was washed with water (10 mL), brine (5 mL), dried (Na₂SO₄) and concentrated to get crude compound. The crude material was purified by column chromatography using 12 g silica column, compound was eluted in neat ethyl acetate, the fractions were collected and concentrated to afford tert-butyl 5-(2-(3,4-dimethoxyphenyl)-3-isopropyl-1H-indole-5-carbonyl)hexahydro pyrrolo[3,4-c]pyrrole-2(1H)-carboxylate (0.101 g, 0.189 mmol, 67% yield) as off white solid. LCMS retention time 1.12 min [G]. MS m/z: 534 [M+H]⁺.

Example 1

To a solution of tert-butyl 5-(2-(3,4-dimethoxyphenyl)-3-isopropyl-1H-indole-5-carbonyl)hexahydropyrrolo[3,4-c]pyrrole-2(1H)-carboxylate (0.190 g, 0.356 mmol) in dioxane (1 mL) was added 4 N HCl in dioxane (0.50 mL, 2.0 mmol) at 0° C. The reaction mixture was stirred at the same temperature for 2 h. The reaction mixture was concentrated, the residue was triturated with diethyl ether (2×5 mL) to afford (2-(3,4-dimethoxyphenyl)-3-isopropyl-1H-indol-5-yl)(hexahydropyrrolo[3,4-c]pyrrol-2(1H)-yl) methanone hydrochloride (0.161 g, 0.343 mmol, 96% yield) as a pale yellow solid. LCMS retention time 0.82 min [G]. MS m/z: 434.2 [M+H]⁺; ¹H NMR (400 MHz, DMSO-d₆) δ ppm 11.24 (s, 1H), 9.22 (bs, 2H), 7.88 (s, 1H), 7.32 (dd, J=8.4, 1.2 Hz, 1H), 7.26 (dd. J=8.4, 1.2 Hz, 1H), 7.15-7.03 (m, 3H), 3.83 (s, 3H), 3.81 (s, 3H), 3.78-3.72 (m, 3H), 3.65-3.51 (m, 2H), 3.48-3.27 (m, 3H), 3.14-2.98 (m, 3H), 1.45-1.42 (m, 6H).

The examples in Table 1 were prepared according to the general procedure described for Example 1.

TABLE 1

| Ex. No. | Structure | Mol Wt. | LCMS MH+ | Ret Time (min) | HPLC Method |
|---|---|---|---|---|---|
| 2 | 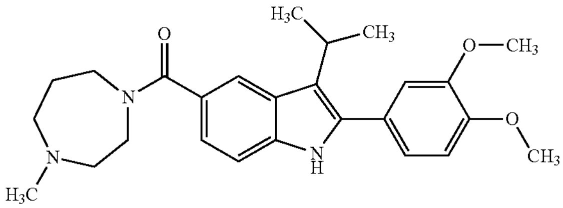 | 435.57 | 436 | 1.398 | E |
| 3 | 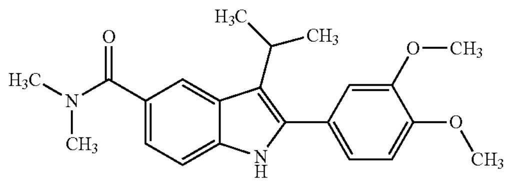 | 366.46 | 367 | 1.633 | F |
| 4 | 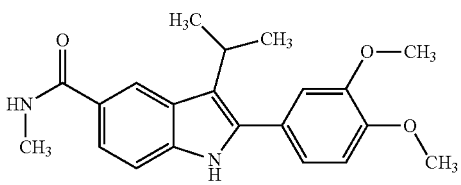 [SMILES: CNC(=O)c1ccc2[nH]c(-c3ccc(OC)c(OC)c3)c(C(C)C)c2c1] | 352.43 | 353 | 1.478 | F |
| 5 | 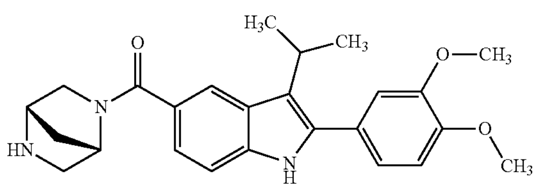 [SMILES: COc1ccc(-c2[nH]c3ccc(C(=O)N4C[C@@H]5C[C@H]4CN5)cc3c2C(C)C)cc1OC] | 419.53 | 420 | 1.26 | E |

Example

2-{5-[2-(3,4-dimethoxyphenyl)-3-(propan-2-yl)-1H-indol-5-carbonyl]-octahydropyrrolo [3,4-c]pyrrol-2-yl}-N,N-dimethylacetamide (6)

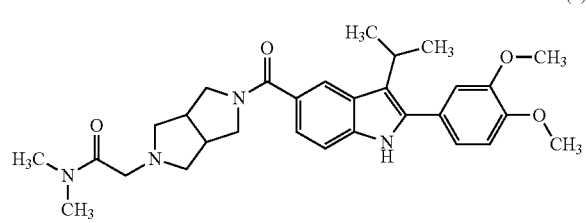

To a solution of (2-(3,4-dimethoxyphenyl)-3-isopropyl-1H-indol-5-yl) (hexahydropyrrolo[3,4-c]pyrrol-2(1H)-yl) methanone hydrochloride (0.040 g, 0.085 mmol) in THF (2.00 mL) and DMF (1.00 mL) were added TEA (0.036 mL, 0.255 mmol) and 2-chloro-N,N-dimethylacetamide (0.016 g, 0.128 mmol) at room temperature. The reaction mixture was stirred at the same temperature for 16 h. Crude LCMS showed formation of product and no starting material. The reaction mixture was concentrated to get crude compound. The crude material was purified by reverse phase prep HPLC using method D2. The fractions containing the compound were combined and evaporated to dryness using Genevac to afford 2-(5-(2-(3,4-dimethoxyphenyl)-3-isopropyl-1H-indole-5-carbonyl)hexahydropyrrolo[3,4-c]pyrrol-2 (1H)-yl)-N,N-dimethylacetamide (0.032 g, 0.059 mmol, 69% yield) as a pale yellow solid. LCMS retention time 2.10 min [H], MS m/z: 519.2 (M+H); $^1$H NMR (400 MHz. CD$_3$OD) δ ppm 7.91 (s, 1H), 7.38 (d, J=8.4 Hz, 1H), 7.25 (dd, J=8.4, 1.2 Hz, 1H), 7.12-7.04 (m, 3H), 3.90 (s, 3H), 3.89 (s, 3H), 3.88-3.82 (m, 3H), 3.38-3.36 (m, 3H), 3.11 (s, 3H), 2.98-2.93 (m, 5H), 2.86-2.42 (m, 5H), 1.45-1.42 (m, 6H).

The example in Table 2 was prepared according to the general procedure described for Example 6

TABLE 2

| Ex. No. | Structure | Mol Wt. | LCMS MH+ | Ret Time (min) | HPLC Method |
|---|---|---|---|---|---|
| 7 | 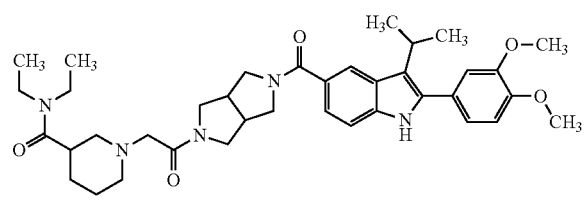 | 504.63 | 505.4 | 1.461 | E |

Example 8

1-(2-{5-[2-(3,4-dimethoxyphenyl)-3-(propan-2-yl)-1H-indole-5-carbonyl]-octahydropyrrolo[3,4-c]pyrrol-2-yl}-2-oxoethyl)-N,N-diethylpiperidine-3-carboxamide (8)

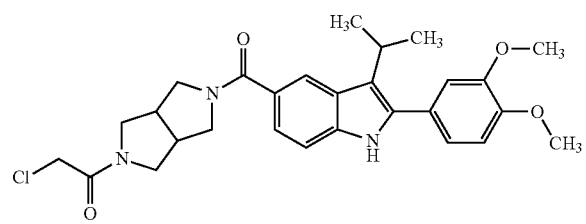

Intermediate 8A: 2-chloro-1-(5-(2-(3,4-dimethoxyphenyl)-3-isopropyl-1H-indole-5-carbonyl)hexahydro pyrrolo[3,4-c]pyrrol-2(1H)-yl)ethanone (8A)

To a solution of (2-(3,4-dimethoxyphenyl)-3-isopropyl-1H-indol-5-yl) (hexahydropyrrolo[3,4-c]pyrrol-2(1H)-yl) methanone hydrochloride (0.160 g, 0.340 mmol) in THF (5.00 mL) (compound was not dissolved completely) was added DIPEA (0.178 mL, 1.021 mmol) at 0° C. (compound was not dissolved completely). The reaction mixture was stirred for 5 min, then chloroacetyl chloride (0.030 mL, 0.374 mmol) was added at the same temperature. Stirring was continued at room temperature for 12 h. Crude LCMS showed formation of product and 12% starting material remained. An additional amount of chloroacetyl chloride (0.2 eq) was added and the reaction was allowed to proceed for another 3 h. Crude LCMS showed formation of product and no starting material. The reaction was quenched with the addition of water. The reaction mixture was extracted with DCM (2×20 mL), combined organic extracts were washed with brine (5 mL), dried ($Na_2SO_4$) and concentrated to afford 2-chloro-1-(5-(2-(3,4-dimethoxyphenyl)-3-isopropyl-1H-indole-5-carbonyl)hexahydropyrrolo[3,4-c] pyrrol-2 (1H)-yl)ethanone (0.168 g, 0.329 mmol, 97% yield) as a gummy solid. LCMS retention time 1.08 min [G]. MS m/z: 510.1 [M+H]+.

Example 8

To a solution of 2-chloro-1-(5-(2-(3,4-dimethoxyphenyl)-3-isopropyl-1H-indole-5-carbonyl)hexahydropyrrolo[3,4-c]pyrrol-2(H)-yl)ethanone (0.100 g, 0.196 mmol) in THF (2.00 mL) were added TEA (0.082 mL, 0.588 mmol) and N,N-diethylnipecotamide (0.055 mL, 0.294 mmol) at room temperature. The mixture was stirred at the same temperature for 16 h and concentrated to yield crude compound. The crude sample was purified by reverse phase prep HPLC using method D2, the product containing fraction was collected, concentrated and lyophilized to afford 1-(2-(5-(2-(3,4-dimethoxyphenyl)-3-isopropyl-1H-indole-5-carbonyl) hexahydropyrrolo[3,4-c]pyrrol-2(1H)-yl)-2-oxoethyl)-N,N-diethylpiperidine-3-carboxamide, TFA (0.072 g, 0.089 mmol, 45% yield) as a pale yellow solid. LCMS retention time 1.08 min [G]. MS m/z: 658.4 [M+H]+; $^1$H NMR (400 MHz, DMSO-$d_6$) δ=11.21 (s, 1H), 9.69-9.46 (br m, 1H), 7.87 (s, 1H), 7.38-7.31 (m, 1H), 7.29-7.22 (m, 1H), 7.15-7.04 (m, 3H), 4.29-2.88 (m, 28H), 1.92-1.78 (m, 4H), 1.42-1.40 (m, 6H), 1.17-1.11 (m, 3H), 1.09-0.93 (m, 3H).

The following Examples were prepared according to the general procedure described for Example 8.

TABLE 3

| Ex. No. | Structure | Mol Wt. | LCMS MH+ | Ret Time (min) | HPLC Method |
|---|---|---|---|---|---|
| 9 | 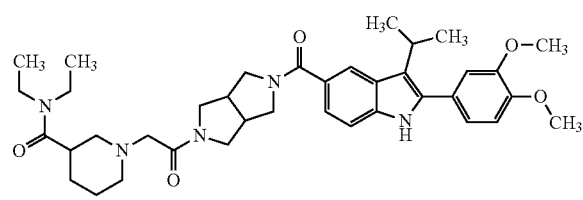 | 518.66 | 519.4 | 1.126 | F |

Examples 10 and 11

1-(2-{5-[2-(3,4-dimethoxyphenyl)-3-(propan-2-yl)-1H-indole-5-carbonyl]-octahydro pyrrolo[3,4-c]pyrrol-2-yl}-2-oxoethyl)-N,N-diethylpiperidine-3-carboxamide (10-11)

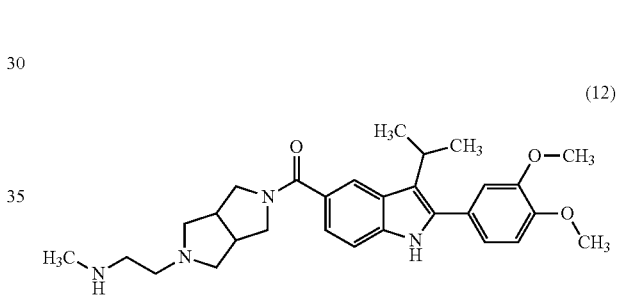

The racemic mixture of Example 8 was separated to afford the two individual enantiomers. Chiral HPLC using column: Chiralpak IA (250×4.6) mm, 5 micron, Run time: 25 min, Flow rate: 0.7 mL/min, mobile phase: 0.2% DEA n-hexane: ethanol:50:50, wave length: 220 racemic. After prep purification, the enantiomers were collected separately, concentrated and lyophilized to afford 1-(2-(5-(2-(3,4-dimethoxyphenyl)-3-isopropyl-1H-indole-5-carbonyl)hexahydropyrrolo[3,4-c] pyrrol-2(1H)-yl)-2-oxoethyl)-N,N-diethyl piperidine-3-carboxamide (0.022 g, 0.032 mmol, 34.0% yield)(Peak-1, Chiral HPLC RT-10.456) as a white solid and 1-(2-(5-(2-(3,4-dimethoxyphenyl)-3-isopropyl-1H-indole-5-carbonyl)hexahydropyrrolo [3,4-c]pyrrol-2 (1H)-yl)-2-oxoethyl)-N,N-diethylpiperidine-3-carboxamide (0.026 g, 0.039 mmol, 42% yield) (Peak-2, Chiral HPLC RT-12.331) as a white solid.

Example 10

Enantiomer 1: LCMS retention time 1.861 min [H], MS m/z: 658.4 (M+H); $^1$H NMR (400 MHz, DMSO-$d_6$) δ 11.21 (s, 1H), 9.69-9.46 (br m, 1H), 7.87 (s, 1H), 7.38-7.31 (m, 1H), 7.29-7.22 (m, 1H), 7.15-7.04 (m, 3H), 4.29-2.88 (m, 28H), 1.92-1.78 (m, 4H), 1.42-1.40 (m, 6H), 1.17-1.11 (m, 3H), 1.09-0.93 (m, 3H).

Example 11

Enantiomer 2: LCMS retention time 1.853 min [H], MS m/z: 658.4 (M+H); $^1$H NMR (400 MHz, DMSO-$d_6$) δ 11.21 (s, 1H), 9.69-9.46 (br m, 1H), 7.87 (s, 1H), 7.38-7.31 (m, 1H), 7.29-7.22 (m, 1H), 7.15-7.04 (m, 3H), 4.29-2.88 (m, 28H), 1.92-1.78 (m, 4H), 1.42-1.40 (m, 6H), 1.17-1.11 (m, 3H), 1.09-0.93 (m, 3H).

Example 12

(2-(3,4-dimethoxyphenyl)-3-isopropyl-1H-indol-5-yl)(5-(2-(methylamino)ethyl) hexahydropyrrolo[3,4-c]pyrrol-2(1H)-yl)methanone (12)

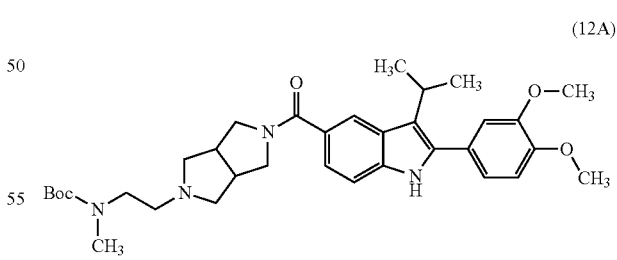

Intermediate 12A: tert-butyl (2-(5-(2-(3,4-dimethoxyphenyl)-3-isopropyl-1H-indole-5-carbonyl) hexahydro pyrrolo [3,4-c]pyrrol-2(1H)-yl)ethylmethyl)carbamate (12A)

To a solution of (2-(3,4-dimethoxyphenyl)-3-isopropyl-1H-indol-5-yl) (hexahydropyrrolo[3,4-c]pyrrol-2(1H)-yl) methanone hydrochloride (0.050 g, 0.106 mmol) in MeOH (3 mL) were added N-Boc-(methylamino)acetaldehyde (0.028 g, 0.160 mmol) and TEA (0.030 mL, 0.213 mmol) at 0° C. The reaction mixture was stirred at room temperature for 3 h. The reaction mixture was cooled to 0° C. and acetic acid (0.20 mL, 3.49 mmol) was added. The reaction mixture was stirred at room temperature for 1 h. Again the reaction mixture was cooled to 0° C. and sodium borohydride (0.012 g, 0.319 mmol) was added. The reaction mixture was left at room temperature overnight. Crude LCMS showed formation of product and no starting material. The reaction was quenched with water (5 mL). Methanol was removed from the mixture using rotavap, the residue was extracted with 10% MeOH in DCM (2×10 mL), combined organic extracts were washed with brine (2 mL), dried (Na$_2$SO$_4$) and concentrated to afford crude tert-butyl (2-(5-(2-(3,4-dimethoxyphenyl)-3-isopropyl-1H-indole-5-carbonyl) hexahydropyrrolo[3,4-c] pyrrol-2(1H)-yl)ethyl)(methyl)carbamate as gummy solid.

LCMS retention time 1.10 min [H], MS m/z: 591.4 (M+H).

Example 12

To a solution of tert-butyl (2-(5-(2-(3,4-dimethoxyphenyl)-3-isopropyl-1H-indole-5-carbonyl)hexahydropyrrolo [3,4-c]pyrrol-2(1H)-yl)ethylmethyl)carbamate (0.063 g, 0.106 mmol) in DCM (2.00 mL) was added TFA (0.5 mL, 6.49 mmol) at 0° C. The reaction mixture was stirred at room temperature for 3 h. Crude LCMS showed formation of product and no starting material. The reaction mass was concentrated to get crude compound. The crude material was purified by Prep LCMS using method D2, fractions containing the product were combined and dried using Genevac centrifugal evaporator to afford (2-(3,4-dimethoxyphenyl)-3-isopropyl-1H-indol-5-yl)(5-(2-(methylamino)ethyl)hexahydro pyrrolo[3,4-c]pyrrol-2(1H)-yl)methanone (0.014 g, 0.028 mmol, 26% yield) as a pale yellow solid. LCMS retention time 1.90 min [E], MS m/z: 491.2 (M+H): $^1$H NMR (400 MHz, DMSO-d) δ ppm 11.20 (s, 1H), 7.82 (s, 1H), 7.35 (d, J=8.4 Hz, 1H), 7.22 (dd, J=8.4, 1.2 Hz, 1H), 7.12-7.04 (m, 3H), 3.85 (s, 3H), 3.83 (s, 3H), 3.76-3.74 (m, 2H), 3.55-3.42 (m, 3H), 2.86-2.74 (m, 4H), 2.66-2.52 (m, 3H), 2.49 (s, 3H), 2.48-2.40 (m, 3H), 1.43 (d, J=12.4 Hz, 6H).

Example 13

(2-(3,4-dimethoxyphenyl)-3-isopropyl-1H-indol-5-yl)(5-methylhexahydro pyrrolo[3,4-c]pyrrol-2(1H)-yl)methanone

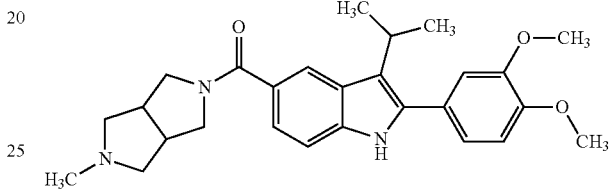

(13)

To a solution of (2-(3,4-dimethoxyphenyl)-3-isopropyl-1H-indol-5-yl) (hexahydropyrrolo[3,4-c]pyrrol-2(1H)-yl) methanone hydrochloride (0.044 g, 0.094 mmol) in MeOH (3.00 mL) were added formaldehyde in water (0.1 mL, 1.271 mmol) and acetic acid (0.016 mL, 0.281 mmol) at 0° C. The reaction mixture was stirred at room temperature for 3 h. Again the reaction mixture was cooled to 0° C. and sodium borohydride (10.63 mg, 0.281 mmol) was added portion wise. The reaction mixture was stirred at room temperature for 16 h. Crude LCMS showed formation of product and no starting material. The reaction was quenched with water (5 mL). Methanol was removed from the reaction mixture using rotavap, the residue was extracted with 10% MeOH in DCM (2×10 mL), combined organic extracts was washed with brine (2 mL), dried (Na$_2$SO$_4$) and concentrated to get crude compound. The crude material was purified by Preparative LCMS using method D2, the fractions containing the product were combined and dried using Genevac centrifugal evaporator to afford (2-(3,4-dimethoxyphenyl)-3-isopropyl-1H-indol-5-yl)(5-methylhexahydro pyrrolo[3,4-c] pyrrol-2(1H)-yl)methanone (0.027 g, 0.058 mmol, 62% yield) as a pale yellow solid. LCMS retention time 1.966 min [E], MS m/z: 448.2 (M+H); $^1$H NMR (400 MHz, CD$_3$OD) δ ppm 7.93 (d, J=0.8 Hz, 1H), 7.39 (d, J=8.4 Hz, 1H), 7.26 (dd, J=8.4, 1.2 Hz, 1H), 7.11-7.06 (m, 3H), 3.92 (s, 3H), 3.90 (s, 3H), 3.89-3.81 (m, 2H), 3.80-3.72 (m, 2H), 3.48-3.37 (m, 1H), 3.09-2.95 (m, 4H), 2.65-2.54 (m, 2H), 2.50 (s, 3H), 1.48 (d, J=6.8 Hz, 6H).

The examples in Table 4 were prepared according to the general procedure described in Example 13.

TABLE 4

| Ex. No. | Structure | Mol Wt. | LCMS MH+ | Ret Time (min) | HPLC Method |
|---|---|---|---|---|---|
| 14 | 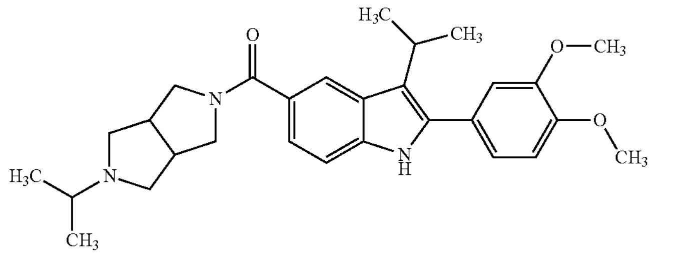 [SMILES: COc1ccc(-c2[nH]c3ccc(C(=O)N4CC5CN(C(C)C)CC5C4)cc3c2C(C)C)cc1OC] | 475.63 | 476.4 | 6.564 | I |
| 15 | 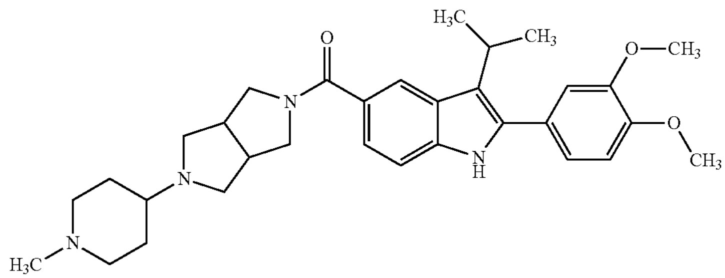 | 530.71 | 531 | 1.356 | E |

Example 16

1-(5-(2-(3,4-dimethoxyphenyl)-3-isopropyl-1H-indole-5-carbonyl)hexahydropyrrolo[3,4-c]pyrrol-2(1H)-yl)-2-(methylamino)ethanone (16)

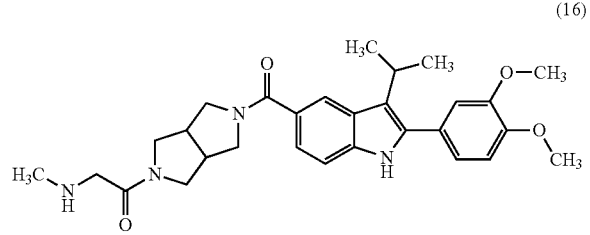

Intermediate 16A: tert-butyl(2-(5-(2-(3,4-dimethoxyphenyl)-3-isopropyl-1H-indole-5-carbonyl)hexahydro pyrrolo[3,4-c]pyrrol-2(1H)-yl)-2-oxoethyl)(methyl)carbamate (16A)

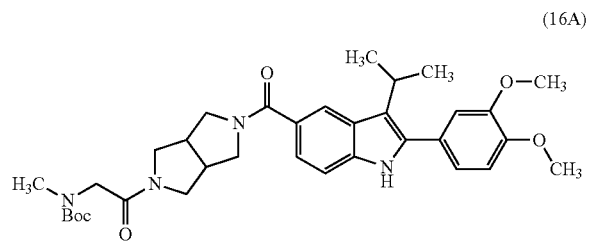

To a solution of (2-(3,4-dimethoxyphenyl)-3-isopropyl-1H-indol-5-yl) (hexahydropyrrolo[3,4-c]pyrrol-2(1H)-yl) methanone hydrochloride (0.030 g, 0.064 mmol) in DMF (3.00 mL) were added TEA (0.027 mL, 0.191 mmol), 2-((tert-butoxycarbonyl)(methyl)amino)acetic acid (0.018 g, 0.096 mmol), and HATU (0.049 g, 0.128 mmol) at 0° C. The reaction mixture was stirred at room temperature for 3 h. Crude LCMS showed formation of product and no starting material. The reaction was quenched with water (5 mL). The reaction mixture was extracted with 10% MeOH in DCM (2×10 mL), combined organic extracts was washed with brine (5 mL), dried ($Na_2SO_4$) and concentrated to afford crude tert-butyl (2-(5-(2-(3,4-dimethoxyphenyl)-3-isopropyl-1H-indole-5-carbonyl)hexahydropyrrolo[3,4-c]pyrrol-2(1H)-yl)-2-oxoethyl) (methyl)carbamate as a gummy solid. LCMS retention time 0.92 min [G]. MS m/z: 505.8 [M+H-Boc]+.

Example 16

To a solution of tert-butyl (2-(5-(2-(3,4-dimethoxyphenyl)-3-isopropyl-1H-indole-5-carbonyl)hexahydropyrrolo[3,4-c]pyrrol-2(1H)-yl)-2-oxoethyl)(methyl)carbamate (0.039 g, 0.064 mmol) in DCM (2.00 mL) was added TFA (0.2 mL, 2.60 mmol) at room temperature. The reaction mixture was stirred at the same temperature for 2 h. Crude LCMS showed formation of product and no starting material. The crude material was purified by Preparative LCMS method D2, the fractions containing the product were combined and dried using Genevac centrifugal evaporator to afford 1-(5-(2-(3,4-dimethoxyphenyl)-3-isopropyl-1H-indole-5-carbonyl)hexahydropyrrolo[3,4-c]pyrrol-2(1H)-yl)-2-(methylamino)ethanone, TFA (0.015 g, 0.024 mmol, 38% yield) as a pale yellow solid. LCMS retention time 1.148 min [E]. MS m/z: 505.4M+H]; $^1$H NMR (400 MHz, DMSO-$d_6$) δ ppm 11.20 (s, 1H), 7.86 (s, 1H), 7.34 (d, J=8.4 Hz, 1H), 7.26 (dd, J=8.4, 1.6 Hz, 1H), 7.11-7.04 (m, 3H), 3.84 (s, 3H), 3.82 (s, 3H), 3.80-3.75 (m, 2H) 3.66-3.58 (m, 2H), 3.46-3.31 (m, 4H), 3.27-3.22 (m, 2H), 3.02-2.97 (m, 1H), 2.91-2.83 (m, 1H), 2.26 (s, 3H), 1.42 (d, J=8.8 Hz, 6H).

Example 17

2-(3,4-dimethoxyphenyl)-N-[2-(dimethylamino)ethyl]-3-ethyl-1H-indole-5-carboxamide

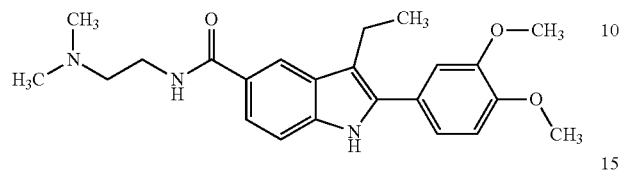

(17)

Intermediate 17A: 1-(5-bromo-1H-indol-3-yl)ethanone

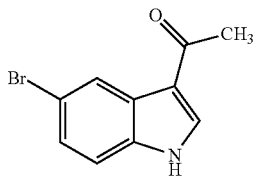

(17A)

To a solution of 5-bromo-1H-indole (1 g, 5.10 mmol) in toluene (10 mL) was added acetyl chloride (0.725 mL, 10.20 mmol) at 0° C. followed by the addition of tin(IV) chloride (10.20 mL, 10.20 mmol) drop wise. The reaction temperature was raised to ambient temperature and the reaction mixture was stirred at the same temperature for 4 h. LC/MS showed completion of reaction. The reaction was quenched with ice cold water. Yellow solid precipitated out and was collected by filtration. The reaction solids were air dried with vacuum filtration. The residue was washed with water and dried under vacuum for 12 h. The dried solid was further triturated with dry toluene and collected to afford 1-(5-bromo-1H-indol-3-yl)ethanone (1 g, 82% yield) as a yellow solid. LCMS retention time 2.13 min [D]. MS m/z: 237 (M+H). $^1$H NMR (300 MHz, DMSO-$d_6$) δ ppm 12.11 (br. s., 1H), 8.37 (s, 1H), 8.33-8.29 (m, 1H), 7.43 (d, J=0.6 Hz, 1H), 7.38-7.30 (m, 1H), 2.45 (s, 3H).

Intermediate 17B: 5-bromo-3-ethyl-1H-indole

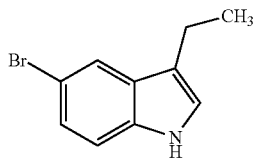

(17B)

To a solution of 1-(5-bromo-1H-indol-3-yl)ethanone (3 g, 12.60 mmol) in THF (30 mL) was added LAH (6.30 mL, 12.60 mmol) at ambient temperature. The reaction mixture was heated to 55° C. The reaction mixture was stirred at same temperature for 1 h. LC/MS showed completion of reaction. The reaction was slowly quenched with ice cold water. White residue precipitated out. The reaction mass was diluted with ethyl acetate and filtered through a pad of celite. The organic layer was concentrated and purified by column chromatography on a 24 g silica column using petroleum ether:ethyl acetate as eluent (8:2). The fractions were collected and concentrated to afford 5-bromo-3-ethyl-1H-indole (1.8 g, 64% yield) as a yellow solid. LCMS retention time 2.35 min [D]. MS m/z: 224 (M+H).

Intermediate 17C: Methyl 3-ethyl-1H-indole-5-carboxylate

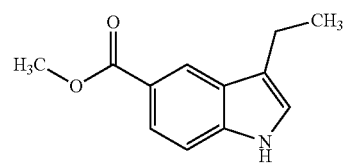

(17C)

To a solution of 5-bromo-3-ethyl-1H-indole (2 g, 8.92 mmol) in methanol (20 mL) and DMSO (20 mL) were added DPPF (0.990 g, 1.785 mmol), Pd(OAc)$_2$ (0.200 g, 0.892 mmol). The solution was degassed for 10 min using argon. The reaction mass was saturated with CO gas, followed by the addition of TEA (3.11 mL, 22.31 mmol). The reaction mass was then heated to 80° C. in the presence of CO for 12 h. LC/MS showed formation of the product. The reaction mass was diluted with ethyl acetate and washed with water, followed by brine, organic layer was separated and dried over sodium sulphate and concentrated to get crude ester, which was further purified by column chromatography using 40 g silica column. The compound was eluted in petroleum ether:ethyl acetate (6:4), the fractions were collected and concentrated to methyl 3-ethyl-1H-indole-5-carboxylate (0.75 g, 41% yield) as a pale yellow solid. LCMS retention time 2.21 min [D]. MS m/z: 204.2 (M+H).

Intermediate 17D: Methyl 2-bromo-3-ethyl-1H-indole-5-carboxylate

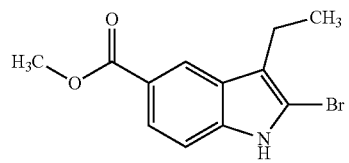

(17D)

To a solution of methyl 3-ethyl-1H-indole-5-carboxylate (0.75 g, 3.69 mmol) in DCE (40 mL) was added NBS (0.657 g, 3.69 mmol) in DCE (40 mL) at ambient temperature. The reaction mixture was stirred for 3 h. LC/MS showed completion of the reaction. The reaction was quenched with 5 mL of sodium sulfite solution. The volatiles were removed. The residue was taken up in DCM (15 mL), filtered and loaded onto a 40 g silica gel column, which was eluted using 0-50% ethyl acetate/hexane. The fractions were collected and concentrated to afford methyl 2-bromo-3-ethyl-1H-indole-5-carboxylate (0.56 g, 53% yield) as a white foam. LCMS retention time 2.36 min [D]. MS m/z: 282 (M+H).

Intermediate 7E: Methyl 2-(3,4-dimethoxyphenyl)-3-ethyl-1H-indole-5-carboxylate

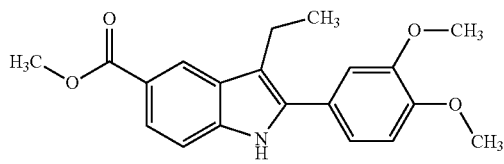

(17E)

Methyl 2-(3,4-dimethoxyphenyl)-3-ethyl-1H-indole-5-carboxylate (0.45 g, 83% yield) was prepared as described in preparation of Intermediate 1C, using methyl 2-bromo-3-ethyl-1H-indole-5-carboxylate (560 mg, 1.985 mmol) as the starting intermediate. LCMS retention time 2.1 min [D]. MS m/z: 340.2 (M+H).

Intermediate 17F: 2-(3,4-dimethoxyphenyl)-3-ethyl-1H-indole-5-carboxylic Acid

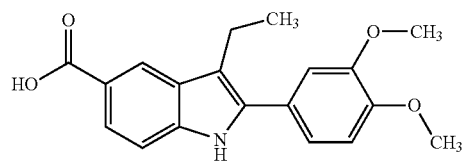

(17F)

2-(3,4-dimethoxyphenyl)-3-ethyl-1H-indole-5-carboxylic acid carboxylate (0.35 g, 81% yield) was prepared according to the general preparation described in Intermediate 1D, using methyl 2-(3,4-dimethoxyphenyl)-3-ethyl-1H-indole-5-carboxylate (0.45 g, 1.326 mmol) as the starting intermediate. LCMS retention time 2.1 min [D]. MS m/z: 326.2 (M+H).

Example 17

To a vial containing 2-(3,4-dimethoxyphenyl)-3-ethyl-1H-indole-5-carboxylic acid (10 mg, 0.031 mmol), HATU (14.02 mg, 0.037 mmol) and the corresponding amine (0.037 mmol), were added DMF (0.5 mL) and DIPEA (0016 mL, 0.092 mmol). The reaction mixture was stirred for 3 h at room temperature. The crude samples was purified by reverse phase prep HPLC using method D2. The fractions containing the compound were combined and evaporated to dryness using Genevac to afford 2-(3,4-dimethoxyphenyl)-N-(2-(dimethylamino)ethyl)-3-ethyl-1H-indole-5-carboxamide (6.1 mg, 0.015 mmol, 50% yield) as a pale solid. LCMS retention time 1.037 min [E]. MS m/z; 396.2 (M+H); $^1$H NMR (400 MHz, DMSO-$d_6$) δ ppm 11.25 (s, 1H), 8.25 (t, J=1.6 Hz, 1H), 8.12 (s, 1H), 7.63 (dd, J=7.2, 1.6 Hz, 1H), 7.35 (d, J=8.8 Hz, 1H), 7.20-7.10 (m, 3H), 3.85 (s, 3H), 3.82 (s, 3H), 3.42-3.36 (m, 2H), 2.92-2.86 (m, 2H), 2.46-2.42 (m, 2H), 2.21 (s, 6H), 1.30 (t, J=7.2 Hz, 3H).

The examples in Table 5 were prepared according to the general procedure described in Example 17.

TABLE 5

| Ex. No. | Structure | Mol Wt. | LCMS MH+ | Ret Time (min) | HPLC Method |
|---|---|---|---|---|---|
| 18 | 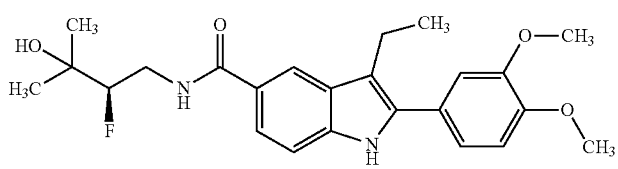 [SMILES: CCc1c(-c2ccc(OC)c(OC)c2)[nH]c2ccc(C(=O)NC[C@@H](F)C(C)(C)O)cc12] | 428.5 | 429 | 1.48 | E |
| 19 | 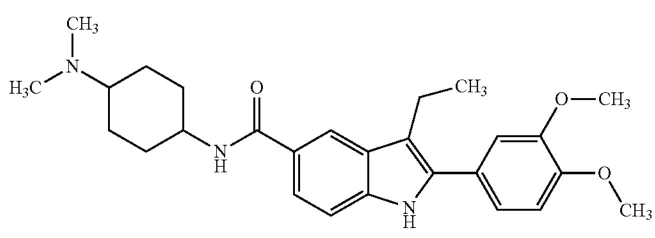 | 449.6 | 450.2 | 1.054 | E |
| 20 | 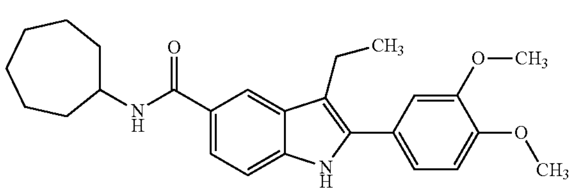 [SMILES: CCc1c(-c2ccc(OC)c(OC)c2)[nH]c2ccc(C(=O)NC3CCCCCC3)cc12] | 420.55 | 421.2 | 3.012 | E |

TABLE 5-continued

| Ex. No. | Structure | Mol Wt. | LCMS MH+ | Ret Time (min) | HPLC Method |
|---|---|---|---|---|---|
| 21 | 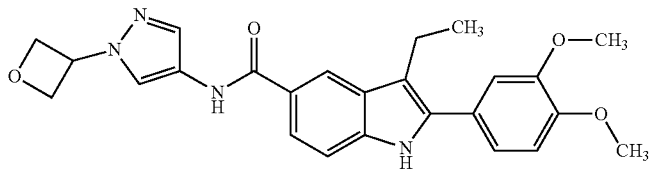 [SMILES: CCc1c(-c2ccc(OC)c(OC)c2)[nH]c2ccc(C(=O)Nc3cnn(C4COC4)c3)cc12] | 446.51 | 447 | 1.42 | E |
| 22 | 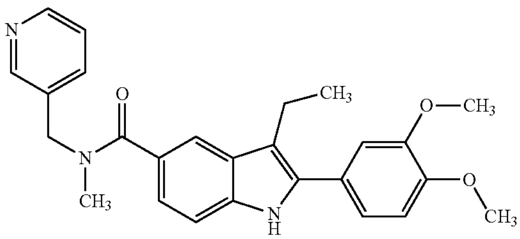 [SMILES: CCc1c(-c2ccc(OC)c(OC)c2)[nH]c2ccc(C(=O)N(C)Cc3cccnc3)cc12] | 429.52 | 430.2 | 2.463 | E |
| 23 | 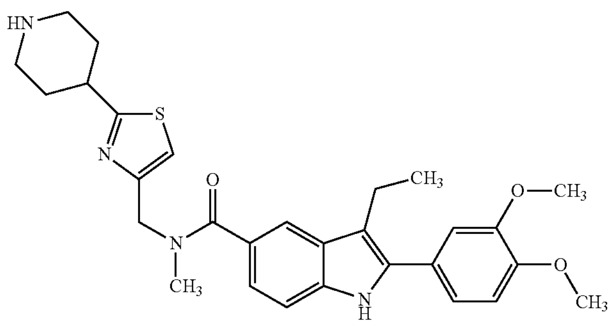 [SMILES: CCc1c(-c2ccc(OC)c(OC)c2)[nH]c2ccc(C(=O)N(C)Cc3csc(C4CCNCC4)n3)cc12] | 518.68 | 519.4 | 1.201 | E |
| 24 | 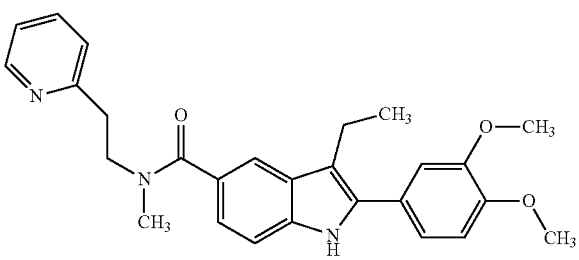 [SMILES: CCc1c(-c2ccc(OC)c(OC)c2)[nH]c2ccc(C(=O)N(C)CCc3ccccn3)cc12] | 443.55 | 444 | 1.58 | E |
| 25 | 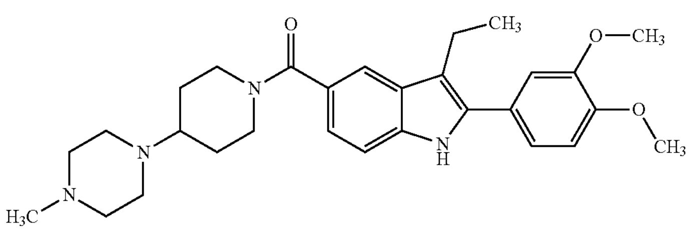 | 490.65 | 491.2 | 1.133 | E |
| 26 | 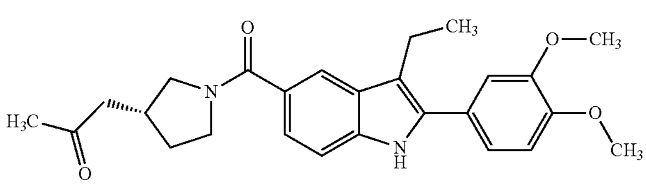 [SMILES: CCc1c(-c2ccc(OC)c(OC)c2)[nH]c2ccc(C(=O)N3CC[C@H](CC(C)=O)C3)cc12] | 435.52 | 436.2 | 2.181 | E |

TABLE 5-continued

| Ex. No. | Structure | Mol Wt. | LCMS MH+ | Ret Time (min) | HPLC Method |
|---|---|---|---|---|---|
| 27 | 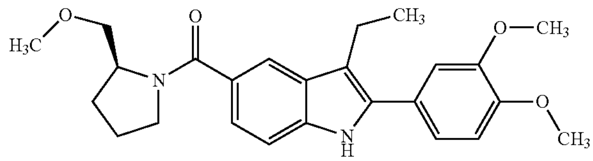 | 422.53 | 423.2 | 2.642 | E |
| 28 | 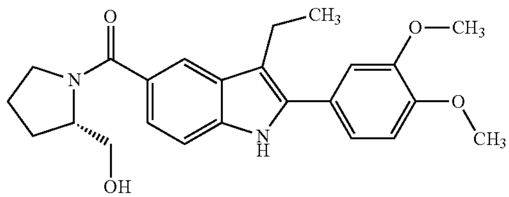 [SMILES: CCc1c(-c2ccc(OC)c(OC)c2)[nH]c2ccc(C(=O)N3CCC[C@H]3CO)cc12] | 408.5 | 409.2 | 2.369 | E |
| 29 | 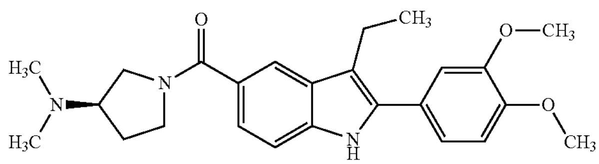 | 421.54 | 422.3 | 1.373 | E |
| 30 | 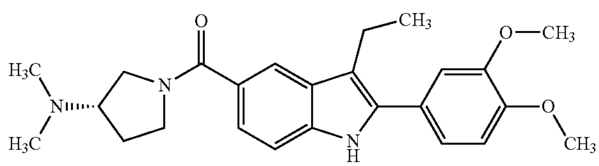 | 421.54 | 422.3 | 1.374 | E |
| 31 | 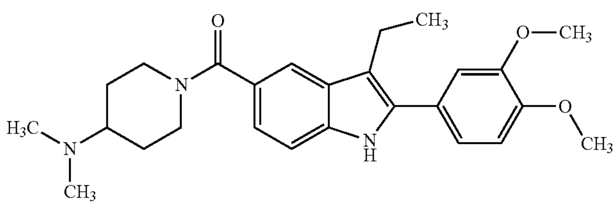 | 435.57 | 436.2 | 1.077 | E |
| 32 | 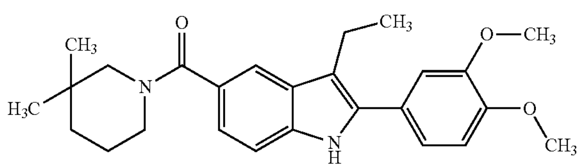 | 420.55 | 421.3 | 2.070 | E |
| 33 | 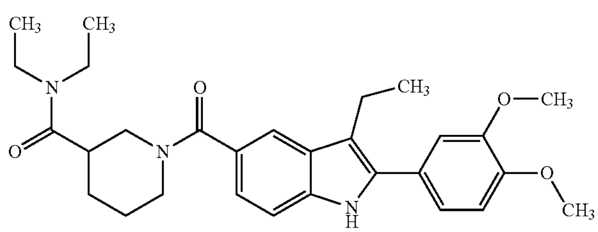 [SMILES: CCc1c(-c2ccc(OC)c(OC)c2)[nH]c2ccc(C(=O)N3CCCC(C(=O)N(CC)CC)C3)cc12] | 491.63 | 492.2 | 2.578 | E |
| 34 | 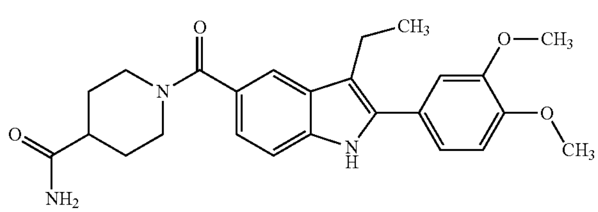 [SMILES: CCc1c(-c2ccc(OC)c(OC)c2)[nH]c2ccc(C(=O)N3CCC(C(N)=O)CC3)cc12] | 435.52 | 436.2 | 2.124 | E |

TABLE 5-continued

| Ex. No. | Structure | Mol Wt. | LCMS MH+ | Ret Time (min) | HPLC Method |
|---|---|---|---|---|---|
| 35 | 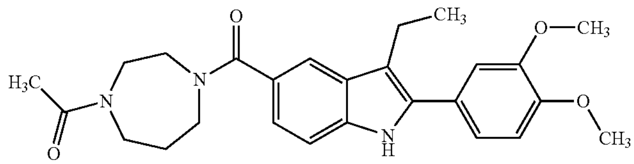 [SMILES: CCc1c(-c2ccc(OC)c(OC)c2)[nH]c2ccc(C(=O)N3CCCN(C(C)=O)CC3)cc12] | 449.55 | 450.2 | 2.229 | E |
| 36 | 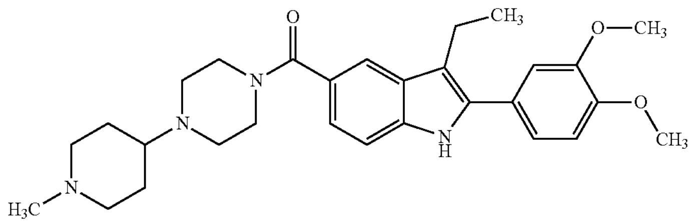 | 490.65 | 491.2 | 2.181 | E |
| 37 | 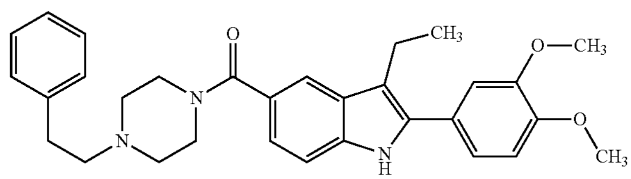 [SMILES: CCc1c(-c2ccc(OC)c(OC)c2)[nH]c2ccc(C(=O)N3CCN(CCc4ccccc4)CC3)cc12] | 497.64 | 498.2 | 2.924 | E |
| 38 | 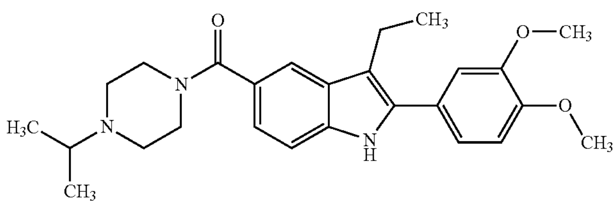 [SMILES: CCc1c(-c2ccc(OC)c(OC)c2)[nH]c2ccc(C(=O)N3CCN(C(C)C)CC3)cc12] | 435.57 | 436.2 | 1.499 | E |
| 39 | 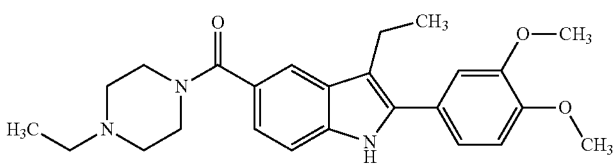 [SMILES: CCc1c(-c2ccc(OC)c(OC)c2)[nH]c2ccc(C(=O)N3CCN(CC)CC3)cc12] | 421.54 | 422.3 | 1.493 | E |
| 40 | 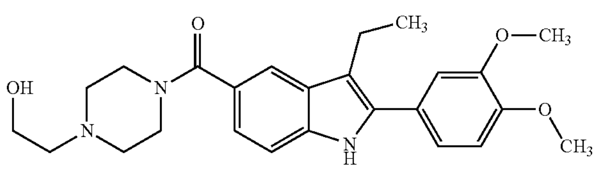 [SMILES: CCc1c(-c2ccc(OC)c(OC)c2)[nH]c2ccc(C(=O)N3CCN(CCO)CC3)cc12] | 437.54 | 438.2 | 2.130 | E |
| 41 | 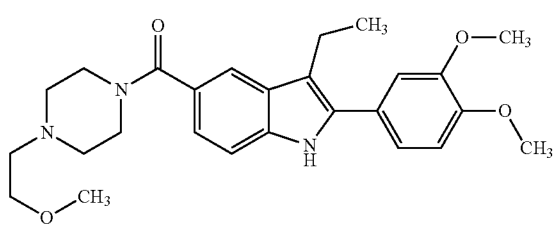 [SMILES: CCc1c(-c2ccc(OC)c(OC)c2)[nH]c2ccc(C(=O)N3CCN(CCOC)CC3)cc12] | 451.57 | 452.3 | 1.481 | E |
| 42 | 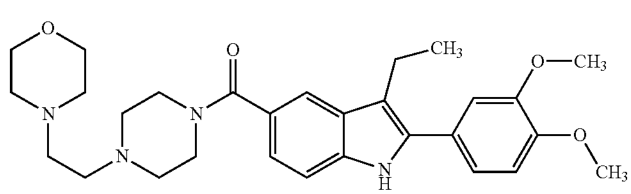 [SMILES: CCc1c(-c2ccc(OC)c(OC)c2)[nH]c2ccc(C(=O)N3CCN(CCN4CCOCC4)CC3)cc12] | 506.65 | 507.4 | 1.353 | E |

TABLE 5-continued

| Ex. No. | Structure | Mol Wt. | LCMS MH+ | Ret Time (min) | HPLC Method |
|---|---|---|---|---|---|
| 43 | 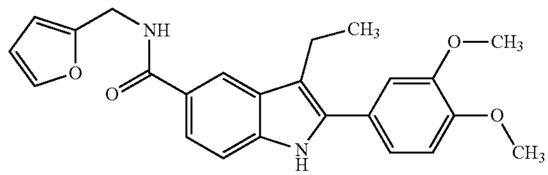 [SMILES: CCc1c(-c2ccc(OC)c(OC)c2)[nH]c2ccc(C(=O)NCc3ccco3)cc12] | 404.47 | 405.3 | 1.681 | E |
| 44 | 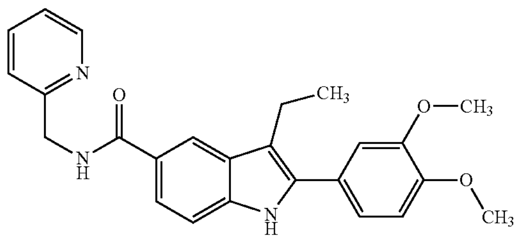 [SMILES: CCc1c(-c2ccc(OC)c(OC)c2)[nH]c2ccc(C(=O)NCc3ccccn3)cc12] | 415.49 | 416.2 | 2.416 | E |
| 45 | 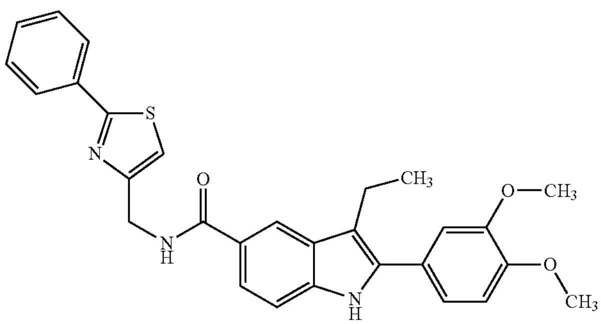 [SMILES: CCc1c(-c2ccc(OC)c(OC)c2)[nH]c2ccc(C(=O)NCc3csc(-c4ccccc4)n3)cc12] | 497.61 | 498.2 | 2.940 | E |
| 46 | 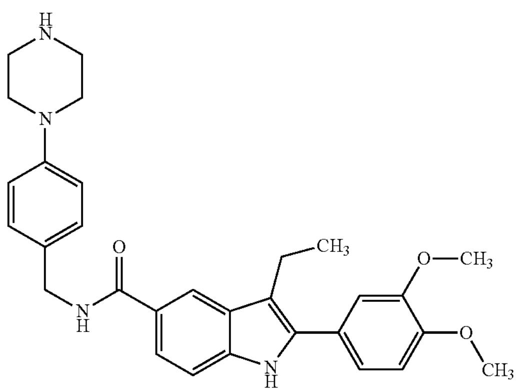 [SMILES: CCc1c(-c2ccc(OC)c(OC)c2)[nH]c2ccc(C(=O)NCc3ccc(N4CCNCC4)cc3)cc12] | 498.63 | 499.4 | 1.262 | E |
| 47 | 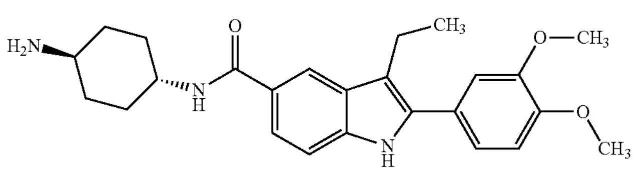 [SMILES: CCc1c(-c2ccc(OC)c(OC)c2)[nH]c2ccc(C(=O)N[C@H]3CC[C@H](N)CC3)cc12] | 421.54 | 422.2 | 0.997 | E |
| 48 | 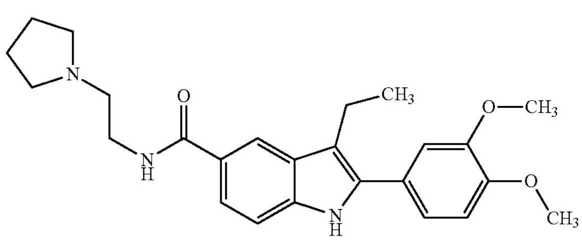 [SMILES: CCc1c(-c2ccc(OC)c(OC)c2)[nH]c2ccc(C(=O)NCCN3CCCC3)cc12] | 421.54 | 422.2 | 1.054 | E |

TABLE 5-continued

| Ex. No. | Structure | Mol Wt. | LCMS MH+ | Ret Time (min) | HPLC Method |
|---|---|---|---|---|---|
| 49 | 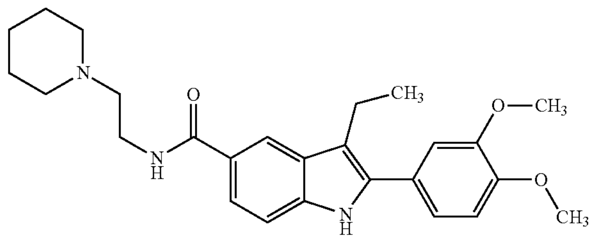 [SMILES: CCc1c(-c2ccc(OC)c(OC)c2)[nH]c2ccc(C(=O)NCCN3CCCCC3)cc12] | 435.57 | 436.2 | 1.203 | E |
| 50 | 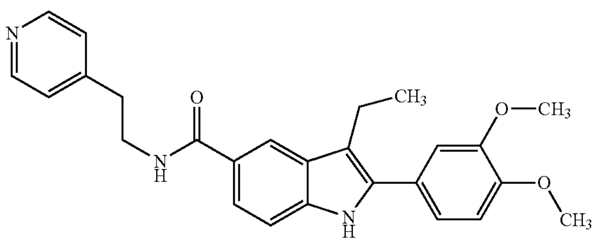 [SMILES: CCc1c(-c2ccc(OC)c(OC)c2)[nH]c2ccc(C(=O)NCCc3ccncc3)cc12] | 429.52 | 430 | 1.366 | E |
| 51 | 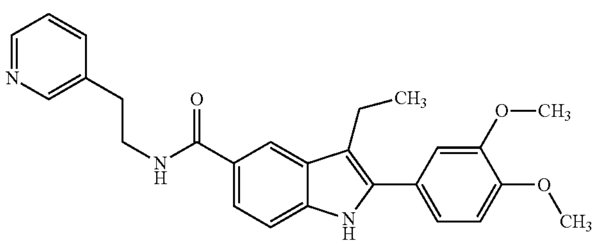 [SMILES: CCc1c(-c2ccc(OC)c(OC)c2)[nH]c2ccc(C(=O)NCCc3cccnc3)cc12] | 429.52 | 430 | 1.383 | E |
| 52 | 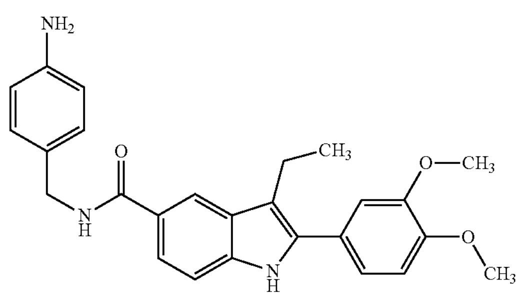 [SMILES: CCc1c(-c2ccc(OC)c(OC)c2)[nH]c2ccc(C(=O)NCc3ccc(N)cc3)cc12] | 429.52 | 430.3 | 1.505 | E |
| 53 | 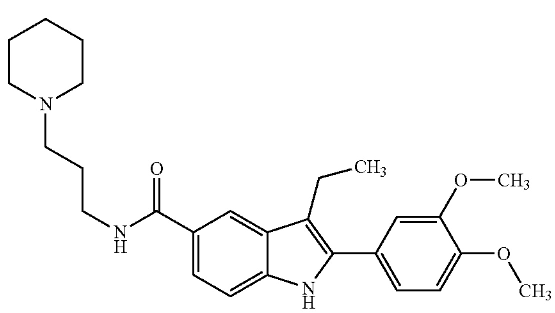 [SMILES: CCc1c(-c2ccc(OC)c(OC)c2)[nH]c2ccc(C(=O)NCCCN3CCCCC3)cc12] | 449.6 | 450.4 | 1.238 | E |

TABLE 5-continued

| Ex. No. | Structure | Mol Wt. | LCMS MH+ | Ret Time (min) | HPLC Method |
|---|---|---|---|---|---|
| 54 | 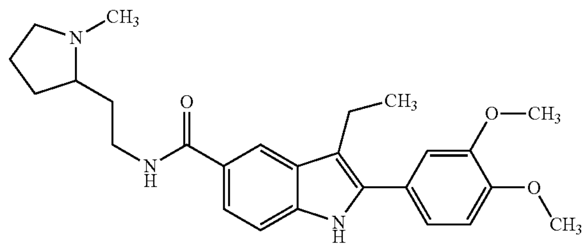 [SMILES: CCc1c(-c2ccc(OC)c(OC)c2)[nH]c2ccc(C(=O)NCCC3CCCN3C)cc12] | 435.57 | 436.2 | 1.086 | E |
| 55 | 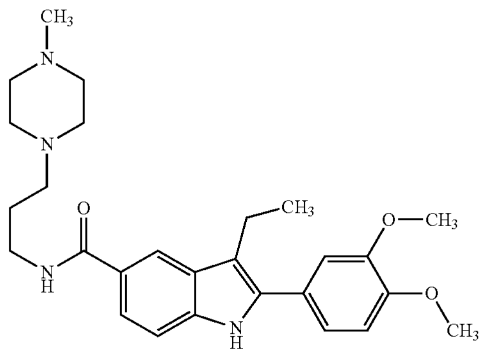 [SMILES: CCc1c(-c2ccc(OC)c(OC)c2)[nH]c2ccc(C(=O)NCCCN3CCN(C)CC3)cc12] | 464.61 | 465.2 | 1.088 | E |
| 56 | 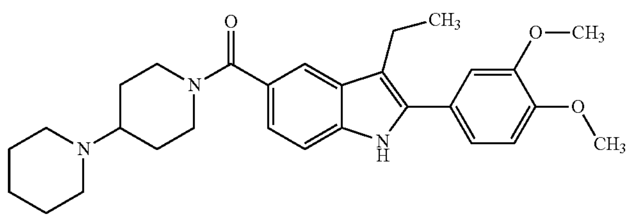 [SMILES: CCc1c(-c2ccc(OC)c(OC)c2)[nH]c2ccc(C(=O)N3CCC(N4CCCCC4)CC3)cc12] | 475.63 | 476.2 | 1.204 | E |
| 57 | 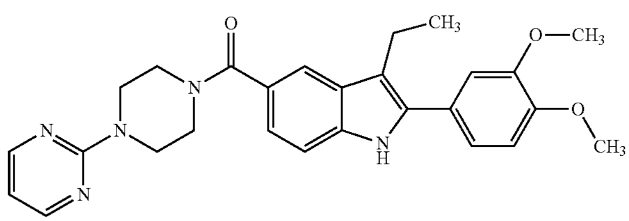 [SMILES: CCc1c(-c2ccc(OC)c(OC)c2)[nH]c2ccc(C(=O)N3CCN(c4ncccn4)CC3)cc12] | 471.56 | 472 | 1.642 | E |
| 58 | 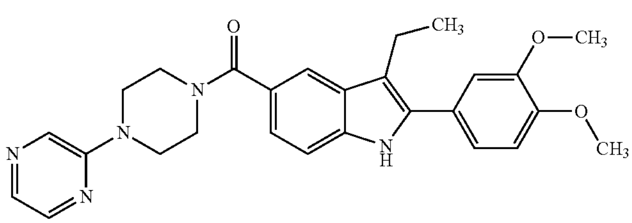 [SMILES: CCc1c(-c2ccc(OC)c(OC)c2)[nH]c2ccc(C(=O)N3CCN(c4cnccn4)CC3)cc12] | 471.56 | 472 | 1.508 | E |
| 59 | 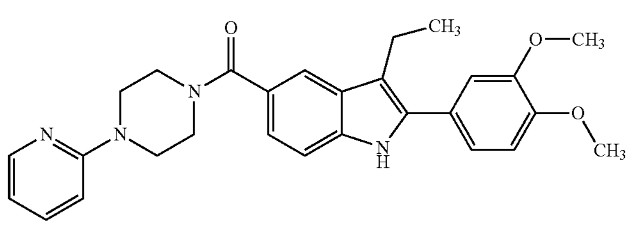 | 470.57 | 471 | 1.711 | E |

TABLE 5-continued

| Ex. No. | Structure | Mol Wt. | LCMS MH+ | Ret Time (min) | HPLC Method |
|---|---|---|---|---|---|
| 60 | 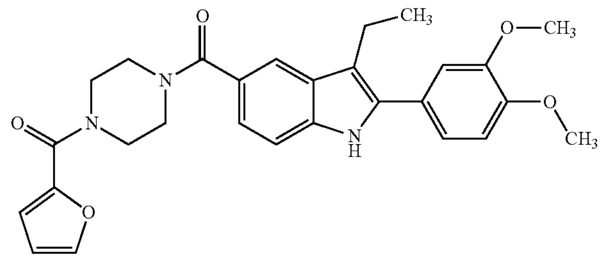 [SMILES: CCc1c(-c2ccc(OC)c(OC)c2)[nH]c2ccc(C(=O)N3CCN(C(=O)c4ccco4)CC3)cc12] | 487.56 | 488.3 | 1.538 | E |
| 61 | 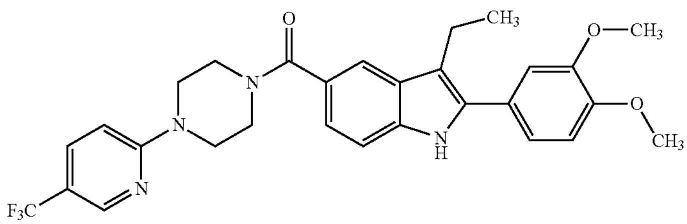 [SMILES: CCc1c(-c2ccc(OC)c(OC)c2)[nH]c2ccc(C(=O)N3CCN(c4ccc(C(F)(F)F)cn4)CC3)cc12] | 538.57 | 539.2 | 3.103 | E |
| 62 | 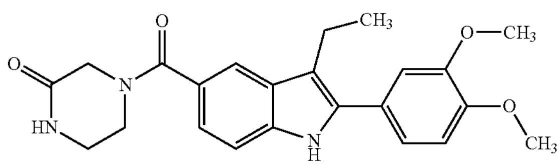 [SMILES: CCc1c(-c2ccc(OC)c(OC)c2)[nH]c2ccc(C(=O)N3CCNC(=O)C3)cc12] | 407.47 | 408.2 | 2.091 | E |
| 63 | 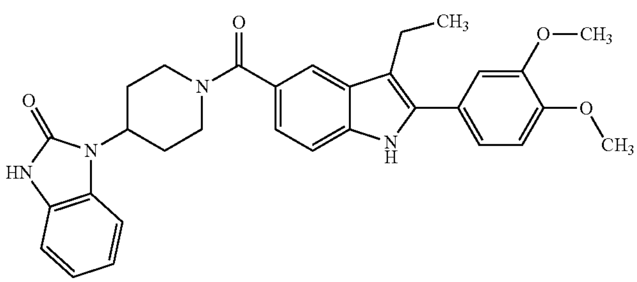 [SMILES: CCc1c(-c2ccc(OC)c(OC)c2)[nH]c2ccc(C(=O)N3CCC(n4c(=O)[nH]c5ccccc54)CC3)cc12] | 524.62 | 525.2 | 2.511 | E |
| 64 | 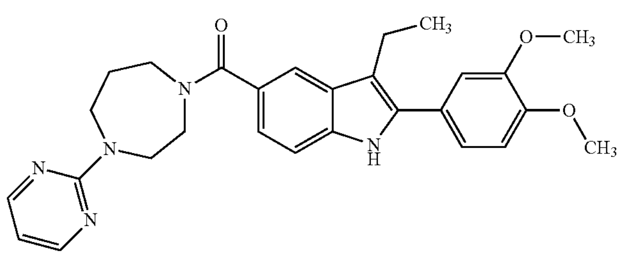 | 485.59 | 486.3 | 1.703 | E |
| 65 | 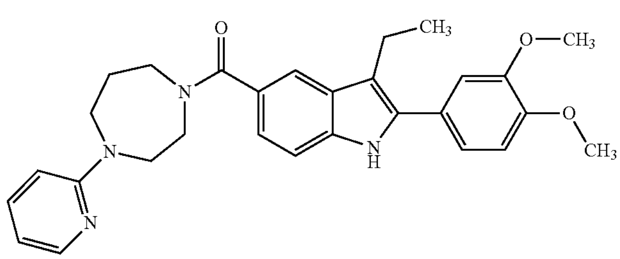 [SMILES: CCc1c(-c2ccc(OC)c(OC)c2)[nH]c2ccc(C(=O)N3CCCN(c4ccccn4)CC3)cc12] | 484.6 | 485.3 | 1.792 | E |

TABLE 5-continued

| Ex. No. | Structure | Mol Wt. | LCMS MH+ | Ret Time (min) | HPLC Method |
|---|---|---|---|---|---|
| 66 | 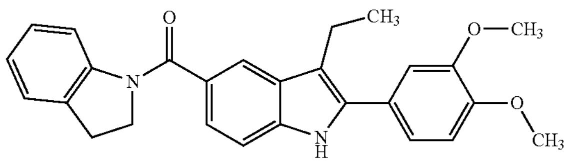 [SMILES: CCc1c(-c2ccc(OC)c(OC)c2)[nH]c2ccc(C(=O)N3CCc4ccccc43)cc12] | 426.52 | 427.3 | 2.057 | E |
| 67 | 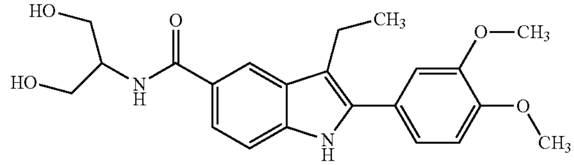 [SMILES: CCc1c(-c2ccc(OC)c(OC)c2)[nH]c2ccc(C(=O)NC(CO)CO)cc12] | 398.46 | 399.2 | 2.070 | E |
| 68 | 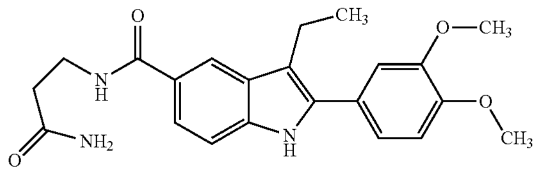 [SMILES: CCc1c(-c2ccc(OC)c(OC)c2)[nH]c2ccc(C(=O)NCCC(N)=O)cc12] | 395.46 | 396 | 1.092 | E |
| 69 | 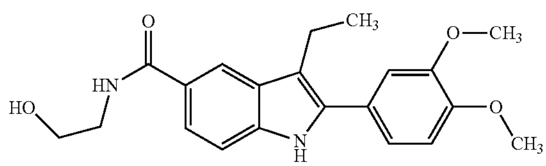 [SMILES: CCc1c(-c2ccc(OC)c(OC)c2)[nH]c2ccc(C(=O)NCCO)cc12] | 368.43 | 369.3 | 1.213 | E |
| 70 | 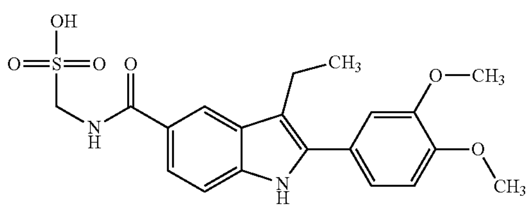 [SMILES: CCc1c(-c2ccc(OC)c(OC)c2)[nH]c2ccc(C(=O)NCS(=O)(=O)O)cc12] | 418.46 | 417 | 1.905 | E |
| 71 | 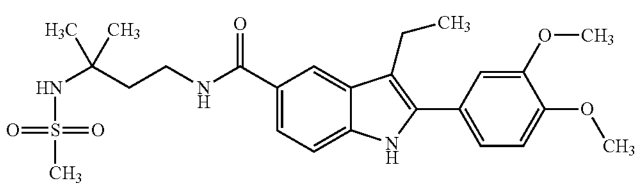 [SMILES: CCc1c(-c2ccc(OC)c(OC)c2)[nH]c2ccc(C(=O)NCCC(C)(C)NS(C)(=O)=O)cc12] | 487.62 | 488 | 1.51 | E |
| 72 | 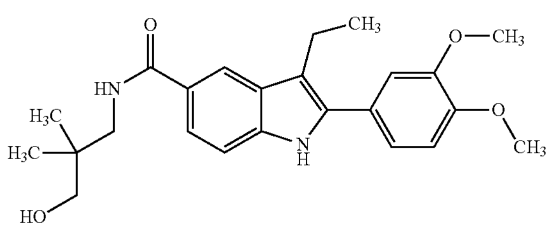 [SMILES: CCc1c(-c2ccc(OC)c(OC)c2)[nH]c2ccc(C(=O)NCC(C)(C)CO)cc12] | 410.51 | 411.3 | 1.570 | E |
| 73 | 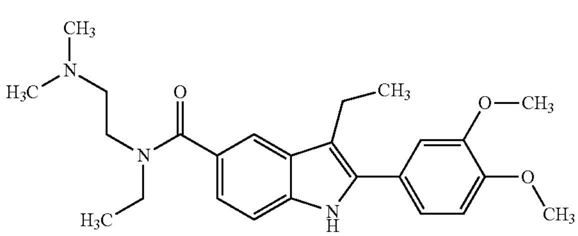 | 423.56 | 424.2 | 1.263 | E |

TABLE 5-continued
| Ex. No. | Structure | Mol Wt. | LCMS MH+ | Ret Time (min) | HPLC Method |
|---|---|---|---|---|---|
| 74 | 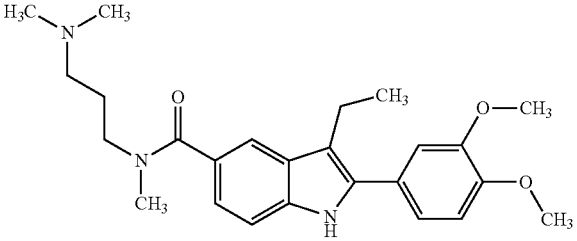 | 423.56 | 424.2 | 1.092 | E |
| 75 | 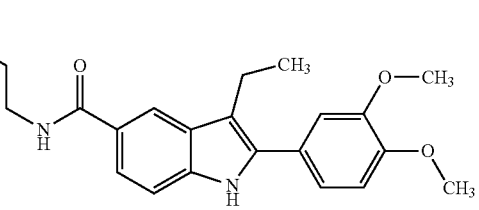 | 409.53 | 410.2 | 2.040 | E |
| 76 | 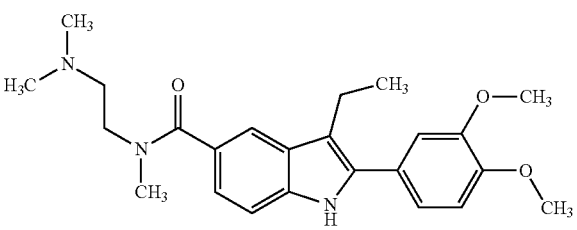 | 409.53 | 410.2 | 1.173 | E |
| 77 | 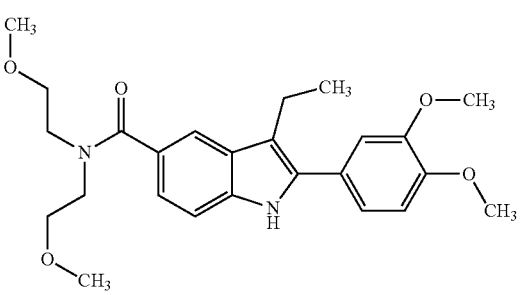 [SMILES: CCc1c(-c2ccc(OC)c(OC)c2)[nH]c2ccc(C(=O)N(CCOC)CCOC)cc12] | 440.54 | 441.2 | 2.539 | E |

Example 78

(2-(3,4-dimethoxyphenyl)-3-ethyl-1H-indol-5-yl)(piperazin-1-yl)methanone hydrochloride

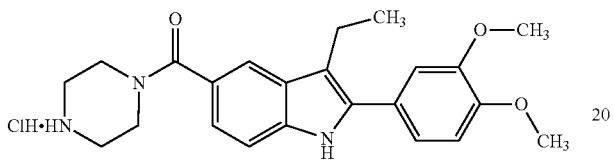

(78)

(2-(3,4-dimethoxyphenyl)-3-ethyl-1H-indol-5-yl)(piperazin-1-yl)methanone hydrochloride (0.035 g, 99% yield) was prepared according to the general procedure described in Example 1 using tert-butyl 4-(2-(3,4-dimethoxyphenyl)-3-ethyl-1H-indole-5-carbonyl)piperazine-1-carboxylate (40 mg, 0.081 mmol) as a starting intermediate. LCMS retention time 2.1 min [G]. MS m/z: 430 [M+H]$^+$; (400 MHz, DMSO-d$_6$): δ ppm 11.25 (s, 1H), 7.56 (s, 1H), 7.36 (d, J=11.20 Hz, 1H), 7.10-7.13 (m, 4H), 3.84 (d, J=12.80 Hz, 6H), 3.51-3.75 (m, 4H), 2.85-2.87 (m, 4H), 2.72-2.77 (m, 2H), 2.60-2.62 (m, 4H), 1.82-1.89 (m, 5H), 1.80 (d, J=8.00 Hz, 2H), 1.35-1.39 (m, 3H), 0.99 (d, J=5.60 Hz, 6H).

The example in Table 6 was prepared according to the general procedure described in Example 78.

TABLE 6

| Ex. No. | Structure | Mol Wt. | LCMS MH$^+$ | Ret Time (min) | HPLC Method |
|---|---|---|---|---|---|
| 79 | 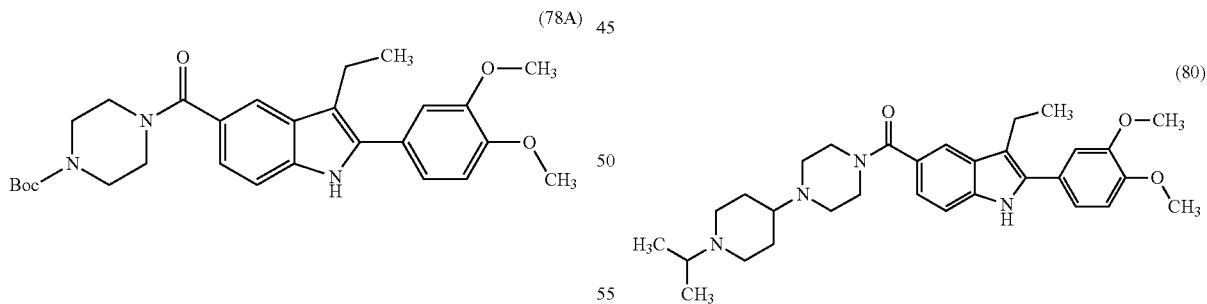 | 419.53 | 420 | 1.02 | E |

Intermediate 78A: tert-butyl 4-(2-(3,4-dimethoxyphenyl)-3-ethyl-1H-indole-5-carbonyl) piperazine-1-carboxylate (78A)

tert-Butyl 4-(2-(3,4-dimethoxyphenyl)-3-ethyl-1H-indole-5-carbonyl piperazine-1-carboxylate (0.025 g, 0.048 mmol, 95% yield) was prepared according to the procedure described in preparation of Intermediate 1E using 2-(3,4-dimethoxyphenyl)-3-ethyl-1H-indole-5-carboxylic acid (0.03 g, 0.092 mmol) and tert-butyl piperazine-1-carboxylate (0.021 g, 0.111 mmol) as a starting materials. LCMS retention time 2.1 min [G]. MS m/z: 494 [M+H]$^+$.

Example 80

(2-(3,4-dimethoxyphenyl)-3-ethyl-1H-indol-5-yl)(4-(1-isopropylpiperidin-4-yl) piperazin-1-yl) methanone (80)

To a solution of (2-(3,4-dimethoxyphenyl)-3-ethyl-1H-indol-5-yl)(piperazin-1-yl)methanone (35 mg, 0.089 mmol) in methanol (2 mL) were added 1-isopropylpiperidin-4-one (12.56 mg, 0.089 mmol), TEA (0.031 mL, 0.222 mmol) and acetic acid (5.09 µL, 0.089 mmol) at room temperature. The mixture was stirred for 45 min, then sodium triacetoxyborohydride (18.85 mg, 0.089 mmol) was added and the mixture was stirred for another 12 h. Crude LC/MS showed formation of the product. The reaction mass was diluted with ethyl acetate, washed with water, followed by brine. The organic layer was separated and dried over sodium sulphate and concentrated to get crude compound. The crude material was purified by Preparative LCMS using method D2, the fractions containing the product were combined and dried using Genevac centrifugal evaporator to afford (2-(3,4-dimethoxyphenyl)-3-ethyl-1H-indol-5-yl)(4-(1-isopropylpiperidin-4-yl) piperazin-1-yl)methanone (0.0027 g, 5.15% yield) as a pale yellow solid. LCMS retention time 1.72 min [E], MS m/z: 519.2 (M+H); $^1$H NMR (400 MHz, DMSO-d$_6$) δ ppm 11.25 (s, 1H), 7.69 (s, 1H), 7.14-7.18 (m, 4H), 3.86 (d, J=7.20 Hz, 6H), 3.77-3.81 (m, 4H), 2.76-2.86 (m, 4H), 2.51-2.64 (m, 4H), 2.49 (d, J=1.60 Hz, 3H), 1.26 (d, J=7.60 Hz, 6H), 0.99-1.13 (m, 6H).

The example in Table 7 was prepared according to the general procedure for Example 80.

TABLE 7

| Ex. No. | Structure | Mol Wt. | LCMS MH+ | Ret Time (min) | HPLC Method |
|---|---|---|---|---|---|
| 81 | 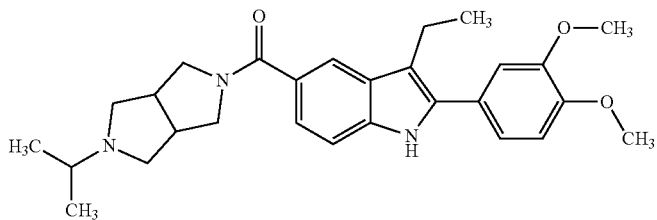 [SMILES: CCc1c(-c2ccc(OC)c(OC)c2)[nH]c2ccc(C(=O)N3CC4CN(C(C)C)CC4C3)cc12] | 461.61 | 462 | 1.28 | E |

Example 82

2-(5-(2-(3,4-dimethoxyphenyl)-3-ethyl-1H-indole-5-carbonyl)hexahydropyrrolo[3,4-c]pyrrol-2(1H)-yl)-N-methylacetamide

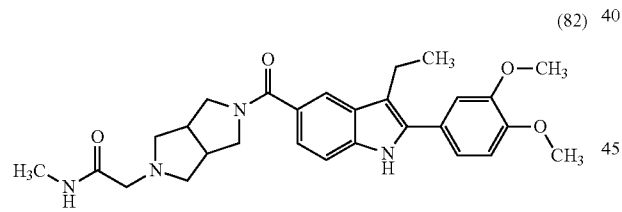
(82)

2-(5-(2-(3,4-dimethoxyphenyl)-3-ethyl-1H-indole-5-carbonyl)hexahydropyrrolo [3,4-c]pyrrol-2(1H)-yl)-N-methylacetamide (0.006 g, 25.4% yield) was prepared according to the general procedure described in Example 6 using (2-(3, 4-dimethoxyphenyl)-3-ethyl-1H-indol-5-yl)(hexahydropyrrolo[3,4-c]pyrrol-2(1H)-yl) methanone (20 mg, 0.048 mmol) as the starting intermediate. LCMS retention time 1.02 min [E], MS m/z: 491 (M+H), $^1$H NMR (400 MHz, DMSO-d$_6$) δ ppm 11.25 (s, 1H), 7.69 (s, 1H), 7.61 (d, J=4.80 Hz, 1H), 7.36 (d, J=8.40 Hz, 1H), 7.25-7.28 (m, 1H), 7.14-7.18 (m, 3H), 3.86 (d, J=7.20 Hz, 6H), 3.77-3.81 (m, 3H), 2.76-2.86 (m, 2H), 2.51-2.64 (m, 2H), 2.49 (d, J=1.60 Hz, 3H), 1.27 (t, J=7.60 Hz, 3H).

Example 83

N-(2-(dimethylamino)ethyl)-N,3-diethyl-2-(1H-pyrrolo[2,3-b]pyridin-4-yl)-1H-indole-5-carboxamide

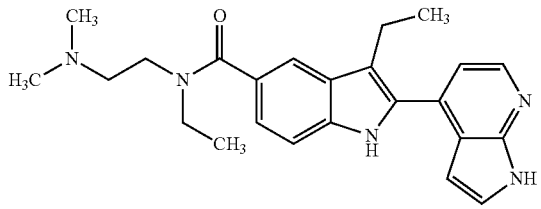
(83)

Intermediate 83A: Methyl 3-ethyl-2-(1H-pyrrolo[2, 3-b]pyridin-4-yl)-1H-indole-5-carboxylate

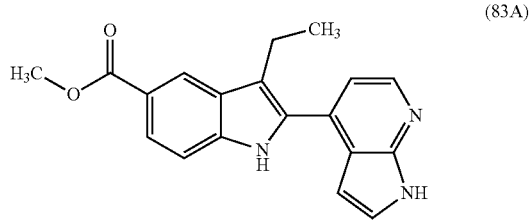 [SMILES: CCc1c(-c2ccnc3[nH]ccc23)[nH]c2ccc(C(=O)OC)cc12]
(83A)

Methyl 3-ethyl-2-(1H-pyrrolo[2,3-b]pyridin-4-yl)-1H-indole-5-carboxylate (0.18 g, 79% yield) was prepared according to the general procedure described in preparation of Intermediate 1C using methyl 2-bromo-3-ethyl-1H-indole-5-carboxylate (0.2 g, 0.709 mmol) as a starting intermediate. LCMS retention time 2.34 min [D]. MS m/z: 320.2 (M+H).

Intermediate 83B: 3-ethyl-2-(1H-pyrrolo[2,3-b]pyridin-4-yl)-1H-indole-5-carboxylic Acid

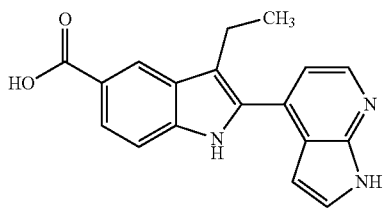
(83B)

3-ethyl-2-(1H-pyrrolo[2,3-b]pyridin-4-yl)-1H-indole-5-carboxylic acid (0.12 g, 60% yield) was prepared according to the general procedure described in the preparation of Intermediate 1D using methyl 3-ethyl-2-(1H-pyrrolo[2,3-b]pyridin-4-yl)-1H-indole-5-carboxylate (0.18 g, 0.564 mmol) as the starting intermediate. LCMS retention time 1.61 min [D]. MS m/z: 306.2 (M+H).

Example 83

N-(2-(dimethylamino)ethyl)-N,3-diethyl-2-(1H-pyrrolo[2,3-b]pyridin-4-yl)-1H-indole-5-carboxamide (0.006 g, 0.048 mmol, 30% yield) was prepared according to the general procedure described in Example 17 using 3-ethyl-2-(H-pyrrolo[2,3-b]pyridin-4-yl)-1H-indole-5-carboxylic acid (15 mg, 0.049 mmol) as the starting intermediate. LCMS retention time 1.06 min [G]. MS m/z: 404 [M+H]$^+$. $^1$H NMR (400 MHz, DMSO-d$_6$) δ ppm 11.83 (s, 1H), 11.37 (s, 1H), 8.32 (d, J=8.00 Hz, 1H), 7.57 (d, J=4.00 Hz, 1H), 7.44 (d, J=8.00 Hz, 1H), 7.17 (d, J=8.00 Hz, 2H), 6.53 (s, 1H), 1.13 (t, J=7.03 Hz, 3H) 1.28 (t, J=7.50 Hz, 3H) 2.57 (s, 3H) 2.65-2.69 (m, 1H) 2.95 (q, J=7.53 Hz, 2H).

Example 84

N-(2-(dimethylamino)ethyl)-N,3-diethyl-2-(2-methylpyridin-4-yl)-1H-indole-5-carboxamide

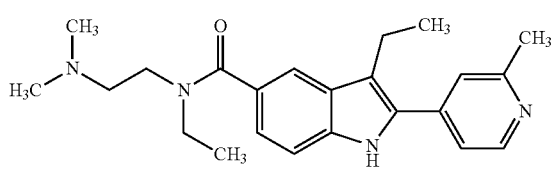
(84)

Intermediate 84A: methyl 3-ethyl-2-(2-methylpyridin-4-yl)-1H-indole-5-carboxylate

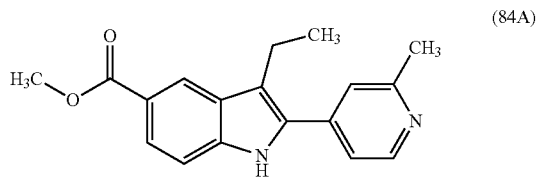
(84A)

Methyl 3-ethyl-2-(1H-pyrrolo[2,3-b]pyridin-4-yl)-1H-indole-5-carboxylate (0.12 g, 62% yield) was prepared according to the general procedure described in preparation of Intermediate 1C using methyl 2-bromo-3-ethyl-1H-indole-5-carboxylate (0.15 g, 0.532 mmol) as the starting intermediate. LCMS retention time 2.38 min [D]. MS m/z: 295.2 (M+H).

Intermediate 84B: 3-ethyl-2-(2-methylpyridin-4-yl)-1H-indole-5-carboxylic Acid

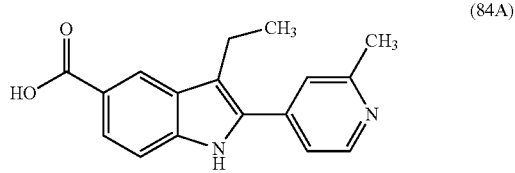 [SMILES: CCc1c(-c2ccnc(C)c2)[nH]c2ccc(C(=O)O)cc12]
(84A)

3-ethyl-2-(2-methylpyridin-4-yl)-1H-indole-5-carboxylic acid (0.1 g, 62% yield) was prepared according to the general procedure described in the preparation of Intermediate 1D using methyl 3-ethyl-2-(2-methylpyridin-4-yl)-1H-indole-5-carboxylate (0.15 g, 0.510 mmol) as the starting intermediate. LCMS retention time 1.61 min [D]. MS m/z: 281.2 (M+H).

Example 84

To a solution of 3-ethyl-2-(2-methylpyridin-4-yl)-1H-indole-5-carboxylic acid (15 mg, 0.054 mmol) in DMF (2 mL) were added N1-ethyl-N2,N2-dimethylethane-1,2-diamine (12.44 mg, 0.107 mmol), DIPEA (0.028 mL, 0.161 mmol) and HATU (30.5 mg, 0.080 mmol) at room temperature. The mixture was stirred at same temperature for 12 h. Crude LCMS showed formation of product. The reaction was quenched with water (5 mL). White solid precipitated from the reaction mixture. The solids were filtered and dried to get crude product. The crude material was purified by Preparative LCMS using method D2, the fractions containing the product were combined and dried using Genevac centrifugal evaporator to afford N-(2-(dimethylamino)ethyl)-N,3-diethyl-2-(2-methylpyridin-4-yl)-1H-indole-5-carboxamide (0.006 g, 0.007 mmol, 35% yield) as an off white solid. LCMS retention time 1.78 min E. MS m/z: 379 [M+H]$^+$; $^1$H NMR (400 MHz, DMSO-d$_6$) δ ppm 11.56 (s, 1H), 8.56 (d, J=5.27 Hz, 1H), 7.66 (s, 1H), 7.50 (s, 1H), 7.42-7.46 (m, 2H), 7.18-7.23 (m, 1H), 2.95 (q, J=7.53 Hz, 2H), 2.65-2.69 (m, 1H), 2.57 (s, 3H), 1.28 (t, J=7.50 Hz, 3H), 1.13 (t, J=7.03 Hz, 3H).

Example 85

(3-ethyl-2-(2-methylpyridin-4-yl)-1H-indol-5-yl)(hexahydropyrrolo[3,4-c]pyrrol-2(1H)-yl)methanone

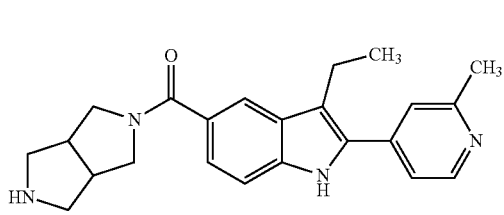

(85)

Intermediate 85A: tert-butyl 5-(3-ethyl-2-(2-methylpyridin-4-yl)-1H-indole-5-carbonyl)hexahydropyrrolo[3,4-c]pyrrole-2(1H)-carboxylate

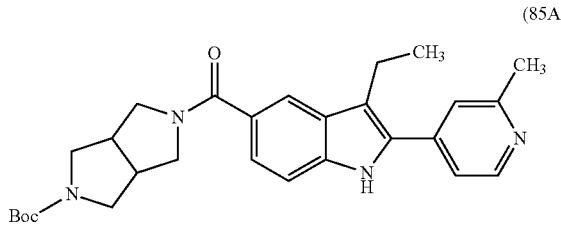

(85A)

tert-Butyl 5-(3-ethyl-2-(2-methylpyridin-4-yl)-1H-indole-5-carbonyl) hexahydropyrrolo[3,4-c]pyrrole-2(1H)-carboxylate was prepared according to the general procedure described in preparation of Example 84 using 3-ethyl-2-(2-methylpyridin-4-yl)-1H-indole-5-carboxylic acid (0.1 g, 62% yield) as the starting intermediate. LCMS retention time 1.91 min [E]. MS m/z: 476 (M+H).

Example 85

(3-Ethyl-2-(2-methylpyridin-4-yl)-1H-indol-5-yl)(hexahydropyrrolo[3,4-c]pyrrol-2(1H)-yl)methanone (0.003 g, 11% yield) was prepared according to the general procedure described in Example 78 using tert-butyl 4-(2-(3,4-dimethoxyphenyl)-3-ethyl-1H-indole-5-carbonyl)piperazine-1-carboxylate (40 mg, 0.081 mmol) as the starting intermediate. LCMS retention time 1.54 min [G]. MS m/z: 375 [M+H]$^+$. $^1$H NMR (400 MHz. DMSO-d$_6$) δ ppm 8.55 (d, J=5.20 Hz, 1H), 7.75 (s, 1H), 7.43 (t, J=4.40 Hz, 1H), 7.40-7.42 (m, 2H), 7.30 (q, J=1.60 Hz, 1H), 4.11 (s, 2H), 3.87-3.99 (m, 3H), 3.10-3.28 (m, 3H), 2.83-2.86 (m, 2H), 2.65 (s, 3H), 2.31-2.49 (m, 2H), 1.91 (s, 2H), 1.27 (t, J=7.60 Hz, 3H).

Example 86

(3-ethyl-2-(2-methylpyridin-4-yl)-1H-indol-5-yl)(5-isopropylhexahydropyrrolo[3,4c]pyrrol-2(1H)-yl)methanone

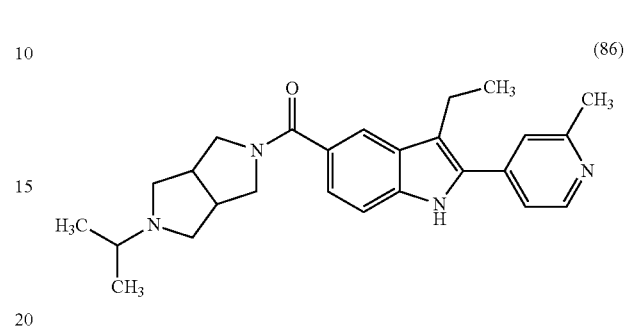

(86)

To a solution of (3-ethyl-2-(2-methylpyridin-4-yl)-1H-indol-5-yl) (hexahydropyrrolo[3,4-c]pyrrol-2(1H)-yl) methanone hydrochloride (20 mg, 0.049 mmol) in methanol (5 mL) were added propan-2-one (7.07 mg, 0.122 mmol), titanium(IV) isopropoxide (0.036 mL, 0.122 mmol), and TEA (0.014 mL, 0.097 mmol) at room temperature. The reaction mixture was stirred at same temperature for 12 h. The reaction mass was cooled to ambient temperature, followed by the addition of sodium cyanoborohydride (7.65 mg, 0.122 mmol) and further stirred at room temperature for 5 h. The reaction mass was diluted with ethyl acetate and filtered through celite, and the filtrate was concentrated to get crude product. The crude material was purified by Preparative LCMS using method D2, the fractions containing the product were combined and dried using Genevac centrifugal evaporator to afford N-(2-(dimethylamino) ethyl)-N,3-diethyl-2-(2-methylpyridin-4-yl)-1H-indole-5-carboxamide (0.007 g, 33% yield) as an off-white solid. LCMS retention time 1.93 min [G]. MS m/z: 417 [M+H]$^+$. $^1$H NMR (400 MHz, DMSO-d$_6$) δ ppm 8.55 (d, J=5.20 Hz, 1H), 7.75 (s, 1H), 7.43 (t, J=4.40 Hz, 1H), 7.40-7.42 (m, 2H), 7.30 (q, J=1.60 Hz, 1H), 4.11 (s, 2H), 3.87-3.99 (m, 3H), 3.10-3.28 (m, 3H), 2.83-2.86 (m, 2H), 2.65 (s, 3H), 2.31-2.49 (m, 2H), 1.89 (s, 2H), 1.21 (t, J=7.60 Hz, 3H), 1.02 (d, J=7.20 Hz, 6H).

Example 87

2-(2-aminopyridin-4-yl)-N-(4-(dimethylamino)cyclohexyl)-3-isopropyl-1H-indole-5-carboxamide

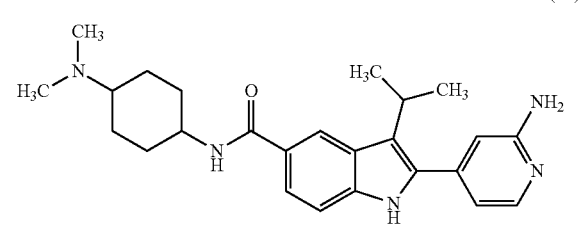

(87)

Intermediate 87A: Methyl 2-(2-aminopyridin-4-yl)-3-isopropyl-1H-indole-5-carboxylate

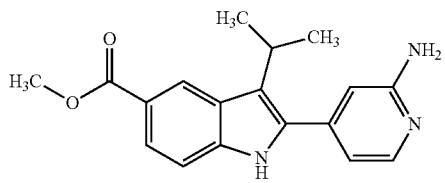
(87A)

Methyl 2-(2-aminopyridin-4-yl)-3-isopropyl-1H-indole-5-carboxylate (350 mg, 67% yield) was prepared according to the general procedure described in Intermediate 1C using methyl 2-bromo-3-isopropyl-1H-indole-5-carboxylate (500 mg, 1.688 mmol) as the starting intermediate. LCMS retention time 1.25 min [D]. MS m/z: 310.2 (M+H).

Intermediate 87B: 2-(2-aminopyridin-4-yl)-3-isopropyl-1H-indole-5-carboxylic Acid

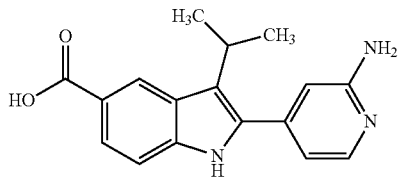
(87B)

2-(2-aminopyridin-4-yl)-3-isopropyl-1H-indole-5-carboxylic acid (250 mg, 0.846 mmol, 82% yield) was prepared according to the general procedure described in Intermediate 1D using methyl 2-(2-aminopyridin-4-yl)-3-isopropyl-1H-indole-5-carboxylate (320 mg, 1.034 mmol) as the starting intermediate. LCMS retention time 0.61 min [D]. MS m/z: 296.3 (M+H).

Example 87

2-(2-Aminopyridin-4-yl)-N-(4-(dimethylamino)cyclohexyl)-3-isopropyl-1H-indole-5-carboxamide (4.7 mg, 0.011 mmol, 11% yield) was prepared according to the general procedure described in Example 17 using 2-(2-aminopyridin-4-yl)-3-isopropyl-1H-indole-5-carboxylic acid (30 mg, 0.102 mmol) as the starting intermediate. LCMS retention time 0.84 min [G]. MS m/z: 420 [M+H]+; $^1$H NMR (400 MHz, DMSO-d$_6$) δ ppm 11.30 (s, 1H), 8.26 (s, 1H), 8.11 (d, J=7.5 Hz, 1H), 8.01 (d, J=5.0 Hz, 1H), 7.66 (dd, J=8.5, 1.5 Hz, 1H), 7.34 (d, J=8.5 Hz, 1H), 6.66-6.55 (m, 2H), 6.06 (s, 2H), 2.81 (d, J=11.0 Hz, 2H), 2.73-2.62 (m, 1H), 2.25-2.10 (m, 2H), 1.85 (s, 6H), 1.65-1.57 (m, 2H), 1.45 (d, J=7.0 Hz, 4H), 0.98 (d, J=6.5 Hz, 6H).

Example 88

(2-(3,4-dimethoxyphenyl)-3-(2,2,2-trifluoroethyl)-1H-indol-5-yl)(hexahydropyrrolo[3,4-c]pyrrol-2(1H)-yl)methanone hydrochloride

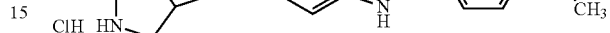
(88)

Intermediate 88A: 1-(3,4-dimethoxyphenyl)-4,4,4-trifluorobutan-1-one

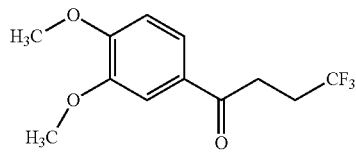
(88A)

To a solution of 4,4,4-trifluorobutanoic acid (10 g, 70.4 mmol) in toluene (100 mL) at 0° C. was added 1,2-dimethoxybenzene (9.00 mL, 70.4 mmol) portion wise. The suspension was stirred for 10 min at 0° C., then polyphosphoric acid (141 mmol) was added. The reaction mixture was heated at 75° C. for 16 h. The reaction was quenched with water (50 mL). The reaction mixture extracted with ethyl acetate (3×100 mL), the combined organic extracts was dried with sodium sulfate and concentrated under reduced pressure to afford the crude compound (15.2 g) a colorless liquid. The crude material was purified with flash chromatography, using 120 g silica column, compound was eluted in 15% ethyl acetate/petroleum ether, the fractions were collected and concentrated to afford 1-(3,4-dimethoxyphenyl)-4,4,4-trifluorobutan-1-one (8 g, 30.5 mmol, 43.3% yield) as an oil. LCMS retention time 2.305 min [D]. MS m/z: 263.2 (M+H).

Intermediate 88B: 5-bromo-2-(3,4-dimethoxyphenyl)-3-(2,2,2-trifluoroethyl)-1H-indole

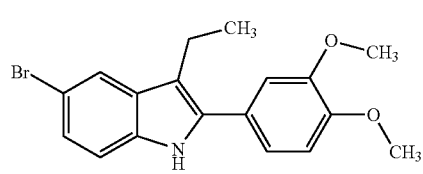
(88B)

To a mixture of (4-bromophenyl)hydrazine (1.070 g, 5.72 mmol), 1-(3,4-dimethoxyphenyl)-4,4,4-trifluorobutan-1-one (1.5 g, 5.72 mmol) and (4-bromophenyl) hydrazine (1.070 g, 5.72 mmol) at room temperature was added polyphosphoric acid (3.40 mL, 5.72 mmol) portion wise. The suspension was stirred for 10 minutes at room temperature, then stirred at 155° C. for 10-20 min. Next, the reaction mixture was quenched with water (20 mL) and extracted with ethyl acetate (3×50 mL), the combined organic extracts was dried with sodium sulfate and concentrated under reduced pressure to get crude compound (15.2 g). The crude material was purified by flash chromatography using a 40 g silica column, compound was eluted in 20-25% ethyl acetate/Pet-Ether, the fractions were collected and concentrated to afford 5-bromo-2-(3,4-dimethoxyphenyl)-3-(2,2,2-trifluoroethyl)-1H-indole (900 mg, 2.173 mmol, 38.00% yield) as a brown solid. LC retention time 2.62 min [D]. MS m/z: 413.0 (M–H).

Intermediate 88C: Methyl 2-(3,4-dimethoxyphenyl)-3-(2,2,2-trifluoroethyl)-1H-indole-5-carboxylate

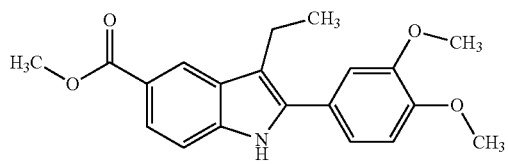

(88C)

Methyl 2-(3,4-dimethoxyphenyl)-3-(2,2,2-trifluoroethyl)-1H-indole-5-carboxylate (650 mg, 1.652 mmol, 86% yield) was prepared according to the general procedure described in Intermediate IA using 5-bromo-2-(3,4-dimethoxyphenyl)-3-(2,2,2-trifluoroethyl)-1H-indole (800 mg, 1.931 mmol) as the starting intermediate. LCMS retention time 1.0 min [D]. MS m/z: 394.1 (M+H).

Intermediate 88D: 2-(3,4-dimethoxyphenyl)-3-(2,2,2-trifluoroethyl)-1H-indole-5-carboxylic Acid

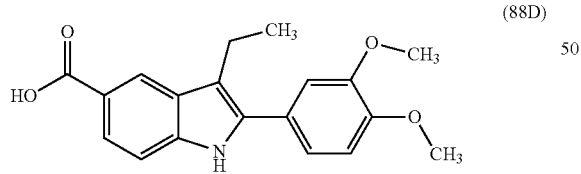

(88D)

2-(3,4-dimethoxyphenyl)-3-(2,2,2-trifluoroethyl)-1H-indole-5-carboxylic acid (160 mg, 0.422 mmol, 83% yield) was prepared according to the general procedure described in Intermediate 1D using 5-bromo-methyl 2-(3,4-dimethoxyphenyl)-3-(2,2,2-trifluoroethyl)-1H-indole-5-carboxylate (200 mg, 0.508 mmol) as the starting intermediate. LCMS retention time 0.86 min [D]. MS m/z: 378.0 (M–H).

Intermediate 88E: tert-Butyl 5-(2-(3,4-dimethoxyphenyl)-3-(2,2,2-trifluoroethyl)-1H-indole-5-carbonyl)hexahydropyrrolo[3,4-c]pyrrole-2(1H)-carboxylate

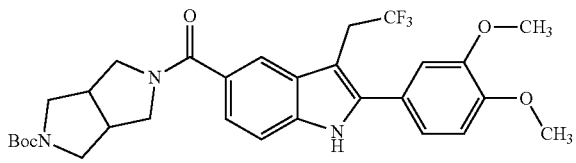

(88E)

Tert-butyl 5-(2-(3,4-dimethoxyphenyl)-3-(2,2,2-trifluoroethyl)-1H-indole-5-carbonyl)hexahydropyrrolo[3,4-c]pyrrole-2(1H)-carboxylate (162 mg, 0.282 mmol, 63.0% yield) was prepared according to the general procedure described in Intermediate 1E, using 2-(3,4-dimethoxyphenyl)-3-(2,2,2-trifluoroethyl)-1H-indole-5-carboxylic acid (170 mg, 0.448 mmol) as the starting intermediate. LCMS retention time 0.99 min [D]. MS m/z: 574.3 (M+H).

Example 88

(2-(3,4-dimethoxyphenyl)-3-(2,2,2-trifluoroethyl)-1H-indol-5-yl) (hexahydropyrrolo[3,4-c]pyrrol-2(1H)-yl)methanone hydrochloride (110 mg, 0.216 mmol, 74% yield) was prepared according to the general procedure described in Example 1, using tert-butyl 5-(2-(3,4-dimethoxyphenyl)-3-(2,2,2-trifluoroethyl)-1H-indole-5-carbonyl)hexahydropyrrolo[3,4-c]pyrrole-2(1H)-carboxylate (168 mg, 0.293 mmol) as the starting intermediate. LCMS retention time 0.71 min [F] MS m/z: 474.3 (M+H); $^1$H NMR (400 MHz, Methanol-$d_4$) δ ppm 7.85 (s, 1H), 7.49 (dd, J=8.4, 0.4 Hz, 1H), 7.40 (d, J=8.4 Hz, 1H), 7.23-7.21 (m, 2H), 7.13 (d, J=8.4 Hz, 1H), 3.98-3.95 (m, 2H), 3.93 (s, 6H), 3.80-3.65 (m, 4H), 3.62-3.51 (m, 2H), 3.24-3.15 (m, 4H).

Example 89

1-(5-(2-(3,4-dimethoxyphenyl)-3-(2,2,2-trifluoroethyl)-1H-indole-5-carbonyl) hexahydropyrrolo[3,4-c]pyrrol-2(1H)-yl)-2-(dimethylamino)ethan-1-one (89)

1-(5-(2-(3,4-dimethoxyphenyl)-3-(2,2,2-trifluoroethyl)-1H-indole-5-carbonyl) hexahydropyrrolo[3,4-c]pyrrol-2(1H)-yl)-2-(dimethylamino)ethan-1-one (15 mg) was prepared according to the general procedure described in Example 17, using (2-(3,4-dimethoxyphenyl)-3-(2,2,2-trifluoroethyl)-1H-indol-5-yl)(hexahydro pyrrolo[3,4-c]pyrrol-2(1H)-yl)methanone hydrochloride (20 mg, 0.039 mmol) as the starting intermediate. LCMS retention time 0.83 min [E].

MS m/z: 559.3 (M+H). ¹H NMR (400 MHz, DMSO-d₆) δ ppm 11.65 (s, 1H), 7.80 (s, 1H), 7.42 (d, J=8.4 Hz, 1H), 7.33 (d, J=8.4 Hz 1H), 7.21-7.13 (m, 3H), 3.85 (s, 6H), 3.78-3.74 (m, 2H), 3.65-3.51 (m, 2H), 3.10-2.91 (m, 4H), 2.25-2.18 (m, 6H).

Example 90

2-(5-(2-(3,4-dimethoxyphenyl)-3-(2,2,2-trifluoroethyl)-1H-indole-5-carbonyl) hexahydropyrrolo[3,4-c]pyrrol-2(1H)-yl)-N,N-dimethylacetamide

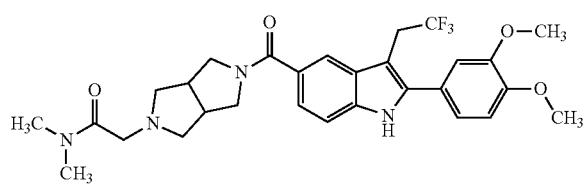

(90)

2-(5-(2-(3,4-dimethoxyphenyl)-3-(2,2,2-trifluoroethyl)-1H-indole-5-carbonyl)hexahydropyrrolo[3,4-c]pyrrol-2(1H)-yl)-N,N-dimethylacetamide (15 mg) was prepared according to the procedure described in Example 6 using (2-(3,4-dimethoxyphenyl)-3-(2,2,2-trifluoroethyl)-1H-indol-5-yl)(hexahydropyrrolo[3,4-c]pyrrol-2(1H)-yl)methanone hydrochloride (20 mg, 0.039 mmol) as the starting intermediate. LCMS retention time 1.467 min [E]. MS m/z: 559.4 (M+H); ¹H NMR (400 MHz, DMSO-d₆) δ ppm 11.63 (s, 1H), 7.74-7.77 (m, 1H) 7.40-7.44 (m, 1H) 7.26-7.30 (m, 1H) 7.18-7.22 (m, 2H) 7.16 (s, 1H) 3.85 (d, J=3.70 Hz, 8H) 3.71-3.80 (m, 2H) 3.21-3.24 (m, 2H) 3.02 (s, 3H) 2.81 (s, 5H).

Example 91

2-(2,6-dimethylpyridin-4-yl)-3-isopropyl-N-(1-isopropylpiperidin-4-yl)-1H-indole-5-carboxamide

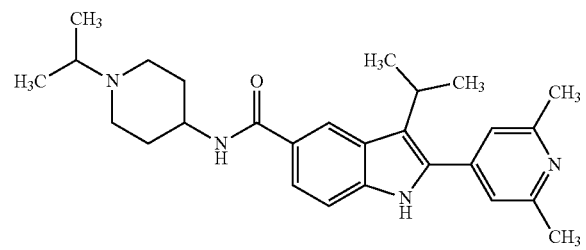

(91)

Intermediate 91A: Methyl 3-isopropyl-2-(4,4,5,5-tetramethyl-1,3,2-dioxaborolan-2-yl)-1H-indole-5-carboxylate

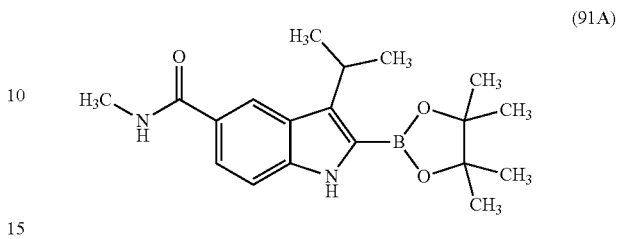

(91A)

TEA (2.131 mL, 15.19 mmol) and pinacolborane (3.95 mL, 25.3 mmol) were added to a degassed solution of methyl 2-bromo-3-isopropyl-1H-indole-5-carboxylate (1.5 g, 5.06 mmol), bis(benzonitrile)palladium(I) chloride (0.194 g, 0.506 mmol) and 2-dicyclohexylphosphino-2',6'-dimethoxybiphenyl (0.208 g, 0.506 mmol) in dioxane (25 mL). The resulting mixture was stirred at 80° C. for 1 h in a sealed tube. The reaction mixture was quenched with ice cold water and diluted with ethyl acetate, filtered and washed with excess ethyl acetate. Combined organic layers were washed with water, brine, dried over sodium sulphate and evaporated to get crude compound. The crude material was purified by column chromatography using 40 g silica column, the compound was eluted with 25% ethyl acetate in petroleum ether, the fraction was collected and concentrated to afford methyl 3-isopropyl-2-(4,4,5,5-tetramethyl-1,3,2-dioxaborolan-2-yl)-1H-indole-5-carboxylate (1.0 g, 2.91 mmol, 57.5% yield) as an off-white solid. LCMS retention time 1.44 min. MS m/z: 344.3 (M+H).

Intermediate 91B: Methyl 2-(2,6-dimethylpyridin-4-yl)-3-isopropyl-1H-indole-5-carboxylate

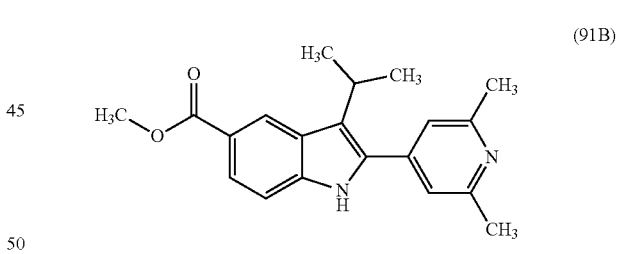

(91B)

A stirred solution of methyl 3-isopropyl-2-(4,4,5,5-tetramethyl-1,3,2-dioxaborolan-2-yl)-1H-indole-5-carboxylate (1.00 g, 2.91 mmol), 4-bromo-2,6-dimethylpyridine (1.084 g, 5.83 mmol) and potassium phosphate tribasic (1.855 g, 8.74 mmol) in dioxane (15.00 mL) and water (5.00 mL) was degassed with nitrogen for 10 min. Next, PdCl₂ (dppf)-CH₂Cl₂ adduct (0.238 g, 0.291 mmol) was added and the reaction mixture was stirred at 90° C. for 2 h. Crude LCMS showed formation of product and no starting material. The reaction mixture was diluted with water (10 mL) and DCM (30 mL). Both the layers were separated and the aqueous layer was extracted with DCM (2×30 mL), the combined organic extracts was washed with brine (10 mL), dried (Na₂SO₄) and concentrated to get crude compound. The crude material was purified by column chromatography using 24 g silica column, compound was eluted in 80% ethyl acetate in hexane, the fractions were collected and concentrated to afford methyl 2-(2,6-dimethylpyridin-4-yl)-3-isopropyl-1H-indole-5-carboxylate (0.860 g, 2.67 mmol, 92% yield) as a off-white solid. LCMS retention time 1.27 min [G]. MS m/z: 323.6 (M+H).

Intermediate 91C: 2-(2,6-dimethylpyridin-4-yl)-3-isopropyl-1H-indole-5-carboxylic Acid

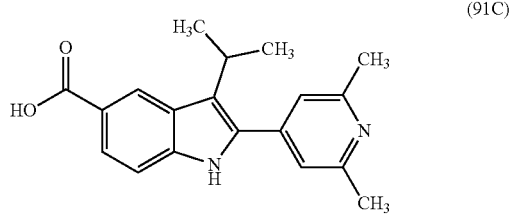 [SMILES: Cc1cc(-c2[nH]c3ccc(C(=O)O)cc3c2C(C)C)cc(C)n1]

(91C)

To a solution of methyl 2-(2,6-dimethylpyridin-4-yl)-3-isopropyl-1H-indole-5-carboxylate (0.250 g, 0.775 mmol) in THF (4.00 mL), MeOH (2.000 mL) and water (1.000 mL) was added lithium hydroxide (0.093 g, 3.88 mmol) at room temperature. The mixture was stirred at 75° C. for 16 h. Crude LCMS showed formation of product and no starting material. The reaction mass was concentrated to remove THF and MeOH, the residue was diluted with water (2 mL), then brought to neutral pH using 0.1 M HCl. The precipitated solid was filtered and washed with water, dried under vacuum to afford 2-(2,6-dimethylpyridin-4-yl)-3-isopropyl-1H-indole-5-carboxylic acid (0.204 g, 0.662 mmol, 85% yield) as an off-white solid. LCMS retention time 0.69 min [G] MS m/z: 309.3 (M+H).

Example 91

To a solution of 2-(2,6-dimethylpyridin-4-yl)-3-isopropyl-1H-indole-5-carboxylic acid, HCl (0.050 g, 0.145 mmol) in DMF (1.500 mL) were added 1-isopropylpiperidin-4-amine (0.031 g, 0.217 mmol), TEA (0.2 mL, 1.435 mmol) and HATU (0.110 g, 0.290 mmol) at room temperature. The mixture was stirred at the same temperature for 3 h. Crude LCMS showed formation of product and no starting material. The reaction mass was concentrated to get crude material. The crude material was purified by Preparative LCMS purification using method D2, fractions containing the product were combined and dried using Genevac centrifugal evaporator to afford 2-(2,6-dimethylpyridin-4-yl)-3-isopropyl-N-(1-isopropylpiperidin-4-yl)-1H-indole-5-carboxamide (0.055 g, 0.123 mmol, 85% yield) as a pale solid. LCMS retention time 1.425 min [E]. MS m/z: 433.3 (M+H); $^1$H NMR (400 MHz, CD$_3$OD) δ ppm 8.37 (d, J=0.4 Hz, 1H), 7.66 (dd, J=8.4.1.6 Hz, 1H), 7.42 (dd, 8.8, 0.4 Hz, 1H), 7.25 (s, 2H), 4.17-4.11 (m, 1H), 3.48-3.34 (m, 4H), 3.16-2.98 (m, 2H), 2.58 (s, 6H), 2.28-2.20 (m, 2H), 1.98-1.88 (m, 2H), 1.53 (d, J=7.2 Hz, 6H), 1.33 (d, J=6.4 Hz, 6H).

The examples in Table 8 were prepared according to the general procedure described in Example 91.

TABLE 8

| Ex. No. | Structure | Mol Wt. | LCMS MH+ | Ret Time (min) | HPLC Method |
|---|---|---|---|---|---|
| 92 | 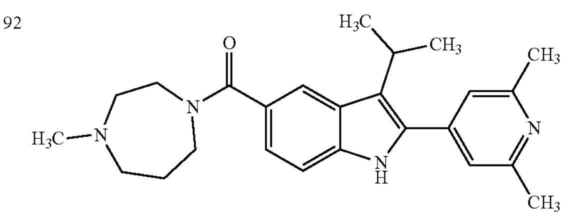 | 404.56 | 405.2 | 0.942 | F |
| 93 | 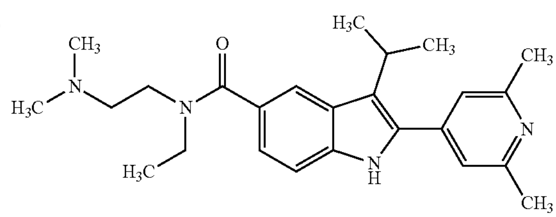 | 406.57 | 407.3 | 1.56 | E |
| 94 | 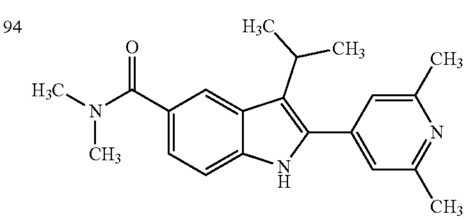 | 335.45 | 336.2 | 1.725 | E |

TABLE 8-continued
| Ex. No. | Structure | Mol Wt. | LCMS MH+ | Ret Time (min) | HPLC Method |
|---|---|---|---|---|---|
| 95 | 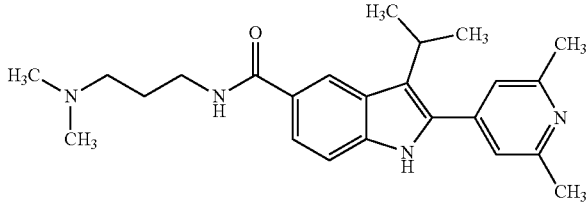 | 392.55 | 393.2 | 1.34 | E |
| 96 | 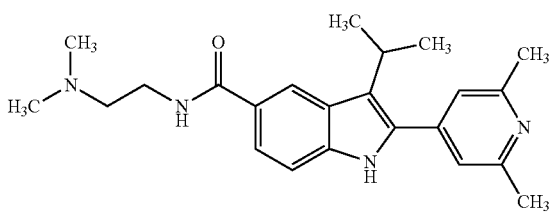 | 378.52 | 379.2 | 1.38 | E |
| 97 | 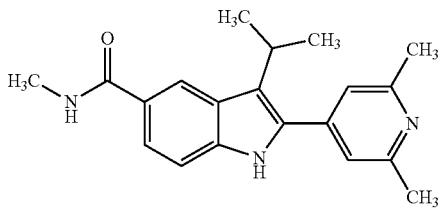 | 321.42 | 322.2 | 1.569 | E |
| 98 | 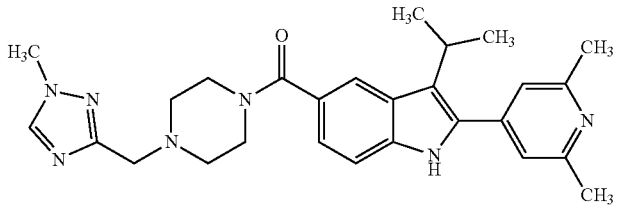 [SMILES: Cc1cc(-c2[nH]c3ccc(C(=O)N4CCN(Cc5ncn(C)n5)CC4)cc3c2C(C)C)cc(C)n1] | 471.61 | 472.4 | 1.36 | QC-ACN-AA-XB |
| 99 | 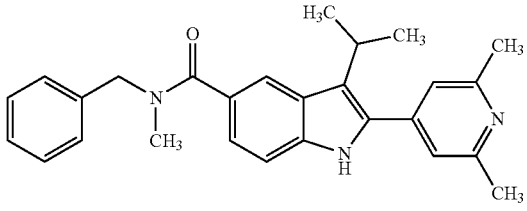 | 411.55 | 412.2 | 2.1 | QC-ACN-AA-XB |
| 100 | 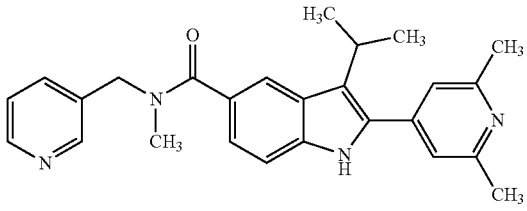 [SMILES: Cc1cc(-c2[nH]c3ccc(C(=O)N(C)Cc4cccnc4)cc3c2C(C)C)cc(C)n1] | 412.54 | 413.1 | 0.95 | QC-ACN-TFA-XB |
| 101 | 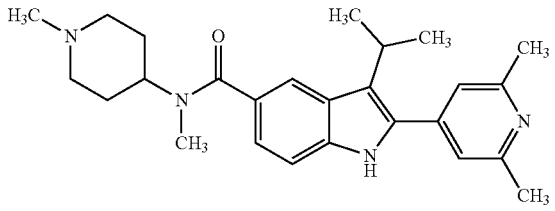 | 418.59 | 419.2 | 0.95 | QC-ACN-TFA-XB |

TABLE 8-continued

| Ex. No. | Structure | Mol Wt. | LCMS MH+ | Ret Time (min) | HPLC Method |
|---|---|---|---|---|---|
| 102 | 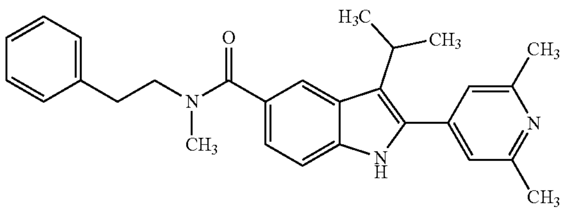 [SMILES: Cc1cc(-c2[nH]c3ccc(C(=O)N(C)CCc4ccccc4)cc3c2C(C)C)cc(C)n1] | 425.58 | 426.2 | 1.58 | QC-ACN-TFA-XB |
| 103 | 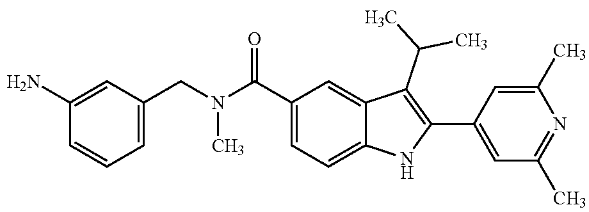 [SMILES: Cc1cc(-c2[nH]c3ccc(C(=O)N(C)Cc4cccc(N)c4)cc3c2C(C)C)cc(C)n1] | 426.56 | 427.4 | 1.03 | QC-ACN-TFA-XB |
| 104 | 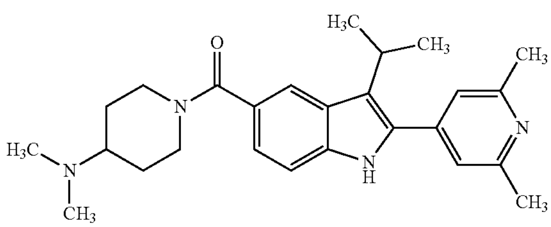 | 418.59 | 419.3 | 0.92 | QC-ACN-TFA-XB |
| 105 | 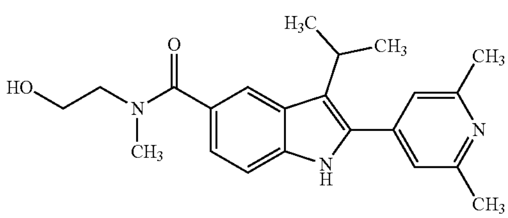 [SMILES: Cc1cc(-c2[nH]c3ccc(C(=O)N(C)CCO)cc3c2C(C)C)cc(C)n1] | 365.48 | 366.2 | 1.47 | QC-ACN-AA-XB |
| 106 | 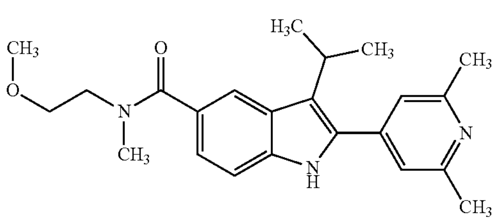 [SMILES: COCCN(C)C(=O)c1ccc2[nH]c(-c3cc(C)nc(C)c3)c(C(C)C)c2c1] | 379.5 | 380.2 | 1.72 | QC-ACN-AA-XB |

Example 107

(2-(2,6-dimethylpyridin-4-yl)-3-isopropyl-1H-indol-5-yl)(hexahydropyrrolo[3,4-c]pyrrol-2(1H)-yl) methanone, HCl (107)

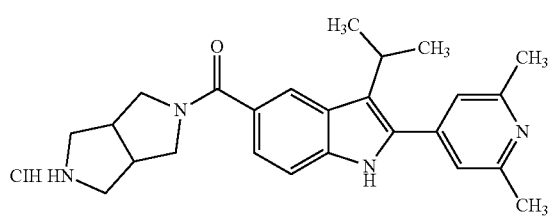

Intermediate 107A: tert-butyl 5-(2-(2,6-dimethylpyridin-4-yl)-3-isopropyl-1H-indole-5-carbonyl)hexahydro pyrrolo[3,4-c]pyrrole-2(1H)-carboxylate (107A)

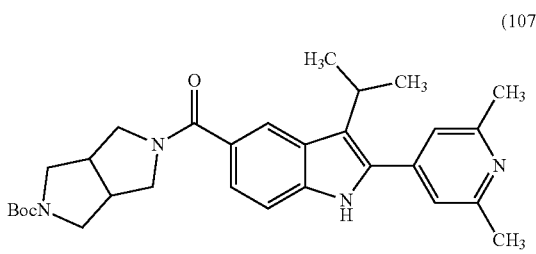

To a solution of 2-(2,6-dimethylpyridin-4-yl)-3-isopropyl-H-indole-5-carboxylic acid, HCl (0.060 g, 0.174 mmol) in DMF (2.00 mL) were added tert-butyl hexahydropyrrolo[3,4-c]pyrrole-2(1H)-carboxylate (0.055 g, 0.261 mmol), TEA (0.2 mL, 1.435 mmol) and HATU (0.132 g, 0.348 mmol) at room temperature. The reaction mixture was stirred at same temperature for 3 h. Crude LCMS showed formation of product and no starting material. The reaction was quenched with water (5 mL). The reaction mixture was extracted with DCM (2×10 mL), the combined organic extracts were dried (Na$_2$SO$_4$) and concentrated to afford crude tert-butyl 5-(2-(2,6-dimethylpyridin-4-yl)-3-isopropyl-1H-indole-5-carbonyl)hexahydropyrrolo[3,4-c]pyrrole-2(1H)-carboxylate as a gummy solid. LCMS retention time 0.78 min [G]. MS m/z: 503.2 [M+H]$^+$.

Example 107

To a solution of tert-butyl 5-(2-(2,6-dimethylpyridin-4-yl)-3-isopropyl-1H-indole-5-carbonyl)hexahydropyrrolo[3,4-c]pyrrole-2(1H)-carboxylate (0.087 g, 0.174 mmol) in dioxane (1.0 mL) was added 4 M HCl in dioxane (1 mL) at room temperature. The mixture was stirred at the same temperature for 2 h. Crude LCMS showed formation of product. The reaction mass was concentrated to get crude compound. The crude material was purified by Prep HPLC method D2, fractions containing the product were combined and dried using Genevac centrifugal evaporator to afford (2-(2,6-dimethylpyridin-4-yl)-3-isopropyl-1H-indol-5-yl)(hexahydropyrrolo[3,4-c]pyrrol-2(1H)-yl)methanone, 2 HCl (0.065 g, 0.137 mmol, 78% yield) as a pale solid. LCMS retention time 1.323 min [E]. MS m/z: 403.2 [M+H]$^+$; $^1$H NMR (400 MHz, CD$_3$OD) δ ppm 8.13 (d, J=0.4 Hz, 1H), 7.75 (s, 2H), 7.56-7.53 (m, 1H), 7.49-7.47 (m, 1H), 4.00-4.93 (m, 2H), 3.76-3.52 (m, 6H), 3.28-3.17 (m, 3H), 2.80 (s, 6H), 1.58 (d, J=6.8 Hz, 6H).

The example in Table 9 was prepared according to the general procedure described in Example 107.

TABLE 9

| Ex. No. | Structure | Mol Wt. | LCMS MH$^+$ | Ret Time (min) | HPLC Method |
|---|---|---|---|---|---|
| 108 | ![structure] | 376.5 | 377.1 | 1.12 | QC-ACN-AA-XB |

Example 109

(2-(2,6-dimethylpyridin-4-yl)-3-isopropyl-1H-indol-5-yl)(5-methylhexahydropyrrolo[3,4-c]pyrrol-2(1H)-yl)methanone

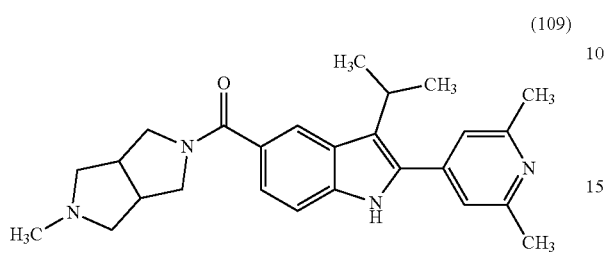

(109)

To a solution of (2-(2,6-dimethylpyridin-4-yl)-3-isopropyl-1H-indol-5-yl) (hexahydropyrrolo[3,4-c]pyrrol-2(1H)-yl)methanone, 2 HCl (0.048 g, 0.101 mmol) in MeOH (3.00 mL) was added formaldehyde in water (0.5 mL, 7.26 mmol). The reaction mixture was cooled to 0° C. and acetic acid (0.20 mL, 3.49 mmol) was added. The reaction mixture was stirred at room temperature for 3 h. Again the reaction mixture was cooled to 0° C. and sodium cyanoborohydride (0.032 g, 0.505 mmol) was added. The reaction was allowed to sit at room temperature for 16 h. Crude LCMS showing no starting material and formation of product. The reaction was quenched with water (5 mL). The reaction mixture was concentrated to remove methanol, extracted with 10% MeOH in DCM (2×10 mL), the combined organic extracts was dried (Na$_2$SO$_4$) and concentrated to get crude compound. The crude material was purified by Prep HPLC method D2, fractions containing the product were combined and dried using Genevac centrifugal evaporator to afford (2-(2,6-dimethylpyridin-4-yl)-3-isopropyl-1H-indol-5-yl)(5-methylhexahydropyrrolo[3,4-c]pyrrol-2(1H)-yl)methanone (0.0181 g, 0.043 mmol, 42.5% yield) as a pale solid. LCMS retention time 1.371 min [E]. MS m/z: 417.2 [M+H]$^+$; $^1$H NMR (400 MHz, CD$_3$OD) δ ppm 7.99 (d, J=1.2 Hz, 1H), 7.44 (d, J=8.4 Hz, 1H), 7.33 (dd, J=8.8, 1.6 Hz, 1H), 7.24 (s, 2H), 3.88-3.81 (m, 2H), 3.78-3.55 (m, 2H), 3.48-3.40 (m, 1H), 3.14-2.92 (m, 4H), 2.58-2.52 (m, 8H), 2.49 (s, 3H), 1.51 (d, J=7.2 Hz, 6H).

The example in Table 10 was prepared according to the general procedure described in Example 109

Example 111

2-(dimethylamino)-1-(5-(2-(2,6-dimethylpyridin-4-yl)-3-isopropyl-1H-indole-5-carbonyl)hexahydropyrrolo[3,4-c]pyrrol-2(1H)-yl)ethanone

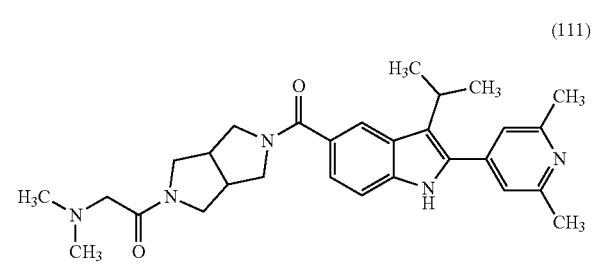

(111)

To a solution of (2-(2,6-dimethylpyridin-4-yl)-3-isopropyl-1H-indol-5-yl) (hexahydropyrrolo[3,4-c]pyrrol-2(1H)-yl)methanone, 2 HCl (0.025 g, 0.053 mmol) and 2-(dimethylamino)acetic acid (8.13 mg, 0.079 mmol) in DMF (2.00 mL) were added TEA (0.1 mL, 0.717 mmol) and HATU (0.040 g, 0.105 mmol) at room temperature. The reaction mixture was stirred at same temperature for 2 h. Crude LCMS showed formation of product and no starting material. The crude material was purified by Prep HPLC method D2, fractions containing the product were combined and dried using Genevac centrifugal evaporator to afford 2-(dimethylamino)-1-(5-(2-(2,6-dimethylpyridin-4-yl)-3-isopropyl-1H-indole-5-carbonyl)hexahydropyrrolo[3,4-c]pyrrol-2 (1H)-yl)ethanone (0.0138 g, 0.027 mmol, 52% yield) as a pale solid. LCMS retention time 1.393 min [E]. MS m/z: 488.3 [M+H]$^+$; $^1$H NMR (400 MHz, CD$_3$OD) δ ppm 8.02 (s, 1H), 7.44 (d, J=8.4 Hz, 1H), 7.35 (dd, J=8.8, 1.6 Hz, 1H), 7.24 (s, 2H), 3.98-3.90 (m, 2H), 3.89-3.51 (m, 8H), 3.49-3.40 (m, 3H), 2.57 (s, 6H), 2.53 (bs, 6H), 1.94 (s, 6H), 1.50 (d, J=7.2 Hz, 6H).

TABLE 10

| Ex. No. | Structure | Mol Wt. | LCMS MH$^+$ | Ret Time (min) | HPLC Method |
|---|---|---|---|---|---|
| 110 | ![structure] | 444.62 | 445.3 | 1.463 | E |

Example 112

(hexahydropyrrolo[3,4-c]pyrrol-2(1H)-yl)(3-isopropyl-2-(2-methyl pyridin-4-yl)-1H-indol-5-yl)methanone, HCl (112)

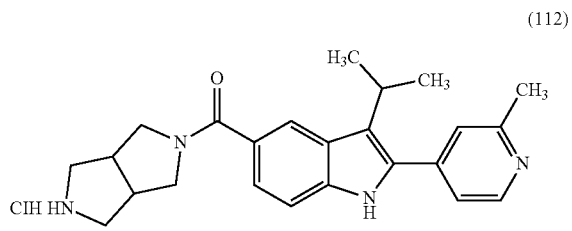

Intermediate 112A: Methyl 3-isopropyl-2-(2-methylpyridin-4-yl)-1H-indole-5-carboxylate (112A)

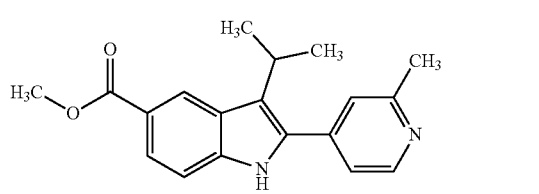

A solution of methyl 2-bromo-3-isopropyl-1H-indole-5-carboxylate (0.400 g, 1.351 mmol), 2-methyl-4-(4,4,5,5-tetramethyl-1,3,2-dioxaborolan-2-yl)pyridine (0.621 g, 2.84 mmol) and cesium carbonate (1.320 g, 4.05 mmol) in dioxane (10.00 mL) and water (2.500 mL) was degassed for 30 min. Next, Pd(Ph$_3$P)$_4$ (0.312 g, 0.270 mmol) was added and the reaction mixture was stirred at 90° C. for 16 h. Crude LCMS showed formation of product and no starting material. The reaction was quenched with water (5 mL). The reaction mixture was extracted with DCM (2×40 mL), the combined organic extracts were washed with brine (10 mL), dried (Na$_2$SO$_4$) and concentrated to get crude compound. The crude material was purified by column chromatography using 40 g silica column, compound was eluted in ethyl acetate, the fractions were collected and concentrated to afford methyl 3-isopropyl-2-(2-methylpyridin-4-yl)-1H-indole-5-carboxylate (0.550 g, 0.856 mmol, 63% yield) as a gummy solid. LCMS retention time 0.76 min [G]. MS m/z: 309.6 (M+H);

Intermediate 112B: 3-isopropyl-2-(2-methylpyridin-4-yl)-1H-indole-5-carboxylic Acid (112B)

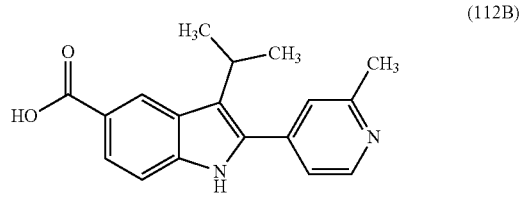 [SMILES: Cc1cc(-c2[nH]c3ccc(C(=O)O)cc3c2C(C)C)ccn1]

To a solution of methyl 3-isopropyl-2-(2-methylpyridin-4-yl)-1H-indole-5-carboxylate (0.552 g, 0.859 mmol) in THF (8.00 mL), MeOH (4.00 mL) and water (2.000 mL) was added lithium hydroxide (0.103 g, 4.30 mmol) at room temperature. The reaction mixture was stirred at 75° C. for 16 h. Crude LCMS showed formation of product and no starting material. The reaction mass was concentrated. The slurry was dissolved in water (10 mL) and the aqueous layer was washed with EtOAc (20 mL). The aqueous layer was acidified with 1.5 N HCl at 0° C. The resulting precipitated solid was filtered, washed with water, then dried under vacuum to afford 3-isopropyl-2-(2-methylpyridin-4-yl)-1H-indole-5-carboxylic acid (0.216 g, 0.734 mmol, 85% yield) as a yellow solid. LCMS retention time 0.60 min [G]. MS m/z: 295.1 (M+H).

Intermediate 112C: tert-butyl 5-(3-isopropyl-2-(2-methylpyridin-4-yl)-1H-indole-5-carbonyl)hexahydropyrrolo[3,4-c]pyrrole-2(1H)-carboxylate (112C)

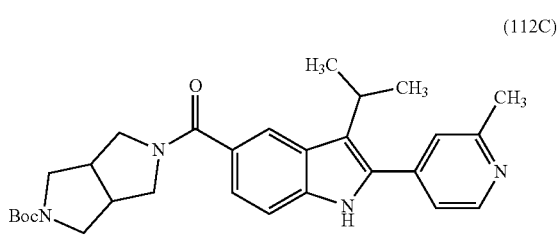 [SMILES: Cc1cc(-c2[nH]c3ccc(C(=O)N4CC5CN(C(=O)OC(C)(C)C)CC5C4)cc3c2C(C)C)ccn1]

To a solution of 3-isopropyl-2-(2-methylpyridin-4-yl)-1H-indole-5-carboxylic acid (0.200 g, 0.679 mmol) and tert-butyl hexahydropyrrolo[3,4-c]pyrrole-2(1H)-carboxylate (0.144 g, 0.679 mmol) in DCM (4.00 mL) and DMF (4.00 mL) was added EDC (0.130 g, 0.679 mmol) at room temperature. The reaction mixture was stirred at same temperature for 4 h. Crude LCMS showed formation of product. The reaction was quenched with water (5 mL). The reaction mixture was extracted with 10% MeOH in DCM (2×20 mL). The combined organic extracts was dried (Na$_2$SO$_4$) and concentrated to get crude compound. The crude material was purified by column chromatography using 12 g silica column. The compound was eluted in ethyl acetate, the fraction was collected and concentrated to afford tert-butyl 5-(3-isopropyl-2-(2-methylpyridin-4-yl)-1H-indole-5-carbonyl) hexahydropyrrolo[3,4-c]pyrrole-2(1H)-carboxylate (0.201 g, 0.411 mmol, 60.5% yield) as a white solid. LCMS retention time 0.88 min [G]. MS m/z: 489.3 (M+H).

Example 12

To a solution of tert-butyl 5-(3-isopropyl-2-(2-methylpyridin-4-yl)-1H-indole-5-carbonyl)hexahydropyrrolo[3,4-c]pyrrole-2(1H)-carboxylate (0.200 g, 0.409 mmol) in dioxane (2 mL) was added 4N HCl in dioxane (1.00 mL, 4.00 mmol) at 0° C. The reaction mixture was stirred at room temperature for 2 h. Crude LCMS showed formation of product and no starting material. The reaction mass was concentrated and the residue was triturated with diethyl ether (2×5 mL) to afford (hexahydropyrrolo[3,4-c]pyrrol-2(1H)-yl)(3-isopropyl-2-(2-methylpyridin-4-yl)-1H-indol-5-yl)methanone, HCl (0.162 g, 0.357 mmol, 87% yield) as a yellow color solid. LCMS retention time 1.74 min [E]. MS m/z: 389.2 [M+H]$^+$; $^1$H NMR (400 MHz, CD$_3$OD) δ ppm 11.52 (s, 0.4H, exchanged with CD$_3$OD), 8.69 (d, J=6.8 Hz, 1H), 8.14 (s, 1H), 8.00-7.97 (m, 2H), 7.56-7.48 (m, 2H), 3.98-3.91 (m, 2H), 3.78-3.51 (m, 5H), 3.34-3.16 (m, 4H), 2.85 (s, 3H), 1.58 (d, J=7.2 Hz, 6H).

The examples in Table 11 were prepared according to the general procedure described for Example 112.

TABLE 11

| Ex. No. | Structure | Mol Wt. | LCMS MH+ | Ret Time (min) | HPLC Method |
|---|---|---|---|---|---|
| 113 | 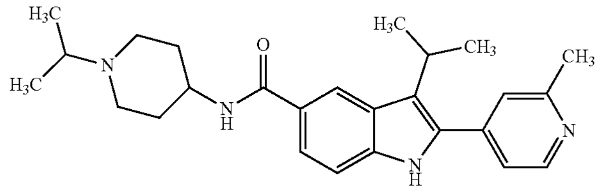 [SMILES: Cc1cc(-c2[nH]c3ccc(C(=O)NC4CCN(C(C)C)CC4)cc3c2C(C)C)ccn1] | 418.59 | 419 | 1 | E |
| 114 | 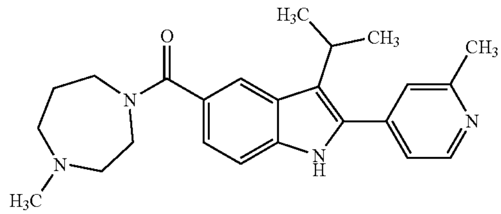 | 390.53 | 391.3 | 0.536 | F |

Example 115

(3-isopropyl-2-(2-methylpyridin-4-yl)-1H-indol-5-yl)(5-methylhexahydropyrrolo[3,4-c]pyrrol-2(1H)-yl)methanone

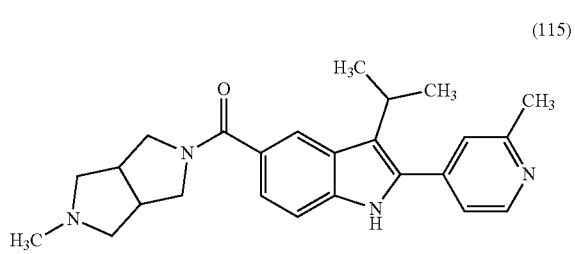

(115)

To a solution of (hexahydropyrrolo[3,4-c]pyrrol-2(1H)-yl)(3-isopropyl-2-(2-methylpyridin-4-yl)-1H-indol-5-yl)methanone hydrochloride (0.021 g, 0.049 mmol) in MeOH (2.50 mL) were added formaldehyde in water (0.1 mL, 1.271 mmol) and acetic acid (0.1 mL, 1.747 mmol) at 0° C. The reaction mixture was stirred at room temperature for 6 h. Again the reaction mixture was cooled to 0° C. and sodium borohydride (5.61 mg, 0.148 mmol) was added portion wise. The reaction mixture was stirred at room temperature for 16 h. Crude LCMS showed formation of product and no starting material. The reaction mass was concentrated to get crude compound. The crude material was purified by Prep HPLC method D2, fractions containing the product were combined and dried using Genevac centrifugal evaporator to afford (3-isopropyl-2-(2-methylpyridin-4-yl)-1H-indol-5-yl)(5-methylhexahydropyrrolo[3,4-c]pyrrol-2(1H)-yl)methanone (0.009 g, 0.022 mmol, 45% yield) as a pale solid. LCMS retention time 1.039 min [E]. MS m/z: 403.3 [M+H]+; $^1$H NMR (400 MHz, CD$_3$OD) δ ppm 8.49 (d, J=5.6 Hz, 1H), 8.00 (d, J=0.8 Hz, 1H), 7.46-7.44 (m, 2H), 7.40 (dc, J=5.2, 1.2 Hz, 1H), 7.34 (dd, J=8.2, 1.2 Hz, 1H), 3.88-3.78 (m, 2H), 3.75-3.54 (m, 2H), 3.50-3.41 (m, 2H), 3.13-2.87 (m, 4H), 2.62 (s, 3H), 2.60-2.51 (m, 1H), 2.47 (s, 3H), 1.51 (d, J=7.2 Hz, 6H).

The following Example was prepared in a similar manner to the product of Example 115

TABLE 12

| Ex. No. | Structure | Mol Wt. | LCMS MH+ | Ret Time (min) | HPLC Method |
|---|---|---|---|---|---|
| 116 | 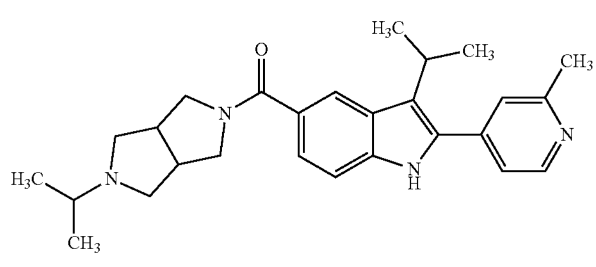 [SMILES: Cc1cc(-c2[nH]c3ccc(C(=O)N4CC5CN(C(C)C)CC5C4)cc3c2C(C)C)ccn1] | 430.6 | 431 | 1.12 | E |

Example 117

2-(5-(3-isopropyl-2-(2-methylpyridin-4-yl)-1H-indole-5-carbonyl)hexahydropyrrolo[3,4-c]pyrrol-2(1H)-yl)-N,N-dimethylacetamide

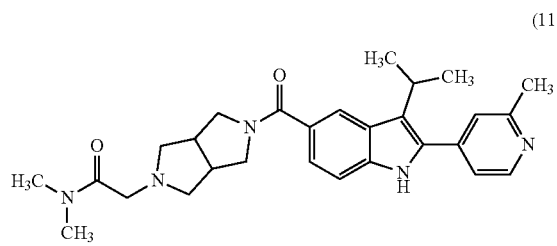

(117)

To a solution of (hexahydropyrrolo[3,4-c]pyrrol-2(H)-yl)(3-isopropyl-2-(2-methylpyridin-4-yl)-1H-indol-5-yl)methanone hydrochloride (0.021 g, 0.049 mmol) in THF (2.00 mL) and DMF (0.500 mL) solvent mixture was added TEA (0.1 mL, 0.717 mmol) at room temperature. The reaction mixture was stirred for 5 min. and then 2-chloro-N,N-dimethylacetamide (9.01 mg, 0.074 mmol) was added. Stirring was continued at same temperature for 16 h. Crude LCMS showed formation of product and no starting material. The reaction mass was concentrated to get crude compound. The crude material was purified by Prep HPLC method D2, fractions containing the product were combined and dried using Genevac centrifugal evaporator to afford 2-(5-(3-isopropyl-2-(2-methylpyridin-4-yl)-1H-indole-5-carbonyl)hexahydropyrrolo[3,4-c]pyrrol-2(1H)-yl)-N,N-dimethylacetamide (0.009 g, 0.018 mmol, 37% yield) as a pale solid. LCMS retention time 1.172 min [E]. MS m/z: 474.4 [M+H]$^+$; $^1$H NMR (400 MHz, DMSO-d$_6$) δ ppm 11.46 (s, 1H), 8.55 (d, J=7.2 Hz, 1H), 7.86 (s, 1H), 7.41-7.38 (m, 2H), 7.31 (dd, 6.0, 1.2 Hz, 1H), 7.26 (dd, 8.4, 1.6 Hz, 1H), 3.74-3.69 (m, 2H), 3.53-3.45 (m, 2H), 3.25 (s, 2H), 3.00 (s, 3H), 2.80 (s, 3H), 2.79-2.72 (m, 2H), 2.60-2.51 (m, 8H), 1.43 (d, J=7.2 Hz, 6H).

The example in Table 13 was prepared according to the general procedure described in Example 117.

Example 119

1-(5-(3-isopropyl-2-(2-methylpyridin-4-yl)-1H-indole-5-carbonyl)hexahydropyrrolo[3,4-c]pyrrol-2(1H)-yl)-2-(methylamino)ethanone

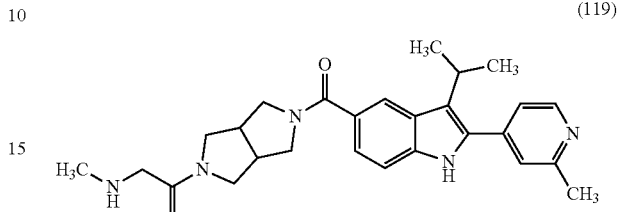

(119)

Intermediate 119A: 2-(5-(3-isopropyl-2-(2-methylpyridin-4-yl)-1H-indole-5-carbonyl) hexahydropyrrolo[3,4-c]pyrrol-2(1H)-yl)-N,N-dimethylacetamide

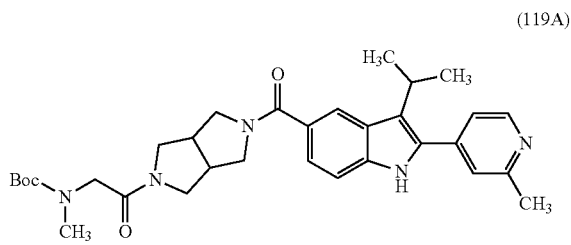 [SMILES: Cc1cc(-c2[nH]c3ccc(C(=O)N4CC5CN(C(=O)CN(C)C(=O)OC(C)(C)C)CC5C4)cc3c2C(C)C)ccn1]

(119A)

To a solution of (hexahydropyrrolo[3,4-c]pyrrol-2(1H)-yl)(3-isopropyl-2-(2-methylpyridin-4-yl)-1H-indol-5-yl)methanone hydrochloride (0.023 g, 0.054 mmol) in DMF (2.00 mL) were added TEA (0.023 mL, 0.162 mmol), 2-((tert-butoxycarbonyl) (methyl)amino)acetic acid (0.015 g, 0.081 mmol) and HATU (0.041 g, 0.108 mmol) at room temperature. The mixture was stirred at the same temperature for 16 h. Crude LCMS showed formation of product and no starting material. The reaction was quenched with water, extracted with 10% MeOH in DCM (2×10 mL), combined organic extracts was washed with brine (5 mL), dried (Na$_2$SO$_4$) and concentrated to afford crude tert-butyl (2-(5-(3-isopropyl-2-(2-methylpyridin-4-yl)-1H-indole-5-carbonyl)hexahydropyrrolo [3,4-c]pyrrol-2(1H)-yl)-2-oxoethyl)

TABLE 13

| Ex. No. | Structure | Mol Wt. | LCMS MH$^+$ | Ret Time (min) | HPLC Method |
|---|---|---|---|---|---|
| 118 | 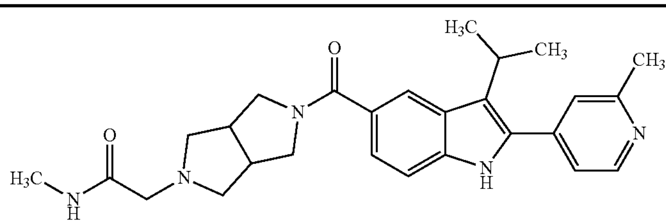 | 459.59 | 460 | 1.2 | E |

(methyl)carbamate (0.039 g, 0.054 mmol, 99% yield) as gummy solid. LCMS retention time 0.71 min [E]. MS m/z: 560.8 [M+H]+.

Example 119

To a solution of tert-butyl (2-(5-(3-isopropyl-2-(2-methylpyridin-4-yl)-1H-indole-5-carbonyl)hexahydropyrrolo[3,4-c]pyrrol-2(1H)-yl)-2-oxoethyl)(methyl)carbamate (0.030 g, 0.054 mmol) in DCM (2.00 mL) was added TFA (0.15 mL, 1.947 mmol) at 0° C. The mixture was stirred at room temperature for 1 h. Crude LCMS showed formation of product and no starting material. The reaction mass was concentrated to get crude compound. The crude material was purified by Prep HPLC method D2, fractions containing the product were combined and dried using Genevac centrifugal evaporator to afford 1-(5-(3-isopropyl-2-(2-methylpyridin-4-yl)-1H-indole-5-carbonyl) hexahydropyrrolo[3,4-c]pyrrol-2(1H)-yl)-2-(methylamino)ethanone, TFA (0.001 g, 1.692 µmol, 3% yield) as a pale solid. LCMS retention time 0.91 min [E]. MS m/z: 460.4 [M+H]+; 1H NMR (400 MHz, DMSO-d6) δ ppm 11.45 (s, 1H), 8.55 (d, J=7.2 Hz, 1H), 7.92 (s, 1H), 7.43-7.38 (m, 2H), 7.33-7.27 (m, 2H), 3.79-3.71 (m, 4H), 3.43-3.34 (m, 3H), 3.32-3.17 (m, 3H), 3.03-2.84 (m, 3H), 2.55 (s, 3H), 2.29 (s, 3H), 1.43 (d, J=7.2 Hz, 6H).

The example in Table 14 was prepared according to the general procedure for Example 119.

Intermediate 121A:
3-isopropyl-1H-indole-5-carboxylic Acid

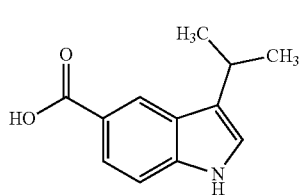

(121A)

To a solution of methyl 3-isopropyl-1H-indole-5-carboxylate (1.350 g, 6.21 mmol) in a solvent mixture of THF (12.00 mL), MeOH (6.00 mL) and THF (12.00 mL) was added LiOH (0.744 g, 31.1 mmol) at room temperature. The reaction mixture was stirred at 75° C. for 5 h. Crude LCMS showed formation of product and no starting material. The reaction mass was concentrated, the residue was dissolved in water (5 mL), brought to acidic pH with 1.5 N HCl, then the precipitated solid was filtered, washed with water and dried under vacuum to afford 3-isopropyl-1H-indole-5-carboxylic acid (1.015 g, 4.99 mmol, 80% yield) as white solid. LCMS retention time 0.81 min [G]. MS m/z: 204.5 [M+H]+

TABLE 14

| Ex. No. | Structure | Mol Wt. | LCMS MH+ | Ret Time (min) | HPLC Method |
|---|---|---|---|---|---|
| 120 | 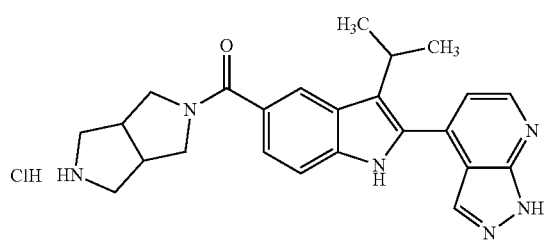 | 473.62 | 474 | 0.99 | E |

Example 121

(hexahydropyrrolo[3,4-c]pyrrol-2(1H)-yl)(3-isopropyl-2-(1H-pyrazolo[3,4-b]pyridin-4-yl)-1H-indol-5-yl)methanone, HCl (121)

Intermediate 121B: tert-butyl 5-(3-isopropyl-1H-indole-5-carbonyl)hexahydropyrrolo [3,4-c]pyrrole-2(1H)-carboxylate

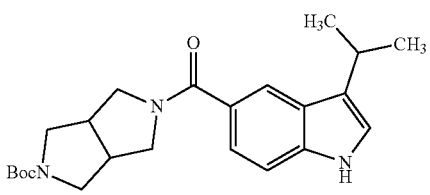

(121B)

To a solution of 3-isopropyl-1H-indole-5-carboxylic acid (0.500 g, 2.460 mmol) and tert-butyl hexahydropyrrolo[3,4-c]pyrrole-2(1H)-carboxylate (0.574 g, 2.71 mmol) in DCM (10.00 mL) and DMF (10.00 mL) solvent was added EDC (0.707 g, 3.69 mmol) at room temperature. The mixture was stirred at the same temperature for 16 h. Crude LCMS showed formation of product and no starting material, the reaction was quenched with water (10 mL), extracted with DCM (2×20 mL), combined organic extracts was washed with brine (5 mL), dried (Na$_2$SO$_4$) and concentrated to get crude compound. The crude material was purified by column chromatography using 24 g silica column, compound was eluted in ethyl acetate, the fractions were collected and concentrated to afford tert-butyl 5-(3-isopropyl-1H-indole-5-carbonyl)hexahydropyrrolo[3,4-c]pyrrole-2(1H)-carboxylate (0.866 g, 2.179 mmol, 89% yield) as a gummy material. LCMS retention time 0.95 min [G]. MS m/z: 342.6 [M+H-tBu]$^+$.

Intermediate 121C: tert-butyl 5-(2-bromo-3-isopropyl-1H-indole-5-carbonyl)hexahydropyrrolo[3,4-c]pyrrole-2(1H)-carboxylate

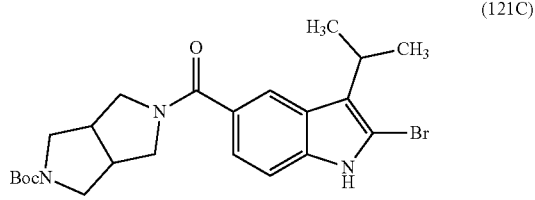 [SMILES: CC(C)c1c(Br)[nH]c2ccc(C(=O)N3CC4CN(C(=O)OC(C)(C)C)CC4C3)cc12]

(121C)

To a solution of tert-butyl 5-(3-isopropyl-1H-indole-5-carbonyl)hexahydropyrrolo [3,4-c]pyrrole-2(1H)-carboxylate (0.510 g, 1.283 mmol) in DCE (25.00 mL) was added dropwise NBS (0.206 g, 1.155 mmol) in DCE (20 mL) at 0° C. The mixture was stirred at room temperature for 15 min. Crude LCMS showed formation of product. The reaction was quenched with water (20 mL). The two layers were separated. The aqueous layer was extracted with DCM (30 mL). The combined organic extracts were dried (Na$_2$SO$_4$) and concentrated to get crude compound. The crude material was purified by ISCO using 24 g silica column, compound was eluted in 90% ethyl acetate in hexanes, the fractions were collected and concentrated to afford tert-butyl 5-(2-bromo-3-isopropyl-1H-indole-5-carbonyl)hexahydropyrrolo[3,4-c]pyrrole-2(1H)-carboxylate (0.164 g, 0.344 mmol, 27% yield) as a white solid. LCMS retention time 1.10 min [G]. MS m/z: 422.1 [M+2)+H-tBu]$^+$.

Intermediate 121D: tert-butyl 5-(3-isopropyl-2-(1-trityl-1H-pyrazolo[3,4-b]pyridin-4-yl)-1H-indole-5-carbonyl) hexahydropyrrolo[3,4-c] pyrrole-2(1H)-carboxylate

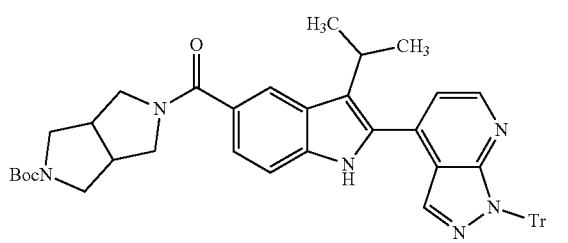

(121D)

To a solution of tert-butyl 5-(2-bromo-3-isopropyl-1H-indole-5-carbonyl) hexahydropyrrolo[3,4-c]pyrrole-2(1H)-carboxylate (0.075 g, 0.157 mmol), potassium phosphate tribasic (0.050 g, 0.236 mmol) and 4-(4,4,5,5-tetramethyl-1,3,2-dioxaborolan-2-yl)-1-trityl-1H-pyrazolo[3,4-b]pyridine (0.092 g, 0.189 mmol) in dioxane (4.00 mL) and water (1.000 mL) was degassed with nitrogen for 20 min. Next, PdCl$_2$(dppf)-CH$_2$Cl$_2$ adduct (6.43 mg, 7.87 µmol) was added and the reaction mixture was stirred at 80° C. for 18 h. Crude LCMS showed no further change in the reaction mass. The reaction mixture was diluted with DCM (20 mL) and water (1 mL) and the two layers were separated. The aqueous layer was extracted with DCM (20 mL). The combined organic extracts was dried (Na$_2$SO$_4$) and concentrated to get crude compound. The crude material was purified by column chromatography using 12 g Silica column, compound was eluted in 80% ethyl acetate in hexane, the fractions were collected and concentrated to afford tert-butyl 5-(3-isopropyl-2-(1-trityl-1H-pyrazolo[3,4-b]pyridin-4-yl)-1H-indole-5-carbonyl)hexahydropyrrolo[3,4-c]pyrrole-2(1H)-carboxylate (0.060 g, 0.079 mmol, 50% yield) as a gummy solid. LCMS retention time 1.10 min [G]. MS m/z: 757.5 [M+H]$^+$:

Example 121

To a solution of tert-butyl 5-(3-isopropyl-2-(1-trityl-1H-pyrazolo[3,4-b]pyridin-4-yl)-1H-indole-5-carbonyl)hexahydropyrrolo[3,4-c]pyrrole-2(1H)-carboxylate (0.032 g, 0.042 mmol) in dioxane (2.00 mL) was added hydrochloric acid 4M in dioxane (1.00 mL, 32.9 mmol) at 0° C. The reaction mixture was stirred at room temperature for 4 h. Crude LCMS showed formation of product and no starting material. The reaction mass was concentrated and triturated with diethyl ether (2×2 mL) to get crude compound. The crude material was purified by Prep HPLC method D2, fractions containing the product were combined and dried using Genevac centrifugal evaporator to afford (hexahydropyrrolo[3,4-c]pyrrol-2(1H)-yl)(3-isopropyl-2-(1H-pyrazolo [3,4-b]pyridin-4-yl)-1H-indol-5-yl)methanone, HCl (0.002 g, 4.43 µmol, 10% yield) as a pale solid. LCMS retention time 1.10 min [E]. MS m/z: 415.3 [M+H]$^+$; $^1$H NMR (400 MHz, CD$_3$OD) δ ppm 8.61 (d, J=4.8 Hz, 1H), 8.16 (s, 1H), 8.08 (d, J=0.8 Hz, 1H), 7.53 (dd, J=8.8, 0.4 Hz, 1H), 7.7.41 (dd, J=8.4, 1.6 Hz, 1H), 7.31 (d, J=4.8 Hz, 1H), 3.98-3.91 (m, 2H), 3.78-3.46 (m, 2H), 3.49-3.38 (m, 3H), 3.18-2.96 (m, 4H), 1.52 (d, J=7.2 Hz, 6H).

Example 122

(3-(2,2-difluoroethyl)-2-(2,6-dimethylpyridin-4-yl)-1H-indol-5-yl)(hexahydropyrrolo [3,4-c]pyrrol-2(1H)-yl)methanone

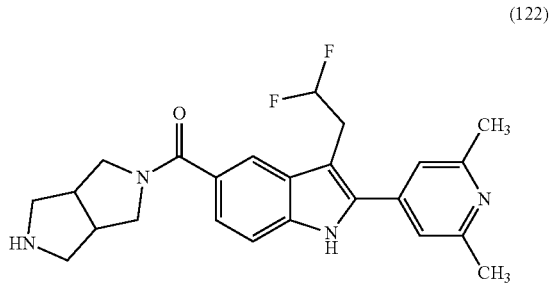 [SMILES: Cc1cc(-c2[nH]c3ccc(C(=O)N4CC5CNCC5C4)cc3c2CC(F)F)cc(C)n1]

(122)

119

Intermediate 122A: 5-bromo-1-tosyl-1H-indole

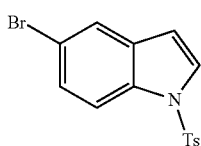

(122A)

To a stirred solution of 5-bromo-1H-indole (5.0 g, 25.5 mmol), TsCl (6.03 g, 31.6 mmol) and tetrabutylammonium hydrogen sulfate (0.63 g, 1.855 mmol) in toluene (100 mL) was added NaOH (50% solution in water, 10.20 g, 255 mmol) dropwise. The reaction mixture was stirred at room temperature for 16 h. The reaction was quenched with water (20 mL). The resulting two layers were separated, the aqueous layer was extracted with EtOAc (2×50 mL), the combined organic extracts was dried ($Na_2SO_4$) and concentrated to get crude material. The crude material was purified by ISCO using 40 g silica column, compound was eluted in 4% ethyl acetate in hexanes, the fractions were collected and concentrated to afford 5-bromo-1-tosyl-1H-indole (7.1 g, 20.27 mmol) as white solid. LCMS retention time=2.230 min [A]. MS m/z: 393.3 (M−H).

Intermediate 122B: 1-(5-bromo-1-tosyl-1H-indol-3-yl)-2,2-difluoroethane-1-one

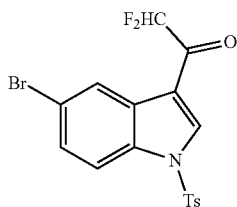

(122B)

Difluoroacetic anhydride (4.47 g, 25.7 mmol) was added to a suspension of $AlCl_3$ (6.85 g, 51.4 mmol) in DCM (50 mL). The reaction mixture was stirred for 15 min, then a solution of 5-bromo-1-tosyl-1H-indole (3 g, 8.57 mmol)) in DCM (30 mL) was added. The reaction mixture was stirred for 1 h at ambient temperature. The reaction was quenched with ice-water. The reaction mixture was extracted with DCM (2×50 mL), combined extracts was washed with aqueous $NaHCO_3$, brine, dried over $MgSO_4$, filtered and concentrated to get crude material. The crude material was purified by column chromatography using silica column, compound was eluted in 10% EtOAc in hexane, the fraction was collected and concentrated to afford 1-(5-bromo-1-tosyl-1H-indol-3-yl)-2,2-difluoroethanone (2.21 g, 4.1 mmol) as a crystalline solid. LCMS retention time=2.732 min [A]. MS m/z: 428.0 (M+H).

120

Intermediate 122C: 1-(5-bromo-1H-indol-3-yl)-2,2-difluoroethane-1-one

(122C)

To a solution of 1-(5-bromo-1-tosyl-1H-indol-3-yl)-2,2-difluoroethanone (0.2 g, 0.467 mmol) in THF (4 mL) and MeOH (4.00 mL) was added $Cs_2CO_3$ (0.45 g, 1.381 mmol) at room temperature. The reaction mixture was stirred at same temperature for 12 h. The reaction mixture was concentrated, the residue was diluted with minimum amount of water and undissolved solids was filtered and dried under vacuum to afford 1-(5-bromo-1H-indol-3-yl)-2,2-difluoroethanone (105 md, 0.244 mmol) as a white solid. LC retention time=2.233 min [A]. MS m/z: 276 (M+2)+H).

Intermediate 122D: 5-bromo-3-(2,2-difluoroethyl)-1H-indole

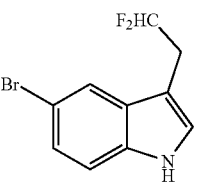

(122D)

To the stirred solution of 1-(5-bromo-1H-indol-3-yl)-2,2-difluoroethanone (0.25 g, 0.912 mmol) in THF (10 mL) was added $BH_3DMS$ (1.368 mL, 2.74 mmol) at 0° C. under nitrogen. The mixture was stirred at 80° C. for 20 h. The reaction mixture was quenched with water (2 mL) at 0° C., diluted with ethyl acetate (100 mL), washed with sodium bicarbonate (2×25 mL) and water (2×25 mL). The combined organic extracts was dried over anhydrous sodium sulphate, filtered and concentrated to get crude compound. The crude material was purified by column chromatography using 24 g silica gel column, compound was eluted at 8% ethyl acetate/hexane, the fractions were collected and concentrated to afford 5-bromo-3-(2,2-difluoroethyl)-1H-indole (120 mg, 0.438 mmol) as an oil. LCMS retention time=2.802 min [D]. MS m/z: 260 (M+H).

Intermediate 122E: Methyl 3-(2,2-difluoroethyl)-1H-indole-5-carboxylate

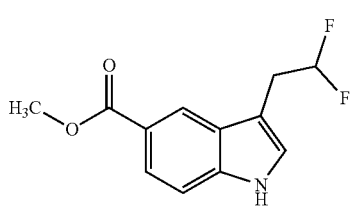

(122E)

To a solution of 5-bromo-3-(2,2-difluoroethyl)-1H-indole (3.0 g, 11.53 mmol) in methanol (100 mL) and DMF (100 mL) were added TEA (3.22 mL, 23.07 mmol), Pd(OAc)$_2$ (0.518 g, 2.307 mmol) and DPPF (1.918 g, 3.46 mmol). The mixture was degassed for 10 min with nitrogen and stirred at 90° C. under carbon monoxide atmosphere (80 psi) for 24 h. The reaction mixture was cooled to room temperature, volatiles was evaporated to get residue. The residue was dissolved in ethyl acetate, filtered and washed with ethyl acetate, combined organic layers were washed with water, brine, dried over sodium sulphate and evaporated to get crude compound. The crude material was purified by column chromatography using silica column 80 g, compound was eluted with 20% ethyl acetate in petroleum ether, the fractions were collected and concentrated to afford methyl 3-(2,2-difluoroethyl)-1H-indole-5-carboxylate (2.4 g, 10.03 mmol, 87% yield) as a light brown liquid. LCMS retention time 0.99 min [D] MS m/z: 240.2 (M+H).

Intermediate 122F: methyl 2-bromo-3-(2,2-difluoroethyl)-1H-indole-5-carboxylate

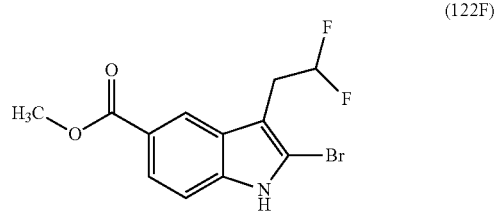 [SMILES: COC(=O)c1ccc2[nH]c(Br)c(CC(F)F)c2c1]

(122F)

A solution of NBS (1.607 g, 9.03 mmol) in DCE (120 mL) was added to a cooled solution of methyl 3-(2,2-difluoroethyl)-1H-indole-5-carboxylate (2.4 g, 10.03 mmol) in DCE (120 mL) at 0° C. The reaction mixture was stirred at the same temperature for 1.5 h. The reaction was quenched with cold water. The mixture was stirred for 15 min, the organic layer was separated, dried over sodium sulphate and concentrated to get crude material. The crude material was purified by ISCO using silica column 40 g, compound was eluted with 25% ethyl acetate in petroleum ether, the fractions were collected and concentrated to afford methyl 2-bromo-3-(2,2-difluoroethyl)-1H-indole-5-carboxylate (1.8 g, 5.66 mmol, 56% yield) as an off-white solid. LCMS retention time 1.05 min, [D] MS m/z: 320.0 ((M+2)+H).

Intermediate 122G: methyl 3-(2,2-difluoroethyl)-2-(4,4,5,5-tetramethyl-1,3,2-dioxa borolan-2-yl)-1H-indole-5-carboxylate

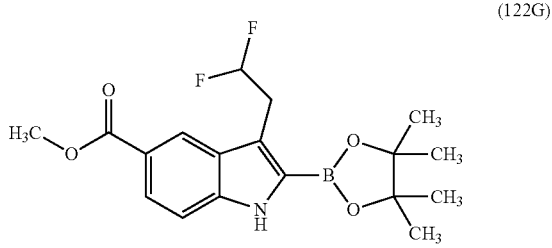

(122G)

To a solution of methyl 2-bromo-3-(2,2-difluoroethyl)-1H-indole-5-carboxylate (1.6 g, 5.03 mmol), bis(benzonitrile)palladium(II) chloride (0.411 g, 0.503 mmol) and SPhos (0.206 g, 0.503 mmol) in dioxane (25 mL) were added TEA (2.117 mL, 15.09 mmol) and pinacolborane (6.51 mL, 25.1 mmol) at room temperature. The mixture was degassed with nitrogen for 5 min. The reaction mixture was stirred at 80° C. for 1 h in a sealed tube. The reaction was quenched with cold water. The reaction mixture was diluted with ethyl acetate, filtered and washed with excess ethyl acetate. The combined organic layers were washed with water, brine, dried over sodium sulphate and evaporated to afford crude compound. The crude material was purified by column chromatography using silica column 40 g, compound was eluted with 25% ethyl acetate in petroleum ether, the fractions were collected and concentrated to afford methyl 3-(2,2-difluoroethyl)-2-(4,4,5,5-tetramethyl-1,3,2-dioxaborolan-2-yl)-1H-indole-5-carboxylate (1.3 g, 3.56 mmol, 71% yield) as an off-white solid. LCMS retention time 1.32 min [G], MS m/z: 366.3 (M+H).

Intermediate 122H: Methyl 3-(2,2-difluoroethyl)-2-(2,6-dimethylpyridin-4-yl)-1H-indole-5-carboxylate

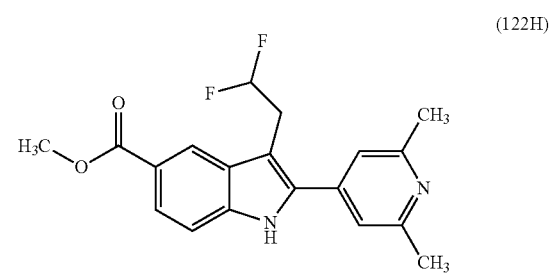

(122H)

To a degassed solution of methyl 3-(2,2-difluoroethyl)-2-(4,4,5,5-tetramethyl-1,3,2-dioxaborolan-2-yl)-1H-indole-5-carboxylate (1.2 g, 3.29 mmol) and 4-bromo-2,6-dimethylpyridine (0.734 g, 3.94 mmol) in dioxane (30.0 mL) and water (5.0 mL) were added PdCl$_2$ (dppf)-CH$_2$Cl$_2$ adduct (0.268 g, 0.329 mmol) and tripotassium phosphate (2.093 g, 9.86 mmol). The resulting reaction mixture was stirred at 95° C. for 5 h in a sealed tube. The reaction mixture was diluted with ethyl acetate, filtered and washed with excess ethyl acetate, combined organic layers were washed with water, brine, dried over sodium sulphate and evaporated to get crude compound. The crude material was purified by column chromatography using silica column 40 g, compound was eluted with 55-65% ethyl acetate in petroleum ether, the fractions were collected and concentrated to afford methyl 3-(2,2-difluoroethyl)-2-(2,6-dimethylpyridin-4-yl)-1H-indole-5-carboxylate (0.850 g, 2.468 mmol, 75% yield) as a off white solid. LCMS retention time 1.07 min [D]. MS m/z: 345.2 (M+H);

123

Intermediate 122I: 3-(2,2-difluoroethyl)-2-(2,6-dimethylpyridin-4-yl)-1H-indole-5-carboxylic Acid

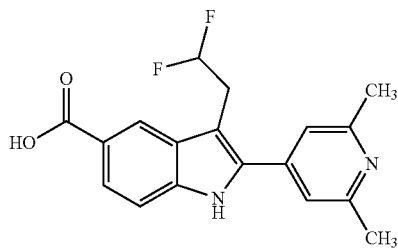

(122I)

A solution of lithium hydroxide (0.087 g, 3.63 mmol) in water (2.0 mL) was added to a solution of methyl 3-(2,2-difluoroethyl)-2-(2,6-dimethylpyridin-4-yl)-1H-indole-5-carboxylate (0.250 g, 0.726 mmol) in THF (5.0 mL) and MeOH (5.0 mL). The reaction mixture was stirred at 70° C. for 16 h. The reaction mixture was cooled to room temperature, volatiles was evaporated, the residue was diluted with water (10 mL), neutralized with 10% HCl, stirred for 30 min, the resulting solid compound was filtered, washed with minimum amount of water and petroleum ether to afford 3-(2,2-difluoroethyl)-2-(2,6-dimethylpyridin-4-yl)-1H-indole-5-carboxylic acid (0.200 g, 0.605 mmol, 83% yield) as an off-white solid. LCMS retention time 0.55 min [G], MS m/z: 331.2 (M+H).

Intermediate 122J: tert-butyl 5-(3-(2,2-difluoroethyl)-2-(2,6-dimethylpyridin-4-yl)-1H-indole-5-carbonyl) hexahydropyrrolo[3,4-c]pyrrole-2(1H)-carboxylate

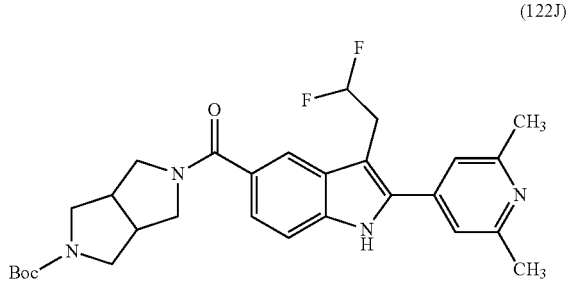 [SMILES: Cc1cc(-c2[nH]c3ccc(C(=O)N4CC5CN(C(=O)OC(C)(C)C)CC5C4)cc3c2CC(F)F)cc(C)n1]

(122J)

124

To a solution of 3-(2,2-difluoroethyl)-2-(2,6-dimethylpyridin-4-yl)-1H-indole-5-carboxylic acid (0.040 g, 0.121 mmol) and tert-butyl hexahydropyrrolo[3,4-c]pyrrole-2(1H)-carboxylate (0.039 g, 0.182 mmol) in DMF (4.0 mL) at 0° C., were added TEA (0.051 mL, 0.363 mmol) and HATU (0.055 g, 0.145 mmol). The mixture was stirred at room temperature for 16 h. Volatiles was evaporated, the residue was dissolved with excess DCM, and washed with water and brine. The organic layer was dried over sodium sulphate and concentrated to afford tert-butyl 5-(3-(2,2-difluoroethyl)-2-(2,6-dimethylpyridin-4-yl)-1H-indole-5-carbonyl)hexahydropyrrolo[3,4-c]pyrrole-2(1H)-carboxylate (0.055 g, 0.105 mmol, 87% yield). LCMS retention time 1.09 min [G]. MS m/z: 525.3 (M+H).

Example 122

To a solution of tert-butyl 5-(3-(2,2-difluoroethyl)-2-(2,6-dimethylpyridin-4-yl)-1H-indole-5-carbonyl)hexahydropyrrolo[3,4-c]pyrrole-2(1H)-carboxylate (0.055 g, 0.105 mmol) in dioxane (3.0 mL) was added 4 M dioxane-HCl (0.655 mL, 2.62 mmol) at room temperature. The mixture was stirred at same temperature for 4 h. The reaction mass was concentrated to get crude product. The crude material was purified by Prep HPLC method D2, fractions containing the product were combined and dried using Genevac centrifugal evaporator to afford (3-(2,2-difluoroethyl)-2-(2,6-dimethylpyridin-4-yl)-1H-indol-5-yl)(hexahydropyrrolo[3,4-c]pyrrol-2(H)-yl)methanone (2.0 mg, 5%) as a pale yellow solid. LCMS retention time 1.08 min [E]. MS m/z: 425.2 (M+H); $^1$H NMR (400 MHz. CD$_3$OD) δ ppm 7.96 (s, 1H), 7.77 (br. s., 2H), 7.60-7.48 (m, 2H), 6.43-6.07 (m, 1H), 3.94 (dd, J=12.1, 7.2 Hz, 2H), 3.64 (td, J=17.7, 3.9 Hz, 8H), 3.35 (s, 2H), 3.24-3.10 (m, 3H), 2.75 (s, 8H), 2.04 (s, 1H), 1.29 (br. s., 2H).

The examples in Table 15 were prepared according to the general procedure for Example 122.

TABLE 15

| Ex. No. | Structure | Mol Wt. | LCMS MH+ | Ret Time (min) | HPLC Method |
|---|---|---|---|---|---|
| 123 | 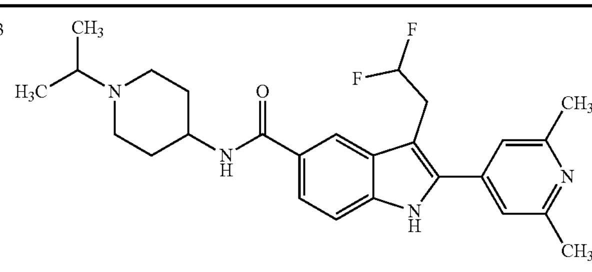 | 454.57 | 455.2 | 1.247 | E |

TABLE 15-continued

| Ex. No. | Structure | Mol Wt. | LCMS MH+ | Ret Time (min) | HPLC Method |
|---|---|---|---|---|---|
| 124 | 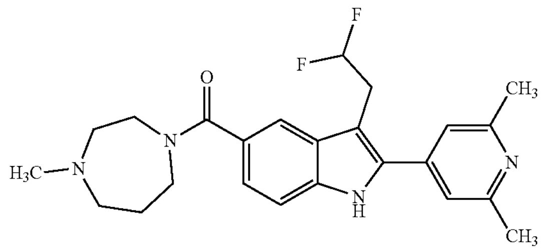 | 426.51 | 427.2 | 1.299 | E |
| 125 | 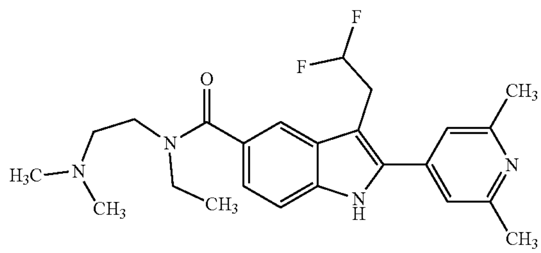 | 428.53 | 429.2 | 1.248 | E |

Example 126

(hexahydropyrrolo[3,4-c]pyrrol-2(1H)-yl)(3-isopropyl-2-(8-methoxy-[1,2,4]triazolo[1,5-a]pyridin-6-yl)-1H-indol-5-yl)methanone (126)

Intermediate 126A: Methyl 3-isopropyl-2-(8-methoxy-[1,2,4]triazolo[1,5-a]pyridin-6-yl)-1H-indole-5-carboxylate

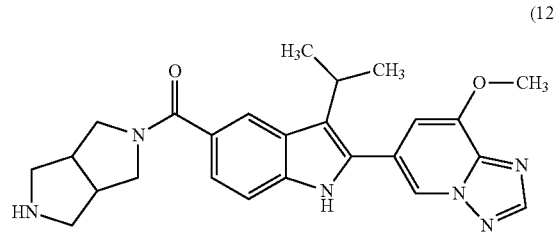

(126A)

To a degassed solution of methyl 2-bromo-3-isopropyl-1H-indole-5-carboxylate (1.0 g, 3.38 mmol) and 8-methoxy-6-(4,4,5,5-tetramethyl-1,3,2-dioxaborolan-2-yl)-[1,2,4]triazolo[1,5-a] pyridine (1.393 g, 5.06 mmol) in dioxane (20.0 mL) and water (5.0 mL) were added PdCl$_2$(dppf)-CH$_2$Cl$_2$ adduct (0.276 g, 0.338 mmol) and potassium phosphate (1.764 g, 10.13 mmol) at room temperature. The resulting reaction mixture was stirred at 95° C. for 4 h in a sealed tube. The reaction mixture was diluted with ethyl acetate, filtered and washed with excess ethyl acetate, combined organic layers were washed with water, brine, dried over sodium sulphate and evaporated to get crude material. The crude material was purified by ISCO using silica column 40 g, compound was eluted with 65% ethyl acetate in petroleum ether, the fractions were collected and concentrated to afford methyl 3-isopropyl-2-(8-methoxy-[1,2,4]triazolo[1,5-a]pyridin-6-yl)-1H-indole-5-carboxylate (0.8 g, 2.195 mmol, 65% yield) as a light yellow solid. LCMS retention time 1.21 min [L]. MS m/z: 365.5 (M+H).

Intermediate 126B: 3-isopropyl-2-(8-methoxy-[1,2,4]triazolo[1,5-a]pyridin-6-yl)-1H-indole-5-carboxylic Acid

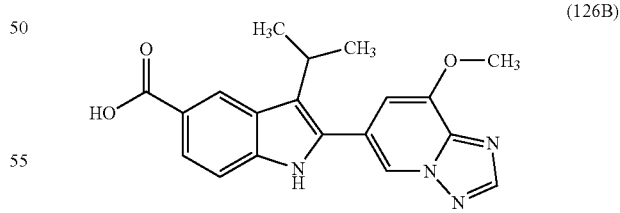

(126B)

To a solution of methyl 3-isopropyl-2-(8-methoxy-[1,2,4]triazolo[1,5-a]pyridin-6-yl)-1H-indole-5-carboxylate (0.620 g, 1.701 mmol) in a solvent mixture of THF (5.0 mL), MeOH (5.0 mL), and water (2.0 mL) was added sodium hydroxide (0.340 g, 8.51 mmol). The resulting mixture was stirred at 65° C. for 2 h, the reaction mixture was cooled to room temperature, volatiles were evaporated, the residue was diluted with water, and brought to acidic pH with 1 N HCl solution. The precipitated solids were filtered and dried under vacuum afford 3-isopropyl-2-(8-methoxy-[1,2,4]triazolo[1,5-a] pyridin-6-yl)-1H-indole-5-carboxylic acid (0.410 g, 1.170 mmol, 69% yield) as a white solid. LCMS retention time 0.59 min [L]. MS m/z: 351.4 (M+H).

Intermediate 126C: tert-butyl 5-(3-isopropyl-2-(8-methoxy-[1,2,4]triazolo[1,5-a]pyridin-6-yl)-1H-indole-5-carbonyl)hexahydropyrrolo[3,4-c]pyrrole-2(1H)-carboxylate

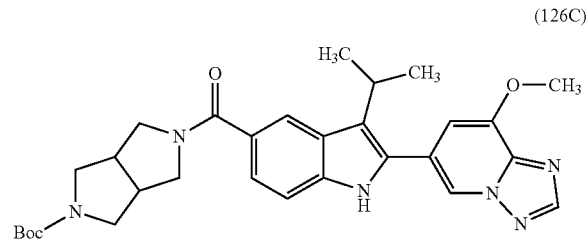 [SMILES: COc1cc(-c2[nH]c3ccc(C(=O)N4CC5CN(C(=O)OC(C)(C)C)CC5C4)cc3c2C(C)C)cn2ncnc12]

(126C)

HATU (0.043 g, 0.114 mmol) was added to a solution of 3-isopropyl-2-(8-methoxy-[1,2,4]triazolo[1,5-a]pyridin-6-yl)-1H-indole-5-carboxylic acid (0.040 g, 0.114 mmol), tert-butyl hexahydropyrrolo[3,4-c] pyrrole-2(1H)-carboxylate (0.032 g, 0.148 mmol), TEA (0.080 mL, 0.571 mmol) in DMF (3.0 mL) at 0° C. The resulting mixture was stirred at room temperature for 16 h. The volatiles was evaporated, residue was dissolved with excess DCM, washed with water, brine, dried over sodium sulphate and concentrated to afford crude tert-butyl 5-(3-isopropyl-2-(8-methoxy-[1,2,4]triazolo[1,5-a]pyridin-6-yl)-1H-indole-5-carbonyl)hexahydropyrrolo[3,4-c]pyrrole-2(1H)-carboxylate (0.065 g, 0.119 mmol, 105% yield) as a brown color semisolid. LCMS retention time 1.20 min. (L), MS m/z: 543.5 (M–H).

Example 126

To a solution of tert-butyl 5-(3-isopropyl-2-(8-methoxy-[1,2,4]triazolo[1,5-a]pyridin-6-yl)-1H-indole-5-carbonyl)hexahydropyrrolo[3,4-c]pyrrole-2(1H)-carboxylate (0.060 g, 0.110 mmol) in dioxane (2.0 mL) was added 4 M HCl in dioxane (0.551 mL, 2.203 mmol) at 10° C. The reaction mixture was stirred at the same temperature for 4 h. The reaction mass was concentrated to get crude product. The crude material was purified by Prep HPLC method D2, fractions containing the product were combined and dried using Genevac centrifugal evaporator to afford (hexahydropyrrolo[3,4-c]pyrrol-2(1H)-yl)(3-isopropyl-2-(8-methoxy-[1,2,4]triazolo[1,5-a]pyridin-6-yl)-1H-indol-5-yl) methanone (32.0 mg, 62.7%) as a pale yellow solid. LCMS retention time 1.05 min [E]. MS m/z: 445.1 (M+H); $^1$H NMR (400 MHz, METHANOL-$d_4$) δ ppm 8.56-8.45 (m, 2H), 8.08 (s, 1H), 7.52 (d, J=8.3 Hz, 1H), 7.42 (d, J=8.6 Hz, 1H), 7.26 (s, 1H), 4.18 (s, 3H), 3.99 (dd, J=12.2, 7.1 Hz, 2H), 3.86-3.70 (m, 5H), 3.63 (br. s., 2H), 3.48-3.37 (m, 1H), 3.25 (br. s., 4H), 1.62-1.39 (m, 6H).

The examples in Table 16 were prepared according to the general procedure described in Example 126.

TABLE 16

| Ex. No. | Structure | Mol Wt. | LCMS MH+ | Ret Time (min) | HPLC Method |
|---|---|---|---|---|---|
| 127 | 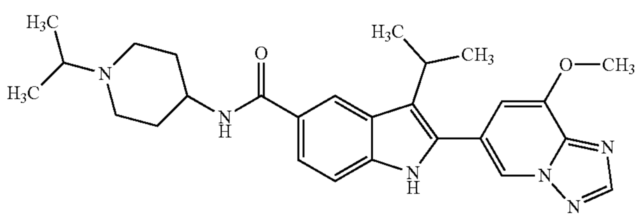 [SMILES: COc1cc(-c2[nH]c3ccc(C(=O)NC4CCN(C(C)C)CC4)cc3c2C(C)C)cn2ncnc12] | 474.61 | 475.2 | 1.217 | E |
| 128 | 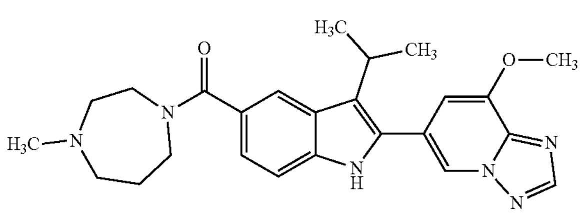 [SMILES: COc1cc(-c2[nH]c3ccc(C(=O)N4CCCN(C)CC4)cc3c2C(C)C)cn2ncnc12] | 446.56 | 447.2 | 1.27 | E |
| 129 | 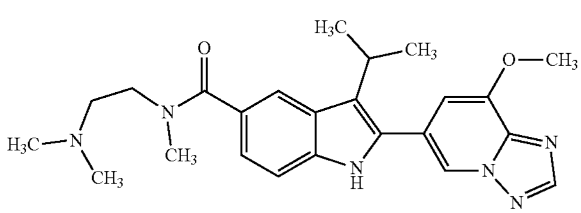 [SMILES: COc1cc(-c2[nH]c3ccc(C(=O)N(C)CCN(C)C)cc3c2C(C)C)cn2ncnc12] | 434.54 | 435.2 | 1.27 | E |

The examples in Table 17 were prepared according to the general procedure for the above examples.

TABLE 17

| Ex. No. | Structure | Mol Wt. | LCMS MH+ | Ret Time (min) | HPLC Method |
|---|---|---|---|---|---|
| 130 | 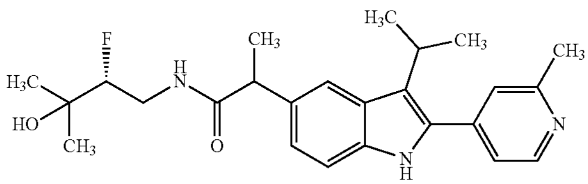 [SMILES: Cc1cc(-c2[nH]c3ccc(C(C)C(=O)NC[C@@H](F)C(C)(C)O)cc3c2C(C)C)ccn1] | 425.55 | 426 | 1.52 | QC-ACN-AA-XB |
| 131 | 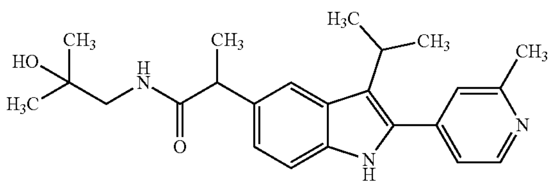 [SMILES: Cc1cc(-c2[nH]c3ccc(C(C)C(=O)NCC(C)(C)O)cc3c2C(C)C)ccn1] | 393.53 | 394.1 | 1.06 | QC-ACN-TFA-XB |
| 132 | 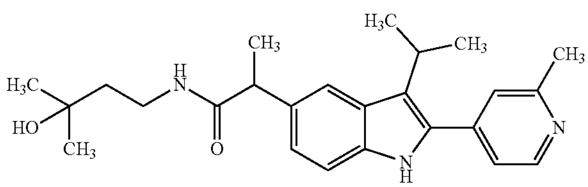 [SMILES: Cc1cc(-c2[nH]c3ccc(C(C)C(=O)NCCC(C)(C)O)cc3c2C(C)C)ccn1] | 407.56 | 408.1 | 1.1 | QC-ACN-TFA-XB |
| 133 | 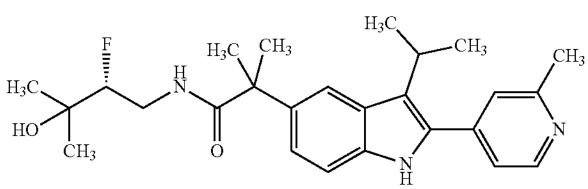 [SMILES: Cc1cc(-c2[nH]c3ccc(C(C)(C)C(=O)NC[C@@H](F)C(C)(C)O)cc3c2C(C)C)ccn1] | 439.58 | 439.9 | 1.38 | QC-ACN-TFA-XB |
| 134 | 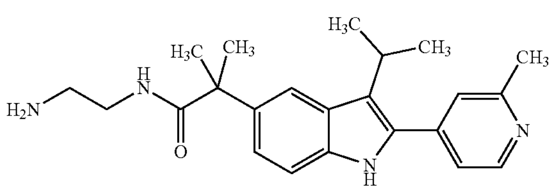 [SMILES: Cc1cc(-c2[nH]c3ccc(C(C)(C)C(=O)NCCN)cc3c2C(C)C)ccn1] | 378.52 | 379.2 | 1.55 | QC-ACN-TFA-XB |
| 135 | 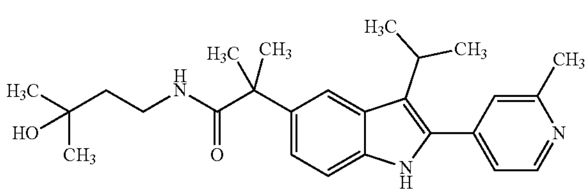 [SMILES: Cc1cc(-c2[nH]c3ccc(C(C)(C)C(=O)NCCC(C)(C)O)cc3c2C(C)C)ccn1] | 421.59 | 422.3 | 1.72 | QC-ACN-AA-XB |
| 136 | 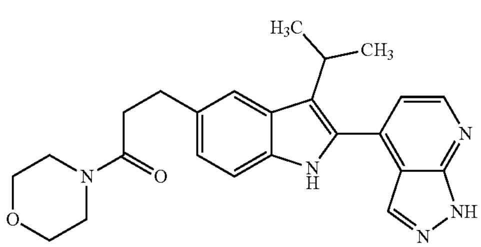 [SMILES: CC(C)c1c(-c2ccnc3[nH]ncc23)[nH]c2ccc(CCC(=O)N3CCOCC3)cc12] | 417.513 | 418.2 | 1.32 | QC-ACN-AA-XB |

TABLE 17-continued
| Ex. No. | Structure | Mol Wt. | LCMS MH+ | Ret Time (min) | HPLC Method |
|---|---|---|---|---|---|
| 137 | 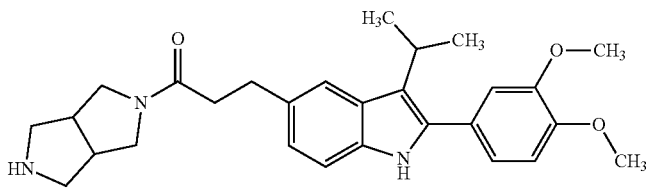 [SMILES: COc1ccc(-c2[nH]c3ccc(CCC(=O)N4CC5CNCC5C4)cc3c2C(C)C)cc1OC] | 461.606 | 462 | 1.2 | QC-ACN-AA-XB |
| 138 | 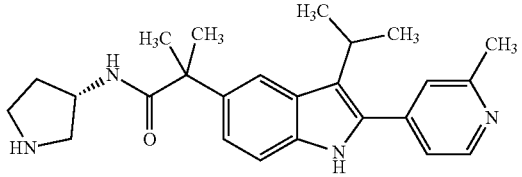 [SMILES: Cc1cc(-c2[nH]c3ccc(C(C)(C)C(=O)N[C@H]4CCNC4)cc3c2C(C)C)ccn1] | 404.558 | 405.3 | 0.9 | QC-ACN-AA-XB |
| 139 | 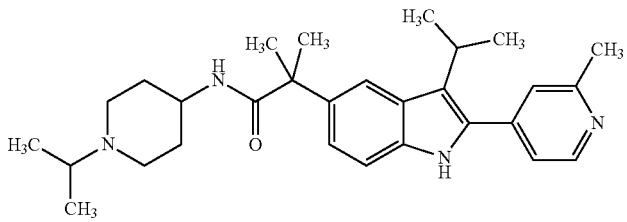 [SMILES: Cc1cc(-c2[nH]c3ccc(C(C)(C)C(=O)NC4CCN(C(C)C)CC4)cc3c2C(C)C)ccn1] | 460.666 | 461.1 | 1.33 | QC-ACN-AA-XB |
| 140 | 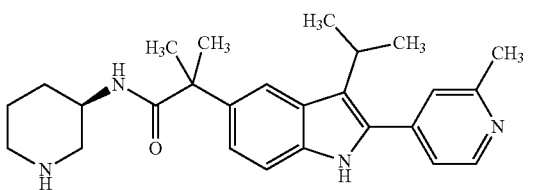 [SMILES: Cc1cc(-c2[nH]c3ccc(C(C)(C)C(=O)N[C@@H]4CCCNC4)cc3c2C(C)C)ccn1] | 418.585 | 419.2 | 1.21 | QC-ACN-TFA-XB |
| 141 | 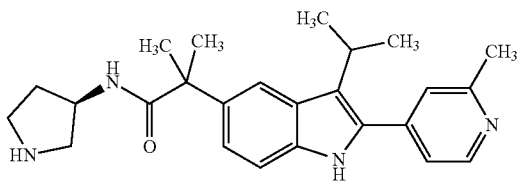 [SMILES: Cc1cc(-c2[nH]c3ccc(C(C)(C)C(=O)N[C@@H]4CCNC4)cc3c2C(C)C)ccn1] | 404.558 | 404.9 | 1.14 | QC-ACN-TFA-XB |
| 142 | 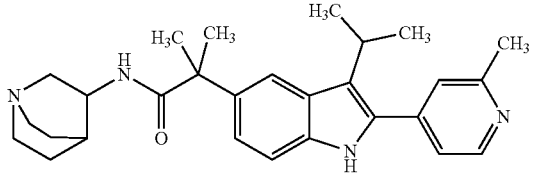 [SMILES: Cc1cc(-c2[nH]c3ccc(C(C)(C)C(=O)NC4CN5CCC4CC5)cc3c2C(C)C)ccn1] | 444.623 | 445.3 | 1.67 | QC-ACN-TFA-XB |
| 143 | 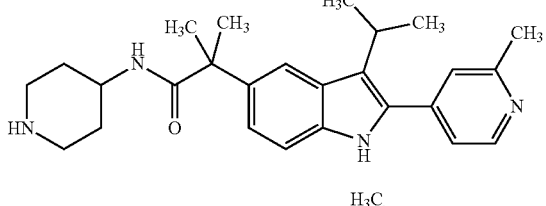 | 418.585 | 419.1 | 0.94 | QC-ACN-TFA-XB |
| 144 | 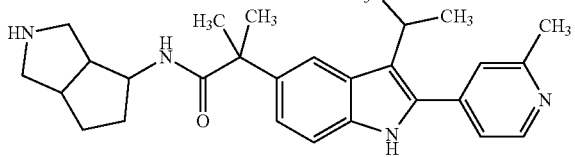 | 444.623 | 445.2 | 1.32 | QC-ACN-AA-XB |

TABLE 17-continued
| Ex. No. | Structure | Mol Wt. | LCMS MH+ | Ret Time (min) | HPLC Method |
|---|---|---|---|---|---|
| 145 | 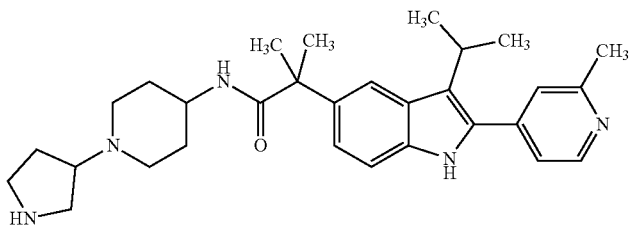 [SMILES: Cc1cc(-c2[nH]c3ccc(C(C)(C)C(=O)NC4CCN(C5CCNC5)CC4)cc3c2C(C)C)ccn1] | 487.69 | 488.4 | 0.92 | QC-ACN-TFA-XB |
| 146 | 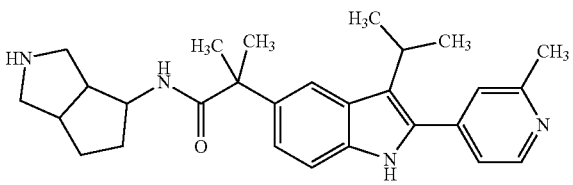 [SMILES: Cc1cc(-c2[nH]c3ccc(C(C)(C)C(=O)NC4CCC5CNCC54)cc3c2C(C)C)ccn1] | 444.62 | 445.5 | 0.67 | B1 |
| 147 | 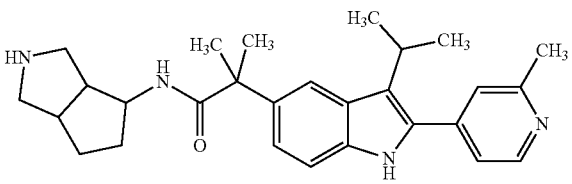 [SMILES: Cc1cc(-c2[nH]c3ccc(C(C)(C)C(=O)NC4CCC5CNCC54)cc3c2C(C)C)ccn1] | 444.62 | 445.5 | 0.67 | B1 |
| 148 | 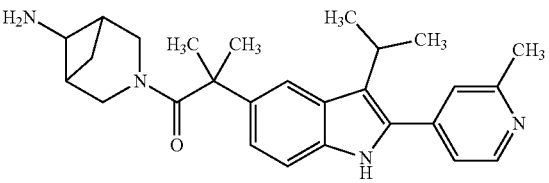 [SMILES: Cc1cc(-c2[nH]c3ccc(C(C)(C)C(=O)N4CC5CC(C4)C5N)cc3c2C(C)C)ccn1] | 430.6 | 431.3 | 1.34 | QC-ACN-AA-XB |
| 149 | 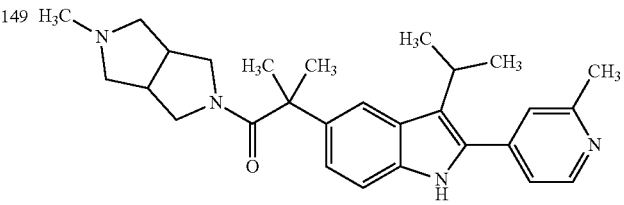 | 444.623 | 445.2 | 1.33 | QC-ACN-AA-XB |
| 150 | 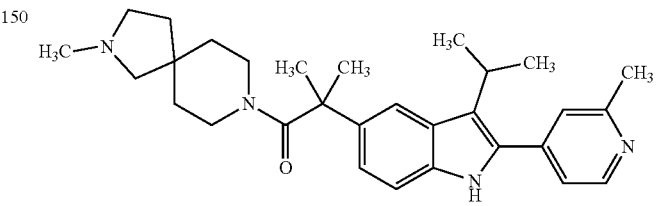 | 472.677 | 473.2 | 0.97 | QC-ACN-TFA-XB |
| 151 | 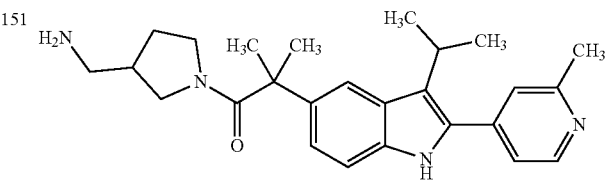 | 418.585 | 419.3 | 0.89 | QC-ACN-TFA-XB |

TABLE 17-continued
| Ex. No. | Structure | Mol Wt. | LCMS MH+ | Ret Time (min) | HPLC Method |
|---|---|---|---|---|---|
| 152 | 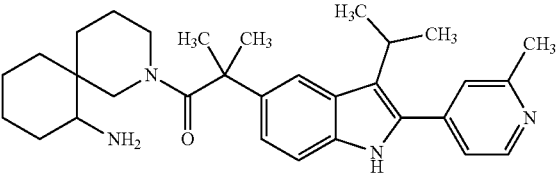 [SMILES: Cc1cc(-c2[nH]c3ccc(C(C)(C)C(=O)N4CCCC5(CCCCC5N)C4)cc3c2C(C)C)ccn1] | 486.704 | 487 | 1.3 | QC-ACN-TFA-XB |
| 153 | 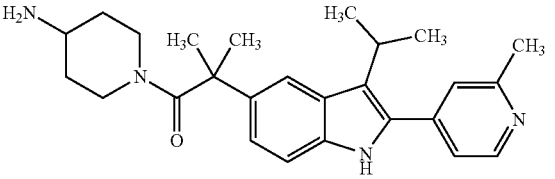 [SMILES: Cc1cc(-c2[nH]c3ccc(C(C)(C)C(=O)N4CCC(N)CC4)cc3c2C(C)C)ccn1] | 418.585 | 419.2 | 0.9 | QC-ACN-AA-XB |
| 154 | 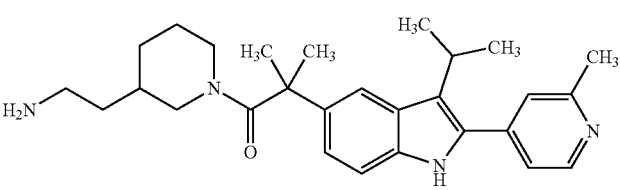 [SMILES: Cc1cc(-c2[nH]c3ccc(C(C)(C)C(=O)N4CCCC(CCN)C4)cc3c2C(C)C)ccn1] | 446.639 | 447.4 | 1.65 | QC-ACN-TFA-XB |
| 155 | 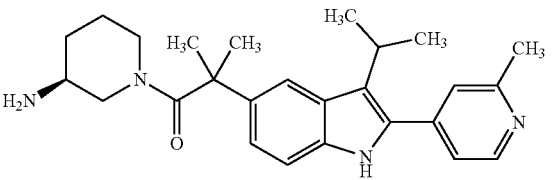 [SMILES: Cc1cc(-c2[nH]c3ccc(C(C)(C)C(=O)N4CCC[C@H](N)C4)cc3c2C(C)C)ccn1] | 418.585 | 419.3 | 1.63 | QC-ACN-TFA-XB |
| 156 | 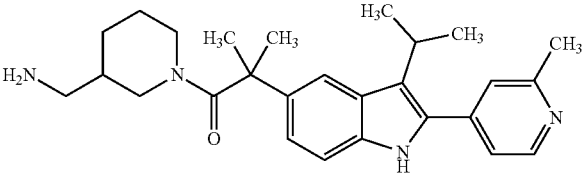 [SMILES: Cc1cc(-c2[nH]c3ccc(C(C)(C)C(=O)N4CCCC(CN)C4)cc3c2C(C)C)ccn1] | 432.612 | 433.2 | 0.94 | QC-ACN-TFA-XB |
| 157 | 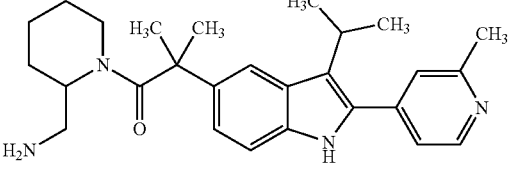 | 432.612 | 433.2 | 1.36 | QC-ACN-AA-XB |
| 158 | 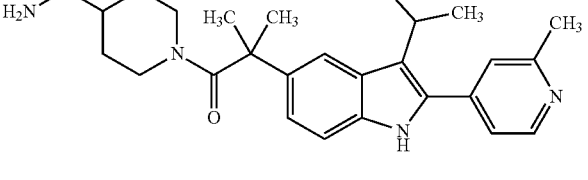 | 432.612 | 433.2 | 0.94 | QC-ACN-TFA-XB |
| 159 | 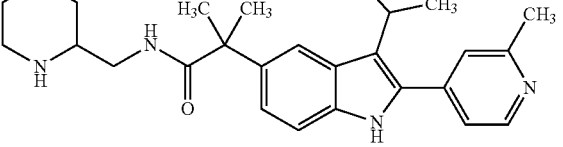 | 432.612 | 433.3 | 0.95 | QC-ACN-AA-XB |

TABLE 17-continued

| Ex. No. | Structure | Mol Wt. | LCMS MH+ | Ret Time (min) | HPLC Method |
|---|---|---|---|---|---|
| 160 | 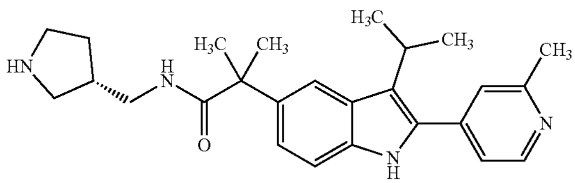 [SMILES: Cc1cc(-c2[nH]c3ccc(C(C)(C)C(=O)NC[C@H]4CCNC4)cc3c2C(C)C)ccn1] | 418.585 | 419.3 | 1.61 | QC-ACN-TFA-XB |
| 161 | 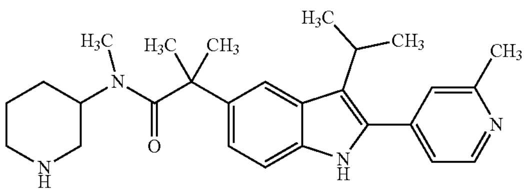 [SMILES: Cc1cc(-c2[nH]c3ccc(C(C)(C)C(=O)N(C)C4CCCNC4)cc3c2C(C)C)ccn1] | 432.612 | 433.2 | 1.25 | QC-ACN-AA-XB |
| 162 | 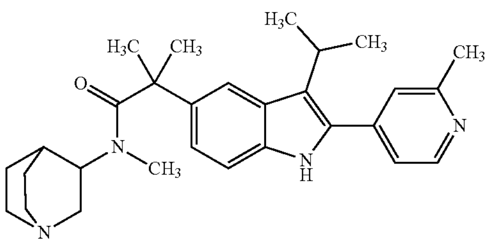 [SMILES: Cc1cc(-c2[nH]c3ccc(C(C)(C)C(=O)N(C)C4CN5CCC4CC5)cc3c2C(C)C)ccn1] | 458.65 | 459.3 | 1 | QC-ACN-AA-XB |
| 163 | 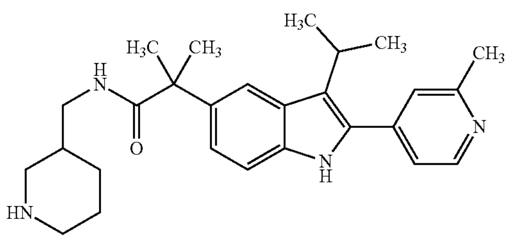 [SMILES: Cc1cc(-c2[nH]c3ccc(C(C)(C)C(=O)NCC4CCCNC4)cc3c2C(C)C)ccn1] | 432.612 | 433 | 1.17 | QC-ACN-TFA-XB |
| 164 | 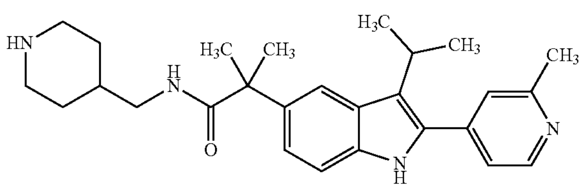 [SMILES: Cc1cc(-c2[nH]c3ccc(C(C)(C)C(=O)NCC4CCNCC4)cc3c2C(C)C)ccn1] | 432.612 | 433 | 1.54 | QC-ACN-AA-XB |
| 165 | 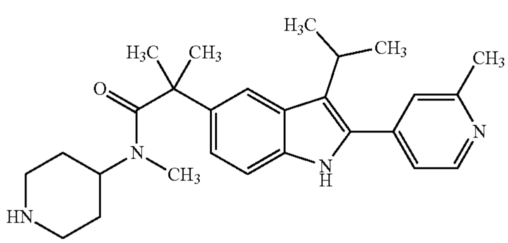 [SMILES: Cc1cc(-c2[nH]c3ccc(C(C)(C)C(=O)N(C)C4CCNCC4)cc3c2C(C)C)ccn1] | 432.612 | 433.2 | 0.93 | QC-ACN-TFA-XB |
| 166 | 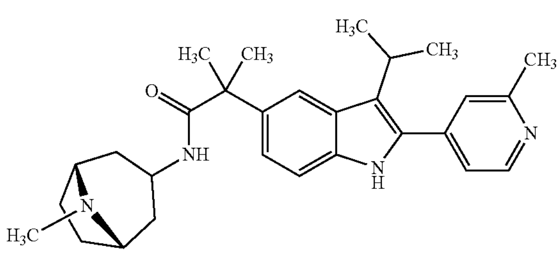 | 458.65 | 459.4 | 0.99 | QC-ACN-AA-XB |

TABLE 17-continued

| Ex. No. | Structure | Mol Wt. | LCMS MH+ | Ret Time (min) | HPLC Method |
|---|---|---|---|---|---|
| 167 | 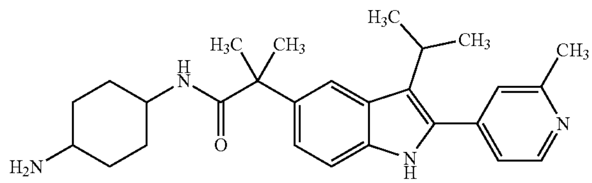 [SMILES: Cc1cc(-c2[nH]c3ccc(C(C)(C)C(=O)NC4CCC(N)CC4)cc3c2C(C)C)ccn1] | 432.612 | 433.4 | 1.62 | QC-ACN-TFA-XB |
| 168 | 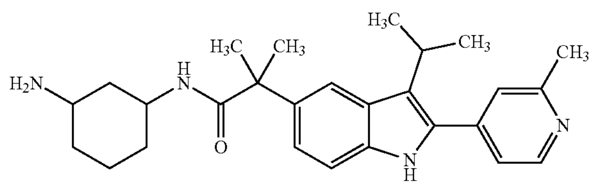 [SMILES: Cc1cc(-c2[nH]c3ccc(C(C)(C)C(=O)NC4CCCC(N)C4)cc3c2C(C)C)ccn1] | 432.612 | 433.2 | 1.26 | QC-ACN-AA-XB |
| 169 | 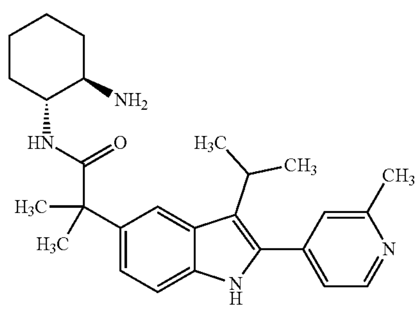 [SMILES: Cc1cc(-c2[nH]c3ccc(C(C)(C)C(=O)N[C@@H]4CCCC[C@H]4N)cc3c2C(C)C)ccn1] | 432.612 | 433.1 | 1.29 | QC-ACN-AA-XB |
| 170 | 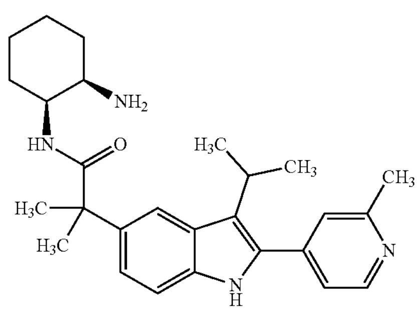 [SMILES: Cc1cc(-c2[nH]c3ccc(C(C)(C)C(=O)N[C@H]4CCCC[C@H]4N)cc3c2C(C)C)ccn1] | 432.612 | 433.2 | 1.4 | QC-ACN-AA-XB |
| 171 | 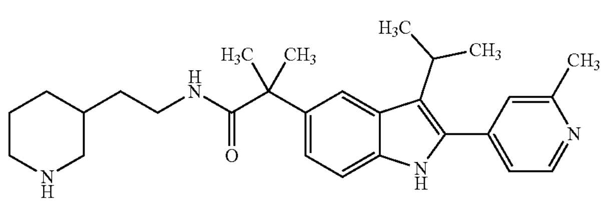 [SMILES: Cc1cc(-c2[nH]c3ccc(C(C)(C)C(=O)NCCC4CCCNC4)cc3c2C(C)C)ccn1] | 446.639 | 447.2 | 1.34 | QC-ACN-AA-XB |
| 172 | 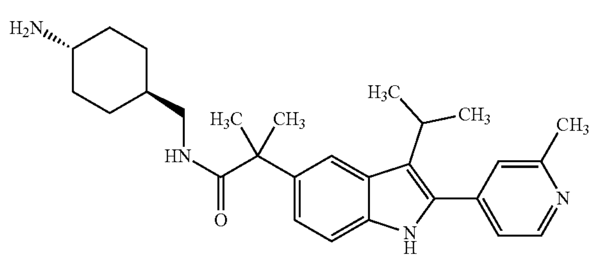 [SMILES: Cc1cc(-c2[nH]c3ccc(C(C)(C)C(=O)NC[C@H]4CC[C@H](N)CC4)cc3c2C(C)C)ccn1] | 446.639 | 447.3 | 1.34 | QC-ACN-AA-XB |

TABLE 17-continued

| Ex. No. | Structure | Mol Wt. | LCMS MH+ | Ret Time (min) | HPLC Method |
|---|---|---|---|---|---|
| 173 | 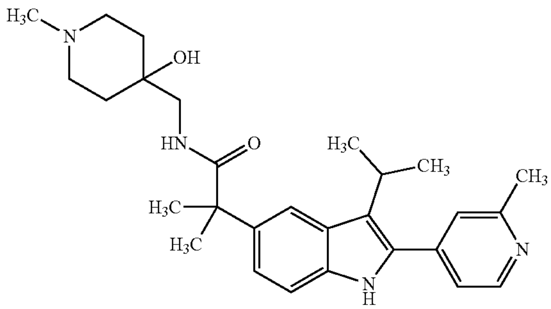 | 462.638 | 463.3 | 1.18 | QC-ACN-TFA-XB |
| 174 | 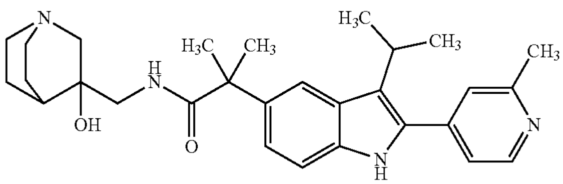 [SMILES: Cc1cc(-c2[nH]c3ccc(C(C)(C)C(=O)NCC4(O)CN5CCC4CC5)cc3c2C(C)C)ccn1] | 474.649 | 475.2 | 1.31 | QC-ACN-AA-XB |
| 175 | 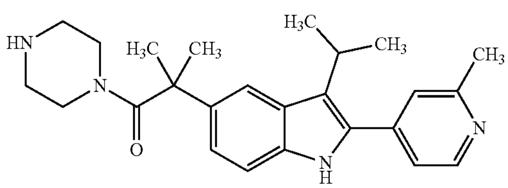 [SMILES: Cc1cc(-c2[nH]c3ccc(C(C)(C)C(=O)N4CCNCC4)cc3c2C(C)C)ccn1] | 404.558 | 405.2 | 0.89 | QC-ACN-AA-XB |
| 176 | 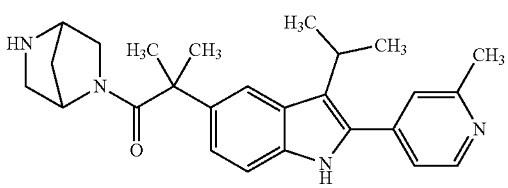 [SMILES: Cc1cc(-c2[nH]c3ccc(C(C)(C)C(=O)N4CC5CC4CN5)cc3c2C(C)C)ccn1] | 416.569 | 417.1 | 1.16 | QC-ACN-TFA-XB |
| 177 | 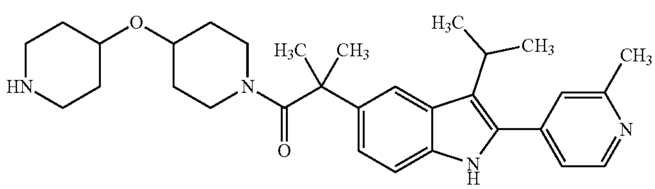 [SMILES: Cc1cc(-c2[nH]c3ccc(C(C)(C)C(=O)N4CCC(OC5CCNCC5)CC4)cc3c2C(C)C)ccn1] | 502.703 | 503.3 | 1 | QC-ACN-TFA-XB |
| 178 | 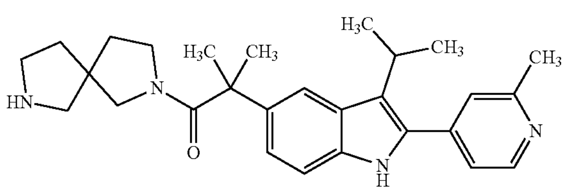 [SMILES: Cc1cc(-c2[nH]c3ccc(C(C)(C)C(=O)N4CCC5(CCNC5)C4)cc3c2C(C)C)ccn1] | 444.623 | 445.2 | 0.92 | QC-ACN-TFA-XB |
| 179 | 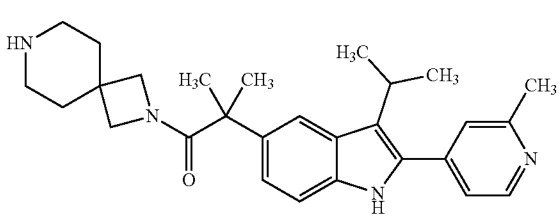 [SMILES: Cc1cc(-c2[nH]c3ccc(C(C)(C)C(=O)N4CC5(CCNCC5)C4)cc3c2C(C)C)ccn1] | 444.623 | 445.3 | 1.26 | QC-ACN-AA-XB |

TABLE 17-continued

| Ex. No. | Structure | Mol Wt. | LCMS MH+ | Ret Time (min) | HPLC Method |
|---|---|---|---|---|---|
| 180 | 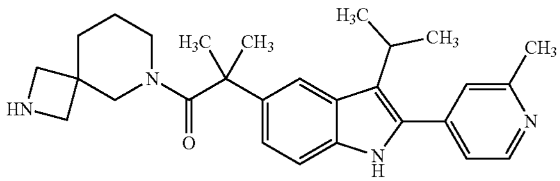 [SMILES: Cc1cc(-c2[nH]c3ccc(C(C)(C)C(=O)N4CCCC5(CNC5)C4)cc3c2C(C)C)ccn1] | 444.623 | 445.2 | 0.96 | QC-ACN-TFA-XB |
| 181 | 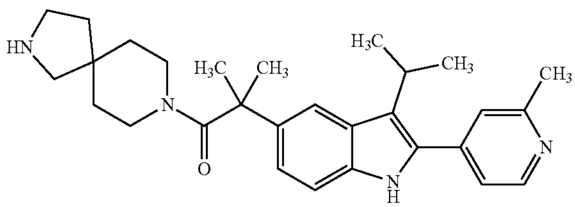 [SMILES: Cc1cc(-c2[nH]c3ccc(C(C)(C)C(=O)N4CCC5(CCNC5)CC4)cc3c2C(C)C)ccn1] | 458.65 | 459.3 | 0.95 | QC-ACN-TFA-XB |
| 182 | 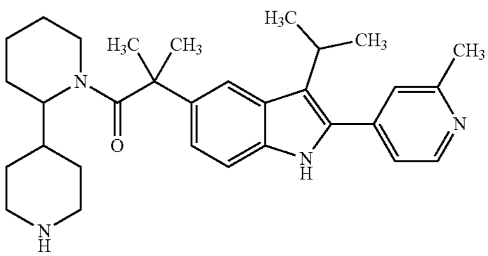 [SMILES: Cc1cc(-c2[nH]c3ccc(C(C)(C)C(=O)N4CCCCC4C4CCNCC4)cc3c2C(C)C)ccn1] | 486.704 | 487.2 | 1.39 | QC-ACN-AA-XB |
| 183 | 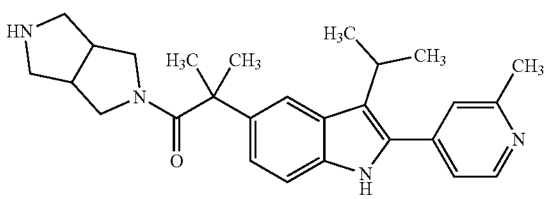 [SMILES: Cc1cc(-c2[nH]c3ccc(C(C)(C)C(=O)N4CC5CNCC5C4)cc3c2C(C)C)ccn1] | 430.596 | 431.2 | 1.25 | QC-ACN-AA-XB |
| 184 | 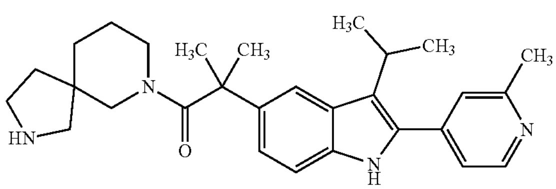 [SMILES: Cc1cc(-c2[nH]c3ccc(C(C)(C)C(=O)N4CCCC5(CCNC5)C4)cc3c2C(C)C)ccn1] | 458.65 | 459.4 | 1.77 | QC-ACN-AA-XB |
| 185 | 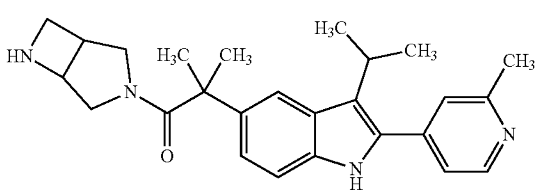 [SMILES: Cc1cc(-c2[nH]c3ccc(C(C)(C)C(=O)N4CC5CNC5C4)cc3c2C(C)C)ccn1] | 416.57 | 417.1 | 0.97 | QC-ACN-TFA-XB |
| 186 | 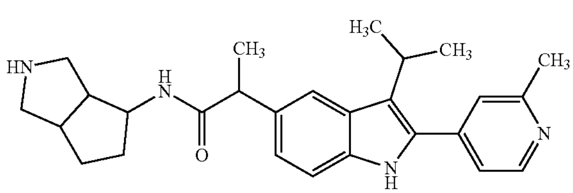 [SMILES: Cc1cc(-c2[nH]c3ccc(C(C)C(=O)NC4CCC5CNCC54)cc3c2C(C)C)ccn1] | 430.6 | 431.1 | 1.11 | QC-ACN-AA-XB |

TABLE 17-continued

| Ex. No. | Structure | Mol Wt. | LCMS MH+ | Ret Time (min) | HPLC Method |
|---|---|---|---|---|---|
| 187 | 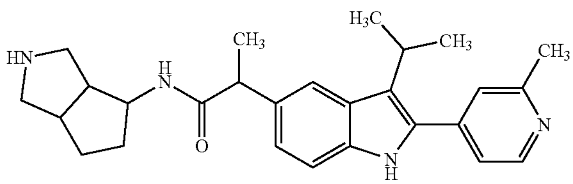 [SMILES: Cc1cc(-c2[nH]c3ccc(C(C)C(=O)NC4CCC5CNCC54)cc3c2C(C)C)ccn1] | 430.6 | 431.1 | 1.18 | QC-ACN-AA-XB |
| 188 | 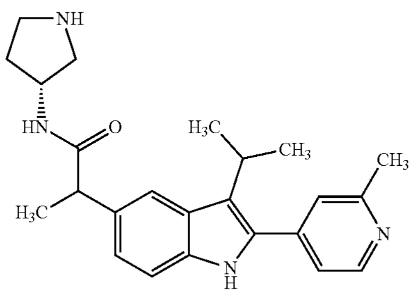 [SMILES: Cc1cc(-c2[nH]c3ccc(C(C)C(=O)N[C@@H]4CCNC4)cc3c2C(C)C)ccn1] | 390.53 | 391.3 | 0.84 | QC-ACN-TFA-XB |
| 189 | 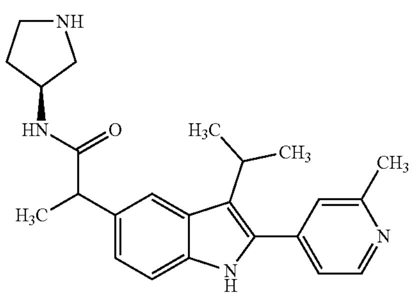 [SMILES: Cc1cc(-c2[nH]c3ccc(C(C)C(=O)N[C@H]4CCNC4)cc3c2C(C)C)ccn1] | 390.53 | 391.3 | 0.84 | QC-ACN-TFA-XB |
| 190 | 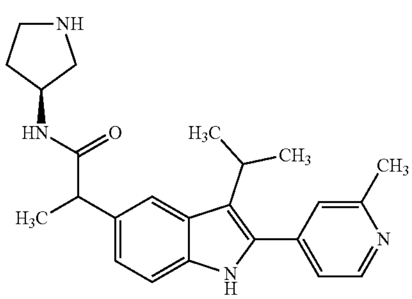 [SMILES: Cc1cc(-c2[nH]c3ccc(C(C)C(=O)N[C@H]4CCNC4)cc3c2C(C)C)ccn1] | 390.53 | 391.3 | 1.51 | QC-ACN-AA-XB |
| 191 | 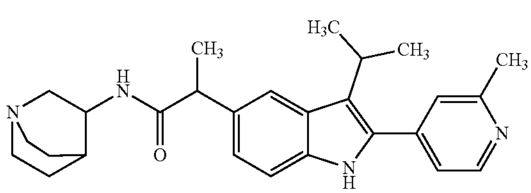 [SMILES: Cc1cc(-c2[nH]c3ccc(C(C)C(=O)NC4CN5CCC4CC5)cc3c2C(C)C)ccn1] | 430.6 | 431.3 | 1.53 | QC-ACN-AA-XB |
| 192 | 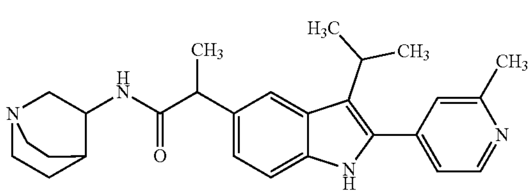 [SMILES: Cc1cc(-c2[nH]c3ccc(C(C)C(=O)NC4CN5CCC4CC5)cc3c2C(C)C)ccn1] | 430.6 | 431.1 | 1.18 | QC-ACN-AA-XB |

TABLE 17-continued

| Ex. No. | Structure | Mol Wt. | LCMS MH+ | Ret Time (min) | HPLC Method |
|---|---|---|---|---|---|
| 193 | 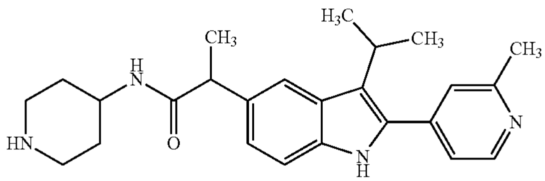 [SMILES: Cc1cc(-c2[nH]c3ccc(C(C)C(=O)NC4CCNCC4)cc3c2C(C)C)ccn1] | 404.558 | 405.3 | 0.83 | QC-ACN-TFA-XB |
| 194 | 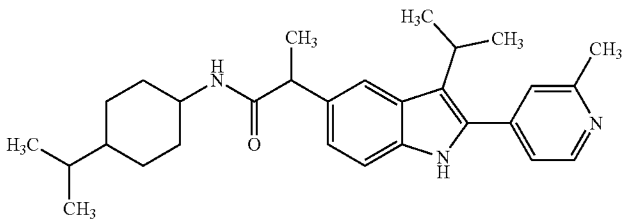 [SMILES: Cc1cc(-c2[nH]c3ccc(C(C)C(=O)NC4CCC(C(C)C)CC4)cc3c2C(C)C)ccn1] | 446.639 | 447.2 | 0.89 | QC-ACN-TFA-XB |
| 195 | 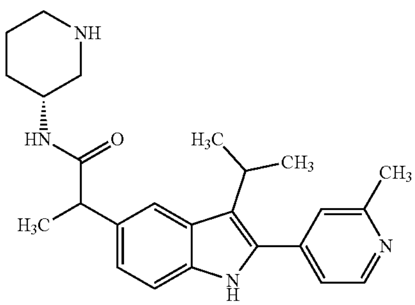 [SMILES: Cc1cc(-c2[nH]c3ccc(C(C)C(=O)N[C@@H]4CCCNC4)cc3c2C(C)C)ccn1] | 404.56 | 405.4 | 1.51 | QC-ACN-AA-XB |
| 196 | 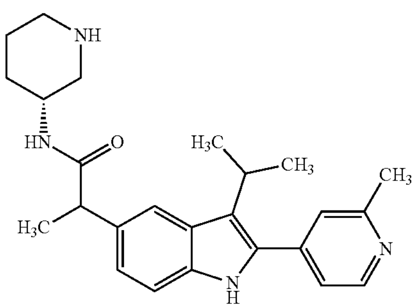 [SMILES: Cc1cc(-c2[nH]c3ccc(C(C)C(=O)N[C@@H]4CCCNC4)cc3c2C(C)C)ccn1] | 404.56 | 405.3 | 0.91 | QC-ACN-TFA-XB |
| 197 | 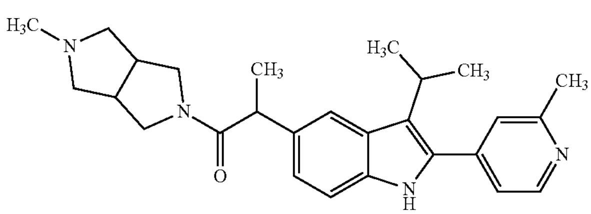 | 430.6 | 431.1 | 1.17 | QC-ACN-AA-XB |
| 198 | 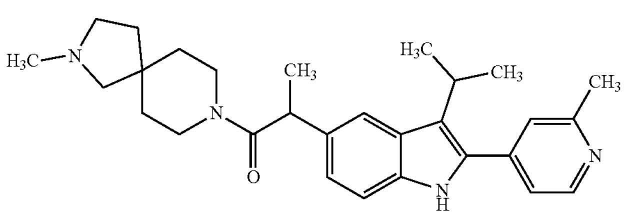 | 458.65 | 459.1 | 1.21 | QC-ACN-AA-XB |

TABLE 17-continued

| Ex. No. | Structure | Mol Wt. | LCMS MH+ | Ret Time (min) | HPLC Method |
|---|---|---|---|---|---|
| 199 | 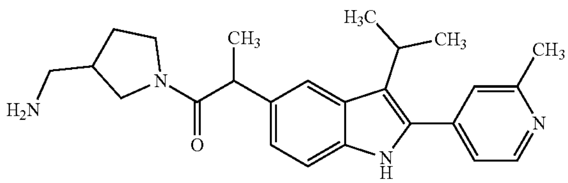 [SMILES: Cc1cc(-c2[nH]c3ccc(C(C)C(=O)N4CCC(CN)C4)cc3c2C(C)C)ccn1] | 404.558 | 405 | 0.84 | QC-ACN-TFA-XB |
| 200 | 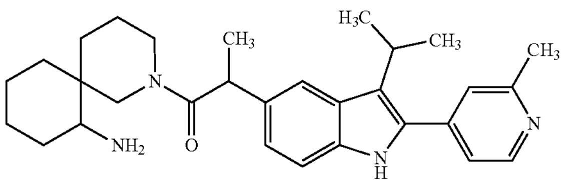 [SMILES: Cc1cc(-c2[nH]c3ccc(C(C)C(=O)N4CCCC5(CCCCC5N)C4)cc3c2C(C)C)ccn1] | 472.677 | 473.4 | 1.01 | QC-ACN-TFA-XB |
| 201 | 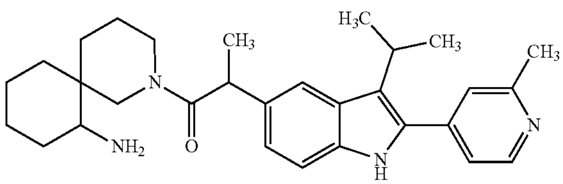 [SMILES: Cc1cc(-c2[nH]c3ccc(C(C)C(=O)N4CCCC5(CCCCC5N)C4)cc3c2C(C)C)ccn1] | 472.667 | 473.4 | 1.81 | QC-ACN-AA-XB |
| 202 | 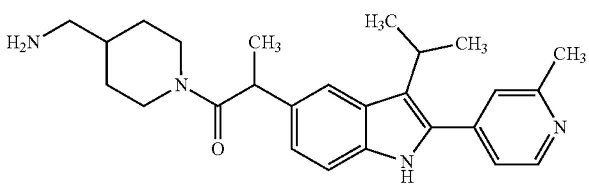 [SMILES: Cc1cc(-c2[nH]c3ccc(C(C)C(=O)N4CCC(CN)CC4)cc3c2C(C)C)ccn1] | 418.585 | 419.4 | 1.48 | QC-ACN-AA-XB |
| 203 | 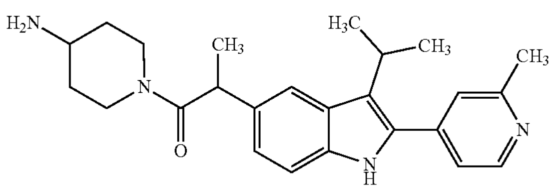 [SMILES: Cc1cc(-c2[nH]c3ccc(C(C)C(=O)N4CCC(N)CC4)cc3c2C(C)C)ccn1] | 404.56 | 405.3 | 1.12 | QC-ACN-AA-XB |
| 204 | 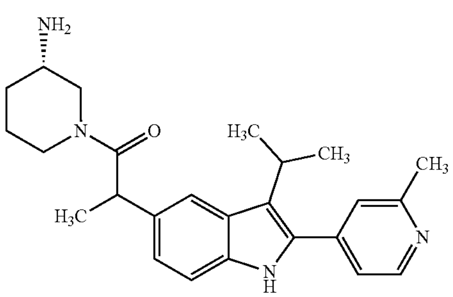 [SMILES: Cc1cc(-c2[nH]c3ccc(C(C)C(=O)N4CCC[C@H](N)C4)cc3c2C(C)C)ccn1] | 404.56 | 405.3 | 0.89 | QC-ACN-TFA-XB |
| 205 | 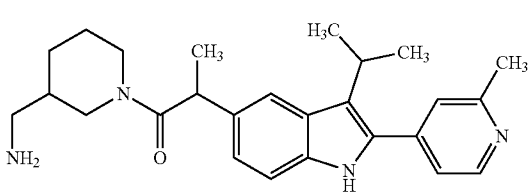 [SMILES: Cc1cc(-c2[nH]c3ccc(C(C)C(=O)N4CCCC(CN)C4)cc3c2C(C)C)ccn1] | 418.585 | 419.1 | 1.25 | QC-ACN-AA-XB |

TABLE 17-continued

| Ex. No. | Structure | Mol Wt. | LCMS MH+ | Ret Time (min) | HPLC Method |
|---|---|---|---|---|---|
| 206 | 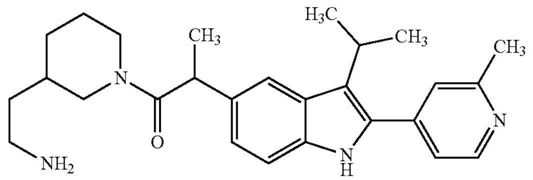 [SMILES: Cc1cc(-c2[nH]c3ccc(C(C)C(=O)N4CCCC(CCN)C4)cc3c2C(C)C)ccn1] | 432.61 | 433.1 | 0.95 | QC-ACN-TFA-XB |
| 207 | 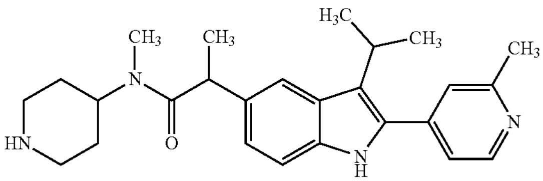 [SMILES: Cc1cc(-c2[nH]c3ccc(C(C)C(=O)N(C)C4CCNCC4)cc3c2C(C)C)ccn1] | 418.585 | 419.3 | 0.87 | QC-ACN-TFA-XB |
| 208 | 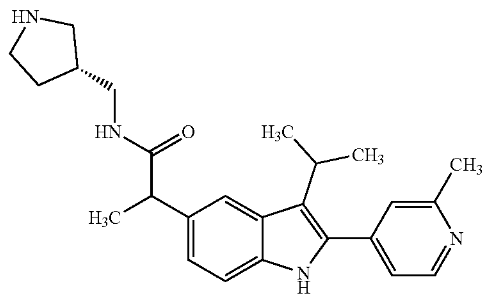 [SMILES: Cc1cc(-c2[nH]c3ccc(C(C)C(=O)NC[C@@H]4CCNC4)cc3c2C(C)C)ccn1] | 404.56 | 405.3 | 1.46 | QC-ACN-AA-XB |
| 209 | 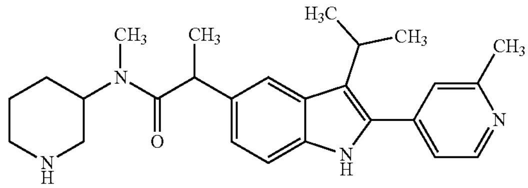 [SMILES: Cc1cc(-c2[nH]c3ccc(C(C)C(=O)N(C)C4CCCNC4)cc3c2C(C)C)ccn1] | 418.59 | 419.1 | 1.22 | QC-ACN-AA-XB |
| 210 | 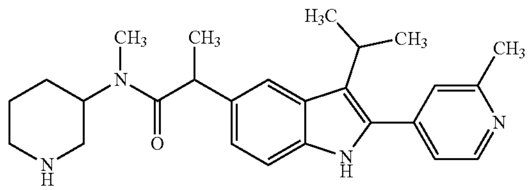 [SMILES: Cc1cc(-c2[nH]c3ccc(C(C)C(=O)N(C)C4CCCNC4)cc3c2C(C)C)ccn1] | 418.59 | 419.1 | 0.88 | QC-ACN-TFA-XB |
| 211 | 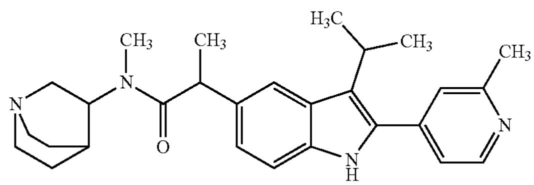 [SMILES: Cc1cc(-c2[nH]c3ccc(C(C)C(=O)N(C)C4CN5CCC4CC5)cc3c2C(C)C)ccn1] | 444.62 | 445.23 | 0.96 | QC-ACN-TFA-XB |
| 212 | 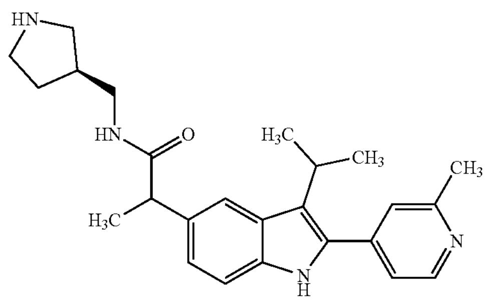 [SMILES: Cc1cc(-c2[nH]c3ccc(C(C)C(=O)NC[C@H]4CCNC4)cc3c2C(C)C)ccn1] | 404.56 | 405.3 | 1.47 | QC-ACN-AA-XB |

TABLE 17-continued

| Ex. No. | Structure | Mol Wt. | LCMS MH+ | Ret Time (min) | HPLC Method |
|---|---|---|---|---|---|
| 213 | 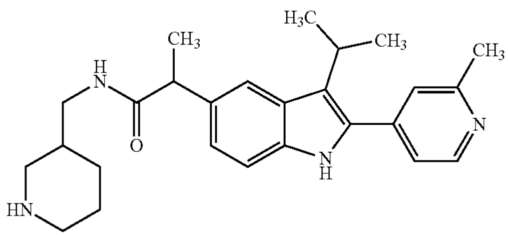 [SMILES: Cc1cc(-c2[nH]c3ccc(C(C)C(=O)NCC4CCCNC4)cc3c2C(C)C)ccn1] | 418.585 | 419.3 | 1.39 | QC-ACN-AA-XB |
| 214 | 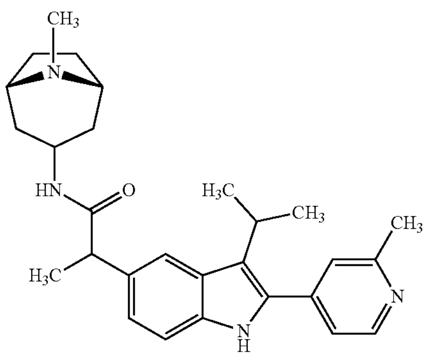 [SMILES: Cc1cc(-c2[nH]c3ccc(C(C)C(=O)NC4C[C@H]5CC[C@@H](C4)N5C)cc3c2C(C)C)ccn1] | 444.62 | 445.1 | 0.91 | QC-ACN-TFA-XB |
| 215 | 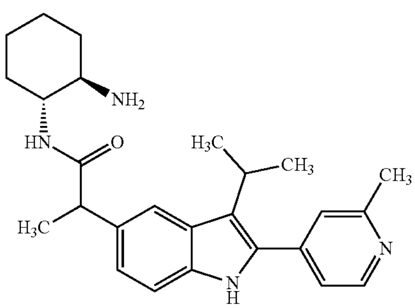 [SMILES: Cc1cc(-c2[nH]c3ccc(C(C)C(=O)N[C@@H]4CCCC[C@H]4N)cc3c2C(C)C)ccn1] | 418.59 | 419.3 | 1.61 | QC-ACN-AA-XB |
| 216 | 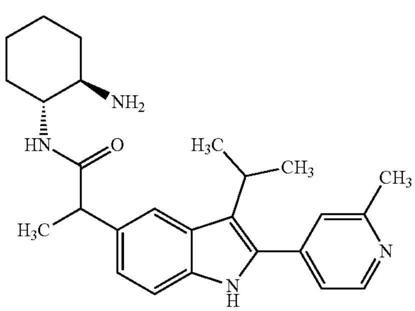 [SMILES: Cc1cc(-c2[nH]c3ccc(C(C)C(=O)N[C@@H]4CCCC[C@H]4N)cc3c2C(C)C)ccn1] | 418.59 | 419.3 | 0.98 | QC-ACN-TFA-XB |
| 217 | 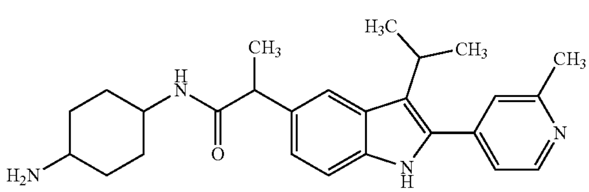 [SMILES: Cc1cc(-c2[nH]c3ccc(C(C)C(=O)NC4CCC(N)CC4)cc3c2C(C)C)ccn1] | 418.59 | 419.1 | 0.9 | QC-ACN-TFA-XB |

TABLE 17-continued

| Ex. No. | Structure | Mol Wt. | LCMS MH+ | Ret Time (min) | HPLC Method |
|---|---|---|---|---|---|
| 218 | 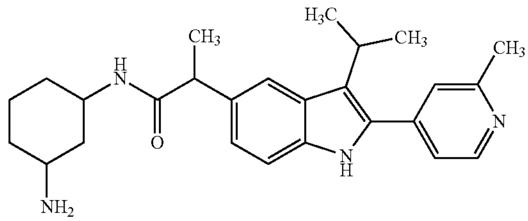 [SMILES: Cc1cc(-c2[nH]c3ccc(C(C)C(=O)NC4CCCC(N)C4)cc3c2C(C)C)ccn1] | 418.59 | 419.3 | 1.54 | QC-ACN-AA-XB |
| 219 | 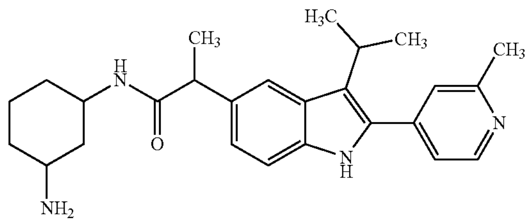 [SMILES: Cc1cc(-c2[nH]c3ccc(C(C)C(=O)NC4CCCC(N)C4)cc3c2C(C)C)ccn1] | 418.59 | 419.1 | 1.18 | QC-ACN-AA-XB |
| 220 | 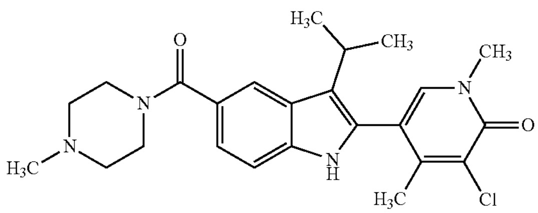 [SMILES: Cc1c(-c2[nH]c3ccc(C(=O)N4CCN(C)CC4)cc3c2C(C)C)cn(C)c(=O)c1Cl] | 440.97 | 441 | 1.17 | QC-ACN-AA-XB |
| 221 | 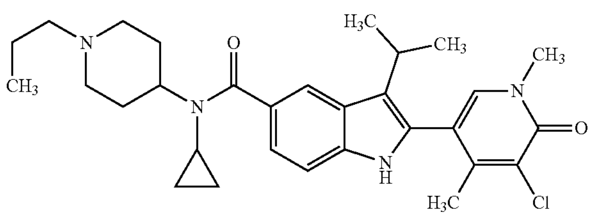 [SMILES: CCCN1CCC(N(C(=O)c2ccc3[nH]c(-c4cn(C)c(=O)c(Cl)c4C)c(C(C)C)c3c2)C2CC2)CC1] | 523.12 | 523.4 | 1.21 | QC-ACN-TFA-XB |
| 222 | 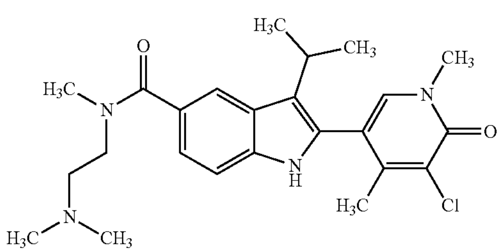 [SMILES: Cc1c(-c2[nH]c3ccc(C(=O)N(C)CCN(C)C)cc3c2C(C)C)cn(C)c(=O)c1Cl] | 442.99 | 443.3 | 1.06 | QC-ACN-AA-XB |

Biological Assays

The pharmacological properties of the compounds of this invention may be confirmed by a number of biological assays. The exemplified biological assays, which follow, have been carried out with compounds of the invention.

TLR7/8/9 Inhibition Reporter Assays

HEK-Blue™-cells (Invivogen) overexpressing human TLR7, TLR8 or TLR9 receptors were used for screening inhibitors of these receptors using an inducible SEAP (secreted embryonic alkaline phosphatase) reporter gene under the control of the IFN-β minimal promoter fused to five NF-κB and AP-1-binding sites. Briefly, cells are seeded into Greiner 384 well plates (15000 cells per well for TLR7, 20,000 for TLR8 and 25,000 for TLR9) and then treated with test compounds in DMSO to yield a final dose response concentration range of 0.05 nM-50 μM. After a 30 minute compound pre-treatment at room temperature, the cells are then stimulated with a TLR7 ligand (gardiquimod at a final concentration of 7.5 μM), TLR8 ligand (R848 at a final concentration of 15.9 μM) or TLR9 ligand (ODN2006 at a final concentration of 5 nM) to activate NF-κB and AP-1 which induce the production of SEAP. After a 22 hour incubation at 37° C., 5% $CO_2$, SEAP levels are determined with the addition of HEK-Blue™ Detection reagent (Invivogen), a cell culture medium that allows for detection of SEAP, according to manufacturer's specifications. The percent inhibition is determined as the % reduction in the HEK-Blue signal present in wells treated with agonist plus DMSO alone compared to wells treated with a known inhibitor.

TABLE 18

TLR7/8/9 Reporter Assay Data
(Ranges: A = <100 nM; B = 100 to 1000 nM;
C = >1000 to 50000 nM; NA-1 = >3125
nM; NA-2 = >50000 nM; NT = not tested)

| Ex. No. | TLR7 IC$_{50}$ (nM) | TLR8 IC$_{50}$ (nM) | TLR9 IC$_{50}$ (nM) |
|---|---|---|---|
| 1 | 30 | 49 | 375 |
| 2 | 45 | 4.0 | 3011 |
| 3 | 153 | 79 | >50000 |
| 4 | 145 | 27 | 30483 |
| 5 | 43 | 43 | 1381 |
| 6 | 180 | 180 | 5227 |
| 7 | 343 | 267 | 4016 |
| 8 | 129 | 126 | 7519 |
| 9 | 76 | 54 | 5348 |
| 10 | 111 | 114 | 7630 |
| 11 | 606 | 645 | 36012 |
| 12 | 274 | 175 | 1216 |
| 13 | 61 | 61 | 2160 |
| 14 | 40 | 26 | 1186 |
| 15 | 99 | 54 | 429 |
| 16 | 280 | 194 | 3937 |
| 17 | 115 | 7.9 | 2506 |
| 18 | 1659 | 260 | 13832 |
| 19 | 104 | NT | 1392 |
| 20 | 2312 | 858 | >50000 |
| 21 | 764 | 132 | 37377 |
| 22 | 356 | 264 | 37579 |
| 23 | 362 | 43 | 885 |
| 24 | 1791 | 581 | 31404 |
| 25 | 186 | 14 | 3710 |
| 26 | 1612 | 931 | >50000 |
| 27 | 1738 | 782 | >50000 |
| 28 | 1351 | 220 | >50000 |
| 29 | 188 | 34 | 6176 |
| 30 | 632 | 191 | 4161 |
| 31 | 296 | NT | 4927 |
| 32 | 1975 | 545 | 5100 |
| 33 | 1116 | 897 | 16753 |
| 34 | 1184 | 218 | >50000 |
| 35 | 595 | 190 | >50000 |
| 36 | 138 | NT | 1934 |
| 37 | 1303 | 14 | 9942 |
| 38 | 299 | 1.2 | 5266 |
| 39 | 367 | 2.2 | 4407 |
| 40 | 545 | 5.7 | 8699 |
| 41 | 1141 | 12 | 26730 |
| 42 | 751 | 15 | 9667 |
| 43 | 2495 | 572 | >50000 |
| 44 | 1941 | 412 | 44839 |
| 45 | 2238 | 1037 | >50000 |
| 46 | 391 | 60 | 931 |
| 47 | 150 | NT | 2794 |
| 48 | 144 | 4.8 | 2696 |
| 49 | 144 | NT | 2409 |
| 50 | 382 | NT | 19866 |
| 51 | 705 | NT | >50000 |
| 52 | 2384 | 243 | >50000 |
| 53 | 258 | 8.1 | 2002 |
| 54 | 206 | 12 | 1814 |
| 55 | 954 | 16 | 2092 |
| 56 | 112 | 13 | 2194 |
| 57 | 577 | 218 | >50000 |
| 58 | 194 | 110 | NT |
| 59 | 1141 | NT | >50000 |
| 60 | 206 | 115 | >50000 |
| 61 | 4124 | 1623 | 10209 |
| 62 | 493 | 381 | >50000 |
| 63 | 801 | 464 | 13592 |
| 64 | 1278 | 2187 | 16637 |
| 65 | 1210 | 1630 | 7245 |
| 66 | 3936 | 1170 | >50000 |
| 67 | 1770 | 412 | >50000 |
| 68 | 1707 | 277 | >50000 |
| 69 | 968 | 274 | >50000 |
| 70 | 441 | 243 | >50000 |
| 71 | 1630 | 439 | >50000 |
| 72 | 579 | 408 | >50000 |
| 73 | 25 | 4.0 | 4336 |
| 74 | 156 | 16 | 5884 |
| 75 | 124 | 7.6 | 250 |
| 76 | 56 | 3.9 | 4888 |
| 77 | 714 | 480 | 40270 |
| 79 | 296 | 124 | 1054 |
| 80 | 177 | 2.9 | 836 |
| 81 | 418 | 87 | 1922 |
| 82 | 515 | 446 | 21907 |
| 83 | 16 | 0.5 | 2348 |
| 84 | 49 | 2.1 | 2521 |
| 85 | 776 | 160 | 386 |
| 86 | 469 | 28 | 1569 |
| 87 | 1049 | 27 | 438 |
| 88 | 401 | 278 | 593 |
| 89 | 914 | 217 | 5865 |
| 90 | 866 | 344 | 4052 |
| 91 | 9.2 | 2.1 | 670 |
| 92 | 32 | 3.2 | 2473 |
| 93 | 2.9 | 1.4 | 594 |
| 94 | 18 | 23 | >50000 |
| 95 | 50 | 3.6 | 516 |
| 96 | 75 | 7.3 | 1501 |
| 97 | 45 | 30 | >50000 |
| 98 | 82 | 45 | >50000 |
| 99 | 201 | 481 | 1833 |
| 100 | 46 | 320 | >50000 |
| 101 | 1.9 | 0.34 | 776 |
| 102 | 185 | 418 | 5062 |
| 103 | 54 | 192 | 27053 |
| 104 | 14 | 12 | 373 |
| 105 | 33 | 59 | 20807 |
| 106 | 51 | 105 | >50000 |
| 107 | 73 | 58 | 264 |
| 108 | 7.3 | 1.5 | 247 |
| 109 | 18 | 2.3 | 116 |
| 110 | 49 | 11 | 410 |
| 111 | 171 | 74 | 668 |
| 112 | 335 | 36 | 334 |
| 113 | 50 | 0.8 | 1269 |
| 114 | 135 | 2.4 | 3626 |
| 115 | 147 | 3.5 | 1579 |
| 116 | 117 | 3.6 | 985 |
| 117 | 730 | 20 | 3696 |
| 118 | 4046 | 165 | 22744 |
| 119 | 2608 | 226 | 2227 |
| 120 | 870 | 47 | 752 |
| 121 | 1596 | 122 | 3333 |
| 122 | 2264 | 5654 | 1460 |
| 123 | 83 | 75 | 231 |
| 124 | 128 | 36 | 1117 |
| 125 | 19 | 23 | 727 |
| 126 | 29 | 233 | 2411 |
| 127 | 2.5 | 1.7 | 916 |
| 128 | 3.8 | 2.6 | 1399 |
| 129 | 1.8 | 2.3 | 3347 |
| 130 | 748 | 818 | >50000 |
| 131 | 657 | 979 | >50000 |
| 132 | 947 | 964 | NT |
| 133 | 284 | 399 | >50000 |
| 134 | 63 | 110 | 1087 |
| 135 | 202 | 551 | >50000 |
| 136 | 1760 | 411 | >50000 |
| 137 | 109 | 32 | 840 |
| 138 | 52 | 64 | 1168 |
| 139 | 25 | 154 | 1144 |
| 140 | 40 | 32 | 1215 |
| 141 | 58 | 68 | 895 |
| 142 | 16 | 120 | 790 |
| 143 | 35 | 147 | 562 |

TABLE 18-continued

TLR7/8/9 Reporter Assay Data
(Ranges: A = <100 nM; B = 100 to 1000 nM;
C = >1000 to 50000 nM; NA-1 = >3125
nM; NA-2 = >50000 nM; NT = not tested)

| Ex. No. | TLR7 IC$_{50}$ (nM) | TLR8 IC$_{50}$ (nM) | TLR9 IC$_{50}$ (nM) |
|---|---|---|---|
| 144 | 26 | 64 | 677 |
| 145 | 554 | 783 | 4495 |
| 146 | 160 | 122 | 979 |
| 147 | 109 | 92 | 1212 |
| 148 | 88 | 79 | 2640 |
| 149 | 17 | 277 | 3051 |
| 150 | 22 | 141 | 1488 |
| 151 | 72 | 175 | 7094 |
| 152 | 31 | 46 | 2638 |
| 153 | 159 | 91 | 566 |
| 154 | 58 | 256 | NT |
| 155 | 113 | 143 | 2037 |
| 156 | 53 | 52 | 927 |
| 157 | 6.3 | 28 | 997 |
| 158 | 79 | 500 | 3026 |
| 159 | 139 | 18 | 855 |
| 160 | 164 | 1028 | 5091 |
| 161 | 42 | 31 | 1738 |
| 162 | 24 | 135 | 3516 |
| 163 | 238 | 676 | 1877 |
| 164 | 331 | 617 | 2530 |
| 165 | 61 | 63 | 908 |
| 166 | 22 | 135 | 8234 |
| 167 | 63 | 36 | 2902 |
| 168 | 96 | 44 | 2674 |
| 169 | 16 | 7.1 | 899 |
| 170 | 11 | 51 | 1663 |
| 171 | 67 | 602 | 5218 |
| 172 | 58 | 325 | 1804 |
| 173 | 57 | 150 | 691 |
| 174 | 54 | 550 | 2055 |
| 175 | 167 | 36 | 1014 |
| 176 | 260 | 211 | 8394 |
| 177 | 128 | 58 | 1465 |
| 178 | 61 | 859 | 1659 |
| 179 | 35 | 1127 | 4931 |
| 180 | 147 | 306 | 1000 |
| 181 | 76 | 1243 | 1947 |
| 182 | 15 | 81 | 716 |
| 183 | 30 | 103 | 387 |
| 184 | 91 | 139 | 533 |
| 185 | 71 | 554 | 11855 |
| 186 | 146 | 100 | 599 |
| 187 | 223 | 496 | 1350 |
| 188 | 458 | 387 | 2621 |
| 189 | 268 | 246 | 1677 |
| 190 | 137 | 211 | 957 |
| 191 | 175 | 209 | 1292 |
| 192 | 71 | 142 | 1533 |
| 193 | 203 | 147 | 3372 |
| 194 | 152 | 106 | 3891 |
| 195 | 273 | 75 | 912 |
| 196 | 51 | 88 | 866 |
| 197 | 200 | 130 | 3289 |
| 198 | 46 | 72 | 1308 |
| 199 | 443 | 303 | 1207 |
| 700 | 12 | 69 | 690 |
| 201 | 74 | 70 | 1869 |
| 202 | 174 | 534 | 1348 |
| 203 | 296 | 365 | 746 |
| 204 | 74 | 119 | 939 |
| 205 | 277 | 341 | 2461 |
| 206 | 517 | 126 | 686 |
| 207 | 172 | 156 | 396 |
| 208 | 1287 | 2571 | 7309 |
| 209 | 103 | 96 | 685 |
| 210 | 280 | 210 | 718 |
| 211 | 50 | 51 | 472 |
| 212 | 821 | 1473 | 4998 |
| 213 | 466 | 241 | 2643 |
| 214 | 107 | 167 | 4674 |
| 215 | 148 | 174 | 1368 |
| 216 | 131 | 159 | 1057 |
| 217 | 167 | 316 | 999 |
| 218 | 803 | 1077 | 1401 |
| 219 | 256 | 182 | 1751 |
| 220 | 141 | 2.1 | NT |
| 221 | 5.2 | 0.7 | 2941 |
| 222 | 22 | 10 | 6920 |

What is claimed is:

1. A compound of Formula (I)

N-oxide, or a salt thereof, wherein:

G is $L_2$ is a bond, —CH(CH$_3$)—, —C(CH$_3$)$_2$—, or —CH$_2$CH$_2$—;

$R_1$ is —CH$_2$CH$_3$, —CH(CH$_3$)$_2$, —CH$_2$CHF$_2$, or —CH$_2$CF$_3$;

each $R_2$ is independently —CH$_3$, —OCH$_3$, or —NH$_2$;

$R_{2a}$ is —CH$_3$;

each $R_{2b}$ is independently H, Cl, or —CH$_3$;

$R_9$ is —CH$_3$, —CH$_2$CH$_2$OH, —CH$_2$C(CH$_3$)$_2$OH, —CH$_2$C(CH$_3$)$_2$CH$_2$OH, —CH$_2$CHFC(CH$_3$)$_2$OH, —CH$_2$CH$_2$C(CH$_3$)$_2$OH, —CH(CH$_2$OH)$_2$, —CH$_2$CH$_2$OCH$_3$, —CH$_2$CH$_2$NH$_2$, —CH$_2$CH$_2$N(CH$_3$)$_2$, —CH$_2$CH$_2$CH$_2$N(CH$_3$)$_2$, —CH$_2$CH$_2$C(O)NH$_2$, —CH$_2$S(O)$_2$OH, —CH$_2$CH$_2$C(CH$_3$)$_2$NHS(O)$_2$CH$_3$, or —(CH$_2$)$_{0-3}$R$_{9a}$;

$R_{9a}$ is cyclohexyl, cycloheptyl, furanyl, phenyl, piperazinyl, piperidinyl, pyrazolyl, pyridinyl, pyrrolidinyl, quinuclidinyl, thiazolyl, or octahydrocyclopenta[c]pyrrolyl, each substituted with zero to 2 substituents independently selected from —OH, $C_{1-3}$ alkyl, —NH$_2$, —N(CH$_3$)$_2$, oxetanyl, phenyl, piperazinyl, piperidinyl, and pyrrolidinyl;

$R_{10}$ is H, —CH$_3$, —CH$_2$CH$_3$, —CH$_2$CH$_2$OCH$_3$, or cyclopropyl;

or $R_9$ and $R_{10}$ together with the nitrogen atom to which they are attached form a heterocyclic ring selected from azabicyclo[3.1.1]heptanyl, azaspiro[5.5]undecanyl, diazabicyclo[2.2.1]heptanyl, diazabicyclo[3.1.1]heptanyl, diazabicyclo[3.2.0]heptanyl, diazaspiro[3.5]nonanyl, diazaspiro[4.4]nonanyl, diazaspiro[4.5]decanyl, diazepanyl, indolinyl, morpholinyl, octahydropyrrolo[3,4-c] pyrrolyl, piperazinonyl, piperazinyl, piperidinyl, and pyrrolidinyl, each substituted with zero to 2 $R_{10}$ a;

each $R_{10a}$ is independently selected from —CH$_3$, —CH$_2$CH$_3$, —CH(CH$_3$)$_2$, —CH$_2$OH, —CH$_2$CH$_2$OH, —CH$_2$OCH$_3$, —CH$_2$CH$_2$OCH$_3$, —CH$_2$NH$_2$, —CH$_2$CH$_2$NH$_2$, —CH$_2$CH$_2$NH(CH$_3$), —CH$_2$C(O)NH(CH$_3$), —CH$_2$C(O)N(CH$_3$)$_2$, —CH$_2$(methyltriazolyl), —CH$_2$CH$_2$(phenyl), —CH$_2$CH$_2$(morpholinyl), —C(O)CH$_3$, —C(O)NH$_2$, —C(O)N(CH$_2$CH$_3$)$_2$, —C(O)CH$_2$NH(CH$_3$), —C(O)CH$_2$N(CH$_3$)$_2$, —NH$_2$, —N(CH$_3$)$_2$, —NHC(O)CH$_3$, —C(O)(furanyl), —O(piperidinyl), —C(O)CH$_2$(diethylcarbamoylpiperidinyl), methylpiperazinyl, piperidinyl, methylpiperidinyl, diethylcarbamoylpiperidinyl, isopropylpiperidinyl, pyridinyl, trifluoromethylpyridinyl, pyrimidinyl, and dihydrobenzo[d]imidazolonyl;

and p is zero, 1, or 2.

2. The compound according to claim 1, N-oxide, or a salt thereof, wherein $R_9$ and $R_{10}$ together with the nitrogen atom to which they are attached form a heterocyclic ring selected from diazaspiro[4.5]decanyl, diazepanyl, octahydropyrrolo[3,4-c]pyrrolyl, piperazinyl, piperidinyl, and pyrrolidinyl, each substituted with zero to 2 $R_{10a}$.

3. The compound according to claim 1, N-oxide, or a salt thereof, wherein $L_2$ is a bond.

4. The compound according to claim 1, N-oxide, or a salt thereof, wherein $L_2$ is —CH(CH$_3$)—, —C(CH$_3$)$_2$—, or —CH$_2$CH$_2$—.

5. The compound according to claim 1, N-oxide, or a salt thereof, wherein G is:

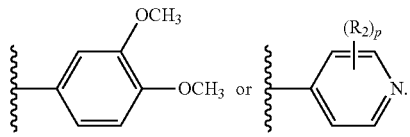

6. A pharmaceutical composition comprising a compound according to claim 1 or a pharmaceutically-acceptable salt thereof; and a pharmaceutically acceptable carrier.

7. A method of treating an autoimmune disease or a chronic inflammatory disease, comprising administering to a mammalian patient having said autoimmune disease or chronic inflammatory disease a compound according to claim 1 or a pharmaceutically acceptable salt thereof, wherein said autoimmune disease or chronic inflammatory disease is selected from systemic lupus erythematosus (SLE), rheumatoid arthritis, multiple sclerosis (MS), and Sjögren's syndrome.

8. A compound or a salt thereof, wherein said compound is:

2-(3,4-dimethoxyphenyl)-5-{octahydropyrrolo [3,4-c] pyrrole-2-carbonyl}-3-(propan-2-yl)-1H-indole (1);

(2-(3,4-dimethoxyphenyl)-3-isopropyl-1H-indol-5-yl)(4-methyl-1,4-diazepan-1-yl) methanone (2);

2-(3,4-dimethoxyphenyl)-3-isopropyl-N,N-dimethyl-1H-indole-5-carboxamide (3);

2-(3,4-dimethoxyphenyl)-3-isopropyl-N-methyl-1H-indole-5-carboxamide (4);

((1S,4S)-2,5-diazabicyclo[2.2.1]heptan-2-yl)(2-(3,4-dimethoxyphenyl)-3-isopropyl-1H-indol-5-yl)methanone (5);

2-{-[2-(3,4-dimethoxyphenyl)-3-(propan-2-yl)-1H-indole-5-carbonyl]-octahydropyrrolo [3,4-c]pyrrol-2-yl}-N,N-dimethylacetamide (6);

2(5-(2-(3,4-dimethoxyphenyl)-3-isopropyl-1H-indole-5-carbonyl) hexahydropyrrolo[3,4-c]pyrrol-2(1H)-yl)-N-methylacetamide (7);

1-(2-{5[2-(3,4-dimethoxyphenyl)-3-(propan-2-yl)-1H-indole-5-carbonyl]-octahydropyrrolo[3,4-c]pyrrol-2-yl}-2-oxoethyl)-N,N-diethylpiperidine-3-carboxamide (8);

1-(5-(2-(3,4-dimethoxyphenyl)-3-isopropyl-1H-indole-5-carbonyl) hexahydropyrrolo[3,4-c]pyrrol-2(1H)-yl)-2-dimethylamino)ethan-1-one (9);

1-(2-{5-[2-(3,4-dimethoxyphenyl)-3-(propan-2-yl)-1H-indole-5-carbonyl]-octahydro pyrrolo[3,4-c]pyrrol-2-yl}-2-oxoethyl)-N,N-diethylpiperidine-3-carboxamide (10-11);

(2(3,4-dimethoxyphenyl)-3-isopropyl-1H-indol-5-yl) (542-(methylamino)ethyl) hexahydropyrrolo[3,4-c] pyrrol-2(1H)-yl)methanone (12);

(2(3,4-dimethoxyphenyl)-3-isopropyl-1H-indol-5-yl)(5-methylhexahydro pyrrolo[3,4-c]pyrrol-2(1H)-yl) methanone (13);

(2-(3,4-dimethoxyphenyl)-3-isopropyl-1H-indol-5-yl)(5-isopropylhexahydropyrrolo[3,4-c]pyrrol-2(1H)-yl) methanone (14);

(2-(3,4-dimethoxyphenyl)-3-isopropyl-1H-indol-5-yl)(5-(1-methylpiperidin-4-yl) hexahydropyrrolo[3,4-c]pyrrol-2(1H)-yl)methanone (15);

1-(5-(2-(3,4-dimethoxyphenyl)-3-isopropyl-1H-indole-5-carbonyl)hexahydro pyrrolo[3,4-c]pyrrol-2(1H)-yl)-2-(methylamino) ethanone (16);

2-(3,4-dimethoxyphenyl)-N-[2-(dimethylamino)ethyl]-3-ethyl-1H-indole-5-carboxamide (17);

(R)-2-(3,4-dimethoxyphenyl)-3-ethyl-N-(2-fluoro-3-hydroxy-3-methylbutyl)-1H-indole-5-carboxamide (18);

2-(3,4-dimethoxyphenyl)-N-(4-(dimethylamino)cyclohexyl)-3-ethyl-1H-indole-5-carboxamide (19);

N-cycloheptyl-2-(3,4-dimethoxyphenyl)-3-ethyl-1H-indole-5-carboxamide (20);

2-(3,4-dimethoxyphenyl)-3-ethyl-N-(1-(oxetan-3-yl)-1H-pyrazol-4-yl)-1H-indole-5-carboxamide (21);

2-(3,4-dimethoxyphenyl)-3-ethyl-N-methyl-N-(pyridin-3-ylmethyl)-1H-indole-5-carboxamide (22);

2-(3,4-dimethoxyphenyl)-3-ethyl-N-methyl-N-((2-(piperidin-4-yl)thiazol-4-yl) methyl)-1H-indole-5-carboxamide (23);

2-(3,4-dimethoxyphenyl)-3-ethyl-N-methyl-N-(2-(pyridin-2-yl)ethyl)-1H-indole-5-carboxamide (24);

(2-(3,4-dimethoxyphenyl)-3-ethyl-1H-indol-5-yl) (4-(4-methylpiperazin-1-yl) piperidin-1-yl)methanone (25);

(R)-1-(1-(2-(3,4-dimethoxyphenyl)-3-ethyl-1H-indole-5-carbonyl)pyrrolidin-3-yl) propan-2-one (26);

(S)-(2-(3,4-dimethoxyphenyl)-3-ethyl-1H-indol-5-yl)(2-(methoxymethyl)pyrrolidin-1-yl) methanone (27);

(S)-(2-(3,4-dimethoxyphenyl)-3-ethyl-1H-indol-5-yl)(2-(hydroxymethyl)pyrrolidin-1-yl)methanone (28);
(R)-(2-(3,4-dimethoxyphenyl)-3-ethyl-1H-indol-5-yl)(3-(dimethylamino) pyrrolidin-1-yl)methanone (29);
(S)-(2-(3,4-dimethoxyphenyl)-3-ethyl-1H-indol-5-yl)(3-(dimethylamino)pyrrolidin-1-yl)methanone (30);
(2-(3,4-dimethoxyphenyl)-3-ethyl-1H-indol-5-yl)(4-(dimethylamino)piperidin-1-yl) methanone (31);
(2-(3,4-dimethoxyphenyl)-3-ethyl-1H-indol-5-yl)(3,3-dimethylpiperidin-1-yl) methanone (32);
1-(2-(3,4-dimethoxyphenyl)-3-ethyl-1H-indole-5-carbonyl)-N,N-diethylpiperidine-3-carboxamide (33);
1-(2-(3,4-dimethoxyphenyl)-3-ethyl-1H-indole-5-carbonyl)piperidine-4-carboxamide (34);
1-(4-(2-(3,4-dimethoxyphenyl)-3-ethyl-1H-indole-5-carbonyl)-1,4-diazepan-1-yl) ethan-1-one (35);
(2-(3,4-dimethoxyphenyl)-3-ethyl-1H-indol-5-yl)(4-(1-methylpiperidin-4-yl) piperazin-1-yl)methanone (36);
(2-(3,4-dimethoxyphenyl)-3-ethyl-1H-indol-5-yl)(4-phenethylpiperazin-1-yl) methanone (37);
(2-(3,4-dimethoxyphenyl)-3-ethyl-1H-indol-5-yl) (4-isopropylpiperazin-1-yl) methanone (38);
(2-(3,4-dimethoxyphenyl)-3-ethyl-1H-indol-5-yl)(4-ethylpiperazin-1-yl)methanone (39);
(2-(3,4-dimethoxyphenyl)-3-ethyl-1H-indol-5-yl) (4-(2-hydroxyethyl)piperazin-1-yl) methanone (40);
(2-(3,4-dimethoxyphenyl)-3-ethyl-1H-indol-5-yl)(4-(2-methoxyethyl)piperazin-1-yl) methanone (41);
(2-(3,4-dimethoxyphenyl)-3-ethyl-1H-indol-5-yl)(4-(2-morpholinoethyl)piperazin-1-yl)methanone (42);
2-(3,4-dimethoxyphenyl)-3-ethyl-N-(furan-2-ylmethyl)-1H-indole-5-carboxamide (43);
2-(3,4-dimethoxyphenyl)-3-ethyl-N-(pyridin-2-ylmethyl)-1H-indole-5-carboxamide (44);
2-(3,4-dimethoxyphenyl)-3-ethyl-N-((2-phenylthiazol-4-yl)methyl)-1H-indole-5-carboxamide (45);
2-(3,4-dimethoxyphenyl)-3-ethyl-N-(4-(piperazin-1-yl)benzyl)-1H-indole-5-carboxamide (46);
N-((1r,4r)-4-aminocyclohexyl)-2-(3,4-dimethoxyphenyl)-3-ethyl-1H-indole-5-carboxamide (47);
2-(3,4-dimethoxyphenyl)-3-ethyl-N-(2-(pyrrolidin-1-yl)ethyl)-1H-indole-5-carboxamide (48);
2-(3,4-dimethoxyphenyl)-3-ethyl-N-(2-(piperidin-1-yl)ethyl)-1H-indole-5-carboxamide (49);
2-(3,4-dimethoxyphenyl)-3-ethyl-N-(2-(pyridin-4-yl)ethyl)-1H-indole-5-carboxamide (50);
2-(3,4-dimethoxyphenyl)-3-ethyl-N-(2-(pyridin-3-yl)ethyl)-1H-indole-5-carboxamide (51);
N-(4-aminobenzyl)-2-(3,4-dimethoxyphenyl)-3-ethyl-1H-indole-5-carboxamide (52);
2-(3,4-dimethoxyphenyl)-3-ethyl-N-(3-(piperidin-1-yl)propyl)-1H-indole-5-carboxamide (53);
2-(3,4-dimethoxyphenyl)-3-ethyl-N-(2-(1-methylpyrrolidin-2-yl)ethyl)-1H-indole-5-carboxamide (54);
2-(3,4-dimethoxyphenyl)-3-ethyl-N-(3-(4-methylpiperazin-1-yl)propyl)-1H-indole-5-carboxamide (55);
[1,4'-bipiperidin]-1'-yl(2-(3,4-dimethoxyphenyl)-3-ethyl-1H-indol-5-yl)methanone (56);
(2-(3,4-dimethoxyphenyl)-3-ethyl-1H-indol-5-yl)(4-(pyrimidin-2-yl)piperazin-1-yl) methanone (57);
(2-(3,4-dimethoxyphenyl)-3-ethyl-1H-indol-5-yl)(4-(pyrazin-2-yl)piperazin-1-yl) methanone (58);
(2-(3,4-dimethoxyphenyl)-3-ethyl-1H-indol-5-yl)(4-(pyridin-2-yl)piperazin-1-yl) methanone (59);
(2-(3,4-dimethoxyphenyl)-3-ethyl-1H-indol-5-yl)(4-(furan-2-carbonyl)piperazin-1-yl) methanone (60);
(2-(3,4-dimethoxyphenyl)-3-ethyl-1H-indol-5-yl)(4-(5-(trifluoromethyl) pyridin-2-yl) piperazin-1-yl)methanone (61);
4-(2-(3,4-dimethoxyphenyl)-3-ethyl-1H-indole-5-carbonyl)piperazin-2-one (62);
1-(1-(2-(3,4-dimethoxyphenyl)-3-ethyl-1H-indole-5-carbonyl)piperidin-4-yl)-1,3-dihydro-2H-benzo[d]imidazol-2-one (63);
(2-(3,4-dimethoxyphenyl)-3-ethyl-1H-indol-5-yl)(4-(pyrimidin-2-yl)-1,4-diazepan-1-yl)methanone (64);
(2-(3,4-dimethoxyphenyl)-3-ethyl-1H-indol-5-yl)(4-(pyridin-2-yl)-1,4-diazepan-1-yl) methanone (65);
(2-(3,4-dimethoxyphenyl)-3-ethyl-1H-indol-5-yl)(indolin-1-yl)methanone (66);
N-(1,3-dihydroxypropan-2-yl)-2-(3,4-dimethoxyphenyl)-3-ethyl-1H-indole-5-carboxamide (67);
N-(3-amino-3-oxopropyl)-2-(3,4-dimethoxyphenyl)-3-ethyl-1H-indole-5-carboxamide (68);
2-(3,4-dimethoxyphenyl)-3-ethyl-N-(2-hydroxyethyl)-1H-indole-5-carboxamide (69);
(2-(3,4-dimethoxyphenyl)-3-ethyl-1H-indole-5-carboxamido) methanesulfonic acid (70);
2-(3,4-dimethoxyphenyl)-3-ethyl-N-(3-methyl-3-(methyl sulfonamido)butyl)-1H-indole-5-carboxamide (71);
2-(3,4-dimethoxyphenyl)-3-ethyl-N-(3-hydroxy-2,2-dimethylpropyl)-1H-indole-5-carboxamide (72);
2-(3,4-dimethoxyphenyl)-N-(2-(dimethylamino)ethyl)-N,3-diethyl-1H-indole-5-carboxamide (73);
2-(3,4-dimethoxyphenyl)-N-(3-(dimethylamino)propyl)-3-ethyl-N-methyl-1H-indole-5-carboxamide (74);
2-(3,4-dimethoxyphenyl)-N-(3-(dimethylamino)propyl)-3-ethyl-1H-indole-5-carboxamide (75);
2-(3,4-dimethoxyphenyl)-N-(2-(dimethylamino)ethyl)-3-ethyl-N-methyl-1H-indole-5-carboxamide (76);
2-(3,4-dimethoxyphenyl)-3-ethyl-N,N-bis(2-methoxyethyl)-1H-indole-5-carboxamide (77);
(2-(3,4-dimethoxyphenyl)-3-ethyl-1H-indol-5-yl)(piperazin-1-yl)methanone hydrochloride (78);
(2-(3,4-dimethoxyphenyl)-3-ethyl-1H-indol-5-yl)(hexahydropyrrolo[3,4-c]pyrrol-2(1H)-yl)methanone (79);
(2-(3,4-dimethoxyphenyl)-3-ethyl-1H-indol-5-yl)(4-(1-isopropylpiperidin-4-yl) piperazin-1-yl) methanone (80);
(2-(3,4-dimethoxyphenyl)-3-ethyl-1H-indol-5-yl)(5-isopropylhexahydropyrrolo[3,4-c]pyrrol-2(1H)-yl)methanone (81);
2-(5-(2-(3,4-dimethoxyphenyl)-3-ethyl-1H-indole-5-carbonyl)hexahydropyrrolo[3,4-c]pyrrol-2(1H)-yl)-N-methylacetamide (82);
N-(2-(dimethylamino)ethyl)-N,3-diethyl-2-(1H-pyrrolo[2,3-b] pyridin-4-yl)-1H-indole-5-carboxamide (83);
N-(2-(dimethylamino)ethyl)-N,3-diethyl-2-(2-methylpyridin-4-yl)-1H-indole-5-carboxamide (84);
(3-ethyl-2-(2-methylpyridin-4-yl)-1H-indol-5-yl)(hexahydropyrrolo[3,4-c]pyrrol-2(1H)-yl)methanone (85);
(3-ethyl-2-(2-methylpyridin-4-yl)-1H-indol-5-yl)(5-isopropylhexahydropyrrolo[3,4c]pyrrol-2(1H)-yl) methanone (86);
2-(2-aminopyridin-4-yl)-N-(4-(dimethylamino)cyclohexyl)-3-isopropyl-1H-indole-5-carboxamide (87);
(2-(3,4-dimethoxyphenyl)-3-(2,2,2-trifluoroethyl)-1H-indol-5-yl) (hexahydropyrrolo[3,4-c]pyrrol-2(1H)-yl) methanone hydrochloride (88);
1-(5-(2-(3,4-dimethoxyphenyl)-3-(2,2,2-trifluoroethyl)-1H-indole-5-carbonyl) hexahydropyrrolo[3,4-c] pyrrol-2(1H)-yl)-2-(dimethylamino)ethan-1-one (89);

2-(5-(2-(3,4-dimethoxyphenyl)-3-(2,2,2-trifluoroethyl)-1H-indole-5-carbonyl) hexahydropyrrolo[3,4-c]pyrrol-2(1H)-yl)-N,N-dimethylacetamide (90);
2-(2,6-dimethylpyridin-4-yl)-3-isopropyl-N-(1-isopropylpiperidin-4-yl)-1H-indole-5-carboxamide (91);
(2-(2,6-dimethylpyridin-4-yl)-3-isopropyl-1H-indol-5-yl)(4-methyl-1,4-diazepan-1-yl)methanone (92);
N-(2-(dimethylamino)ethyl)-2-(2,6-dimethylpyridin-4-yl)-N-ethyl-3-isopropyl-1H-indole-5-carboxamide (93);
2-(2,6-dimethylpyridin-4-yl)-3-isopropyl-N,N-dimethyl-1H-indole-5-carboxamide (94);
N-(3-(dimethylamino)propyl)-2-(2,6-dimethylpyridin-4-yl)-3-isopropyl-1H-indole-5-carboxamide (95);
N-(2-(dimethylamino)ethyl)-2-(2,6-dimethylpyridin-4-yl)-3-isopropyl-1H-indole-5-carboxamide (96);
2-(2,6-dimethylpyridin-4-yl)-3-isopropyl-N-methyl-1H-indole-5-carboxamide (97);
(2-(2,6-dimethylpyridin-4-yl)-3-isopropyl-1H-indol-5-yl)(4-((l-methyl-1H-1,2,4-triazol-3-yl)methyl)piperazin-1-yl)methanone (98);
N-benzyl-2-(2,6-dimethylpyridin-4-yl)-3-isopropyl-N-methyl-1H-indole-5-carboxamide (99);
2-(2,6-dimethylpyridin-4-yl)-3-isopropyl-N-methyl-N-(pyridin-3-ylmethyl)-1H-indole-5-carboxamide (100);
2-(2,6-dimethylpyridin-4-yl)-3-isopropyl-N-methyl-N-(1-methylpiperidin-4-yl)-1H-indole-5-carboxamide (101);
2-(2,6-dimethylpyridin-4-yl)-3-isopropyl-N-methyl-N-phenethyl-1H-indole-5-carboxamide (102);
N-(3-aminobenzyl)-2-(2,6-dimethylpyridin-4-yl)-3-isopropyl-N-methyl-1H-indole-5-carboxamide (103);
(4-(dimethylamino)piperidin-1-yl)(2-(2,6-dimethylpyridin-4-yl)-3-isopropyl-1H-indol-5-yl) methanone (104);
2-(2,6-dimethylpyridin-4-yl)-N-(2-hydroxyethyl)-3-isopropyl-N-methyl-1H-indole-5-carboxamide (105);
2-(2,6-dimethylpyridin-4-yl)-3-isopropyl-N-(2-methoxyethyl)-N-methyl-1H-indole-5-carboxamide (106);
(2-(2,6-dimethylpyridin-4-yl)-3-isopropyl-1H-indol-5-yl)(hexahydropyrrolo[3,4-c] pyrrol-2(1H)-yl)methanone, HCl (107);
(2-(2,6-dimethylpyridin-4-yl)-3-isopropyl-1H-indol-5-yl)(piperazin-1-yl)methanone (108);
(2-(2,6-dimethylpyridin-4-yl)-3-isopropyl-1H-indol-5-yl)(5-methylhexahydropyrrolo[3,4-c] pyrrol-2(1H)-yl)methanone (109);
(2-(2,6-dimethylpyridin-4-yl)-3-isopropyl-1H-indol-5-yl)(5-isopropylhexahydropyrrolo[3,4-c]pyrrol-2(1H)-yl)methanone (110);
2-(dimethylamino)-1-(5-(2-(2,6-dimethylpyridin-4-yl)-3-isopropyl-1H-indole-5-carbonyl)hexahydropyrrolo[3,4-c]pyrrol-2(1H)-yl)ethanone (111);
(hexahydropyrrolo[3,4-c]pyrrol-2(1H)-yl)(3-isopropyl-2-(2-methyl pyridin-4-yl)-1H-indol-5-yl)methanone, HCl (112);
3-isopropyl-N-(1-isopropylpiperidin-4-yl)-2-(2-methylpyridin-4-yl)-1H-indole-5-carboxamide (113);
(3-isopropyl-2-(2-methylpyridin-4-yl)-1H-indol-5-yl)(4-methyl-1,4-diazepan-1-yl) methanone (114);
(3-isopropyl-2-(2-methylpyridin-4-yl)-1H-indol-5-yl)(5-methylhexahydropyrrolo[3,4-c]pyrrol-2(1H)-yl) methanone (115);
(3-isopropyl-2-(2-methylpyridin-4-yl)-1H-indol-5-yl)(5-isopropylhexahydropyrrolo[3,4-c]pyrrol-2(1H)-yl) methanone (116);
2-(5-(3-isopropyl-2-(2-methylpyridin-4-yl)-1H-indole-5-carbonyl) hexahydropyrrolo[3,4-c]pyrrol-2(1H)-yl)-N,N-dimethylacetamide (117);
2-(5-(3-isopropyl-2-(2-methylpyridin-4-yl)-1H-indole-5-carbonyl)hexahydropyrrolo[3,4-c]pyrrol-2(1H)-yl)-N-methylacetamide (118);
1-(5-(3-isopropyl-2-(2-methylpyridin-4-yl)-1H-indole-5-carbonyl) hexahydropyrrolo[3,4-c]pyrrol-2(1H)-yl)-2-(methylamino)ethanone (119);
2-(dimethylamino)-1-(5-(3-isopropyl-2-(2-methylpyridin-4-yl)-1H-indole-5-carbonyl) hexahydropyrrolo[3,4-c]pyrrol-2(1H)-yl)ethan-1-one (120);
(hexahydropyrrolo[3,4-c]pyrrol-2(1H)-yl)(3-isopropyl-2-(1H-pyrazolo[3,4-b]pyridin-4-yl)-1H-indol-5-yl) methanone, HCl (121);
(3-(2,2-difluoroethyl)-2-(2,6-dimethylpyridin-4-yl)-1H-indol-5-yl) (hexahydropyrrolo[3,4-c]pyrrol-2(1H)-yl) methanone (122);
3-(2,2-difluoroethyl)-2-(2,6-dimethylpyridin-4-yl)-N-(1-isopropylpiperidin-4-yl)-1H-indole-5-carboxamide (123);
(3-(2,2-difluoroethyl)-2-(2,6-dimethylpyridin-4-yl)-1H-indol-5-yl)(4-methyl-1,4-diazepan-1-yl)methanone (124);
3-(2,2-difluoroethyl)-N-(2-(dimethylamino)ethyl)-2-(2,6-dimethylpyridin-4-yl)-N-ethyl-1H-indole-5-carboxamide (125);
(hexahydropyrrolo[3,4-c]pyrrol-2(1H)-yl)(3-isopropyl-2-(8-methoxy-[1,2,4]triazolo[1,5-a]pyridin-6-yl)-1H-indol-5-yl)methanone (126);
3-isopropyl-N-(1-isopropylpiperidin-4-yl)-2-(8-methoxy-[1,2,4]triazolo[1,5-a] pyridin-6-yl)-1H-indole-5-carboxamide (127);
(3-isopropyl-2-(8-methoxy-[1,2,4]triazolo[1,5-a]pyridin-6-yl)-1H-indol-5-yl)(4-methyl-1,4-diazepan-1-yl) methanone (128);
N-(2-(dimethylamino)ethyl)-3-isopropyl-2-(8-methoxy-[1,2,4]triazolo[1,5-a]pyridin-6-yl)-N-methyl-1H-indole-5-carboxamide (129);
N-((R)-2-fluoro-3-hydroxy-3-methylbutyl)-2-(3-isopropyl-2-(2-methylpyridin-4-yl)-1H-indol-5-yl)propanamide (130);
N-(2-hydroxy-2-methylpropyl)-2-(3-isopropyl-2-(2-methylpyridin-4-yl)-1H-indol-5-yl)propanamide (131);
N-(3-hydroxy-3-methylbutyl)-2-(3-isopropyl-2-(2-methylpyridin-4-yl)-1H-indol-5-yl) propanamide (132);
(R)—N-(2-fluoro-3-hydroxy-3-methylbutyl)-2-(3-isopropyl-2-(2-methylpyridin-4-yl)-1H-indol-5-yl)-2-methylpropanamide (133);
N-(2-aminoethyl)-2-(3-isopropyl-2-(2-methylpyridin-4-yl)-1H-indol-5-yl)-2-methylpropanamide (134);
N-(3-hydroxy-3-methylbutyl)-2-(3-isopropyl-2-(2-methylpyridin-4-yl)-1H-indol-5-yl)-2-methylpropanamide (135);
3-(3-isopropyl-2-(1H-pyrazolo[3,4-b]pyridin-4-yl)-1H-indol-5-yl)-1-morpholinopropan-1-one (136);
3-(2-(3,4-dimethoxyphenyl)-3-isopropyl-1H-indol-5-yl)-1-(hexahydropyrrolo[3,4-c] pyrrol-2(1H)-yl)propan-1-one (137);
(S)-2-(3-isopropyl-2-(2-methylpyridin-4-yl)-1H-indol-5-yl)-2-methyl-N-(pyrrolidin-3-yl)propanamide (138);
2-(3-isopropyl-2-(2-methylpyridin-4-yl)-1H-indol-5-yl)-N-(1-isopropylpiperidin-4-yl)-2-methylpropanamide (139);
(R)-2-(3-isopropyl-2-(2-methylpyridin-4-yl)-1H-indol-5-yl)-2-methyl-N-(piperidin-3-yl)propanamide (140);

(R)-2-(3-isopropyl-2-(2-methylpyridin-4-yl)-1H-indol-5-yl)-2-methyl-N-(pyrrolidin-3-yl)propanamide (141);
2-(3-isopropyl-2-(2-methylpyridin-4-yl)-1H-indol-5-yl)-2-methyl-N-(quinuclidin-3-yl)propanamide (142);
2-(3-isopropyl-2-(2-methylpyridin-4-yl)-1H-indol-5-yl)-2-methyl-N-(piperidin-4-yl) propanamide (143);
2-(3-isopropyl-2-(2-methylpyridin-4-yl)-1H-indol-5-yl)-2-methyl-N-(octahydrocyclopenta[c]pyrrol-4-yl)propanamide (144);
2-(3-isopropyl-2-(2-methylpyridin-4-yl)-1H-indol-5-yl)-2-methyl-N-(1-(pyrrolidin-3-yl)piperidin-4-yl)propanamide (145);
2-(3-isopropyl-2-(2-methylpyridin-4-yl)-1H-indol-5-yl)-2-methyl-N-(octahydrocyclopenta[c]pyrrol-4-yl)propanamide (146);
2-(3-isopropyl-2-(2-methylpyridin-4-yl)-1H-indol-5-yl)-2-methyl-N-(octahydrocyclopenta[c]pyrrol-4-yl)propanamide (147);
1-(6-amino-3-azabicyclo[3.1.1]heptan-3-yl)-2-(3-isopropyl-2-(2-methylpyridin-4-yl)-1H-indol-5-yl)-2-methylpropan-1-one (148);
2-(3-isopropyl-2-(2-methylpyridin-4-yl)-1H-indol-5-yl)-2-methyl-1-(5-methylhexahydropyrrolo[3,4-c]pyrrol-2(1H)-yl)propan-1-one (149);
2-(3-isopropyl-2-(2-methylpyridin-4-yl)-1H-indol-5-yl)-2-methyl-1-(methyl-2,8-diazaspiro[4.5]decan-8-yl)propan-1-one (150);
1-(3-(aminomethyl)pyrrolidin-1-yl)-2-(3-isopropyl-2-(2-methylpyridin-4-yl)-1H-indol-5-yl)-2-methylpropan-1-one (151);
1-(7-amino-2-azaspiro[5.5]undecan-2-yl)-2-(3-isopropyl-2-(2-methylpyridin-4-yl)-1H-indol-5-yl)-2-methylpropan-1-one (152);
1-(4-aminopiperidin-1-yl)-2-(3-isopropyl-2-(2-methylpyridin-4-yl)-1H-indol-5-yl)-2-methylpropan-1-one (153);
1-(3-(2-aminoethyl)piperidin-1-yl)-2-(3-isopropyl-2-(2-methylpyridin-4-yl)-1H-indol-5-yl)-2-methylpropan-1-one (154);
(S)-1-(3-aminopiperidin-1-yl)-2-(3-isopropyl-2-(2-methylpyridin-4-yl)-1H-indol-5-yl)-2-methylpropan-1-one (155);
1-(3-(aminomethyl)piperidin-1-yl)-2-(3-isopropyl-2-(2-methylpyridin-4-yl)-1H-indol-5-yl)-2-methylpropan-1-one (156);
1-(2-(aminomethyl)piperidin-1-yl)-2-(3-isopropyl-2-(2-methylpyridin-4-yl)-1H-indol-5-yl)-2-methylpropan-1-one (157);
1-(4-(aminomethyl)piperidin-1-yl)-2-(3-isopropyl-2-(2-methylpyridin-4-yl)-1H-indol-5-yl)-2-methylpropan-1-one (158);
2-(3-isopropyl-2-(2-methylpyridin-4-yl)-1H-indol-5-yl)-2-methyl-N-(piperidin-2-ylmethyl)propanamide (159);
(S)-2-(3-isopropyl-2-(2-methylpyridin-4-yl)-1H-indol-5-yl)-2-methyl-N-(pyrrolidin-3-ylmethyl)propanamide (160);
2-(3-isopropyl-2-(2-methylpyridin-4-yl)-1H-indol-5-yl)-N,2-dimethyl-N-(piperidin-3-yl)propanamide (161);
2-(3-isopropyl-2-(2-methylpyridin-4-yl)-1H-indol-5-yl)-N,2-dimethyl-N-(quinuclidin-3-yl)propanamide (162);
2-(3-isopropyl-2-(2-methylpyridin-4-yl)-1H-indol-5-yl)-2-methyl-N-(piperidin-3-ylmethyl)propanamide (163);
2-(3-isopropyl-2-(2-methylpyridin-4-yl)-1H-indol-5-yl)-2-methyl-N-(piperidin-4-ylmethyl)propanamide (164);
2-(3-isopropyl-2-(2-methylpyridin-4-yl)-1H-indol-5-yl)-N,2-dimethyl-N-(piperidin-4-yl)propanamide (165);
2-(3-isopropyl-2-(2-methylpyridin-4-yl)-1H-indol-5-yl)-2-methyl-N-((1R,5S)-8-methyl-8-azabicyclo[3.2.1]octan-3-yl)propanamide (166);
N-(4-aminocyclohexyl)-2-(3-isopropyl-2-(2-methylpyridin-4-yl)-1H-indol-5-yl)-2-methylpropanamide (167);
N-(3-aminocyclohexyl)-2-(3-isopropyl-2-(2-methylpyridin-4-yl)-1H-indol-5-yl)-2-methylpropanamide (168);
N-((1R,2R)-2-aminocyclohexyl)-2-(3-isopropyl-2-(2-methylpyridin-4-yl)-1H-indol-5-yl)-2-methylpropanamide (169);
N-((1S,2R)-2-aminocyclohexyl)-2-(3-isopropyl-2-(2-methylpyridin-4-yl)-1H-indol-5-yl)-2-methylpropanamide (170);
2-(3-isopropyl-2-(2-methylpyridin-4-yl)-1H-indol-5-yl)-2-methyl-N-(2-(piperidin-3-yl)ethyl)propanamide (171);
N-(((1R,4R)-4-aminocyclohexyl)methyl)-2-(3-isopropyl-2-(2-methylpyridin-4-yl)-1H-indol-5-yl)-2-methylpropanamide (172);
N-((4-hydroxy-1-methylpiperidin-4-yl)methyl)-2-(3-isopropyl-2-(2-methylpyridin-4-yl)-1H-indol-5-yl)-2-methylpropanamide (173);
N-((3-hydroxyquinuclidin-3-yl)methyl)-2-(3-isopropyl-2-(2-methylpyridin-4-yl)-1H-indol-5-yl)-2-methylpropanamide (174);
2-(3-isopropyl-2-(2-methylpyridin-4-yl)-1H-indol-5-yl)-2-methyl-1-(piperazin-1-yl) propan-1-one (175);
1-(2,5-diazabicyclo[2.2.1]heptan-2-yl)-2-(3-isopropyl-2-(2-methylpyridin-4-yl)-1H-indol-5-yl)-2-methylpropan-1-one (176);
2-(3-isopropyl-2-(2-methylpyridin-4-yl)-1H-indol-5-yl)-2-methyl-1-(4-(piperidin-4-yloxy)piperidin-1-yl)propan-1-one (177);
2-(3-isopropyl-2-(2-methylpyridin-4-yl)-1H-indol-5-yl)-2-methyl-1-(2,7-diazaspiro[4.4]nonan-2-yl)propan-1-one (178);
2-(3-isopropyl-2-(2-methylpyridin-4-yl)-1H-indol-5-yl)-2-methyl-1-(2,7-diazaspiro[3.5]nonan-2-yl)propan-1-one (179);
2-(3-isopropyl-2-(2-methylpyridin-4-yl)-1H-indol-5-yl)-2-methyl-1-(2,6-diazaspiro[3.5]nonan-6-yl)propan-1-one (180);
2-(3-isopropyl-2-(2-methylpyridin-4-yl)-1H-indol-5-yl)-2-methyl-1-(2,8-diazaspiro[4.5]decan-8-yl)propan-1-one (181);
1-([2,4'-bipiperidin]-1-yl)-2-(3-isopropyl-2-(2-methylpyridin-4-yl)-1H-indol-5-yl)-2-methylpropan-1-one (182);
1-(hexahydropyrrolo[3,4-c]pyrrol-2(1H)-yl)-2-(3-isopropyl-2-(2-methylpyridin-4-yl)-1H-indol-5-yl)-2-methylpropan-1-one (183);
2-(3-isopropyl-2-(2-methylpyridin-4-yl)-1H-indol-5-yl)-2-methyl-1-(2,7-diazaspiro[4.5]decan-7-yl)propan-1-one (184);
1-(3,6-diazabicyclo[3.2.0]heptan-3-yl)-2-(3-isopropyl-2-(2-methylpyridin-4-yl)-1H-indol-5-yl)-2-methylpropan-1-one (185);
2-(3-isopropyl-2-(2-methylpyridin-4-yl)-1H-indol-5-yl)-N-(octahydrocyclopenta[c]pyrrol-4-yl)propanamide (186);
2-(3-isopropyl-2-(2-methylpyridin-4-yl)-1H-indol-5-yl)-N-(octahydrocyclopenta[c]pyrrol-4-yl)propanamide (187);
2-(3-isopropyl-2-(2-methylpyridin-4-yl)-1H-indol-5-yl)-N-((R)-pyrrolidin-3-yl) propanamide (188);
2-(3-isopropyl-2-(2-methylpyridin-4-yl)-1H-indol-5-yl)-N-((S)-pyrrolidin-3-yl) propanamide (189);

2-(3-isopropyl-2-(2-methylpyridin-4-yl)-1H-indol-5-yl)-N-((S)-pyrrolidin-3-yl) propanamide (190);
2-(3-isopropyl-2-(2-methylpyridin-4-yl)-1H-indol-5-yl)-N-(quinuclidin-3-yl) propanamide (191);
2-(3-isopropyl-2-(2-methylpyridin-4-yl)-1H-indol-5-yl)-N-(quinuclidin-3-yl) propanamide (192);
2-(3-isopropyl-2-(2-methylpyridin-4-yl)-1H-indol-5-yl)-N-(piperidin-4-yl) propanamide (193);
2-(3-isopropyl-2-(2-methylpyridin-4-yl)-1H-indol-5-yl)-N-(1-isopropylpiperidin-4-yl) propanamide (194);
2-(3-isopropyl-2-(2-methylpyridin-4-yl)-1H-indol-5-yl)-N-((R)-piperidin-3-yl) propanamide (195);
2-(3-isopropyl-2-(2-methylpyridin-4-yl)-1H-indol-5-yl)-N-((R)-piperidin-3-yl) propanamide (196);
2-(3-isopropyl-2-(2-methylpyridin-4-yl)-1H-indol-5-yl)-1-(5-methylhexahydropyrrolo[3,4-c]pyrrol-2(1H)-yl) propan-1-one (197);
2-(3-isopropyl-2-(2-methylpyridin-4-yl)-1H-indol-5-yl)-1-(2-methyl-2,8-diazaspiro[4.5]decan-8-yl)propan-1-one (198);
1-(3-(aminomethyl)pyrrolidin-1-yl)-2-(3-isopropyl-2-(2-methylpyridin-4-yl)-1H-indol-5-yl)propan-1-one (199);
1-(7-amino-2-azaspiro[5.5]undecan-2-yl)-2-(3-isopropyl-2-(2-methylpyridin-4-yl)-1H-indol-5-yl)propan-1-one (200);
1-(7-amino-2-azaspiro[5.5]undecan-2-yl)-2-(3-isopropyl-2-(2-methylpyridin-4-yl)-1H-indol-5-yl)propan-1-one (201);
1-(4-(aminomethyl)piperidin-1-yl)-2-(3-isopropyl-2-(2-methylpyridin-4-yl)-1H-indol-5-yl)propan-1-one (202);
1-(4-aminopiperidin-1-yl)-2-(3-isopropyl-2-(2-methylpyridin-4-yl)-1H-indol-5-yl) propan-1-one (203);
1-((S)-3-aminopiperidin-1-yl)-2-(3-isopropyl-2-(2-methylpyridin-4-yl)-1H-indol-5-yl)propan-1-one (204);
1-(3-(aminomethyl)piperidin-1-yl)-2-(3-isopropyl-2-(2-methylpyridin-4-yl)-1H-indol-5-yl)propan-1-one (205);
1-(3-(2-aminoethyl)piperidin-1-yl)-2-(3-isopropyl-2-(2-methylpyridin-4-yl)-1H-indol-5-yl)propan-1-one (206);
2-(3-isopropyl-2-(2-methylpyridin-4-yl)-1H-indol-5-yl)-N-methyl-N-(piperidin-4-yl) propanamide (207);
2-(3-isopropyl-2-(2-methylpyridin-4-yl)-1H-indol-5-yl)-N-(((R)-pyrrolidin-3-yl) methyl)propanamide (208);
2-(3-isopropyl-2-(2-methylpyridin-4-yl)-1H-indol-5-yl)-N-methyl-N-(piperidin-3-yl) propanamide (209);
2-(3-isopropyl-2-(2-methylpyridin-4-yl)-1H-indol-5-yl)-N-methyl-N-(piperidin-3-yl) propanamide (210);
2-(3-isopropyl-2-(2-methylpyridin-4-yl)-1H-indol-5-yl)-N-methyl-N-(quinuclidin-3-yl)propanamide (211);
2-(3-isopropyl-2-(2-methylpyridin-4-yl)-1H-indol-5-yl)-N-(((S)-pyrrolidin-3-yl) methyl)propanamide (212);
2-(3-isopropyl-2-(2-methylpyridin-4-yl)-1H-indol-5-yl)-N-(piperidin-3-ylmethyl) propanamide (213);
2-(3-isopropyl-2-(2-methylpyridin-4-yl)-1H-indol-5-yl)-N-((1R,5S)-8-methyl-8-azabicyclo[3.2.1]octan-3-yl) propanamide (214);
N-((1R,2R)-2-aminocyclohexyl)-2-(3-isopropyl-2-(2-methylpyridin-4-yl)-1H-indol-5-yl)propanamide (215);
N-((1R,2R)-2-aminocyclohexyl)-2-(3-isopropyl-2-(2-methylpyridin-4-yl)-1H-indol-5-yl)propanamide (216);
N-(4-aminocyclohexyl)-2-(3-isopropyl-2-(2-methylpyridin-4-yl)-1H-indol-5-yl) propanamide (217);
N-(3-aminocyclohexyl)-2-(3-isopropyl-2-(2-methylpyridin-4-yl)-1H-indol-5-yl) propanamide (218);
N-(3-aminocyclohexyl)-2-(3-isopropyl-2-(2-methylpyridin-4-yl)-1H-indol-5-yl) propanamide (219);
3-chloro-5-(3-isopropyl-5-(4-methylpiperazine-1-carbonyl)-1H-indol-2-yl)-1,4-dimethylpyridin-2(1H)-one (220);
2-(5-chloro-1,4-dimethyl-6-oxo-1,6-dihydropyridin-3-yl)-N-cyclopropyl-3-isopropyl-N-(1-propylpiperidin-4-yl)-1H-indole-5-carboxamide (221); or
2-(5-chloro-1,4-dimethyl-6-oxo-1,6-dihydropyridin-3-yl)-N-(2-(dimethylamino) ethyl)-3-isopropyl-N-methyl-1H-indole-5-carboxamide (222).

9. The compound according to claim 1, N-oxide, or a salt thereof, wherein

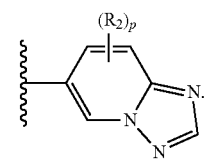

* * * * *

UNITED STATES PATENT AND TRADEMARK OFFICE
CERTIFICATE OF CORRECTION

PATENT NO. : 11,420,973 B2  
APPLICATION NO. : 16/954543  
DATED : August 23, 2022  
INVENTOR(S) : Alaric Dyckman et al.

Page 1 of 1

It is certified that error appears in the above-identified patent and that said Letters Patent is hereby corrected as shown below:

In the Claims

Claim 1, Column 161, Line 16, delete "$R_{10}$ a;" and insert -- $R_{10a}$; --.

Claim 8, Column 162, Line 14, delete "2-{-[2-" and insert -- 2-{5-[2- --.

Claim 8, Column 162, Line 17, delete "2(5" and insert -- 2-(5 --.

Claim 8, Column 162, Line 20, delete "1-(2-{5[2-(3,4" and insert -- 1-(2-{5-[2-(3,4 --.

Claim 8, Column 162, Line 25, delete "dimethylamino)" and insert -- (dimethylamino) --.

Claim 8, Column 162, Line 30, delete "(2(3,4" and insert -- (2-(3,4 --.

Claim 8, Column 162, Line 31, delete "(542" and insert -- (5-(2 --.

Claim 8, Column 162, Line 33, delete "(2(3,4" and insert -- (2-(3,4 --.

Claim 8, Column 166, Line 48, delete "(R)—" and insert -- (R)- --.

Signed and Sealed this  
Sixteenth Day of September, 2025

Coke Morgan Stewart  
*Acting Director of the United States Patent and Trademark Office*